(12) United States Patent
Flynn et al.

(10) Patent No.: US 7,790,756 B2
(45) Date of Patent: Sep. 7, 2010

(54) KINASE INHIBITORS USEFUL FOR THE TREATMENT OF MYLEOPROLIFERATIVE DISEASES AND OTHER PROLIFERATIVE DISEASES

(75) Inventors: Daniel L. Flynn, Lawrence, KS (US); Peter A Petillo, Lawrence, KS (US); Michael D Kaufman, Lawrence, KS (US)

(73) Assignee: Deciphera Pharmaceuticals, LLC, Lawrence, KS (US)

( * ) Notice: Subject to any disclaimer, the term of this patent is extended or adjusted under 35 U.S.C. 154(b) by 0 days.

(21) Appl. No.: 11/870,388

(22) Filed: Oct. 10, 2007

(65) Prior Publication Data

US 2008/0090856 A1 Apr. 17, 2008

Related U.S. Application Data

(60) Provisional application No. 60/850,834, filed on Oct. 11, 2006.

(51) Int. Cl.
*A61K 31/44* (2006.01)

(52) U.S. Cl. .................. 514/341; 546/143; 546/162; 546/268.1; 548/375.1

(58) Field of Classification Search .................. 514/341; 546/143, 162, 268.1; 548/375.1
See application file for complete search history.

(56) References Cited

U.S. PATENT DOCUMENTS

| | | |
|---|---|---|
| 3,528,980 A | 9/1970 | Islip |
| 3,818,024 A | 6/1974 | Krenzer |
| 3,939,122 A | 2/1976 | Merten et al. |
| 3,949,002 A | 4/1976 | Feasey et al. |
| 4,093,624 A | 6/1978 | Revankar et al. |
| 4,296,237 A | 10/1981 | Cragoe, Jr. et al. |
| 4,366,189 A | 12/1982 | Burdeska et al. |
| 4,432,992 A | 2/1984 | Cragoe, Jr. et al. |
| 4,525,450 A | 6/1985 | Itoh et al. |
| 4,816,454 A | 3/1989 | Zoller et al. |
| 5,103,014 A | 4/1992 | Musser et al. |
| 5,162,360 A | 11/1992 | Creswell et al. |
| 5,319,099 A | 6/1994 | Kamata et al. |
| 5,494,925 A | 2/1996 | Court et al. |
| 5,514,691 A | 5/1996 | Chan et al. |
| 5,621,010 A | 4/1997 | Sueda et al. |
| 5,721,231 A | 2/1998 | Moriwaki et al. |
| 5,811,456 A | 9/1998 | Seman et al. |
| 6,020,357 A | 2/2000 | Pinto et al. |
| 6,080,763 A | 6/2000 | Regan et al. |
| 6,197,599 B1 | 3/2001 | Chin et al. |
| 6,235,786 B1 | 5/2001 | Dai et al. |
| 6,294,573 B1 | 9/2001 | Curtin et al. |
| 6,319,921 B1 | 11/2001 | Cirillo et al. |
| 6,410,254 B1 | 6/2002 | Finer et al. |
| 6,500,628 B1 | 12/2002 | Robison |
| 6,525,046 B1 | 2/2003 | Cirillo et al. |
| 6,645,990 B2 | 11/2003 | Askew et al. |
| 6,916,924 B2 | 7/2005 | Tan et al. |
| 7,135,550 B2 | 11/2006 | Come et al. |
| 7,144,911 B2 | 12/2006 | Flynn et al. |
| 7,202,257 B2 | 4/2007 | Flynn et al. |
| 7,211,575 B2 | 5/2007 | Moss et al. |
| 7,342,037 B2 | 3/2008 | Flynn et al. |
| 7,531,566 B2 | 5/2009 | Flynn et al. |
| 2002/0058678 A1 | 5/2002 | Cirillo et al. |
| 2002/0165394 A1 | 11/2002 | Dumas et al. |
| 2002/0193405 A1 | 12/2002 | Askew |
| 2003/0060455 A1 | 3/2003 | Moss et al. |
| 2003/0144278 A1 | 7/2003 | Riedl et al. |
| 2003/0181442 A1 | 9/2003 | Riedl et al. |
| 2004/0043388 A1 | 3/2004 | Come et al. |
| 2004/0102636 A1 | 5/2004 | Miller et al. |
| 2004/0157827 A1 | 8/2004 | Pevarello et al. |
| 2004/0171075 A1 | 9/2004 | Flynn et al. |
| 2004/0180906 A1 | 9/2004 | Flynn et al. |
| 2005/0165024 A1 | 7/2005 | Milanov et al. |
| 2005/0165031 A1 | 7/2005 | Grotzfeld et al. |
| 2005/0192314 A1 | 9/2005 | Mehta et al. |
| 2005/0197371 A1 | 9/2005 | Milanov et al. |
| 2005/0267182 A1 | 12/2005 | Milanov et al. |
| 2005/0288286 A1 | 12/2005 | Flynn et al. |
| 2007/0078121 A1 | 4/2007 | Flynn et al. |
| 2007/0191336 A1 | 8/2007 | Flynn et al. |

(Continued)

FOREIGN PATENT DOCUMENTS

DE 1115350 10/1961

(Continued)

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Branford et al., "High frequency of point mutations clustered within the adenosine triphosphate-binding region of BCR/ABL in patients with chronic myeloid leukemia or Ph-positive acute lymphoblastic leukemia who develop imatinib (ST1571)resistance," *Blood* (2002) vol. 99, pp. 3472-3475.
Carr, J.B. et al, "Isoxazole Anthelmintics," *J. Med. Chem* (1977) vol. 20, No. 7, pp. 934-939.
Chan, "Promotion of Reaction of N-H Bonds with Triarylbismuth and Cupric Acetate," *Tetrahedron Letters* (1996) vol. 37, No. 50, pp. 9013-9016.

(Continued)

*Primary Examiner*—James O Wilson
*Assistant Examiner*—Douglas M Willis
(74) *Attorney, Agent, or Firm*—Wilmer Cutler Pickering Hale and Dorr LLP

(57) ABSTRACT

The present invention is concerned with novel compounds useful in the treatment of hyperproliferative diseases and mammalian cancers, especially human cancers. The invention also pertains to methods of modulating kinase activities, pharmaceutical compositions, and methods of treating individuals, incorporating or using the compounds. The preferred compounds are active small molecules set forth in formulae Ia-Iww.

22 Claims, No Drawings

U.S. PATENT DOCUMENTS

| | | |
|---|---|---|
| 2007/0244120 A1 | 10/2007 | Dumas et al. |
| 2008/0009527 A1 | 1/2008 | Dumas et al. |
| 2008/0045531 A1 | 2/2008 | Flynn et al. |
| 2008/0045706 A1 | 2/2008 | Flynn et al. |
| 2008/0090856 A1 | 4/2008 | Flynn et al. |
| 2008/0113967 A1 | 5/2008 | Flynn et al. |
| 2008/0132506 A1 | 6/2008 | Flynn et al. |
| 2008/0187978 A1 | 8/2008 | Flynn et al. |
| 2008/0220497 A1 | 9/2008 | Flynn et al. |
| 2008/0248487 A1 | 10/2008 | Flynn et al. |
| 2008/0248548 A1 | 10/2008 | Flynn et al. |
| 2009/0069310 A1 | 3/2009 | Flynn et al. |
| 2009/0075986 A1 | 3/2009 | Flynn et al. |
| 2009/0105230 A1 | 4/2009 | Flynn et al. |
| 2009/0137021 A1 | 5/2009 | Flynn et al. |
| 2009/0312349 A1 | 12/2009 | Flynn et al. |

FOREIGN PATENT DOCUMENTS

| | | |
|---|---|---|
| DE | 4343831 | 6/1995 |
| EP | 0021228 | 1/1981 |
| EP | 0025232 | 3/1981 |
| EP | 0154190 A1 | 9/1985 |
| EP | 0661276 | 7/1995 |
| EP | 0692483 | 1/1996 |
| EP | 0739884 A2 | 10/1996 |
| EP | 0867435 | 9/1998 |
| EP | 0927555 | 7/1999 |
| EP | 928790 A1 | 7/1999 |
| EP | 0956855 | 11/1999 |
| EP | 1281399 | 2/2003 |
| FR | 2337554 | 8/1977 |
| FR | 2396549 | 2/1979 |
| GB | 971307 | 9/1964 |
| GB | 1410279 A | 10/1975 |
| GB | 2220206 | 1/1990 |
| JP | 59-15247 | 1/1984 |
| JP | 9221476 A | 8/1997 |
| JP | 107804 | 1/1998 |
| JP | 2000275886 | 10/2000 |
| JP | 20012687 A | 7/2002 |
| WO | WO-91/19708 | 12/1991 |
| WO | WO-92/08693 | 5/1992 |
| WO | WO-94/18176 | 8/1994 |
| WO | WO 94/21617 | 9/1994 |
| WO | WO-94/24095 | 10/1994 |
| WO | WO-95/15954 | 6/1995 |
| WO | WO-95/29902 | 11/1995 |
| WO | WO-95/34540 | 12/1995 |
| WO | WO-96/16046 | 5/1996 |
| WO | WO-96/19477 | 6/1996 |
| WO | WO-97/34900 | 9/1997 |
| WO | WO-9740028 | 10/1997 |
| WO | WO-98/22103 | 5/1998 |
| WO | WO-98/52558 | 11/1998 |
| WO | WO-99/15164 | 4/1999 |
| WO | WO-99/23091 | 5/1999 |
| WO | WO-99/23093 | 5/1999 |
| WO | WO 99/32106 | 7/1999 |
| WO | WO 99/32110 | 7/1999 |
| WO | WO 99/32111 | 7/1999 |
| WO | WO 99/32455 | 7/1999 |
| WO | WO-99/37622 A1 | 7/1999 |
| WO | WO-99/59959 | 11/1999 |
| WO | WO-00/06550 | 2/2000 |
| WO | WO-00/07980 | 2/2000 |
| WO | WO-00/18738 | 4/2000 |
| WO | WO-00/21927 A2 | 4/2000 |
| WO | WO 00/41698 | 7/2000 |
| WO | WO 00/42012 | 7/2000 |
| WO | WO-00/43384 | 7/2000 |
| WO | WO-00/55139 | 9/2000 |
| WO | WO-00/59506 A1 | 10/2000 |
| WO | WO-01/12621 | 2/2001 |
| WO | WO-01/14372 | 3/2001 |
| WO | WO-01/74771 | 10/2001 |
| WO | WO-01/96298 | 12/2001 |
| WO | WO 02/00647 | 1/2002 |
| WO | WO-02/14291 | 2/2002 |
| WO | WO 02/14311 | 2/2002 |
| WO | WO-02/28835 | 4/2002 |
| WO | WO-02/34727 | 5/2002 |
| WO | WO-02/060869 | 8/2002 |
| WO | WO-02/060876 | 8/2002 |
| WO | WO 02/062763 | 8/2002 |
| WO | WO-02/070662 | 9/2002 |
| WO | WO-03/005999 | 1/2003 |
| WO | WO-03/053368 | 7/2003 |
| WO | WO-03/059373 | 7/2003 |
| WO | WO-03/068223 | 8/2003 |
| WO | WO 03/068223 | 8/2003 |
| WO | WO-03/072577 | 9/2003 |
| WO | WO-03/084539 | 10/2003 |
| WO | WO 2004/004720 | 1/2004 |
| WO | WO-2004/056783 | 7/2004 |
| WO | WO-2004/060306 | 7/2004 |
| WO | WO-2004/061084 | 7/2004 |
| WO | WO 2004/061084 | 7/2004 |
| WO | WO 2004/078128 | 9/2004 |
| WO | WO-2004/113352 | 12/2004 |
| WO | WO 2005/002673 | 1/2005 |
| WO | WO 2005/048948 | 6/2005 |
| WO | WO-2005/110994 | 11/2005 |
| WO | WO-2006/014290 | 2/2006 |
| WO | WO 2006/039718 | 4/2006 |
| WO | WO-2006/071940 | 7/2006 |
| WO | WO 2006/071940 | 7/2006 |
| WO | WO 2006/072589 | 7/2006 |
| WO | WO 2006/081034 | 8/2006 |
| WO | WO-2007/008917 | 1/2007 |
| WO | WO 2007/064872 * | 6/2007 |
| WO | WO 2007/076473 | 7/2007 |
| WO | WO-2008/046003 | 4/2008 |

OTHER PUBLICATIONS

Chan et al., "Copper promoted C-N and C-O bond cross-coupling with phenyl and pyridylboronates," *Tetrahedron Letters* (2003) vol. 44, pp. 3863-3865.

Daley et al., "Induction of Chronic Myelogenous Leukemia in Mice by the P210[bcr/abl] Gene of the Philadelphia Chromosome," *Science* (Feb. 16, 1990) vol. 247, pp. 824-830.

Dumas et al., "Recent developments in the discovery of protein kinase inhibitors from the urea class," *Current Opinion in Drug Discovery & Development* (2004) vol. 7, No. 5, pp. 600-616.

Ettmayer et al, "Lessons Learned from Marketed and Investigational Prodrugs," *Journal of Medicinal Chemistry* (May 6, 2004) vol. 47, No. 10, pp. 2393-2404.

Faderl et al., "The Biology of Chronic Myeloid Leukemia," *The New England Journal of Medicine* (Jul. 15, 1999) vol. 341, No. 3, pp. 164-172.

Gishizky et al., "Efficient transplantation of BCR-ABL-induced chronic myelogenous leukemia-like syndrome in mice," *Proc. Natl. Acad. Sci.* (Apr. 1993) vol. 90, pp. 3755-3759.

Gorre et al., "Clinical Resistance to STI-571Cancer Therapy Caused by BCR-ABL Gene Mutation or Amplification," *Science* (Aug. 3, 2001) vol. 293, pp. 876-880.

Hackler et al., "The Syntheses of 5-Amino-3- t-butylisothiazole and 3-Amino-5- t-butylisothiazole," *J. Heterocyclic Chem.* (Nov.-Dec. 1989) vol. 26, pp. 1575-1578.

Huse et al., "The Conformational Plasticity of Protein Kinases," *Cell* (May 3, 2002) vol. 109, pp. 275-282.

Konopka et al., "Cell lines and clinical isolates derived from Ph[1]—positive chronic myelogenous leukemia patients express c-*abl* proteins with a common structural alteration," *Proc. Natl. Acad. Sci.* (Mar. 1985) vol. 82, pp. 1810-1814.

Li et al, "The P190, P210, and P230 Forms of the BCR/ABL Oncogene Induce a Similar Chronic Myeloid Leukemia-like Syndrome in Mice but Have Different Lymphoid Leukemogenic Activity," *J. Exp. Med.* (1999) vol. 189, No. 9, pp. 1399-1412.

Lorenzi et al., "Amino Acid Ester Prodrugs of 2-Bromo-5, 6-dichloro-1-(β-D-ribofuranosyl)benzimidazole Enhance Metabolic Stability In Vitro and In Vivo," *The Journal of Pharmacology and Experimental Therapeutics* (2005) vol. 314, No. 2, pp. 883-890.

Lowinger et al., "Design and Discovery of Small Molecules Targeting Raf-1 Kinase," *Current Pharmaceutical Design* (2002) vol. 8, No. 25, pp. 2269-2278.

Nagar et al., "Structural Basis for the Autoinhibition of c-Abl Tyrosine Kinase," *Cell* (Mar. 21, 2003) vol. 112, pp. 859-871.

Nowell et al., "A Minute Chromosome in Human Chronic Granulocytic Leukemia," *Science* (Nov. 18, 1960) vol. 132, p. 1497.

Pluk et al., "Autoinhibition of c-Abl," *Cell* (Jan. 25, 2002) vol. 108, pp. 247-259.

Rowley, "A New Consistent Chromosomal Abnormality in Chronic Myelogenous Leukaemia identified by Quinacrine Flourescence and Giemsa Staining," *Nature* (Jun. 1, 1973) vol. 243, pp. 290-293.

Sawyers, "Chronic Myeloid Leukemia," *The New England Journal of Medicine* (Apr. 29, 1999) vol. 340, No. 17, pp. 1330-1340.

Schindler et al., "Structural Mechanism for STI-571 Inhibition of Abelson Tyrosine Kinase," *Science* (Sep. 15, 2000) vol. 289, pp. 1938-1942.

Shah et al., "Overriding Imatinib Resistance with a Novel ABL Kinase Inhibitor," *Science* (Jul. 16, 2004) vol. 305, pp. 399-401.

Sircar et al., "Synthesis of 4-Hydroxy-*N*-[5-(hydroxymethyl)-3-isoxazolyl]2-methyl-2*H*-1,2-bsnzo-thiazine-3-carboxamide 1,1-Dioxide and [(5-Methyl-3-isoxazolyl)amino]oxoacetic Acid. Major Metabolites of Isoxicam," *J. Org. Chem.* (1985) vol. 50, pp. 5723-5727.

Takase et al., "Practical Synthesis of 3-Amino-5-*tert*-Butylisoxazole from 4,4-Dimethyl-3-Oxopentanenitrile with Hydroxylamine," *Heterocycles* (1991) vol. 32, No. 6, pp. 1153-1158.

Van Etten, "Cycling, stressed-out and nervous: cellular functions of c-Abl," *Trends in Cell Biology* (May 1999) vol. 9, pp. 179-186.

von Bubnoff et al., "BCR-ABL gene mutations in relation to clinical resistance of Philadelphia-chromosome-positive leukemia to STI571: a prospective study," *The Lancet* (Feb. 9, 2002) vol. 359, pp. 487-491.

Wan et al., "Mechanism of Activation of the RAF-ERK Signaling Pathway by Oncogenic Mutations of B-RAF," *Cell* (Mar. 19, 2004) vol. 116, pp. 855-867.

"Additions and Corrections", Journal of Medicinal Chemistry, 32(12):2583 (1989).

"NHLBI LBC Computational Biophysics Scetion", CHARMM Documentation Index, http://www.lobos.nih.gov/Charmm/chmdoc.html, printed Mar. 4, 2005 (1 page).

"Trilateral Project WM4 -Comparative Studies in New Technologies: Report on Comparative Study on Protein 3-Dimensional Structure Related Claims—ANNEX 3: Comments of the USPTO", Vienna, Austria, Nov. 4-8, 2002, pp. 58-79.

Aklilu, et al., "Increased PTHRP Production by a Tyrosine Kinase Oncogene, Tpr-Met: Rose of the Ras Signaling Pathway", The American Physiological Society, pp. E277-E283 (1996).

Albericio, et al., "Synthesis of a Sulfaydantion Library", J. Comb. Chem., 3:290-300 (2001).

Almerico, et al., "On the Preparation of 1-aryl-2-heteroaryl- and 2-aryl-1-heteroaryl-pyrroles as Useful Building Blocks for Biologically Interesting Heterocycles", ARKIVOC, Rudy Abramovitch Issue, pp. 129-142 (2001).

Anzai, et al., "Alkyl- and Arylthiation of Uracil and Indole", J. Heterocyclic Chem., 16:567-569 (1979).

Askew, et al., "Molecular Recognition with Convergent Functional Groups: 6. Synthetic and Structural Studies with a Model Receptor for Nucleic Acid Components", J. Am. Chem., 111:1082-1090 (1989).

Bais, et al., "Inhibition of Endogenous Wxalate Production: Biochemical Consideration of the Roles of Glycollate Oxidase and Lactate Dehydrogenase", Clinical Science, 76:303-309 (1989).

Baker, et al., "Irreversible Enzyme Inhibitors. 188. Inhibition of Mammalian Thymidine Phosphorylase", Journal of Medicinal Chemistry, 14:612-616 (1971).

Barker, et al., "Characterization of pp60c-src Tyrosine Kinase Activities Using a Continuous Assay: Autoactivation of the Enzyme is an Intermolecular Autophosphorylation Process", Biochemistry, 35:14843-14851 (1995).

Bausch, et al., "Proton-Transfer Chemistry of Urazoles and Related Imides, and Diacyl Hydrazides", J. Org. Chem., 56:5643-5651 (1991).

Benvenuti, et al., "Crystallization of Soluble Proteins in Vapor Diffusion for X-Ray Crystallography", Nature Protocols, 2(7):1633-1651 (2007).

Bosca, et al., "Circular Dichroism Analysis of Ligand-Induced Conformational Changes in Protein Kinase C", Biochem J., 290:827-832 (1993).

Boschelli, et al., "4-Anilino-3-quinolinecarbonitriles: An Emerging Class of Kinase Inhibitors", Current Topics in Medicinal Chemistry, 2:1051-1063 (2002).

Bourdonnec, et al., "Synthesis and Pharmacological Evaluation of New Pyrazolidine-3,5-diones as $AT_1$ Angiotensin II Receptor Antagonists", J. Med. Chem., 43:2685-2697 (2000).

Boyer, "Small Molecule Inhibitors of KDR (VEGFR-2) Kinase: An Overview of Structure Activity Relationships", Current Topics in Medicinal Chemisty, 2:973-1000 (2002).

Brady, et al., "Fast Prediction and Visualization of Protein Binding Pockets with PASS". Journal of Computer-Aided Molecular Design, 14:383-401 (2000).

Brasher, et al., "C-Abul has High Intrinsic Tyrosine Kinase Activity that is Stimulated by Mutation of the Src Homology 3 Domain and by Autophosphorylation at Two Distinct Regulatory Tyrosines", Journal of Biological Chemistry, 275:35631-35637 (2000).

Bullock, et al., "Prospects for Kinase Activity Modulators in the Treatment of Diabetes and Diabetic Complications", Current Topics in Medicinal Chemistry, 2:915-938 (2002).

Byron, et al., "The Synthesis of some Substituted Biphenyl-4-carboxylic Acids, 4-Biphenylylacetic Acids, and 4-Aminobiphenyls", J. Chem. Soc. (C), Organic, pp. 840-845 (1966).

Cardillo, et al., "Sulle 1,2-difenil-3.5-dichetopirazolidine", Gazz. Chim., Ital., 9:973-985 (1966)—Italian Language.

Chen, et al., "Biochemical Evidence for the Autophosphorylation and Transphosphorylation of Transforming Growth Factor β Receptor Kinases", Proc. Natl. Acad. Sci. USA, 92:1565-1569 (1995).

Cheng, et al., "Novel Solution Phase Strategy for the Synthesis of Chemical Libraries Containing Small Organic Molecules", J. Am. Chem. Soc., 118:2567-2573 (1996).

Cheng, et al., "Synthesis and SAR of Heteroaryl-phenyl-substituted Pyrazole Derivatives as Highly Selective and Potent Canine COX-2 Inhibitors", Bioorganic & Medicinal Chemistry Letters, 16:2076-2080 (2006).

Chu, et al., "Using Affinity Capillary Electrophoresis to Determine Binding Stoichiometries of Protein-Ligand Interactions", Biochemistry, 33:10616-10621 (1994).

Cirillo, et al. "The Non-Diaryl Heterocycle Classes of p38 MAP Kinase Inhibitors", Current Topics in Medicinal Chemistry, 2:1021-1035 (2002).

Closier, et al., "Nitrofuryl Heterocyclics. 1", Journal of Medicinal Chemistry, 13(4):638-640 (1970).

Cockerill, et al., "Small Molecule Inhibitors of the Class 1 Receptor Tyrosine Kinase Family", Current Topics in Medicinal Chemistry, 2:1001-1010 (2002).

Colton, et al., "Affinity Capillary Electrophoresis: A Physical-Organic Tool for Studying Interactions in Biomolecular Recognition", Electrophoresis, 19:367-382 (1998).

Cortes, et al., "Results of Imatinib Mesylate Therapy in Patients with Refractory or Recurrent Acute Myeloid Leukemia, High-Risk Myelodysplastic Syndrime, and Myeloproliferative Disorders", Cancer, 97(11):2760-2766 (2003).

Cross, et al., "Inhibition of Glycogen Synthase Kinase-3 by Insulin Mediated by Protein Kinase B", Nature, 378:785-789 (1995).

Cudney, "Preface: Protein Crystallization and Dumb Luck", The Rigaku Journal, 16(1):1-7 (1999).
Dajani, et al., "Crystal Structur of Glycogen Synthase Kinas 3β: Structural Basis for Phosphate-Primed Substrate Specificity and Autoinhibition", Cell, 105:721-732 (2001).
Dajani, et al., "Structural Basis for Recruitment of Glycogen Synthase Kinase 3β to the Axin-APC Scaffold Complex", EMBO, 22(3):494-501 (2003).
Davis, et al., "Iterative Size-Exclusion Chromatography Coupled with Liquid Chromatographic Mass Spectrometry to Enrich and Identify Tight-Binding Ligands from Complex Mixtures", Tetrahedron, 55:11653-11667 (1999).
de Boer, et al., "Synthesis and Characterization of Conjugated Mono- and Dithiol Oligomers and Characterization of Their Self-Assembled Monolayers", Langmuir, 19:4272-4284 (2003).
de Silva, et al., "Gastrointestinal Stromal Tumors (GIST): C-kin Mutations, CD117 Expression, Differential Diagnosis and Targeted Cancer Therapy with Imatinib", Pathology Oncology Research, 9(1):13-19 (2003).
Deng, et al., "Expression, Characterization, and Crystallization of the Pyrophosphate-Dependent Phosphofructo-1-Kinase of *Borrelia burgdorferi*", Archives of Biochemistry and Biophysics, 371(2):326-331 (1999).
Dess, et al., "A Useful 12-I-5 Triacetoxyperiodiane (the Dess-Martin Periodiane) for Selective Oxidation of Primary or Secondary Alcohols and a Variety of Related 12-I-5 Species", J. Am. Chem., Soc., 113:7277-7287 (1991).
Dumas, "Preface", *Current Topics in Medicinal Chemistry* (2002) (1 Page).
Dumas, "Protein Kinase Inhibitors: Emerging Pharmacophores", Exp. Opin. Ther. Patent, 11:405-429 (2001).
Dumas, et al., "Discovery of a New Class of p38 Kinase Inhibitors", Bioorganic & Medicinal Chemistry Letters, 10:2047-2050 (2000).
Ewing, "Critical Evaluation of Search Algorithms for Automated Molecular Docking and Database Screening", Journal of Computational Chemistry, 18(9):1175-1189 (1997).
Farooqui, et al., "Interactions Between Neural Membrane Glycerophospholipid and Sphingolipid Mediators: A Recipe for Neural Cell Survival or Suicide", Journal of Neuroscience Research, 85:1834-1850 (2007).
Fathalla, "Synthesis of New Pyrazolo[1,5-a]pyrimidine Derivative Using 5-Aminouracil and Ketene Dithiacetal", Arch Pharm Res, 22(6):571-574 (1999).
Fathalla, et al., "Synthesis of New Uracil-5-Sulfonamide Derivatives and Immuno-Stimulatory Effect of a Chemically Modified Hemolymph of *Biomphalaria alexandrina* on *Schistosoma manosi* Infected Mice", Arch Pharm Res., 26(5):358-366 (2003).
Fathalla, et al., "Synthesis of New Uracil-5-Sulphonamide-p-Phenyl Derivatives and Their Effect on *Biomphalaria alexandrina* Snail's Nucleoproteins", Arch. Pharm. Res., 23(2):128-138 (2000).
Flatt, et al., "Synthesis of Thiol Substituted Oligoanilines for Molecular Device Candidates", Tetrahedron Letters, 44:6699-6702 (2003).
Fletcher, et al., "Diagnosis of Gastrointestinal Stromal Tumors: A Consensus Approach", 33(5):459-465 (2002).
Frame, et al., "A Common Phosphate Binding Site Explains the Unique Substrate Specificity of GSK3 and Its Inactivation by Phosphorylation", Molecular Cell, 7:1321-1327 (2001).
Furyua, et al., "Addition of 4-Ethoxyimidazoles to Dimethyl Acetylenedicarboxylate and Transformation of the Adducts to Pyrimidian-5-yl Acetates", Chem. Pharm. Bull., 36(5):1669-1675 (1988).
Garcia-Tellado, et al., "Molecular Recognition in the Solid Waste State: Controlled Assembly of Hydrogen-Bonded Molecular Sheets", J. Am. Chem. Soc., 113:9265-9269 (1991).
Greene, et al., "Chapter 7: Protection for the Amino Group", in Protective Groups in Organic Synthesis, Third Edition, pp. 494-653 (1999).
Griffith, et al., "TPAP: Tetra-n-propylammonium Perruthenate, A Mild and Convenient Oxidant for Alcohols", Aldrichimica Acta, 23(1):13-19 (1990).

Guzel, "Investigation of the Relationship Between the Inhibitory Activity of Glycolic Acid Oxidase (GAO) and its Chemical Structure: Electron-Topological Approach", Journal of Molecular Structure, 366:131-137 (1996).
Haar, et al., "Structure of GSK3β Reveals a Primed Phosphorylation Mechanism", Nature Structural Biology, 8(7):593-596 (2001).
Haesslein, et al., "Recent Advances in Cyclin-Dependent Kinase Inhibition. Purine-Based Derivatives as Anti-Cancer Agents. Roles and Perspectives for the Future", Current Topics in Medicinal Chemistry, 2:1037-1050 (2002).
Heegaard, et al., "Affinity Capillary Electrophoresis: Important Application Areas and Some Recent Developments", Journal of Chromatography B, 715:29-54 (1998).
Honda, et al., "Determination of the Association Constant of Monovalent Mode Protein-Sugar Interaction by Capillary Zone Electrophoresis", Journal of Chromatography, 597:377-382 (1992).
Hu, et al., "Capillary Electrophoresis for the Analysis of Biopolymers", Anal., Chem., 74:2833-2850 (2002).
Huang, et al., "Inhibition of Nucleoside Transport by Protein Kinase Inhibitors", The Journal of Pharmacology and Experimental Therapeutics, 304(2):753-760 (2003).
Hubbard, "Crystal Structure of the Activated Insulin Receptor Tyrosine Kinase in Complex with Peptide Substrate and ATP Analog", EMBO, 16(18):5573-5581 (1997).
Hubbard, et al., "Crystal Structure of the Tyrosine Kinase Domain of the Human Insulin Receptor", Nature, 374:746-754 (1994).
Hughes, et al., "Modulation of the Glycogen Synthase Kinase-3 Family by Tyrosine Phosphorylation", EMBO, 12(2):803-808 (1993).
Huse, et al., "Crystal Structure of the Cytoplasmic Domain of the Type I TGFβ Receptor in Complex with FKBP12", Cell, 96:425-436 (1999).
Huse, et al., "The TGFβ Receptor Activation Process: An Inhibitor- to Substrate-Binding Switch", Molecular Cell, 8:671-682 (2001).
Igarashi, et al., "Antimicrobial Activities of 2-arylthio-N-alkylmaleimides", Journal of Industrial Microbiology, 9:91-96 (1992).
International Human Genome Sequencing Consortium, "Initial Sequencing and Analysis of the Human Genome", Nature, 409:860-921 (2001).
International Search Report issued for PCT/US2008/060833 mailed Sep. 30, 2008 (5 pages).
International Search Report issued for PCT/US2008/060867, mailed Sep. 29, 2008 (5 pages).
International Search Report issued for PCT/US2008/060896, mailed Sep. 29, 2008 (5 pages).
Ishida, et al., "Molecular Arrangement and Electrical Conduction of Self-Assembled Monolayers Made from Terphenyl Thiols", Surface Sciences, 514:187-193 (2002).
Islip, et al., "Nitrofuryl Heterocyclics 3", Journal of Medicinal Chemistry, 16(11):1309-1310 (1973).
Jackson, et al., "N-Terminal Mutations Activate the Leukemogenic Potential of the Myristoylated form of c-abl", EMBO, 8(2):449-456 (1989).
Jackson, et al., "Pyridinylimidazole Based p38 MAP Kinase Inhibitors", Current Topics in Medicinal Chemistry, 2:1011-1020 (2002).
Jiang, et al., ""Soft Docking": Matching of Molecular Surface Cubes", J. Mol. Biol., 219:79-102 (1991).
Jiang, et al., "Synthesis and SAR Investigations for Novel Melanin-Concentrating Hormone 1 Receptor (MCH$_1$) Antagonists Part 1. The Discovery of Arylacetamides as Viable Replacements for the Dihydropyrimidione Moiety of an HTS Hit", J. Med. Chem., 50:3870-3882 (2007).
Johnson, "Circular Dichroism Spectroscopy and the Vacuum Ultraviolet Region", Ann. Rev. Phys. Chem., 29:93-114 (1978).
Johnson, "Protein Secondary Structure and Circular Dichroism: A Practical Guide", Proteins: Structure, Function, and Genetics, 7:205-214 (1990).
Johnson, et al., "An Evaluation of the Effect of Light Stabilisers on the Exterior Durability of Polyester Powder Coatings for the Architectural Market", Surface Coatings International, 3:134-141 (1999).

Johnson, et al., "The Stereochemistry of Oxidation at Sulfur Oxidation of 2- Thiabicyclo[2.2.1]Hpetane", Tetrahedron, 25:5649-5653 (1969).

Katritzky, et al., "Novel Chromophoric Heterocycles Based on Maleimide and Naphthoquinone", J. Heterocyclic Chem., 26:885-892 (1989).

Kern, et al., "Synthese von Makromolekeln einheitlicher Broβe. II Mitt: Syntheses neuer Diol-oligo-urethane nach dem Duplikationsverfahren", Makromolekulara Chemie, 16:89-107 (1955)—English Summary (20 pages).

Kim, et al., "Solid Phase Synthesis of Benzamidine and Butylamine-Derived Hydantoin Libraries", Molecular Diversity, 3:129-132 (1998).

Klayman, et al., "The Reaction of S-Methiodide Derivatives of Activated Thioureas with Hydroxylic Compounds. A Novel Synthesis of Mercaptans", J. Org. Chem., 37(10):1532-1537 (1972).

Kleywegt, et al., "Detection, Delineation, Measurement and Display of Cavities in Macromolecular Structures", Acta Cryst, D50:178-185 (1994).

Koch, et al., "QSAR and Molecular Modelling for a Series of Isomeric X-Sulfanilamido-1-phenylpyrazoles", Quant. Struct. Act. Relat., 12:373-382 (1993).

Krasovitskii, et al., "Synthesis and Spectral-Luminescence Properties of Hetarylethylene Derivatives of 2,5-Diphenyloxazole and 2,5-Diphenyl-1,3,4-Oxadiazole", Khimiya Geterotsiklicheskikh Soedinenii, 5:617-621 (1982)—English Translation (10 pages).

Kuhn, et al., "The Genesis of High-Throughput Structure-Based Drug Discovery using Protein Crystallography", Analytical Techniques, Current Opinion in Chemical Biology, 6:704-710 (2002).

Kumar, et al., "P38 Map Kinases: Key Signalling Molecules as Therapeutic Targets for Inflammatory Diseases", Nature Reviews Drug Discovery, 2:717-726 (2003).

Kundrot, "Which Strategy for a Protein Crystallization Project", CMLS, Cell. Mol. Life Sci., 61:525-536 (2004).

Kundu, et al., "Depropargylation Under Palladium-Copper Catatlysis: Synthesis of Diaryl Sulfides", Tetrahedron, 57:5885-5895 (2001).

Kurogi, et al., "Discovery of Novel Mesangial Cell Proliferation Inhibitors Using a Three-Dimensional Database Searching Method", J. Med. Chem., 44:2304-2307 (2001).

Kwong, et al., "A General, Efficient, and Inexpensive Catalyst System for the Coupling Aryl Iodides and Thiols", Organic Letters, 4(20):3517-3520 (2002).

Laskowski, "SURFNET: A Program for Visualizing Molecular Surfaces, Cavities, and Intermolecular Interactions", Journal of Molecular Graphics, 13:323-330 (1995).

Leca, et al., "A New Practical One-Pot Access to Sulfonimidates", Organic Letters, 4(23):4093-4095 (2002).

Lefevre, et al., "Roles of Stem Cell Factor/c-Kit and Effects of Glivec®/STI571 in Human Uveal Melanoma Cell Turmorigenesis", Journal of Biological Chemistry, 279(30):31769-31779 (2004).

Lesort, et al., "Insulin Transiently Increases Tau Phosphorylation: Involvement of Glycogen Synthase Kinase-3β and Fyn Tyrosine Kinase", Journal of Neurochemistry, 72(2):576-584 (1999).

Leung, et al., "The Difluoromethylensulfonic Acid Groups as a Monoanionic Phosphate Surrogate for Obtaining PTP1B Inhibitors", Bioorganic & Medicinal Chemistry, 10:2309-2323 (2002).

Li, et al., "Targeting Serine/Threonine Protein Kinase B/Akt and Cell-cycle Checkpoint Kinases for Treating Cancer", Current Topics in Medicinal Chemistry, 2:939-971 (2002).

Li, et al., "The P190, {210, and P230 Forms of the BCR/ABL Oncogene Induce a Similar Chronic Myeloid Leukemia-like Syndrome in Mice but Have Different Lymphoid Leukemogenic Activity", J. Exp. Med., 189(9):1399-1412 (1999).

Link, et al., "Synthesis of 8-Substituted 5-Deazaflavins", J. Heterocyclic Chem, 22:841-848 (1985).

Lipinski, et al., "Experimental and Computational Approaches to Estimate Solubility and Permeability in Drug Discovery and Development Settings", Advanced Drug Delivery Reviews, 23:3-25 (1997).

Loren, et al., "NH-1,2,3-Triazoles from Azidomethyl Pivalate and Carbamates: Base-Labile N-Protecting Groups", SYNLETT, 18:2847-2850 (2005).

Lorenzi, et al., "Amino Acid Ester Prodrugs of 2-Bromo-5,6-dichloro-1-(β-D-ribofuranosyl)benzimidazole Enhance Metabolic Stability in Vitro and in Vivo", Journal of Pharmacology and Experimental Therapeutics, 314(2):883-890 (2005).

Lowinger, et al., "Design and Discovery of Small Molecules Targeting Raf-1 Kinase", Current Pharmaceutical Design, 8:2269-2278 (2002) (11 pages).

Ma, et al., "c-Met Mutational Analysis in Small Cell Lung Cancer: Novel Juxtamembrane Domain Mutations Regulating Cytoskeletal Functions", Cancer Research, 63:6272-6281 (2003).

Ma, et al., "c-Met: Structure, Functions and Potential for Therapeutic Inhibition", Cancer and Metastasis Reviews, 22:309-325 (2003).

Mallakpour, et al., "Uncatalyzed Polymerization of Bistriazolinediones with Electron-Rich Aromatic Compounds via Electrophilic Aromatic Substitution", Journal of Polymer Science: Part A: Polymer Chemistry, 27:217-235 (1989).

Mamaev, et al., "Synthesis of 2,5'-Bipyrimidines from Substituted 5-Cyanopyrimidines", Khimiya Geterotsiklicheskikh Soedinenni, 24(3):371-375- (1988)—English Translation.

*March's Advanced Organic Chemistry: Reactions, Mechanisms, and Structure, Fifth Edition*, Smith and March Editors, Wiley-Interscience Publication (2001) (4 pages).

Martinez, et al., "First Non-ATP Competitive Glycogen Synthase Kinase 3β (GSK-3β) Inhibitors: Thiadizolidinones (TDZD) as Potential Drugs for the Treatment of Alzheimers Disease", J. Med. Chem., 45(2002)1292-1299 (2002).

Mattsson, et al., "Six X-Linked Agammaglobulinemia-Causing Missense Mutations in the Src Homology 2 Domain of Bruton's Tyrosine Kinase: Phosphotyrosine-Binding and Circular Dichroism Analysis", Journal of Immunology, pp. 4170-4177 (2000).

McPherson, "Current Approaches to Macromolecular Crystallization", Eur. J. Biochem, 189:1-23 (1990).

Medebielle, et al., "A Convenient Synthesis of Perfluoroalkylated and Fluorinated-Aryl Nitrogen Bases by Electrochemically Induced SRN1 Substitution", J. Org. Chem., 61:1331-1340 (1996).

Medebielle, et al., "A New Convenient Synthesis of 5-Aryl Uracils Using SRN1 Aromatic Nucleophilic Substitution", Tetrahedron Letters, 34(21):3409-3412 (1993).

Mikhaleva, et al., "Relative Reactivities of the Chlorine Atoms of 2,2',4-Trichloro-4',5-Dipyrimidinyl in its Reaction with Piperidine", Khimiya Geterotsiklicheskikh Soedinenii, 6:821-826 (1979)—English Translation (12 pages).

Morris, et al., "Automated Docking of Flexible Ligands to Macromolecules", AutoDock Website, www.scripps.edu/mb/olson/doc/autodock/, printed Mar. 3, 2005 (3 pages).

Morris, et al., "Automated Docking Using a Lamarckian Genetic Algorithm and an Empirical Binding Free Energy Function", Journal of Computational Chemistry, 19(14):1639-1662 (1998).

Morstyn, et al., "Stem Cell Factor Is a Potent Synergistic Factor in Hematopoiesis", Oncology, 51:205-214 (1994).

Moss, et al., Basic Terminology of Stereochemistry, Pure & Appl. Chem., 6812):2193-2222 (1996).

Muller, "Glossary of Terms Used in Physical Organic Chemistry", Pure & Appl. Chem., 66(5):1077-1184 (1994).

Muller, et al., "A General Synthesis of 4-Substituted 1,1-Dioxo-1,2,5-thiadiazolidin-3-ones Derived from α-Amino Acids", J. Org. Chem., 54:4471-473 (1989).

Murayama, et al., "JNK (c-Jun $NH_2$ Terminal Kinase) and p38 During Ischemia Reperfusion Injury in the Small Intestine" Transplantation, 81(9):1325-1330 (2006).

Mutlib, et al., "Disposition of 1-[3-(Aminomethyl)phenyl]-N-[3-fluoro-2'-(methylsulfonyl)-[1,1'-biphenyl]-4-yl]-3(trifluomethyl)-1H-pyrazole-5-carboxamide (DPC 423) by Novel Metabolic Pathways. Characterization of Unusual Metabolites by Liquid Chromatography/Mass Spectrometry and NMR", Chem. Res. Toxicol., 15:48-62 (2002).

Mutlib, et al., "P450-Mediated Metabolism of 1[3-(Aminomethyl)phenyl]-N-[3-fluoro-2'-(methylsulfonyl)-[1,1'-biphenyl]-4-yl]-3(trifluomethyl)-1H-pyrazole-5-carboxamide (DCP 423) and Its Analogues to Aldoximes. Characterization of Glutathione Conjugates of Postulated Intermediates Derived from Aloximes", Chem. Res. Toxicol., 15:63-75 (2002).

Nagano, M. et al. "Studies on Organic Sulfur Compounds. XIV. The Reaction of N-alkoxy-carbonyl-N'-(2-thiazolyl)thioureas with some oxidants." Chemical and Pharmaceutical Bulletin. vol. 21, No. 11, pp. 2408-2416. ISSN: 0009-2363. Nov. 1973.

Nagar, et al., "Crystal Structures of the Kinase Domain of c-Abl in Complex with the Small Molecule Inhibitors PD173955 and Imatinib (STI-571)", Cancer Research, 62:4236-4243 (2002).

Nakopoulou, et al., "c-Met Tyrosine Kinase Receptor Expression is Associated with Abnormal β-catenin Expression and Favourable Prognostic Factors in Invasive Breast Carcinoma", Histopathology, 36:313-325 (2000).

Nantaka-Namirski, et al., "Condensation Reaction of Ethyl (4-Uracil)-Acetate with Ethyl Orthoformate", ACTA Polon. Pharm XXVII, 28(5):455-463 (1971).

National Academy of Sciences, "Abstracts of Papers Presented at the Autumn Meeting, Nov. 14-16, 1960", Science, 132:1488-1501 (1960) (15 pages).

Nicolaou, et al.,"Molecular Design and Chemical Synthesis of a Highly Potent Epothilone", ChemMedChem, 1:41-44 (2006).

Nikolaev, et al., "Solubility Polytherm in the System $HNO_3$-$H_2O$-$(C_4H_9O)PO(C_4H_9)_2$", Doklady Akademii Nauk SSSR, 160(4):841-844 (1965)—English Translation.

Nofal, et al., "Synthesis of Novel Uracil-5-Sulphonamide Derivatives of Possible Biological Activity", Egypt J. Chem., 33(4):375-380 (1990).

O'Dell, et al., "Treatment of Rheumatoid Arthritis with Methotrexate Alone, Sulfasalazine and Hydroxychloroquine, or a Combination of All Three Medications", New England J. Med., 334(20):1287-1291(1996).

O'Neill, "Targeting Signal Transduction as a Strategy to Treat Inflammatory Diseases", Nature Review Drug Discovery, Published Online Jun. 9, 2006, www.nature.com/reviews/drugdisc (15 pages).

Okano, et al., "o-Bromophenylzinc Compound: A Readily Available and Efficient Synthetic Equivalent of o-Phenylene 1-Anion 2-Cation", Tetrahedron Letters 39:3001-3004 (1998).

Okishio, et al., "Differential Ligand Recognition by the Src and Phosphatidylinositol 3-Kinase Src Homology 3 Domains: Circular Dichroism and Ultraviolet Resonance Raman Studies", Biochemistry, 42:208-216 (2003).

Okishio, et al., "Identification of Tyrosine Residues Involved in Ligand Recognition by the Phosphatidylinositol 3-Kinase Src Homology 3 Domain: Circular Dichroism and UV Resonance Raman Studies", Biochemistry, 40:15797-15804 (2001).

Okishio, et al., "Role of the Conserved Acidic Residue Asp21 in the Structure of Phosphatidylinositol 3-Kinase Src Homolgy 3 Domain: Circular Dichroism and Nuclear Magnetic Resonance Studies", Biochemistry 40:119-129 (2001).

Parang, et al., "Mechanism-based Design of a Protein Kinase Inhibitor", Nature Structural Biology, 8(1):37-41 (2001).

Pargellis, et al., "Inhibition of p38 MAP Kinase by Utilizing a Novel Allosteric Binding Site", Nature Structural Biology, 9(4):268-272 (2002).

Park, et al., "Mechanism of *met* Oncogene Activation", Cell, 45:895-904 (1986).

Pedersen, "The Preparation of Some N-Methyl-1,2,3-Triazoles", Acta Chimica Scandinavica, 13(5):888-892 (1959).

Peng, et al., "Identification of Novel Inhibitors of BCR-ABL Tyrosine Kinase via Virtual Screening", Bioorganic & Medicinal Chemistry Letters, 13:3693-3699 (2003).

Pereira, et al., "The Role of c-kit and Imatinib Mesylate in Uveal Melonoma", Journal of Carcinogenesis, 4:19 (2005), downloaded from www.carcinogenesis.com/content/4/1/19, Sep. 3, 2008 (8 pages).

Picard, et al., "Inhibitors of Acyl-CoA: Cholesterol O-Acyltrasferase. 17. Structure-Activity Relationships of Several Series of Compounds Derived from N-Chlorosulfonyl Isocyanate", J. Med. Chem., 39:1243-1252 (1996).

Ponzetto, et al., "A Novel Recognition Motif for Phosphatidylinositol 3-Kinase Binding Mediates Its Association with the Hepatocyte Growth Factor/Scatter Factor Receptor", Molecular and Cellular Biology, 13(8):4600-4608 (1993).

Raimbault, et al., "Effects of pH and KCl on the Conformations of Creatine Kinase from Rabbit Muscle", Eur. J. Biochem., 234:570-578 (1995).

Rebek, et al. "Convergent Functional Groups: Synthetic and Structural Studies", J. Am. Chem. Soc., 107:7476-7481 (1985).

Rebek, et al., "Convergent Functional Groups. 2. Structure and Selectivity in Olefin Epoxidation with Peracids", J. Org. Chem., 51:1649-1653 (1986).

Reed, et al., "Circular Dichroic Evidence for an Ordered Sequence Ligand/Binding Site Interactions in the Catalytic Reaction of the cAMP-Dependent Protein Kinase", Biochemistry, 24:2967-2973 (1985).

Regan, et al., "Pyrazole Urea-Based Inhibitors of p38 MAP Kinase: From Lead Compound to Clinical Candidate", J. Med. Chem., 45:2994-3008 (2002).

Regan, et al., "Structure-Activity Relationships of the p38α MAP Kinase Inhibitor 1-(5-*tert*-Butyl-2-*p*-tolyl-2*H*-pyrazol-3-yl)-3-[4-(2-morpholin-4-yl-ethoxy)naph-thalen-1-yl]urea (BIRB 796)", J. Med. Chem., 46:4676-4686 (2003).

Rooney, et al., "Inhibitors of Gylcolic Acid Oxidase. 4-Substituted 3-Hydroxy-1H-pyrrole-2,5-dione Derivatives", J. Med. Chem., 26(5):700-714 (1983).

Roux, et al., "ERK and p38 MAPK-Activated Protein Kinases: a Family of Protein Kinases with Diverse Biological Functions", Microbiology and Molecular Biology Reviews, 68(2):320-344 (2004).

Russell, et al., "3-[3-(Piperdin-1-yl)propyl]indoles as Highly Selective h5-$HT_{1D}$ Receptor", J. Med. Chem., 42:4981-5001 (1999).

Saiga, et al., "Consecutive Cross-Coupling of o-Phenylenedizinc Compound with Acyl and/or Aryl Halides in the Presence of Pd(0)-tris(2,4,6-trimethoxyphenyl)phosphine", Tetrahedron Letters, 41:4629-4632 (2000).

Sakamoto, et al., "Condensed Heteroaromatic Ring Systems. XIX. Synthesis and Reactions of 5-(Tributylstannyl)Isoxazoles", Tetrahedron, 47(28):5111-5118 (1991).

Sakuma, et al., "*c-kit* Gene Mutations in Intracranial Germinomas", Cancer Sci, 95(9):716-720 (2004).

Satsangi, et al., "1-(4-Substituted-thiazol-2-yl)hydatoins as Anti-inflammatory and CNS-Active Agents", Pharmazie, 38:341-342 (1983).

Schmidt, et al., "Germline and Somatic Mutations in the Tyrosine Kinase Domain of the MET proto-oncogene in Papillary Renal Carcinomas", Nature Genetics, 16:68-73 (1997).

Schmidt, et al., "Novel Mutations of the MET Proto-oncogene in Papillary Renal Carcinomas", Oncogene, 18:2343-2350 (1999).

Seimiya, et al., "Telomere Shortening and Growth Inhibition of Human Cancer Cells by Novel Synthetic Telomerase Inhibitors MST-312, MST-295, and MST-199", Molecular Cancer Therapeutics, 1:657-665 (2002).

Seminario, et al., "Theoretical Study of a Molecular Resonant Tunneling Diode", J. Am. Chem. Soc., 122:3015-3020 (2000).

Shah, et al., "Circular Dichroic Studies of Protein Kinase C and its Interactions with Calcium and Lipid Vesicles", Biochimica et Biophysica Acta, 1119:19-26 (1992).

Shi, et al., "Abnormal Diels-Alder Reaction of 5-Alkoxythiazoles with Highly Reactive Dienophiles; 4-Phenyl-3H-1,2,4-triazole-3,5(4H)-dione, Diethyl Azodicarboxylate, and Diethyl Oxomalonate", Bull. Chem. Soc. Jpn., 65:3315-3321 (1992).

Shinkai, et al., "Coenzyme Models, Part 45. Synthesis of Atropisomeric Flavins and their Novel Redox-induced Racemisation", J. Chem. Soc. Perkin Trans., pp. 313-319 (1988).

Shiozaki, et al., "Impaired Differentiation of Endocrine and Exocrine Cells of the Pancreas in Transgenic Mouse Expressing the Truncated Type II Activin Receptor", Biochimica et Biophysica Acta, 1450:1-11 (1999).

Stout, et al., "High-Throughput Structural Biology in Drug Discovery: Protein Kinases", Current Pharmaceutical Design, 10:1069-1082 (2004).

Sugden, et al., ""Stress-Responsive" Mitogen-Activated Protein Kinases (c-Jun N-Terminal Kinases and p38 Mitogen-Activated Protein Kinases) in the Myocardium", Circulation Research—Journal of the American Heart Association, 83:345-352 (1998).

Tanis, et al., "Two Distinct Phosphorylation Pathways Have Additive Effects on Abl Family Kinase Activation", Molecular and Cellular Biology, 23(11):3884-3896 (2003).

Teague, "Implications of Protein Flexibility for Drug Discovery", Nature Reviews, 2:527-541 (2003).

Tominaga, et al., "General model for Estimation of the Inhibition of Protein Kinases Using Monte Carlo Simulations", J. Med. Chem., 47:2534-2549 (2004).

Tremblay, et al., "Efficient Solid-Phase Synthesis of Sulfahydantoins", J. Comb. Chem., 4:429-435 (2002).

Tsuzuki, et al., "Synthesis and Structure-Activity Relationships of Novel 7-Substituted 1,4-Dihydro-4-oxo-1-(2-thiazolyl)-1,8-napthyridine-3-carboxylic Acids as Antitumor Agents. Part 2", J. Med. Chem., 47:2097-2109 (2004).

Venter, et al., "The Sequence of the Human Genome", Science, 291:1304-1351, Feb. 16, 2001; Erratum, Jun. 8, 2001 (49 pages).

Waetzig, et al., "Review Article: Mitogen-Activated Protein Kinases in Chronic Intestinal Inflammation—Targeting Ancient Pathways to Treat Modern Diseases", Aliment Pharmacol Ther, 18:17-32 (2003).

Welker, et al., "Glucocorticoid-Induced Modulation of Cytokine Secretion from Normal and Leukemic Human Myelomonocytic Cells", Int. Arch. Allergy Immunol, 109:110-115 (1996).

Wentland, et al., "3-Quinolinecarboxamides. A Series of Novel Orally-Active Antiherpetic Agents", J. Med. Chem., 36:1580-1596 (1993).

Wilson, et al., "The Structural Basis for the Specificity of Pyridinylimidazole Inhibitors of p38 MAP Kinase", Chemistry & Biology, 4(6):423-431 (1997).

Wilson, et el., "Laser-Jet Delayed Trapping: Electron-Transfer Trapping of the Photoenol from 2-Methylbenzophenone", J. Am. Chem. Soc., 109:4743-4745 (1987).

Wolter, et al., "Copper-Catalyzed Coupling of Aryl Iodides with Aliphatic Alcohols", Organic Letters, 4(6):973-976 (2002).

Wrana, et al., "Mechanism of Activation of the TGF-β Receptor", Nature, 370:341-347 (1994).

Wu, et al., "Discovery of a Novel Family of CDK Inhibitors with the Program LIDAEUS: Structual Basis for Ligand-Induced Disordering of the Acivation Loop", Structure, 11:399-410 (2003).

Yang, et al., "Molecular Mechanism for the Regulation of Protein Kinase B/Akt by Hydrophobic Motif Phosphorylation", Molecular Cell, 9:1227-1240 (2002).

Yang, et al., "Palladium-Catalyzed Amination of Arly Halides and Sulfonates", Journal of Organometallic Chemistry, 576:125-146 (1999).

Yarden, et al., "Human Proto-oncogene c-kit: a New Cell Surface Receptor Tyrosine Kinase for an Unidentified Ligand", The EMBO Journal, 6(11):3341-3351 (1987).

Yoneda, et al., "A New Synthesis of Purines", J.C.S. Chem. Comm., p. 551 (1974).

Yonezawa, et al., "Synthesis of Sequentially Controlled Isomeric, Wholly aromatic Polyketones Composed of 2-trifluoromethylbiphenylene and 2,2'-dimethoxybiphenylene Units", Reactive & Functional Polymers, 52:19-30 (2002).

Yoshimoto, et al., "Correlation Analysis of Baker's Studies on Enzyme Inhibition. 2. Chymotrypsin, Trypsin, Thymidine Phosphorylase, Uridine Phosphorylase, Thimidylate Synthetase, Cytosine Nucleoside Deaminase, Dihodrofolate Reductase, Malate Dehydrogenase, Glutamate Dehydrogenase, Lactate Dehydrogenase, and Glyceraldehyde-phosphate Dehydrogenase", Journal of Medicinal Chemistry, 19(1):71-98 (1976).

Yoshino, et al., "Organic Phosphorous Compounds. 2. Synthesis and Coronary Vasodilator Activity of (Benzothiazolybenzyl) Phosphonate Derivatives", J. Med. Chem., 32:1528-1532 (1989).

Yu, et al., "Frequency of TPR-MET Rearrangement in Patients with Gastric Carcinoma and in First-Degree Relatives", Cancer, 88(8):1801-1806 (2000).

Zaidi, et al., "New Anti-Mycobacterial Hydantoins", Pharmazie, 35:755-756 (1980).

Zhen, et al., "Structural and Functional Domains Critical for Constitutive Activation of the HGF-Receptor (Met)", Oncogene, 9(6):1691-1697 (1994).

Zinner, et al., "Zur Weiteren Kenntnis Bicyclischer 3.5-Dioxopyrazolidine", Die Pharmazie, 25(5):309-312 (1970).

Zvilichovsky, et al., "Aminolysis and Polymerization of 3-(p-Toluenesulfonoxy) Hydantoin", Israel Journal of Chemistry, 7:547-554 (1969).

* cited by examiner

KINASE INHIBITORS USEFUL FOR THE TREATMENT OF MYLEOPROLIFERATIVE DISEASES AND OTHER PROLIFERATIVE DISEASES

CROSS REFERENCE TO RELATED APPLICATION

This application claims the benefit of Provisional Application 60/850,834 filed Oct. 11, 2006. This application is incorporated by reference herein.

FIELD OF THE INVENTION

The present invention relates to novel kinase inhibitors and modulator compounds useful for the treatment of various diseases. More particularly, the invention is concerned with such compounds, methods of treating diseases, and methods of synthesis of the compounds. Preferably, the compounds are useful for the modulation of kinase activity of C-Abl, c-Kit, VEGFR, PDGFR, Flt-3, c-MET, the HER family, the Raf kinase family and disease polymorphs thereof.

BACKGROUND OF THE INVENTION

Several members of the protein kinase family have been clearly implicated in the pathogenesis of various proliferative and myeloproliferative diseases and thus represent important targets for treatment of these diseases. Some of the proliferative diseases relevant to this invention include cancer, rheumatoid arthritis, atherosclerosis, and retinopathies. Important examples of kinases which have been shown to cause or contribute to the pathogensis of these diseases include C-Abl kinase and the oncogenic fusion protein bcr-Abl kinase; c-Kit kinase, c-MET, the HER family, PDGF receptor kinase, VEGF receptor kinases, Flt-3 kinase and the Raf kinase family.

C-Abl kinase is an important non-receptor tyrosine kinase involved in cell signal transduction. This ubiquitously expressed kinase—upon activation by upstream signaling factors including growth factors, oxidative stress, integrin stimulation, and ionizing radiation—localizes to the cell plasma membrane, the cell nucleus, and other cellular compartments including the actin cytoskeleton (Van Etten, *Trends Cell Biol.* (1999) 9: 179). There are two normal isoforms of Abl kinase: Abl-1A and Abl-1B. The N-terminal half of c-Abl kinase is important for autoinhibition of the kinase domain catalytic activity (Pluk et al, *Cell* (2002) 108: 247). Details of the mechanistic aspects of this autoinhibition have recently been disclosed (Nagar et al, *Cell* (2003) 112: 859). The N-terminal myristolyl amino acid residue of Abl-1B has been shown to intramolecularly occupy a hydrophobic pocket formed from alpha-helices in the C-lobe of the kinase domain. Such intramolecular binding induces a novel binding area for intramolecular docking of the SH2 domain and the SH3 domain onto the kinase domain, thereby distorting and inhibiting the catalytic activity of the kinase. Thus, an intricate intramolecular negative regulation of the kinase activity is brought about by these N-terminal regions of c-Abl kinase. An aberrant dysregulated form of c-Abl is formed from a chromosomal translocation event, referred to as the Philadelphia chromosome (P. C. Nowell et al, *Science* (1960) 132: 1497; J. D. Rowley, *Nature* (1973) 243: 290). This abnormal chromosomal translocation leads aberrant gene fusion between the Abl kinase gene and the breakpoint cluster region (BCR) gene, thus encoding an aberrant protein called bcr-Abl (G. Q. Daley et al, *Science* (1990) 247: 824; M. L. Gishizky et al, *Proc. Natl. Acad. Sci. USA* (1993) 90: 3755; S. Li et al, *J. Exp. Med.* (1999) 189: 1399). The bcr-Abl fusion protein does not include the regulatory myristolyation site (B. Nagar et al, *Cell* (2003) 112: 859) and as a result functions as an oncoprotein which causes chronic myeloid leukemia (CML). CML is a malignancy of pluripotent hematopoietic stem cells. The p210 form of bcr-Abl is seen in 95% of patients with CML, and in 20% of patients with acute lymphocytic leukemia. A p185 form has also been disclosed and has been linked to being causative of up to 10% of patients with acute lymphocytic leukemia.

The majority of small molecule kinase inhibitors that have been reported have been shown to bind in one of three ways. Most of the reported inhibitors interact with the ATP binding domain of the active site and exert their effects by competing with ATP for occupancy. Other inhibitors have been shown to bind to a separate hydrophobic region of the protein known as the "DFG-in-conformation" pocket, and still others have been shown to bind to both the ATP domain and the "DFG-in-conformation" pocket. Examples specific to inhibitors of Raf kinases can be found in Lowinger et al, *Current Pharmaceutical Design* (2002) 8: 2269-2278; Dumas, J. et al., *Current Opinion in Drug Discovery & Development* (2004) 7: 600-616; Dumas, J. et al, WO 2003068223 A1 (2003); Dumas, J., et al, WO 9932455 A1 (1999), and Wan, P. T. C., et al, *Cell* (2004) 116: 855-867.

Physiologically, kinases are regulated by a common activation/deactivation mechanism wherein a specific activation loop sequence of the kinase protein binds into a specific pocket on the same protein which is referred to as the switch control pocket (see WO 200380110049 for further details). Such binding occurs when specific amino acid residues of the activation loop are modified for example by phosphorylation, oxidation, or nitrosylation. The binding of the activation loop into the switch pocket results in a conformational change of the protein into its active form (Huse, M. and Kuriyan, J. *Cell* (109) 275-282).

BRIEF SUMMARY OF THE INVENTION

Compounds of the present invention find utility in the treatment of hyperproliferative diseases, mammalian cancers and especially human cancers including but not limited to malignant, melanomas, glioblastomas, ovarian cancer, pancreatic cancer, prostate cancer, lung cancers, breast cancers, kidney cancers, cervical carcinomas, thyroid cancer metastasis of primary solid tumor secondary sites, myeloproliferative diseases, chronic myelogenous leukemia, acute lymphocytic leukemia, other myeloproliferative disorders, papillary thyroid carcinoma, non small cell lung cancer, mesothelioma, hypereosinophilic syndrome, gastrointestinal stromal tumors, colonic cancers, ocular diseases characterized by hyperproliferation leading to blindness including various retinopathies, i.e. diabetic retinopathy and age-related macular degeneration, rheumatoid arthritis, asthma, chronic obstructive pulmonary disorder, human inflammation, rheumatoid spondylitis, ostero-arthritis, asthma, gouty arthritis, sepsis, septic shock, endotoxic shock, Gram-negative sepsis, toxic shock syndrome, adult respiratory distress syndrome, stroke, reperfusion injury, neural trauma, neural ischemia, psoriasis, restenosis, chronic obstructive pulmonary disease, bone resorptive diseases, graft-versus-host reaction, Chron's disease, ulcerative colitis, inflammatory bowel disease, pyresis, and combinations thereof, a disease caused by c-Abl kinase, oncogenic forms thereof, aberrant fusion proteins thereof and polymorphs thereof, a disease caused by a Raf kinase, oncogenic forms thereof, aberrant fusion proteins thereof and polymorphs thereof, c-Kit kinase, oncogenic forms thereof, aberrant fusion proteins thereof and polymorphs thereof, Flt-3 kinase, oncogenic forms thereof, aberrant fusion proteins thereof and polymorphs thereof, VEGFR kinase, oncogenic forms thereof, aberrant fusion proteins thereof and polymorphs thereof, PDGFR kinase, oncogenic forms thereof, aberrant fusion proteins thereof and polymorphs thereof, c-MET kinase, oncogenic forms thereof, aberrant fusion proteins thereof and polymorphs thereof and a disease caused by a HER kinase, oncogenic forms thereof, aberrant fusion proteins thereof and polymorphs thereof.

DETAILED DESCRIPTION OF THE INVENTION

The following descriptions refer to various compounds and moieties thereof.

Carbocyclyl refers to carbon rings taken from cyclopropyl, cyclobutyl, cyclopentyl, cyclohexyl, cycloheptanyl, cyclooctanyl, norboranyl, norborenyl, bicyclo[2.2.2]octanyl, and bicyclo[2.2.2]octenyl;

Halogen refers to fluorine, chlorine, bromine and iodine;

Aryl refers to monocyclic or fused bicyclic ring systems characterized by delocalized π electrons (aromaticity) shared among the ring carbon atoms of at least one carbocyclic ring; preferred aryl rings are taken from phenyl, naphthyl, tetrahydronaphthyl, indenyl, and indanyl;

Heteroaryl refers to monocyclic or fused bicyclic ring systems characterized by delocalized π electrons (aromaticity) shared among the ring carbon or heteroatoms including nitrogen, oxygen, or sulfur of at least one carbocyclic or heterocyclic ring; heteroaryl rings are taken from, but not limited to, pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyridinyl, pyrimidinyl, pyrazinyl, pyridazinyl, triazinyl, indolyl, indolinyl, isoindolyl, isoindolinyl, indazolyl, benzofuranyl, benzothienyl, benzothiazolyl, benzothiazolonyl, benzoxazolyl, benzoxazolonyl, benzisoxazolyl, benzisothiazolyl, benzimidazolyl, benzimidazolonyl, benztriazolyl, imidazopyridinyl, pyrazolopyridinyl, imidazolonopyridinyl, thiazolopyridinyl, thiazolonopyridinyl, oxazolopyridinyl, oxazolonopyridinyl, isoxazolopyridinyl, isothiazolopyridinyl, triazolopyridinyl, imidazopyrimidinyl, pyrazolopyrimidinyl, imidazolonopyrimidinyl, thiazolopyridiminyl, thiazolonopyrimidinyl, oxazolopyridiminyl, oxazolonopyrimidinyl, isoxazolopyrimidinyl, isothiazolopyrimidinyl, triazolopyrimidinyl, dihydropurinonyl, pyrrolopyrimidinyl, purinyl, pyrazolopyrimidinyl, phthalimidyl, phthalimidinyl, pyrazinylpyridinyl, pyridinopyrimidinyl, pyrimidinopyrimidinyl, cinnolinyl, quinoxalinyl, quinazolinyl, quinolinyl, isoquinolinyl, phthalazinyl, benzodioxyl, benzisothiazoline-1,1,3-trionyl, dihydroquinolinyl, tetrahydroquinolinyl, dihydroisoquinolyl, tetrahydroisoquinolinyl, benzoazepinyl, benzodiazepinyl, benzoxapinyl, and benzoxazepinyl;

Heterocyclyl refers to monocyclic rings containing carbon and heteroatoms taken from oxygen, nitrogen, or sulfur and wherein there is not delocalized π electrons (aromaticity) shared among the ring carbon or heteroatoms; heterocyclyl rings include, but are not limited to, oxetanyl, azetadinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl;

Poly-aryl refers to two or more monocyclic or fused aryl bicyclic ring systems characterized by delocalized π electrons (aromaticity) shared among the ring carbon atoms of at least one carbocyclic ring wherein the rings contained therein are optionally linked together;

Poly-heteroaryl refers to two or more monocyclic or fused bicyclic systems characterized by delocalized π electrons (aromaticity) shared among the ring carbon or heteroatoms including nitrogen, oxygen, or sulfur of at least one carbocyclic or heterocyclic ring wherein the rings contained therein are optionally linked together, wherein at least one of the monocyclic or fused bicyclic rings of the poly-heteroaryl system is taken from heteroaryl as defined broadly above and the other rings are taken from either aryl, heteroaryl, or heterocyclyl as defined broadly above;

Poly-heterocyclyl refers to two or more monocyclic or fused bicyclic ring systems containing carbon and heteroatoms taken from oxygen, nitrogen, or sulfur and wherein there is not delocalized π electrons (aromaticity) shared among the ring carbon or heteroatoms wherein the rings contained therein are optionally linked, wherein at least one of the monocyclic or fused bicyclic rings of the poly-heteroaryl system is taken from heterocyclyl as defined broadly above and the other rings are taken from either aryl, heteroaryl, or heterocyclyl as defined broadly above;

Lower alkyl refers to straight or branched chain C1-C6alkyls;

Substituted in connection with a moiety refers to the fact that a further substituent may be attached to the moiety to any acceptable location on the moiety.

The term salts embraces pharmaceutically acceptable salts commonly used to form alkali metal salts of free acids and to form addition salts of free bases. The nature of the salt is not critical, provided that it is pharmaceutically-acceptable. Suitable pharmaceutically-acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, and heterocyclyl containing carboxylic acids and sulfonic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methane sulfonic, ethanesulfonic, 2-hydroxyethanesulfonic, benzenesulfonic, pantothenic, toluenesulfonic, 2-hydroxyethanesulfonic, sulfanilic, cyclohexylaminosulfonic, algenic, 3-hydroxybutyric, galactaric and galacturonic acid. Suitable pharmaceutically-acceptable salts of free acid-containing compounds of the invention include metallic salts and organic salts. More preferred metallic salts include, but are not limited to appropriate alkali metal (group Ia) salts, alkaline earth metal (group IIa) salts and other physiological acceptable metals. Such salts can be made from aluminum, calcium, lithium, magnesium, potassium, sodium and zinc. Preferred organic salts can be made from primary amines, secondary amines, tertiary amines and quaternary ammonium salts, including in part, tromethamine, diethylamine, tetra-N-methylammonium, N,N'-dibenzylethylenediamine, chloroprocaine, choline, diethanolamine, ethylenediamine, meglumine (N-methylglucamine) and procaine.

The term prodrug refers to derivatives of active compounds which revert in vivo into the active form. For example, a carboxylic acid form of an active drug may be esterified to create a prodrug, and the ester is subsequently converted in vivo to revert to the carboxylic acid form. See Ettmayer et. al, *J. Med. Chem.*, 2004, 47(10), 2393-2404 and Lorenzi et. al, *J. Pharm. Exp. Therpeutics*, 2005, 883-8900 for reviews.

1. First Aspect of the Invention—Compounds, Methods, Preparations and Adducts

The invention includes compounds of the formula Ia:

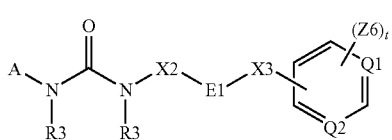

wherein Q1 and Q2 are each individually and independently selected from the group consisting of N and C—Z6, provided that both Q1 and Q2 are not simultaneously C—Z6;

E1 is selected from the group consisting cyclopropyl, cyclobutyl, cyclopentyl, cyclohexyl, pyrrolidinyl piperidinyl, phenyl, thienyl, oxazolyl, thiazolyl, isoxazolyl, isothiazolyl, pyrrolyl, pyrazolyl, oxadiazolyl, thiadiazolyl, furyl, imidazolyl, pyridyl, pyrimidinyl and naphthyl and wherein the E1 ring is substituted with one or more R16 moieties and wherein the E1 ring is substituted with one or more R18 moieties;

wherein A is selected from the group consisting of phenyl, C3-C8carbocyclyl, pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl, pyridinyl, pyrimidinyl, and G4;

G1 is a heteroaryl taken from the group consisting of pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl, pyridinyl, and pyrimidinyl;

G2 is a fused bicyclic heteroaryl taken from the group consisting of indolyl, indolinyl, isoindolyl, isoindolinyl, indazolyl, benzofuranyl, benzothienyl, benzothiazolyl, benzothiazolonyl, benzoxazolyl, benzoxazolonyl, benzisoxazolyl, benzisothiazolyl, benzimidazolyl, benzimidazolonyl, benztriazolyl, imidazopyridinyl, pyrazolopyridinyl, imidazolonopyridinyl, thiazolopyridinyl, thiazolonopyridinyl, oxazolopyridinyl, oxazolonopyridinyl, isoxazolopyridinyl, isothiazolopyridinyl, triazolopyridinyl, imidazopyrimidinyl, pyrazolopyrimidinyl, imidazolonopyrimidinyl, thiazolopyridiminyl, thiazolonopyrimidinyl, oxazolopyriminyl, oxazolonopyrimidinyl, isoxazolopyrimidinyl, isothiazolopyrimidinyl, triazolopyrimidinyl, dihydropurinonyl, pyrrolopyrimidinyl, purinyl, pyrazolopyrimidinyl, phthalimidyl, phthalimidinyl, pyrazinylpyridinyl, pyridinopyrimidinyl, pyrimidinopyrimidinyl, cinnolinyl, quinoxalinyl, quinazolinyl, quinolinyl, isoquinolinyl, phthalazinyl, benzodioxyl, benzisothiazoline-1,1,3-trionyl, dihydroquinolinyl, tetrahydroquinolinyl, dihydroisoquinolyl, tetrahydroisoquinolinyl, benzoazepinyl, benzodiazepinyl, benzoxapinyl, and benzoxazepinyl;

G3 is a non-fused bicyclic heteroaryl taken from the group consisting of pyridylpyridiminyl pyrimidinylpyrimidinyl, oxazolylpyrimidinyl, thiazolylpyrimidinyl, imidazolylpyrimidinyl, isoxazolylpyrimidinyl, isothiazolylpyrimidinyl, pyrazolylpyrimidinyl, triazolylpyrimidinyl, oxadiazoylpyrimidinyl, thiadiazoylpyrimidinyl, morpholinylpyrimidinyl, dioxothiomorpholinylpyrimidinyl, and thiomorpholinylpyrimidinyl;

G4 is a heterocyclyl taken from the group consisting of oxetanyl, azetadinyl, tetrahydrofuranyl, pyrrolidinyl, oxazolinyl, oxazolidinyl, imidazolonyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl;

The A ring is substituted at any substitutable position with one A1 moiety, wherein A1 is selected from the group consisting of A2, A3 and A4;

A2 is selected from the group consisting of

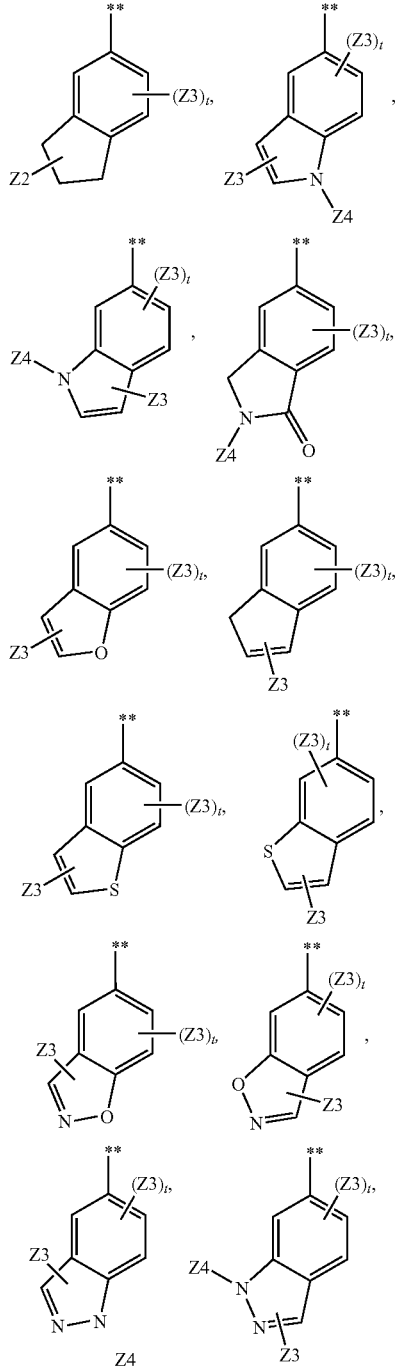

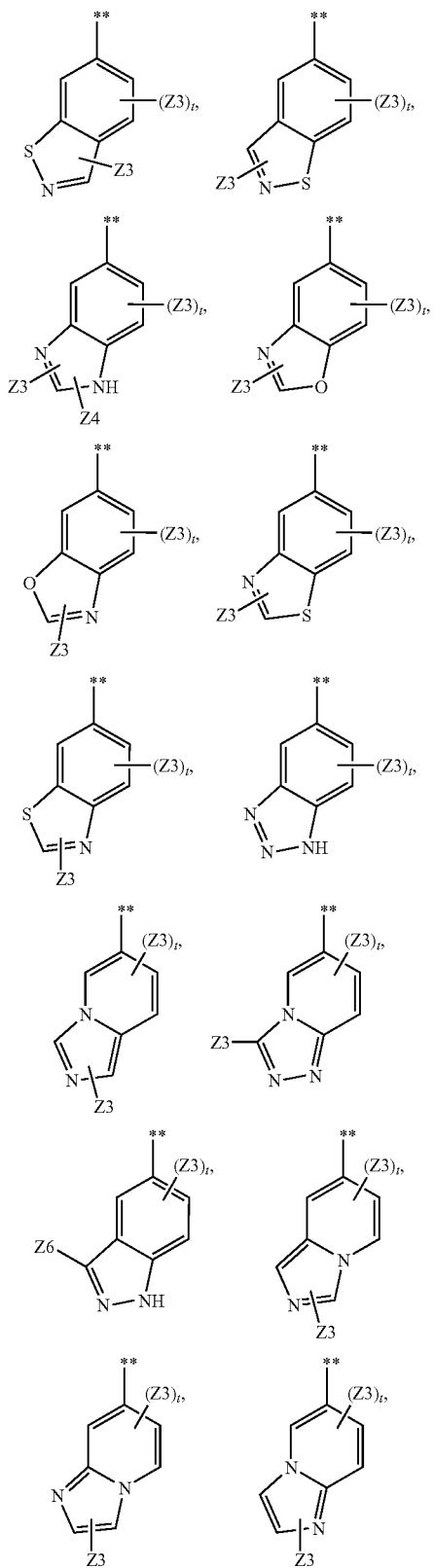
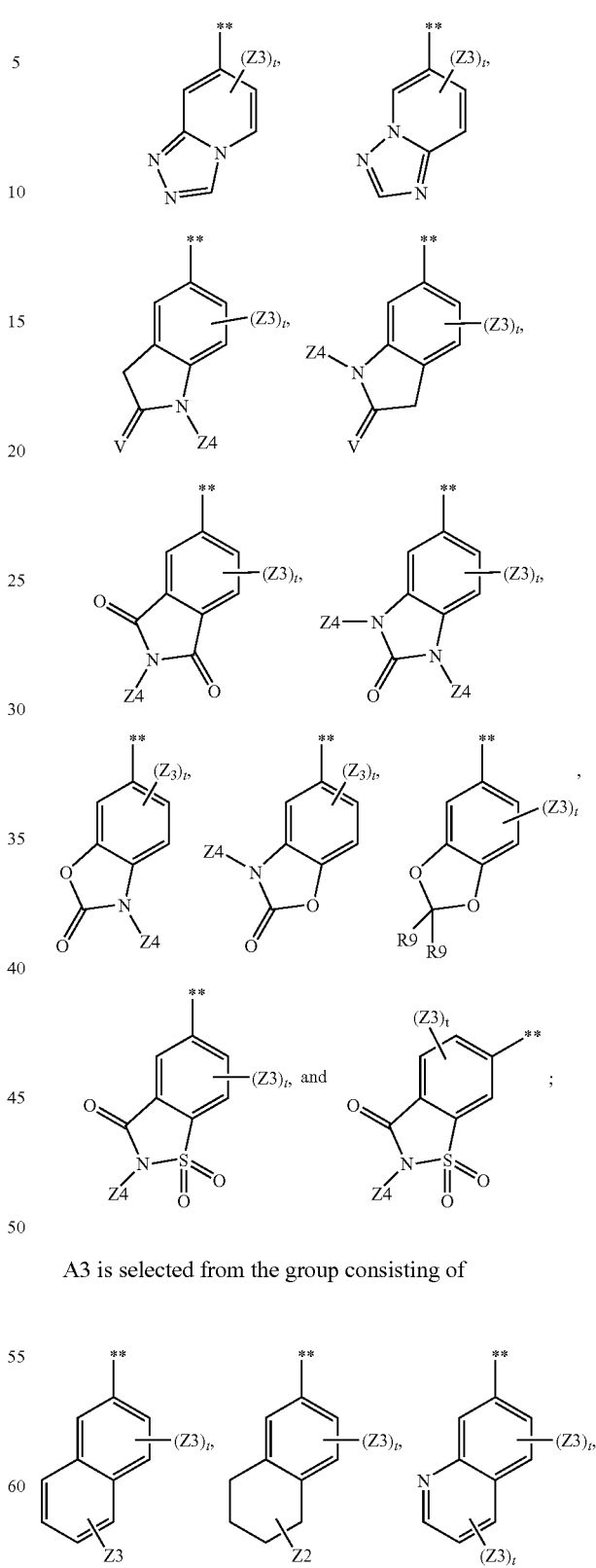
A3 is selected from the group consisting of

-continued
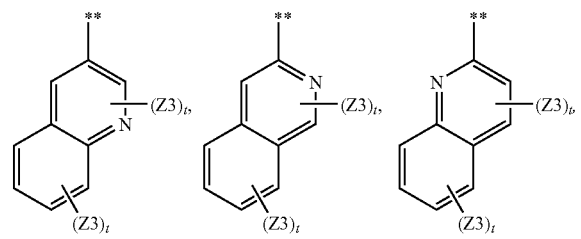
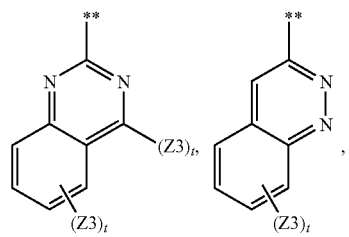
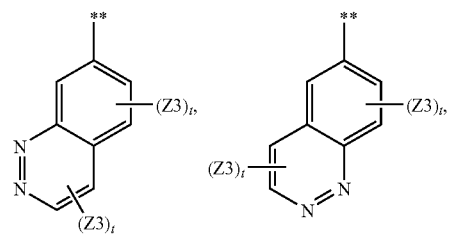
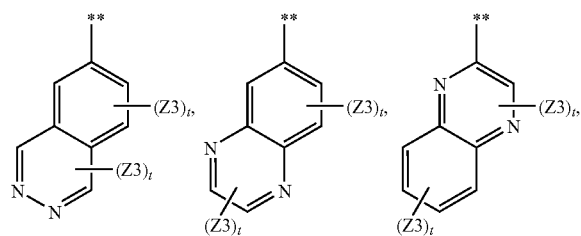
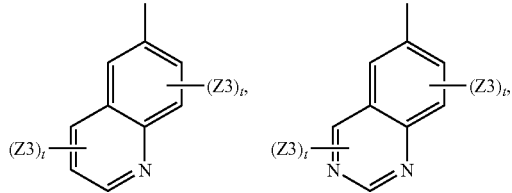
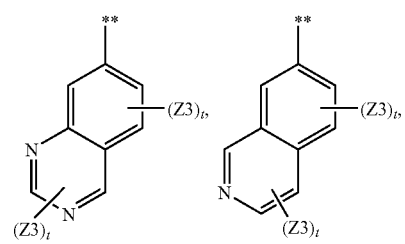
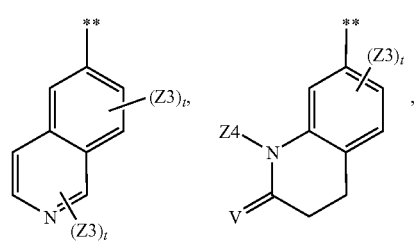
-continued
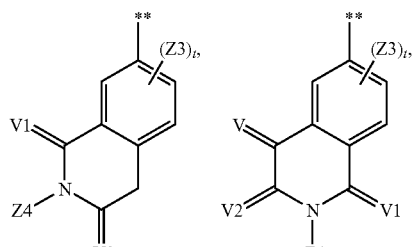
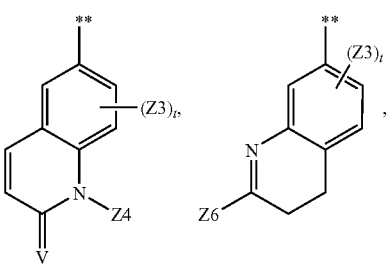
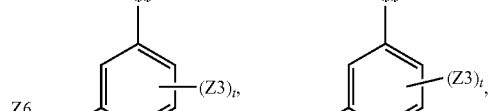
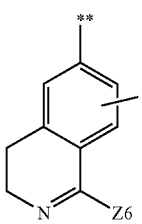
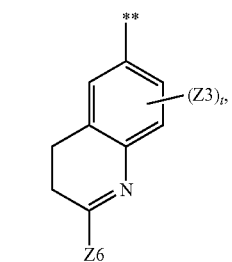
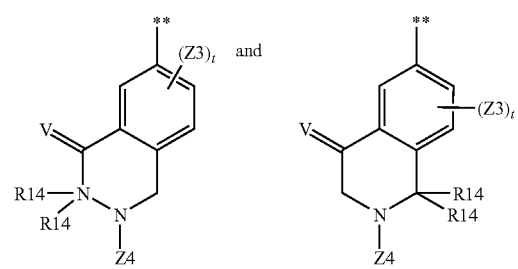
A4 is selected from the group consisting of
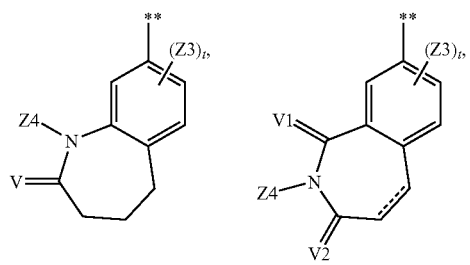

-continued

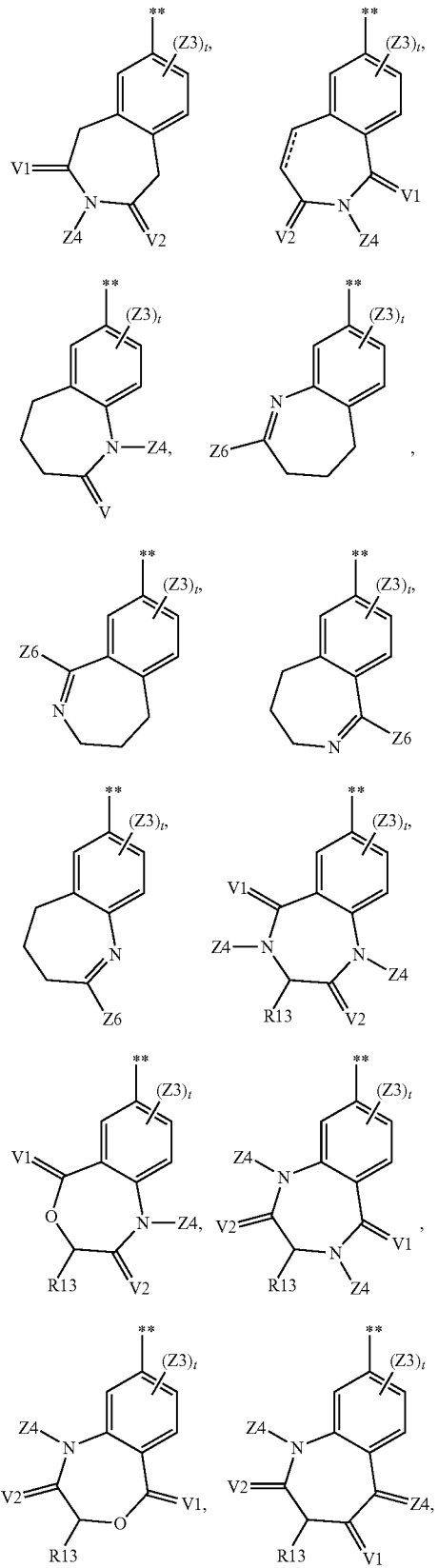
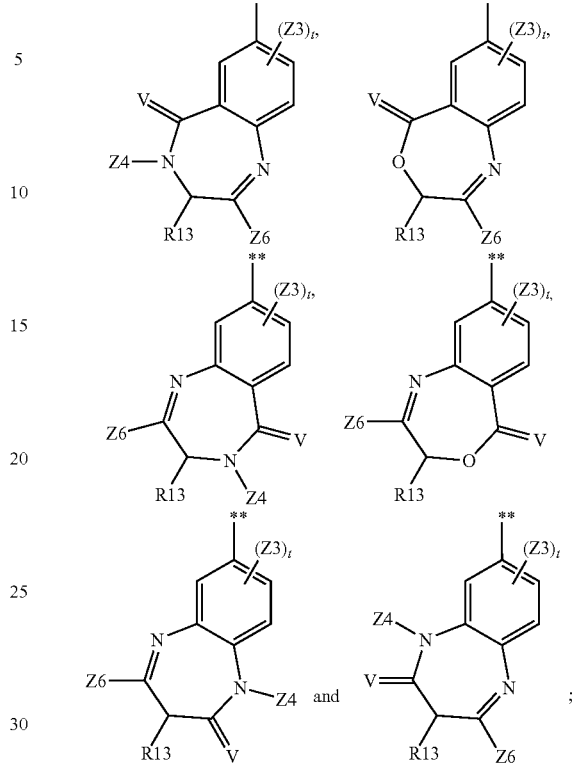

and wherein the symbol (**) is the point of attachment to the A ring of formula Ia; and wherein ---- indicates either a saturated or unsaturated bond;

the A ring is optionally substituted with one or more R2 moieties;

X2 is selected from the group consisting of C1-C6 alkyl, C2-C6 branched alkyl, and a direct bond wherein E1 is directly linked to the NR3 group of formula Ia;

X3 is selected from the group consisting of —C(=O)—, —O—, —O—(CH$_2$)$_n$—, —S—(CH$_2$)$_n$—, —NR3—(CH$_2$)$_n$—, —O—(CH$_2$)$_q$—O—, —O—(CH$_2$)$_q$—NR3—, —N(R3)—(CH$_2$)$_q$—N(R3)—, —(CH$_2$)$_n$—N(R4)-C(=O)—, —(CH$_2$)$_n$—N(R4)—C(=O)(CH$_2$)$_n$—, —(CH$_2$)$_n$—C(=O)N(R4)—, —(CH$_2$)$_p$—, C2-C5alkenyl, C2-C5alkynyl, and C3-C6cycloalkyl and wherein the carbon atoms of —(CH$_2$)$_n$—, —(CH$_2$)$_q$—, —(CH$_2$)$_p$—, C2-C5alkenyl, and C2-C5alkynyl moieties of X3 may be further substituted by one or more C1-C6alkyl;

V, V1, and V2 are each independently and respectively selected from the group consisting of O and H$_2$;

each Z2 is independently and individually selected from the group consisting of hydrogen, aryl, C1-C6alkyl, C3-C8carbocyclyl, hydroxyl, hydroxyC1-C6alkyl-, cyano, (R3)$_2$N—, (R4)$_2$N—, (R4)$_2$NC1-C6alkyl-, (R4)$_2$NC2-C6alkylN(R4)-(CH$_2$)$_n$—, (R4)$_2$NC2-C6alkylO(CH$_2$)$_n$—, (R3)$_2$NC(O)—, (R4)$_2$NC(O)—, (R4)$_2$NC(O)C1-C6alkyl-, carboxyl, carboxyC1-C6alkyl-, C1-C6alkoxycarbonyl-, C1-C6alkoxycarbonylC1-C6alkyl-, (R3)$_2$NSO$_2$—, (R4)$_2$NSO$_2$—, —SO$_2$R5, —SO$_2$R8, —(CH$_2$)$_n$N(R4)C(O)R8, —C(O)R8, =O, =NOH, =N(OR6), —(CH$_2$)$_n$G1, —(CH$_2$)$_n$G4, —(CH$_2$)$_n$O(CH$_2$)$_n$G1, —(CH$_2$)$_n$O(CH$_2$)$_n$G4, —(CH$_2$)$_n$NR3(CH$_2$)$_n$-aryl,     —(CH$_2$)$_n$NR3(CH$_2$)$_n$G1, —(CH$_2$)$_n$NR3(CH$_2$)$_n$G4,     —(CH$_2$)$_n$NHC(O)NHS(O)$_2$R8, —(CH$_2$)$_n$NHS(O)$_2$NHC(O)R8,     —C(O)NHS(O)$_2$R8, —(CH$_2$)NHC(O)(CH$_2$)$_n$R5,     —(CH$_2$)$_n$NHS(O)$_2$R5, —(CH$_2$)$_n$C(O)NH(CH$_2$)$_q$R5, —(CH$_2$)$_n$C(O)R5, —(CH$_2$)$_n$OC(O)R5, and —(CH$_2$)$_n$R5;

in the event that Z2 contains an alkyl or alkylene moiety, such moieties may be further substituted with one or more C1-C6alkyls;

each Z3 is independently and individually selected from the group consisting of H, C$_1$-C6alkyl, branched C3-C7alkyl, C3-C8-carbocyclyl, halogen, fluoroC1-C6alkyl wherein the alkyl moiety can be partially or fully fluorinated, cyano, hydroxyl, methoxy, oxo, (R3)$_2$NC(O)—, (R4)$_2$NC(O)—, —N(R4)C(O)R8, (R3)$_2$NSO$_2$—, (R4)$_2$NSO$_2$—, —N(R4)SO$_2$R5, —N(R4)SO$_2$R8, —(CH$_2$)$_n$N(R3)$_2$, —(CH$_2$)$_n$N(R4)$_2$, —O(CH$_2$)$_q$N(R4)$_2$, —O(CH$_2$)$_q$O—C1-C6alkyl, —N(R3)(CH$_2$)$_q$O—C1-C6alkyl, —N(R3)(CH$_2$)$_q$N(R4)$_2$, —O(CH$_2$)$_q$R5, —NR3(CH$_2$)$_q$R5, —C(O)R5, —C(O)R8, —R5, and nitro;

in the event that Z3 contains an alkyl or alkylene moiety, such moieties may be further substituted with one or more C1-C6alkyls;

each Z4 is independently and individually selected from the group consisting of H, C$_1$-C6alkyl, hydroxyC2-C6alkyl, C1-C6alkoxyC2-C6alkyl-, (R4)$_2$N—C2-C6alkyl-, (R4)$_2$N—C2-C6alkylN(R4)-C2-C6alkyl-, (R4)$_2$N—C2-C6alkyl-O—C2-C6alkyl-, (R4)$_2$NC(O)—C1-C6alkyl-, carboxyC1-C6alkyl-, C1-C6alkoxycarbonylC1-C6alkyl-, —C2-C6alkylN(R4)C(O)R8, R8-C(=NR3)-, —SO$_2$R8, —COR8, —(CH$_2$)$_n$G1, —(CH$_2$)$_n$G4, —(CH$_2$)$_q$—O(CH$_2$)$_n$G1, —(CH$_2$)$_q$O(CH$_2$)$_n$G4, —(CH$_2$)$_q$NR3(CH$_2$)$_n$G1, —(CH$_2$)$_q$NR3(CH$_2$)$_n$G4, —(CH$_2$)$_q$NHC(O)(CH$_2$)$_n$R5, —(CH$_2$)$_q$C(O)NH(CH$_2$)$_q$R5, —(CH$_2$)$_q$C(O)R5, —(CH$_2$)$_q$OC(O)R5, —(CH$_2$)$_q$R5, —(CH$_2$)$_q$NR4(CH$_2$)$_q$R5, and —(CH$_2$)$_q$O(CH$_2$)$_q$R5;

in the event that Z4 contains an alkyl or alkylene moiety, such moieties may be further substituted with one or more C1-C6alkyls;

each Z6 is independently and individually selected from the group consisting of H, C1-C6alkyl, branched C3-C7alkyl, hydroxyl, hydroxyC1-C6alkyl, hydroxyC2-C6 branched alkyl-, C1-C6alkoxy, C1-C6alkoxyC1-C6alkyl-, C1-C6alkoxyC2-C6 branched alkyl-, branched C2-C6alkoxy-, C1-C6alkylthio, (R3)$_2$N—, —N(R3)COR8, (R4)$_2$N—, —R5, —N(R4)C(O)R8, —N(R3)SO$_2$R6, —C(O)N(R3)$_2$, —C(O)N(R4)$_2$, —C(O)R5, —SO$_2$NHR4, halogen, fluoroC1-C6alkyl wherein the alkyl is fully or partially fluorinated, cyano, fluoroC1-C6alkoxy wherein the alkyl is fully or partially fluorinated, —O(CH$_2$)$_q$N(R4)$_2$, —N(R3)(CH$_2$)$_q$N(R4)$_2$, —O(CH$_2$)$_q$O—C1-C6alkyl, —O(CH$_2$)$_q$N(R4)$_2$, —N(R3)(CH$_2$)$_q$O-DC1-C6alkyl, —N(R3)(CH$_2$)$_q$N(R4)$_2$, —O(CH$_2$)$_q$R5, and —N(R3)(CH$_2$)$_q$R5, —(NR3)$_r$R17, —(O)$_r$R17, —(S)$_r$R17, —(CH$_2$)$_n$R17, —(CH$_2$)$_n$G1, —(CH$_2$)$_n$G4, —(CH$_2$)$_q$O(CH$_2$)$_n$G1, —(CH$_2$)$_q$O(CH$_2$)$_n$G4, —(CH$_2$)$_q$N(R3)(CH$_2$)$_n$G1, and —(CH$_2$)$_q$NR3(CH$_2$)$_n$G4;

each R2 is selected from the group consisting of Z3-substituted aryl, Z3-substituted G1, Z3-substituted G4, C1-C6alkyl, branched C3-C8alkyl, R19 substituted C3-C8carbocyclyl, hydroxylC1-C6alky, hydroxyl branched C3-C6alkyl-, hydroxyl substituted C3-C8carbocyclyl-, cyanoC1-C6 alkyl-, cyano substituted branched C3-C6alkyl-, cyano substituted C3-C8carbocyclyl-, (R4)$_2$NC(O)C1-C6alkyl-, (R4)$_2$NC(O) substituted branched C3-C6alkyl-, (R4)$_2$NC(O) substituted C3-C8-carbocyclyl-, fluoroC1-C6alkyl wherein the alkyl is fully or partially fluorinated, halogen, cyano, C1-C6alkoxy, and fluoroC1-C6alkoxy wherein the alkyl group is fully or partially fluorinated;

each R3 is independently and individually selected from the group consisting of H, C$_1$-C6alkyl, branched C3-C7alkyl, C3-C7cycloalkyl, and Z3-substituted phenyl-;

each R4 is independently and individually selected from the group consisting of H, C$_1$-C$_6$alkyl, hydroxyC1-C6alkyl-, dihydroxyC1-C6alkyl-, C1-C6alkoxyC1-C6alkyl-, branched C3-C7alkyl-, branched hydroxyC1-C6alkyl-, branched C1-C6alkoxyC1-C6alkyl-, branched dihydroxyC2-C6alkyl-, —(CH$_2$)$_p$N(R7)$_2$, —(CH$_2$)$_p$R5, —(CH$_2$)$_p$C(O)N(R7)$_2$, —(CH$_2$)$_n$C(O)R5, —(CH$_2$)$_n$C(O)OR3, C3-C8-carbocyclyl, hydroxyl substituted C3-C8carbocyclyl-, alkoxy substituted C3-C8carbocyclyl-, dihydroxyl substituted C3-C 8carbocyclyl-, and —(CH$_2$)$_n$R17;

each R5 is independently and individually selected from the group consisting of

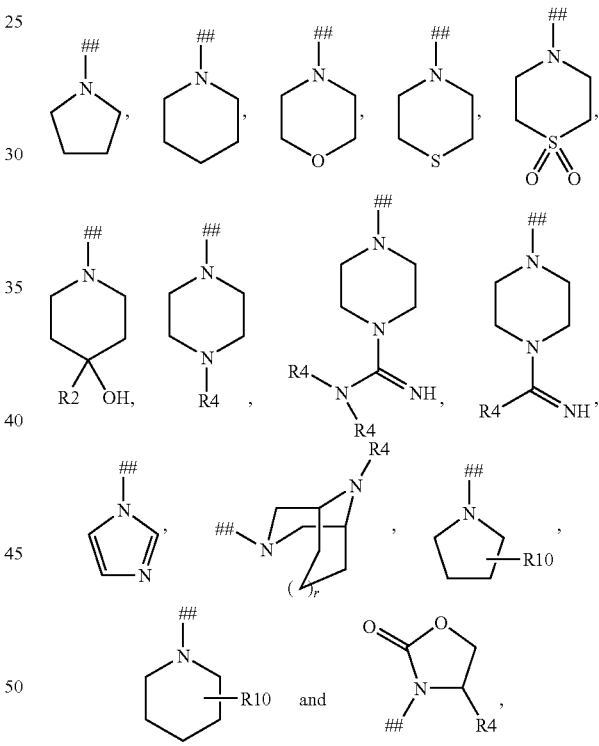

and wherein the symbol (##) is the point of attachment of the R5 moiety;

each R6 is independently and individually selected from the group consisting of C$_1$-C6alkyl, branched C3-C7alkyl, C3-C8carbocyclyl, phenyl, G1, and G4;

each R7 is independently and individually selected from the group consisting of H, C$_1$-C$_6$alkyl, hydroxyC2-C6alkyl-, dihydroxyC2-C6alkyl-, C2-C6alkoxyC2-C6alkyl-, branched C3-C7alkyl-, branched hydroxyC2-C6 alkyl-, branched C2-C6alkoxyC2-C6alkyl-, branched dihydroxyC2-C6alkyl-, —(CH$_2$)$_q$R5, —(CH$_2$)$_n$C(O)R5, —(CH$_2$)$_n$C(O)OR3, C3-C8-carbocyclyl, hydroxyl substituted C3-C8carbocyclyl-, alkoxy substituted C3-C8carbocyclyl-, dihydroxy substituted C3-C8carbocyclyl, and —(CH$_2$)$_n$R17;

each R8 is independently and individually selected from the group consisting of C$_1$-C6alkyl, branched C3-C7alkyl, fluoroC1-C6alkyl wherein the alkyl moiety is partially or fully fluorinated, C3-C8carbocyclyl, Z3-substituted phenyl-, Z3-substituted phenylC$_1$-C6alkyl-, Z3-substituted G1-, Z3-substituted G1-C1-C6alkyl-, Z2-substituted G4-, Z2-substituted G4-C1-C6alkyl-, OH, C1-C6alkoxy, N(R3)$_2$, N(R4)$_2$, and R5;

each R9 is independently and individually selected from the group consisting of H, F, C$_1$-C6alkyl, branched C3-C7alkyl, C3-C7cycloalkyl, phenyl, phenyl-C1-C6alkyl-, —(CH$_2$)$_n$ G1, and —(CH$_2$)$_n$G4;

each R10 is independently and individually selected from the group consisting of CO$_2$H, CO$_2$C1-C6alkyl, —C(O)N(R4)$_2$, OH, C1-C6alkoxy, and —N(R4)$_2$;

each R13 is independently and individually selected from the group consisting of H, C$_1$-C6alkyl, branched C3-C7alkyl, carbocyclyl, hydroxyC2-C7alkyl, C1-C6alkoxyC2-C7alkyl-, (R4)$_2$NC(O)—, (R4)$_2$NC(O)C1-C6alkyl-, carboxyC1-C6alkyl-, C$_1$-C$_6$alkoxycarbonyl-, C1-C6alkoxycarbonylC1-C6alkyl-, (R4)$_2$N—C2-C6alkyl-, (R4)$_2$N—C2-C6alkylN(R4)(CH$_2$)$_q$—, R5-C2-C6alkylN (R4)(CH$_2$)$_q$—, (R4)$_2$N—C2-C6alkylO(CH$_2$)$_q$—, R5-C2-C6alkylO(CH$_2$)$_q$—, —(CH$_2$)$_q$N(R4)C(O)R8, aryl, arylC1-C6alkyl, aryloxyC2-C6alkyl-, arylaminoC2-C6alkyl-, C1-C6alkoxycarbonylC1-C6alkyl-, —C2-C6alkylN(R4)C (O)R8, R8C(=NR3)-, —SO$_2$R8, —COR8, —(CH$_2$)$_n$G1, —(CH$_2$)$_n$-G4, —(CH$_2$)$_n$)(CH$_2$)$_n$G1, —(CH$_2$)$_n$O(CH$_2$)$_n$G4, —(CH$_2$)$_n$N(R3)(CH$_2$)$_n$G1, and —(CH$_2$)$_n$N(R3)(CH$_2$)$_n$G4;

each R14 is independently and respectively selected from the group consisting of H, C$_1$-C6alkyl, branched C3-C6alkyl, and C3-C7-carbocyclyl;

each R16 is independently and individually selected from the group consisting of C1-C6alkyl, branched C3-C7alkyl, C$_3$-C$_8$ carbocyclyl, halogen, fluoro C1-C6alkyl wherein the alkyl moiety can be partially or fully fluorinated, cyano, hydroxyl, C1-C6alkoxy, fluoroC1-C6alkoxy wherein the alkyl moiety can be partially or fully fluorinated, —N(R3)$_2$, —N(R4)$_2$, and nitro;

each R17 is taken from the group comprising phenyl, naphthyl, pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl, oxetanyl, azetadinyl, tetrahydrofuranyl, oxazolinyl, oxazolidinyl, pyranyl, thiopyranyl, tetrahydropyranyl, dioxalinyl, azepinyl, oxepinyl, diazepinyl, pyrrolidinyl, and piperidinyl;

wherein R17 can be further substituted with one or more Z2, Z3 or Z4 moieties;

R18 is independently and individually selected from the group consisting of hydrogen, C1-C6alkyl, branched C3-C7alkyl, C3-C8carbocyclyl, halogen, fluoroC1-C6alkyl wherein the alkyl moiety can be partially or fully fluorinated, cyano, hydroxyl, C1-C6alkoxy, fluoroC1-C6alkoxy wherein the alkyl moiety can be partially or fully fluorinated, —N(R3)$_2$, —N(R4)$_2$, C2-C$_3$alkynyl, and nitro;

R19 is H or C1-C6alkyl;

wherein two R3 or R4 moieties are independently and individually taken from the group consisting of C1-C6alkyl and branched C3-C6alkyl, hydroxyalkyl, and alkoxyalkyl and are attached to the same nitrogen atom, said moieties may cyclize to form a C3-C7 heterocyclyl ring;

and n is 0-6; p is 1-4; q is 2-6; r is 0 or 1; t is 1-3, v is 1 or 2;

with the proviso that compounds of formula Ia can not be

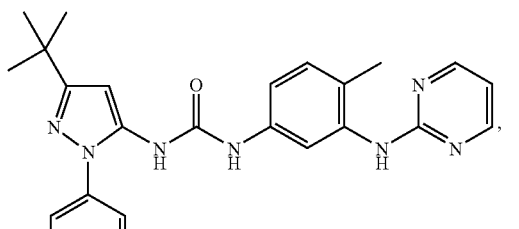

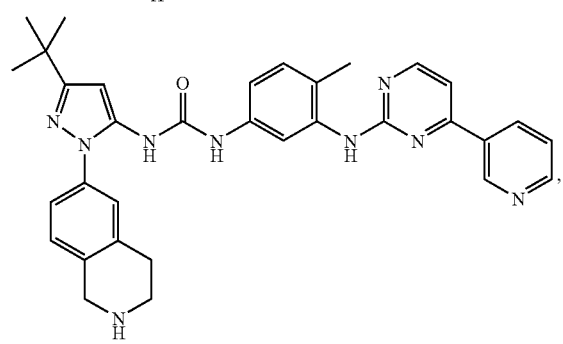

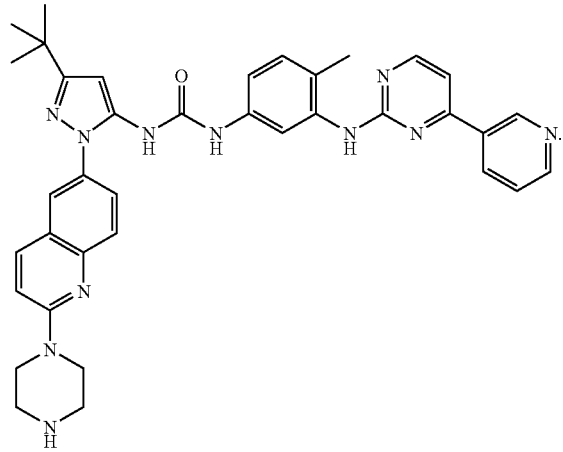

1.1 Compounds of Formula Ia which Exemplify Preferred A and X2-E1 Moieties

In a preferred embodiment of compounds of formula Ia, said compounds have structures of formula I-Ib:

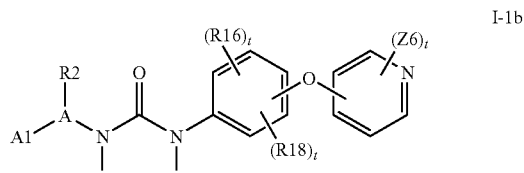

wherein the A ring is pyrazolyl.

1.1.1 Compounds of Formula I-1b which Exemplify Preferred A1 Moieties

In a preferred embodiment of compounds of formula I-1b, said compounds have structures of formula I-1c:

I-1c

1.1.2 Compounds of Formula Ib which Exemplify Preferred A1 Moieties

In a preferred embodiment of compounds of formula I-1b, said compounds have structures of formula I-1d I-1d

1.1.3 Compounds of Formula I-1b which Exemplify Preferred A1 Moieties

In a preferred embodiment of compounds of formula I-1b, said compounds have structures of formula I-1e I-1e

1.1.4 More Preferred Compounds of Section 1.1

In a preferred embodiment of compounds from Section 1.1, said compounds have structures of formula I-1f:

I-1f

1.1.5 Compounds of Section 1.1.4 with Preferred R16 Moieties

In a preferred embodiment of compounds from Section 1.1.4, said compounds have structures of formula I-1g:

I-1g

1.1.6 Compounds of Section 1.1.5 with a More Preferred A1 Moieties

In a more preferred embodiment of compounds from Section 1.1.5, said compounds have structures of formula I-1 h:

I-1h

Wherein A1 is selected from the group consisting of

-continued

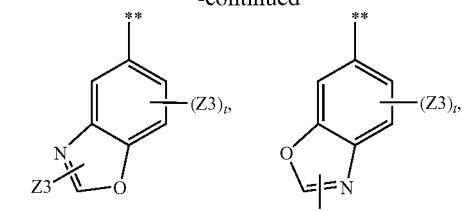

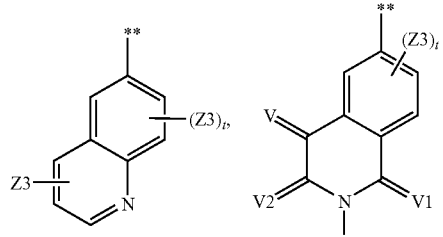

and

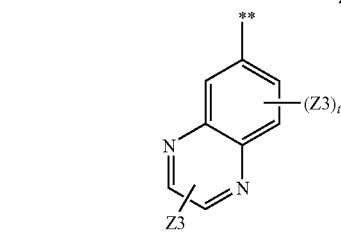

1.1.7 Compounds of Section 1.1.5 with a More Preferred Z6 Moieties

In a more preferred embodiment of compounds from Section 1.1.5, said compounds have structures of formula I-1i:

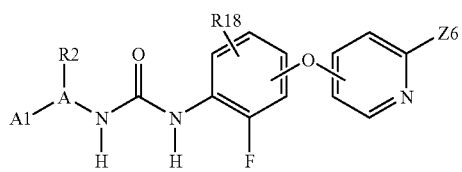

I-1i wherein Z6 is —C(O)NHR4, —NHR4 or R19 substituted pyrazole;

1.2 Compounds of Formula Ia which Exemplify Preferred A and X2-E1 Moieties

In a preferred embodiment of compounds of formula Ia, said compounds have structures of formula I-2a:

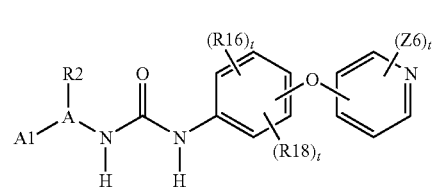

I-2a

Where in the A ring is isoxazolyl.

1.2.1 Compounds of Formula I-2a which Exemplify Preferred A1 Moieties

In a preferred embodiment of compounds of formula I-2a, said compounds have structures of formula I-2b:

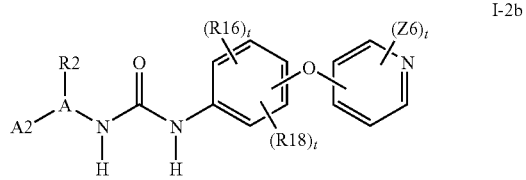

I-2b

1.2.2 Compounds of Formula I-2a which Exemplify Preferred A1 Moieties

In a preferred embodiment of compounds of formula I-2a, said compounds have structures of formula I-2c:

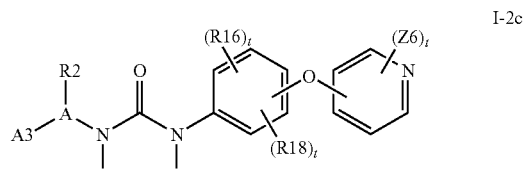

I-2c

1.2.3 Compounds of Formula I-2a which Exemplify Preferred A1 Moieties

In a preferred embodiment of compounds of formula I-2a, said compounds have structures of formula I-2d:

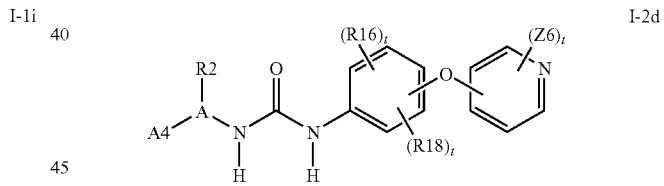

I-2d

1.2.4 More Preferred Compounds of Section 1.2

In a preferred embodiment of compounds from Section 1.2, said compounds have structures of formula I-2e:

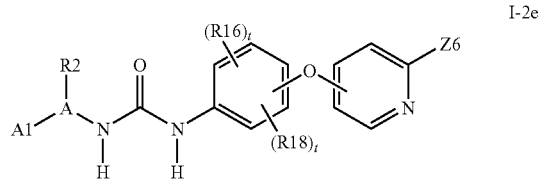

I-2e

1.2.5 Compounds of Section 1.2.4 with Preferred R16 Moieties

In a preferred embodiment of compounds from Section 1.2.4, said compounds have structures of formula I-2f:

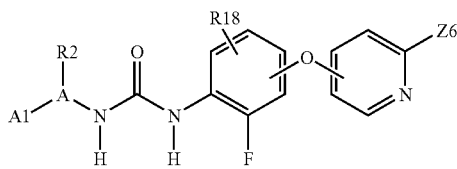

I-2f

1.2.6 Compounds of Section 1.2.5 with a more Preferred A1 Moieties

In a more preferred embodiment of compounds from Section 1.2.5, said compounds have structures of formula I-2g:

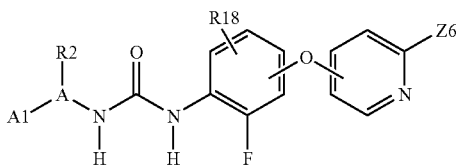

I-1g

Wherein A1 is selected from the group consisting of

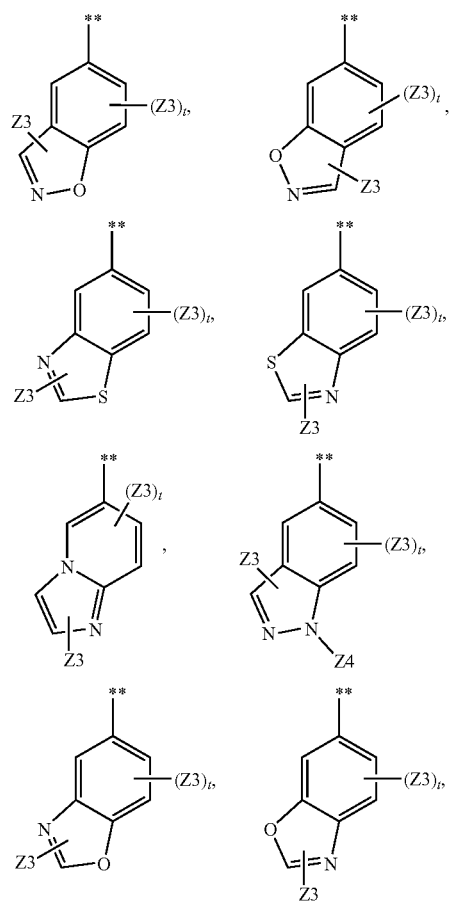

-continued

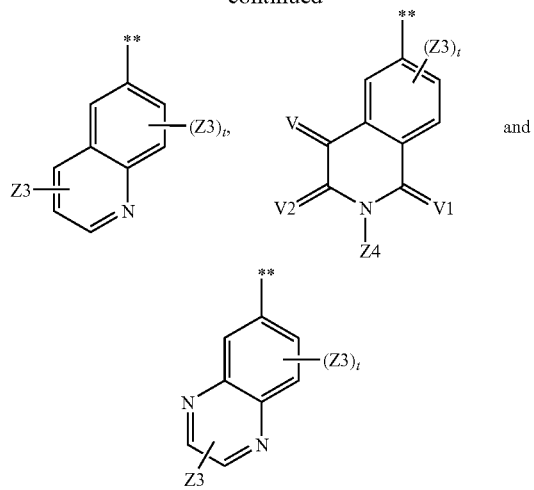

and

1.2.7 Compounds of Section 1.2.5 with a More Preferred Z6 Moieties

In a more preferred embodiment of compounds from Section 1.2.5, said compounds have structures of formula I-2h:

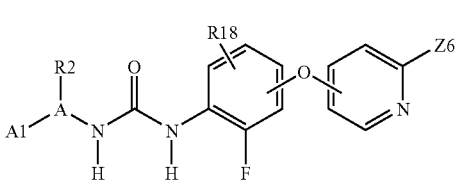

I-2h wherein Z6 is —C(O)NHR4, —NHR4 or R19 substituted pyrazole;

1.3 Compounds of Formula Ia which Exemplify Preferred A and X2-E1 Moieties

In a preferred embodiment of compounds of formula Ia, said compounds have structures of formula I-3a:

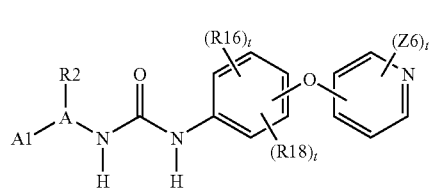

I-3a wherein the A ring is thienyl.

1.3.1 Compounds of Formula I-3a which Exemplify Preferred A1 Moieties

In a preferred embodiment of compounds of formula I-3a, said compounds have structures of formula I-3b:

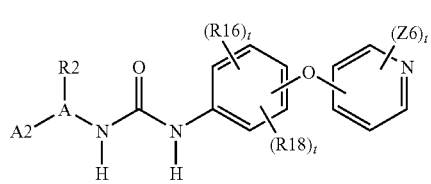
I-3b

1.3.2 Compounds of Formula Ix which Exemplify Preferred A1 Moieties

In a preferred embodiment of compounds of formula I-3a, said compounds have structures of formula I-3c:

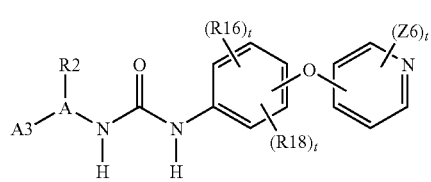
I-3c

1.3.3 Compounds of Formula I-3a which Exemplify Preferred A1 Moieties

In a preferred embodiment of compounds of formula I-3a, said compounds have structures of formula I-3d:

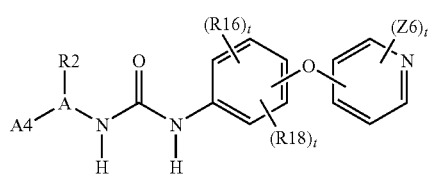
I-3d

1.3.4 More Preferred Compounds of Section 1.3

In a preferred embodiment of compounds from Section 1.3, said compounds have structures of formula I-3e:

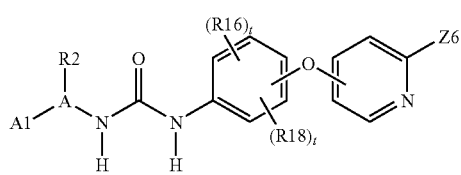
I-3e

1.3.5 Compounds of Section 1.3.4 with Preferred R16 Moieties

In a preferred embodiment of compounds from Section 1.3.4, said compounds have structures of formula I-3f:

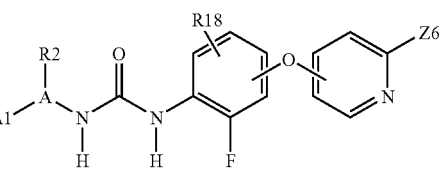
I-3f

1.3.6 Compounds of Section 1.3.5 with a More Preferred A1 Moieties

In a more preferred embodiment of compounds from Section 1.3.5, said compounds have structures of formula I-3g:

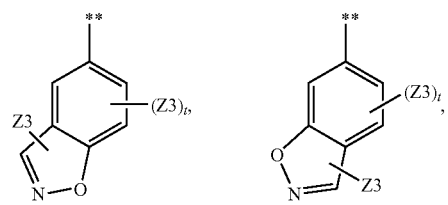
I-3g

Wherein A1 is selected from the group consisting of

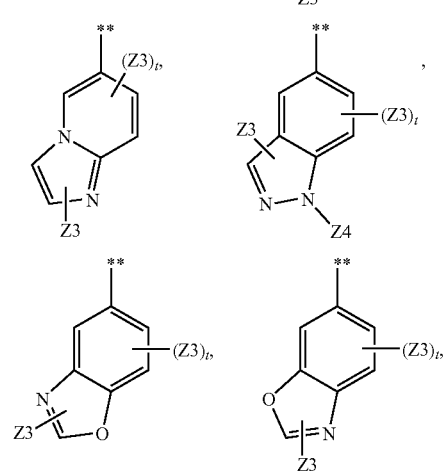

-continued

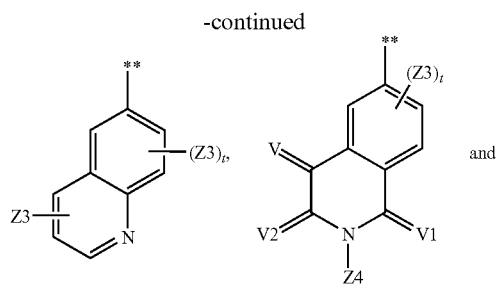

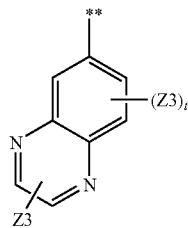

1.3.7 Compounds of Section 1.3.5 with a More Preferred Z6 Moieties

In a more preferred embodiment of compounds from Section 1.3.5, said compounds have structures of formula I-3h:

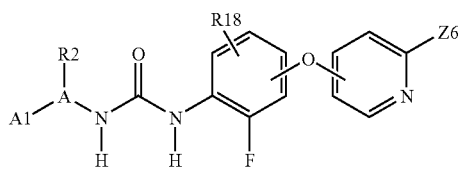

I-3h wherein Z6 is —C(O)NHR4, —NHR4 or R19 substituted pyrazole;

1.4 Compounds of Formula Ia which Exemplify Preferred A and X2-E1 Moieties

In a preferred embodiment of compounds of formula Ia, said compounds have structures of formula I-4-a:

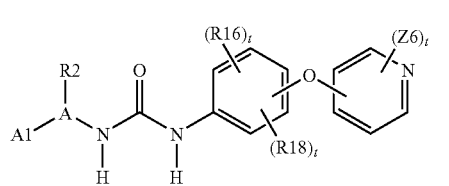

I-4a wherein the A ring is furyl.

1.4.1 Compounds of Formula Iii which Exemplify Preferred A1 Moieties

In a preferred embodiment of compounds of formula I-4-a, said compounds have structures of formula I-4-b:

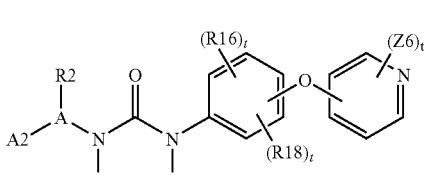

I-4b

1.4.2 Compounds of Formula Iii which Exemplify Preferred A1 Moieties

In a preferred embodiment of compounds of formula I-4-a, said compounds have structures of formula I-4-c:

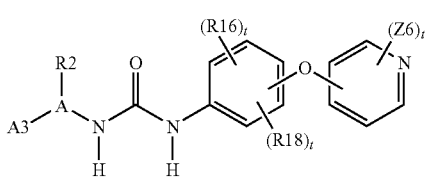

I-4c

1.4.3 Compounds of Formula Im which Exemplify Preferred A1 Moieties

In a preferred embodiment of compounds of formula I-4-a, said compounds have structures of formula I-4-d:

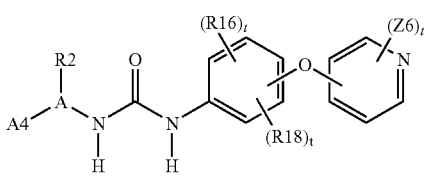

I-4d

1.4.4 More Preferred Compounds of Section 1.4

In a preferred embodiment of compounds from Section 1.4, said compounds have structures of formula I-4-e:

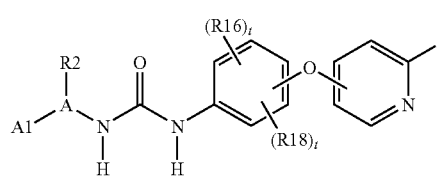

I-4e

1.4.5 Compounds of Section 1.4.4 with Preferred R16 Moieties

In a preferred embodiment of compounds from Section 1.4.4, said compounds have structures of formula I-4-f:

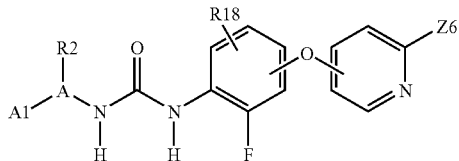

I-4f

1.4.6 Compounds of Section 1.4.5 with a More Preferred A1 Moieties

In a more preferred embodiment of compounds from Section 1.4.5, said compounds have structures of formula I-4-g:

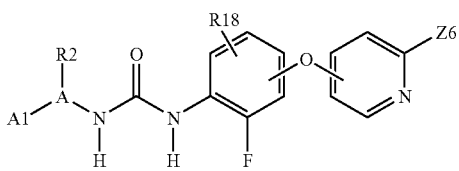

I-4g

Wherein A1 is selected from the group consisting of

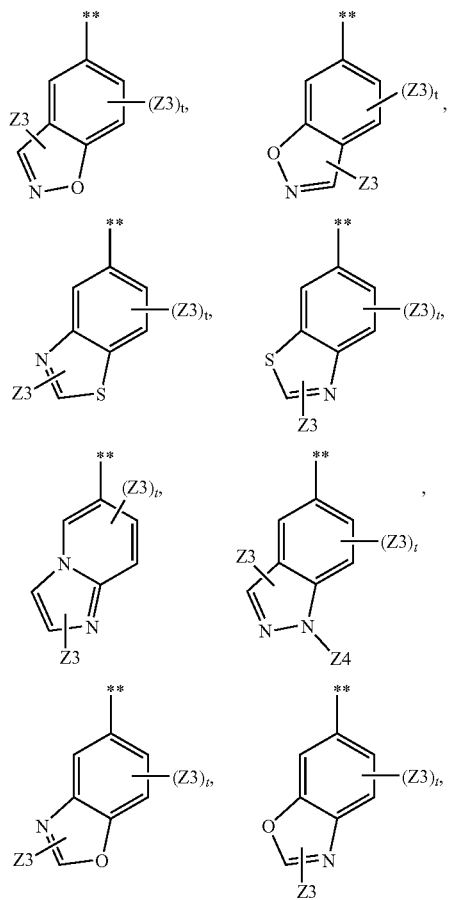

-continued

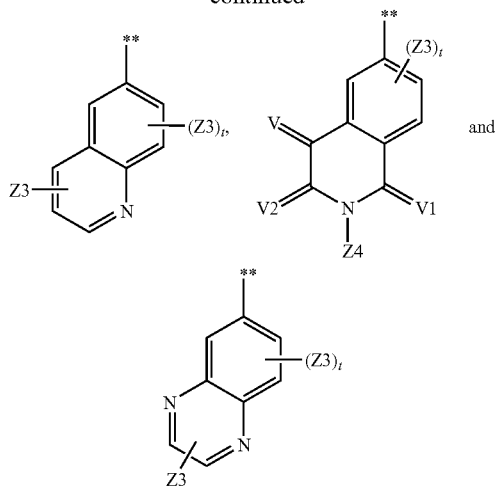

and

1.4.7 Compounds of Section 1.4.5 with a More Preferred Z6 Moieties

In a more preferred embodiment of compounds from Section 1.4.5, said compounds have structures of formula I-4-h:

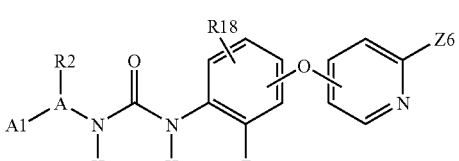

I-4h wherein Z6 is —C(O)NHR4, —NHR4 or R19 substituted pyrazole;

1.5 Compounds of Formula Ia which Exemplify Preferred A and X2-E1 Moieties

In a preferred embodiment of compounds of formula Ia, said compounds have structures of formula I-5a:

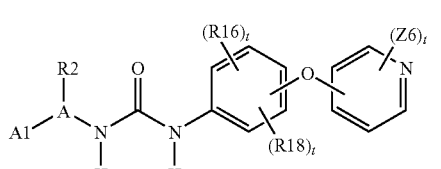

I-5a wherein the A ring is pyrrolyl.

1.5.1 Compounds of Formula I-5a which Exemplify Preferred A1 Moieties

In a preferred embodiment of compounds of formula I-5a, said compounds have structures of formula I-5b:

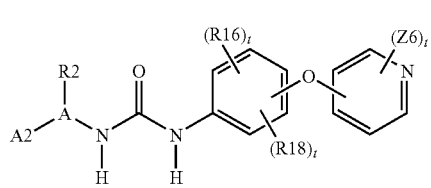

I-5b

1.5.2 Compounds of Formula I-5a which Exemplify Preferred A1 Moieties

In a preferred embodiment of compounds of formula I-5a, said compounds have structures of formula I-5c:

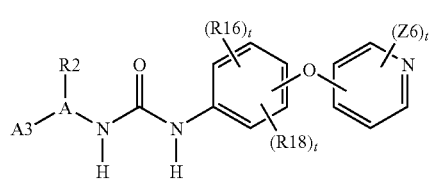

I-5c

1.5.3 Compounds of Formula-5a which Exemplify Preferred A1 Moieties

In a preferred embodiment of compounds of formula I-5a, said compounds have structures of formula I-5d:

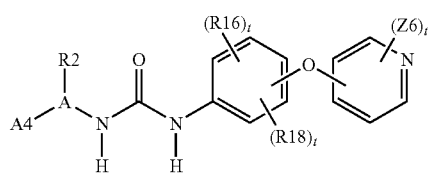

I-5d

1.5.4 More Preferred Compounds of Section 1.5

In a preferred embodiment of compounds from Section 1.5, said compounds have structures of formula I-5e:

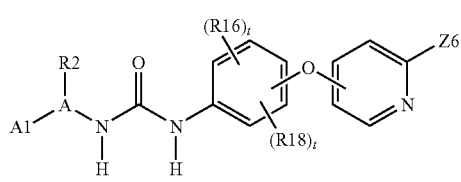

I-5e

1.5.5 Compounds of Section 1.5.4 with Preferred R16 Moieties

In a preferred embodiment of compounds from Section 1.5.4, said compounds have structures of formula I-5f:

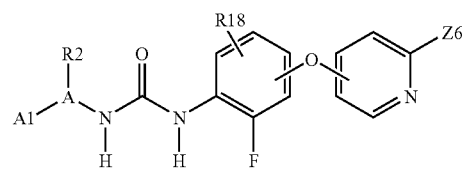

I-5f

1.5.6 Compounds of Section 1.5.5 with a More Preferred A1 Moieties

In a more preferred embodiment of compounds from Section 1.5.5, said compounds have structures of formula I-5g:

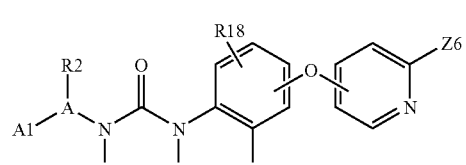

I-5g

Wherein A1 is selected from the group consisting of

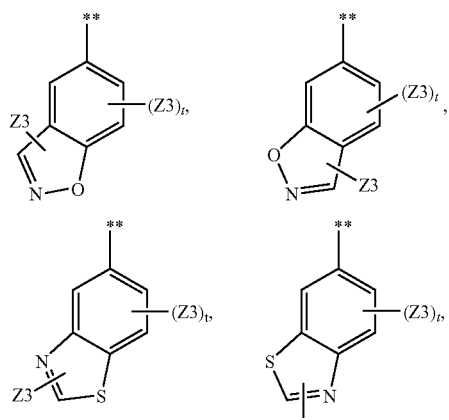

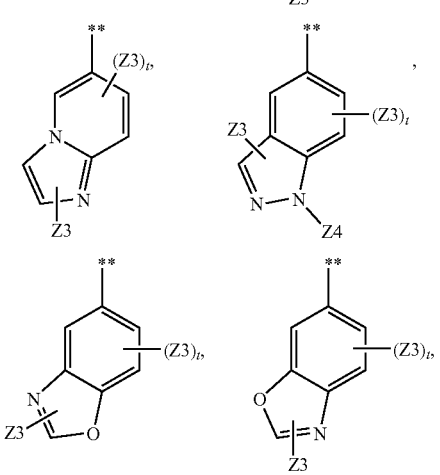

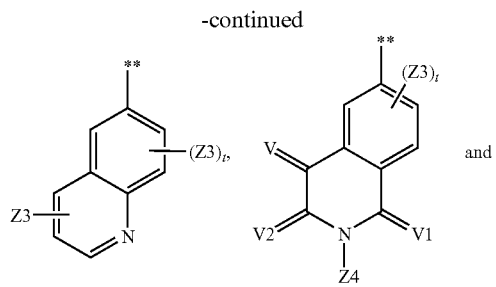

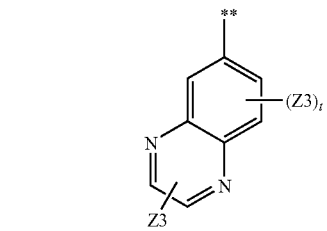

1.5.7 Compounds of Section 1.5.5 with a More Preferred Z6 Moieties

In a more preferred embodiment of compounds from Section 1.5.5, said compounds have structures of formula I-5h:

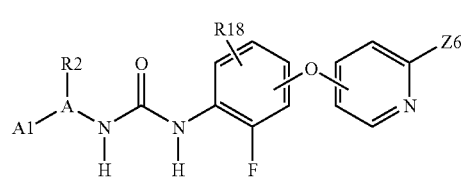

I-5h wherein Z6 is —C(O)NHR4, —NHR4 or R19 substituted pyrazole;

1.6 Compounds of Formula Ia which Exemplify Preferred A and X2-E1 Moieties

In a preferred embodiment of compounds of formula Ia, said compounds have structures of formula I-6a:

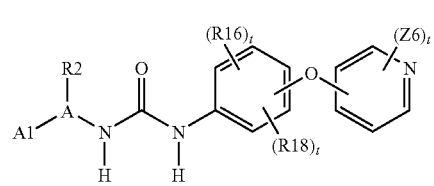

I-6a wherein the A ring is imidazolyl.

1.6.1 Compounds of Formula I-6a which Exemplify Preferred A1 Moieties

In a preferred embodiment of compounds of formula I-6a, said compounds have structures of formula I-6b:

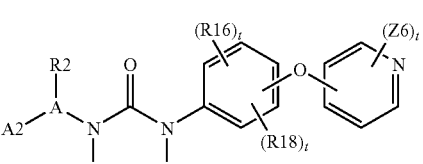

I-6b

1.6.2 Compounds of Formula I-6a which Exemplify Preferred A1 Moieties

In a preferred embodiment of compounds of formula I-6a, said compounds have structures of formula I-6c:

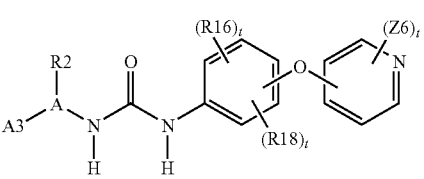

I-6c

1.6.3 Compounds of Formula I-6a which Exemplify Preferred A1 Moieties

In a preferred embodiment of compounds of formula I-6a, said compounds have structures of formula I-6d:

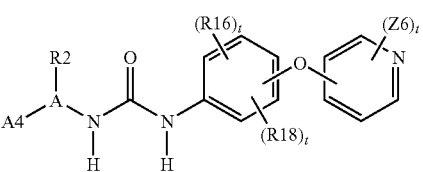

I-6d

1.6.4 More Preferred Compounds of Section 1.6

In a preferred embodiment of compounds from Section 1.6, said compounds have structures of formula I-6e:

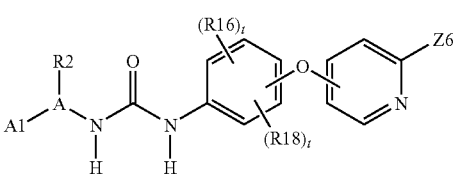

I-6e

1.6.5 Compounds of Section 1.6.4 with Preferred R16 Moieties

In a preferred embodiment of compounds from Section 1.6.4, said compounds have structures of formula I-6f:

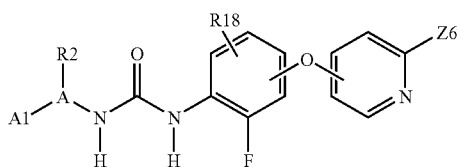

I-6f

1.6.6 Compounds of Section 1.6.5 with a More Preferred A1 Moieties

In a more preferred embodiment of compounds from Section 1.6.5, said compounds have structures of formula I-6g:

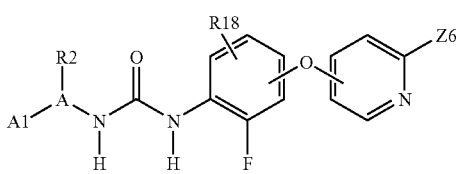

I-6g

Wherein A1 is selected from the group consisting of

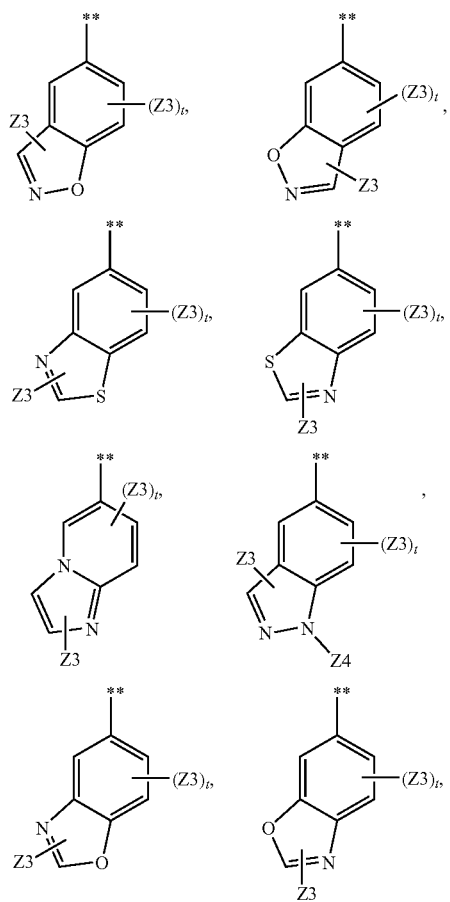

-continued

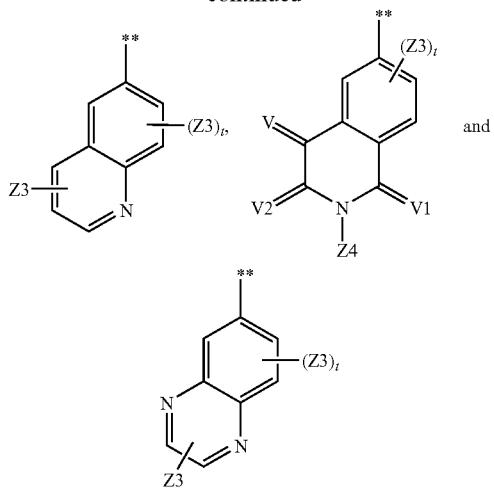

and

1.6.7 Compounds of Section 1.6.5 with a More Preferred Z6 Moieties

In a more preferred embodiment of compounds from Section 1.6.5, said compounds have structures of formula I-6h:

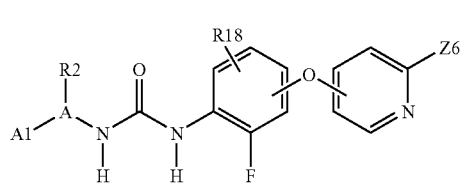

I-6h wherein Z6 is —C(O)NHR4, —NHR4 or R19 substituted pyrazole;

1.7 Compounds of Formula Ia which Exemplify Preferred A and X2-E1 Moieties

In a preferred embodiment of compounds of formula Ia, said compounds have structures of formula I-7a:

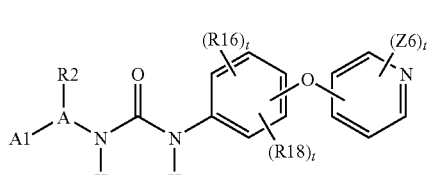

I-7a wherein the A ring is thiazolyl.

1.7.1 Compounds of Formula I-7a which Exemplify Preferred A1 Moieties

In a preferred embodiment of compounds of formula I-7a, said compounds have structures of formula I-7b:

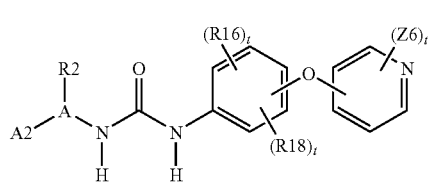
I-7b

1.7.2 Compounds of Formula I-7a which Exemplify Preferred A1 Moieties

In a preferred embodiment of compounds of formula I-7a, said compounds have structures of formula I-7c:

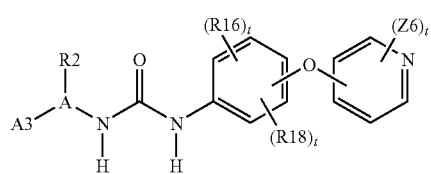
I-7c

1.7.3 Compounds of Formula I-7a which Exemplify Preferred A1 Moieties

In a preferred embodiment of compounds of formula I-7a, said compounds have structures of formula I-7d:

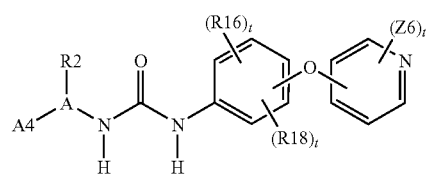
I-7d

1.7.4 More Preferred Compounds of Section 1.7

In a preferred embodiment of compounds from Section 1.7, said compounds have structures of formula I-7e:

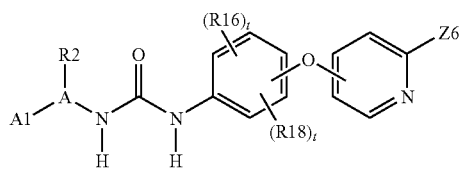
I-7e

1.7.5 Compounds of Section 1.7.4 with Preferred R16 Moieties

In a preferred embodiment of compounds from Section 1.7.4, said compounds have structures of formula I-7f:

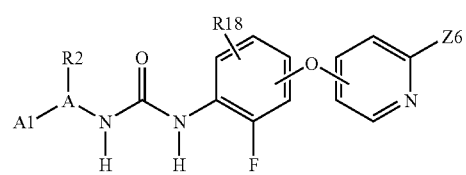
I-7f

1.7.6 Compounds of Section 1.7.5 with a More Preferred A1 Moieties

In a more preferred embodiment of compounds from Section 1.7.5, said compounds have structures of formula I-7g:

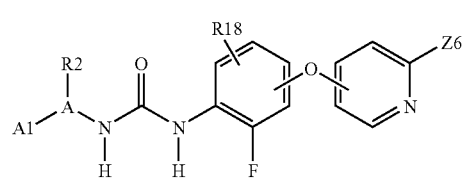
I-7g

Wherein A1 is selected from the group consisting of

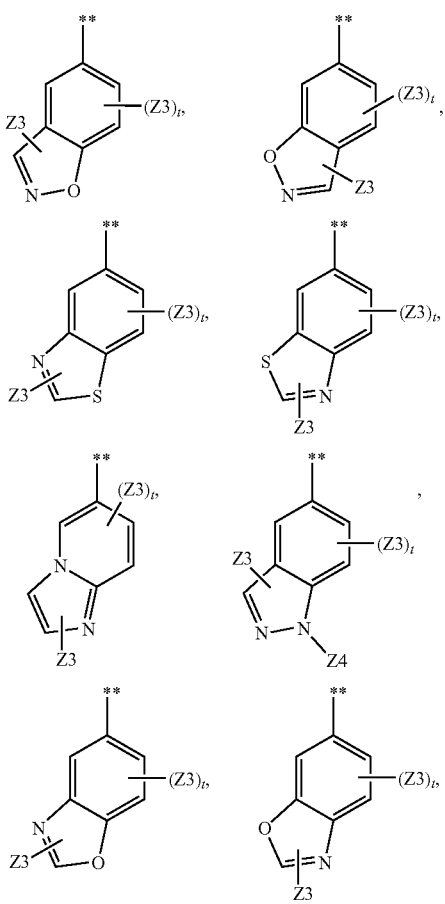

-continued

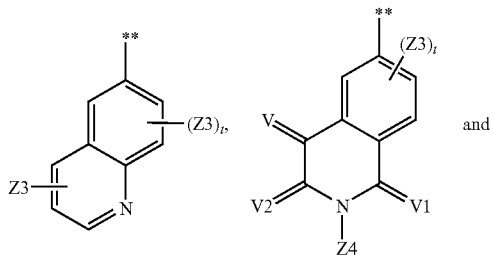

and

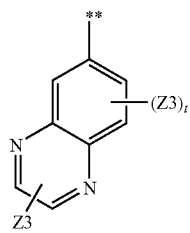

1.7.7 Compounds of Section 1.7.5 with a More Preferred Z6 Moieties

In a more preferred embodiment of compounds from Section 1.7.5, said compounds have structures of formula I-7h:

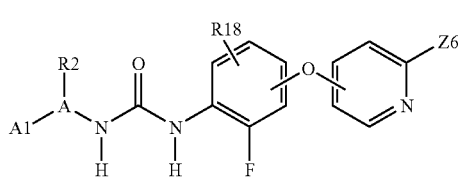

I-7h wherein Z6 is —C(O)NHR4, —NHR4 or R19 substituted pyrazole;

1.8 Compounds of Formula Ia which Exemplify Preferred A and X2-E1 Moieties

In a preferred embodiment of compounds of formula Ia, said compounds have structures of formula I-8a:

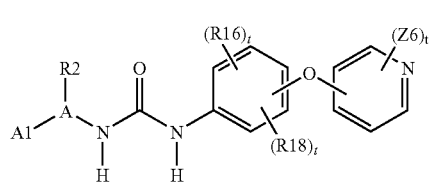

I-8a wherein the A ring is oxazolyl.

1.8.1 Compounds of Formula I-8a which Exemplify Preferred A1 Moieties

In a preferred embodiment of compounds of formula I-8a, said compounds have structures of formula I-8b:

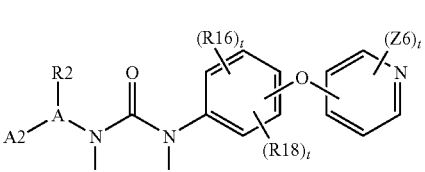

I-8b

1.8.2 Compounds of Formula I-8a which Exemplify Preferred A1 Moieties

In a preferred embodiment of compounds of formula I-8a, said compounds have structures of formula I-8c:

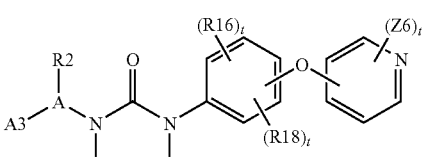

I-8c

1.8.3 Compounds of Formula I-8a which Exemplify Preferred A1 Moieties

In a preferred embodiment of compounds of formula I-8a, said compounds have structures of formula I-8d:

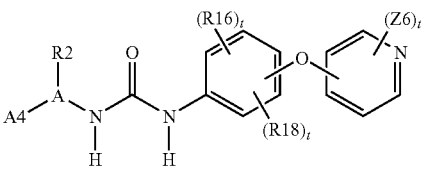

I-8d

1.8.4 More Preferred Compounds of Section 1.8

In a preferred embodiment of compounds from Section 1.8, said compounds have structures of formula I-8e:

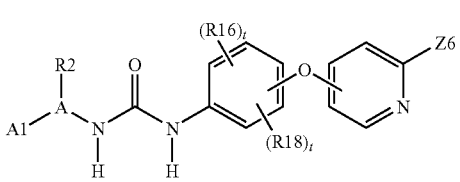

I-8e

1.8.5 Compounds of Section 1.8.4 with Preferred R16 Moieties

In a preferred embodiment of compounds from Section 1.8.4, said compounds have structures of formula I-8f:

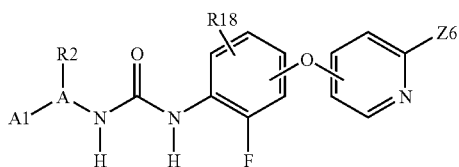

I-8f

1.8.6 Compounds of Section 1.8.5 with a More Preferred A1 Moieties

In a more preferred embodiment of compounds from Section 1.8.5, said compounds have structures of formula I-8g:

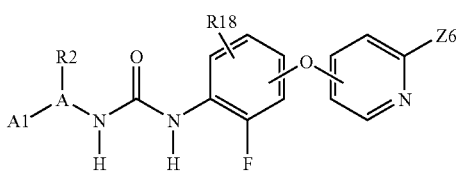

I-8g

Wherein A1 is selected from the group consisting of

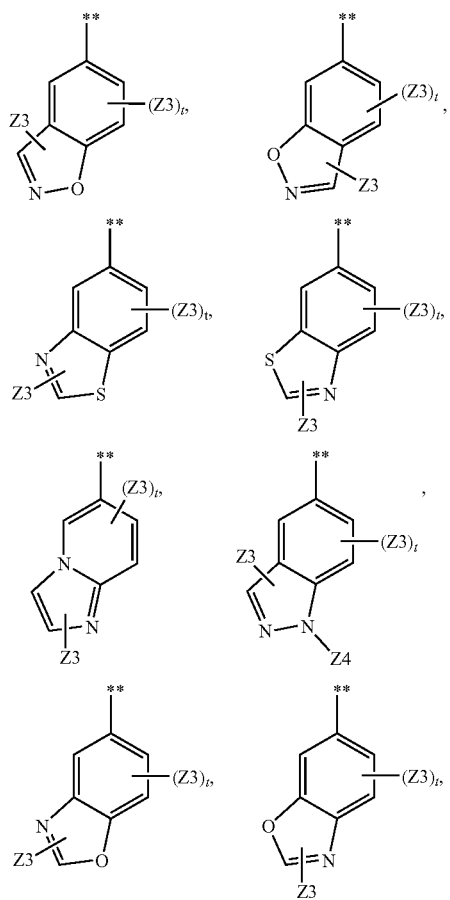

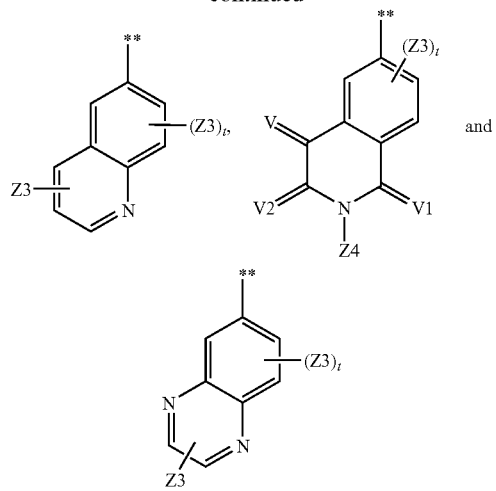

1.8.7 Compounds of Section 1.8.5 with a More Preferred Z6 Moieties

In a more preferred embodiment of compounds from Section 1.8.5, said compounds have structures of formula I-8h:

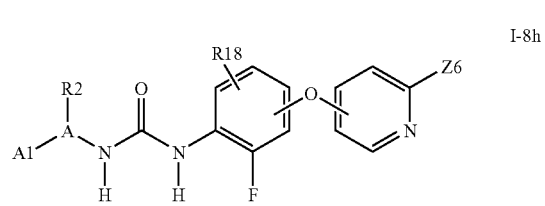

I-8h wherein Z6 is —C(O)NHR4, —NHR4 or R19 substituted pyrazole;

1.9 Compounds of Formula Ia which Exemplify Preferred A and X2-E1 Moieties

In a preferred embodiment of compounds of formula Ia, said compounds have structures of formula I-9a:

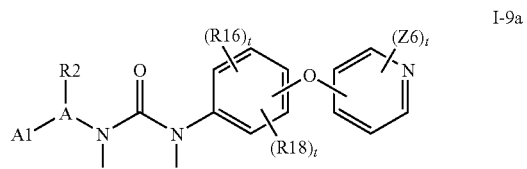

I-9a wherein the A ring is isothiazolyl.

1.9.1 Compounds of Formula I-9a which Exemplify Preferred A1 Moieties

In a preferred embodiment of compounds of formula I-9a, said compounds have structures of formula I-9b:

1.9.2 Compounds of Formula-9a which Exemplify Preferred A1 Moieties

In a preferred embodiment of compounds of formula I-9a, said compounds have structures of formula I-9c:

*[Structure I-9c: urea with A3-A group, R2, linked via NH-C(O)-NH to phenyl bearing (R16)$_t$ and (R18)$_t$, connected through O to pyridine bearing (Z6)$_t$]*

1.9.3 Compounds of Formula I-9a which Exemplify Preferred A1 Moieties

In a preferred embodiment of compounds of formula I-9a, said compounds have structures of formula I-9d:

*[Structure I-9d: urea with A4-A group, R2, linked via NH-C(O)-NH to phenyl bearing (R16)$_t$ and (R18)$_t$, connected through O to pyridine bearing (Z6)$_t$]*

1.9.4 More Preferred Compounds of Section 1.9

In a preferred embodiment of compounds from Section 1.9, said compounds have structures of formula I-9e:

*[Structure I-9e: urea with A1-A group, R2, linked via NH-C(O)-NH to phenyl bearing (R16)$_t$ and (R18)$_t$, connected through O to pyridine bearing Z6]*

1.9.5 Compounds of Section 1.9.4 with Preferred R16 Moieties

In a preferred embodiment of compounds from Section 1.9.4, said compounds have structures of formula I-9f:

*[Structure I-9f: urea with A1-A group, R2, linked via NH-C(O)-NH to phenyl bearing R18 and F, connected through O to pyridine bearing Z6]*

1.9.6 Compounds of Section 1.9.5 with a More Preferred A1 Moieties

In a more preferred embodiment of compounds from Section 1.9.5, said compounds have structures of formula I-9g:

*[Structure I-9g: urea with A1-A group, R2, linked via NH-C(O)-NH to phenyl bearing R18 and F, connected through O to pyridine bearing Z6]*

Wherein A1 is selected from the group consisting of

*[Eight heterocyclic structures shown with attachment points (**) and (Z3)$_t$ substituents: benzisoxazole (two isomers), benzothiazole (two isomers), imidazopyridine, indazole with Z4, benzoxazole (two isomers)]*

-continued

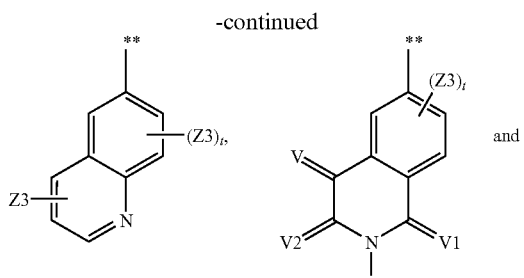

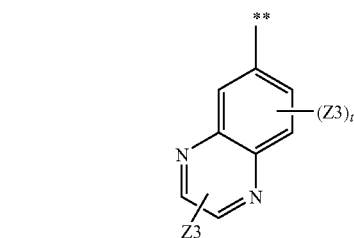

1.9.7 Compounds of Section 1.9.5 with a More Preferred Z6 Moieties

In a more preferred embodiment of compounds from Section 1.9.5, said compounds have structures of formula I-9h:

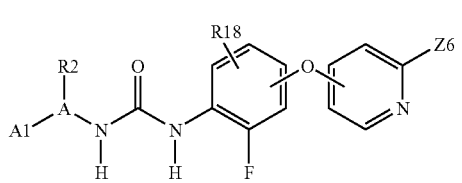
I-9h wherein Z6 is —C(O)NHR4, —NHR4 or R19 substituted pyrazole;

1.10 Compounds of Formula Ia which Exemplify Preferred A and X2-E1 Moieties

In a preferred embodiment of compounds of formula Ia, said compounds have structures of formula I-10a:

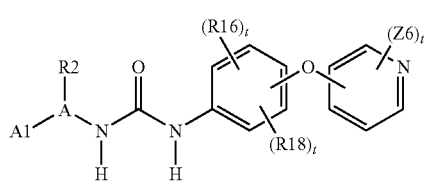
I-10a wherein the A ring is phenyl.

1.10.1 Compounds of Formula I-10a which Exemplify Preferred A1 Moieties

In a preferred embodiment of compounds of formula I-10a, said compounds have structures of formula I-10b:

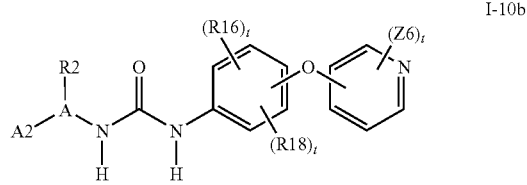
I-10b

1.10.2 Compounds of Formula I-10a which Exemplify Preferred A1 Moieties

In a preferred embodiment of compounds of formula I-10a, said compounds have structures of formula I-10c:

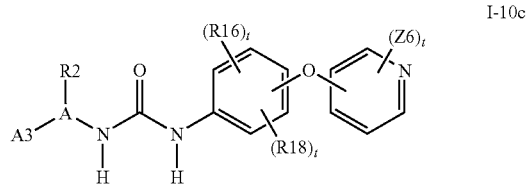
I-10c

1.10.3 Compounds of Formula I-10a which Exemplify Preferred A1 Moieties

In a preferred embodiment of compounds of formula I-10a, said compounds have structures of formula I-10d:

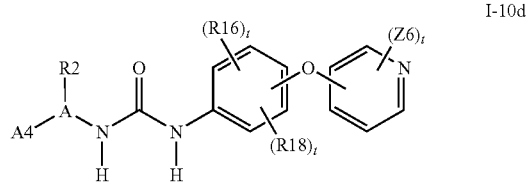
I-10d

1.10.4 More Preferred Compounds of Section 1.10

In a preferred embodiment of compounds from Section 1.10, said compounds have structures of formula I-10e:

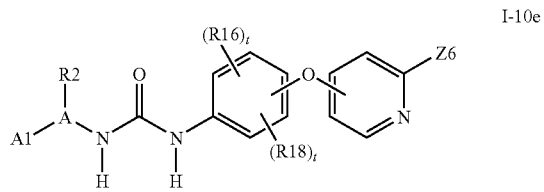
I-10e

1.10.5 Compounds of Section 1.10.4 with Preferred R16 Moieties

In a preferred embodiment of compounds from Section 1.10.4, said compounds have structures of formula I-10f:

I-10f

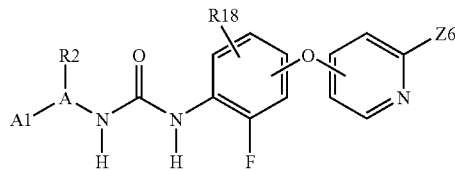

1.10.6 Compounds of Section 1.10.5 with a More Preferred A1 Moieties

In a more preferred embodiment of compounds from Section 1.10.5, said compounds have structures of formula I-10g:

I-10g

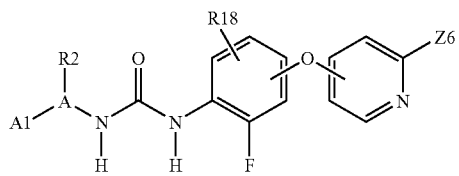

Wherein A1 is selected from the group consisting of

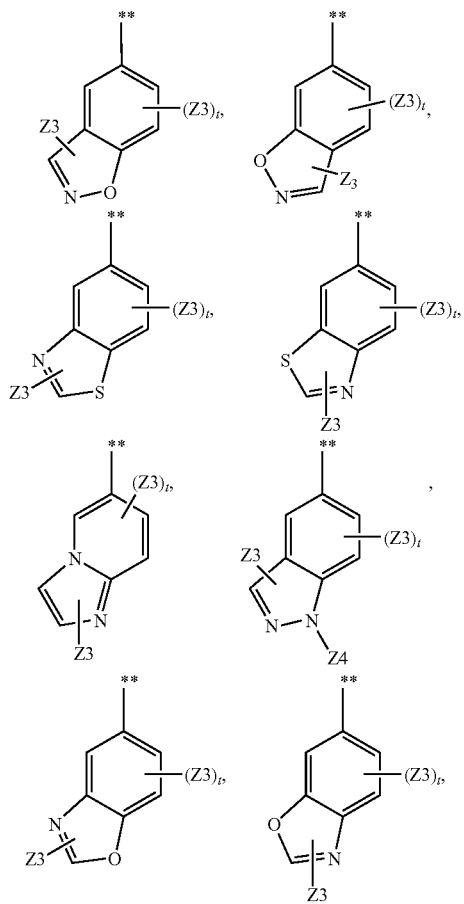

-continued

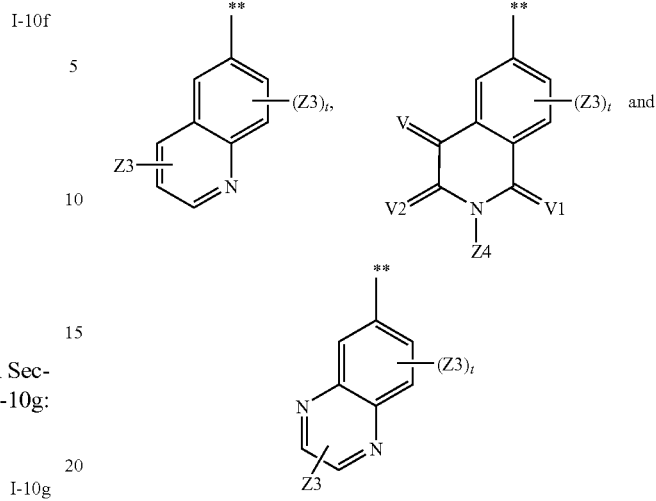

1.10.7 Compounds of Section 1.10.5 with a More Preferred Z6 Moieties

In a more preferred embodiment of compounds from Section 1.10.5, said compounds have structures of formula I-10h:

I-10h

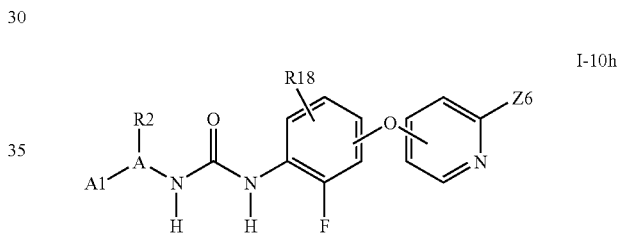

wherein Z6 is —C(O)NHR4, —NHR4 or R19 substituted pyrazole;

1.11 Compounds of Formula Ia which Exemplify Preferred A and X2-E1 Moieties

In a preferred embodiment of compounds of formula Ia, said compounds have structures of formula I-11a:

I-11a

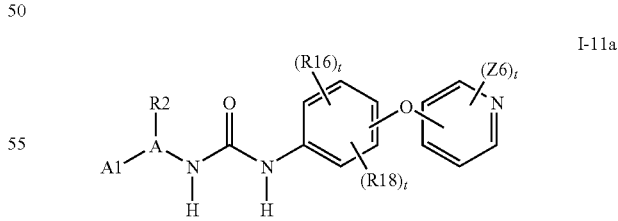

wherein the A ring is pyrimidinyl.

1.11.1 Compounds of Formula I-11a which Exemplify Preferred A1 Moieties

In a preferred embodiment of compounds of formula I-11a, said compounds have structures of formula I-11b:

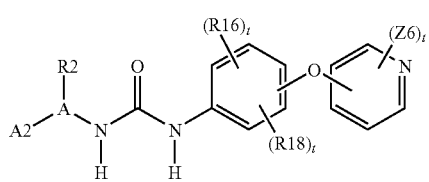
I-11b

1.11.2 Compounds of Formula I-11a which Exemplify Preferred A1 Moieties

In a preferred embodiment of compounds of formula I-11a, said compounds have structures of formula I-11c:

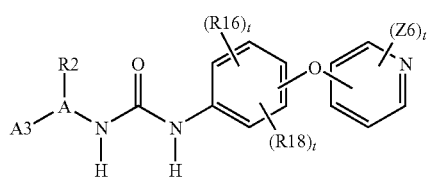
I-11c

1.11.3 Compounds of Formula I-11a which exemplify preferred A1 Moieties

In a preferred embodiment of compounds of formula I-11a, said compounds have structures of formula I-11d:

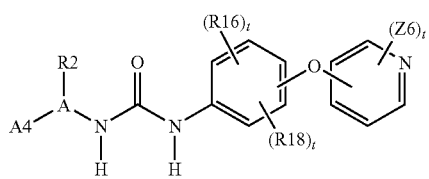
I-11d

1.11.4 More Preferred Compounds of Section 1.11

In a preferred embodiment of compounds from Section 1.11, said compounds have structures of formula I-11e:

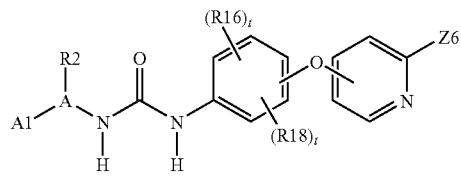
I-11e

1.11.5 Compounds of Section 1.11.4 with Preferred R16 Moieties

In a preferred embodiment of compounds from Section 1.11.4, said compounds have structures of formula I-11f:

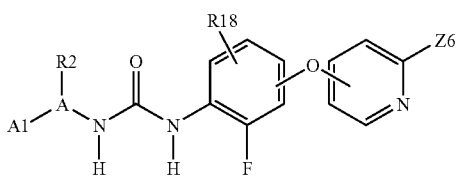
I-11f

1.11.6 Compounds of Section 1.11.5 with a More Preferred A1 Moieties

In a more preferred embodiment of compounds from Section 1.11.5, said compounds have structures of formula I-11g:

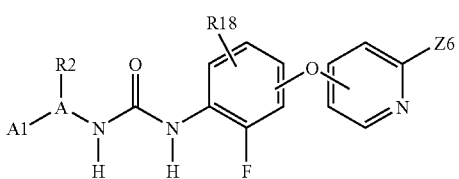
I-11g

Wherein A1 is selected from the group consisting of

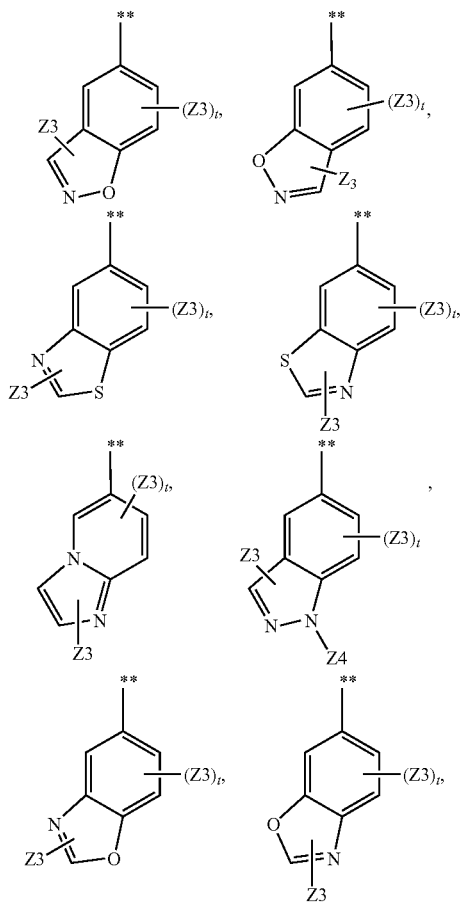

-continued

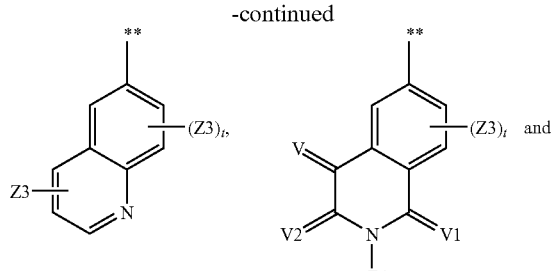

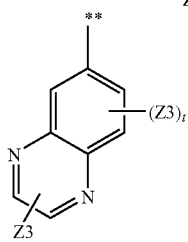

1.11.7 Compounds of Section 1.11.5 with a More Preferred Z6 Moieties

In a more preferred embodiment of compounds from Section 1.11.5, said compounds have structures of formula I-11h:

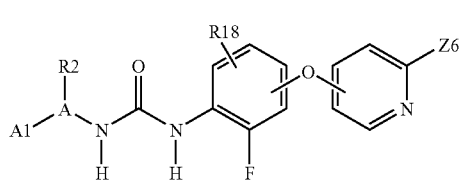
I-11h wherein Z6 is —C(O)NHR4, —NHR4 or R19 substituted pyrazole;

1.12 Compounds of Formula Ia which Exemplify Preferred A and X2-E1 Moieties

In a preferred embodiment of compounds of formula Ia, said compounds have structures of formula I-12a:

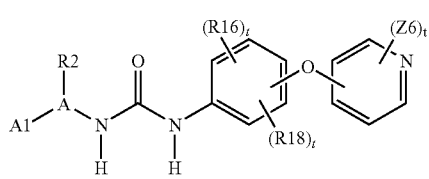
I-12a wherein the A ring is pyridinyl.

1.12.1 Compounds of Formula I-12a which Exemplify Preferred A1 Moieties

In a preferred embodiment of compounds of formula I-12a, said compounds have structures of formula I-12b:

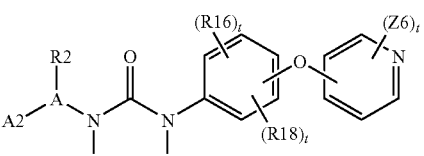
I-12b

1.12.2 Compounds of Formula I-12a which Exemplify Preferred A1 Moieties

In a preferred embodiment of compounds of formula I-12a, said compounds have structures of formula I-12c:

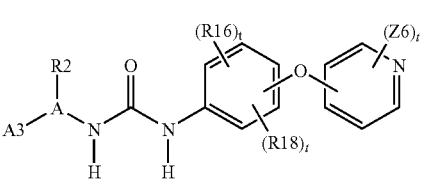
I-12c

1.12.3 Compounds of Formula I-12a which Exemplify Preferred A1 Moieties

In a preferred embodiment of compounds of formula I-12a, said compounds have structures of formula I-12d:

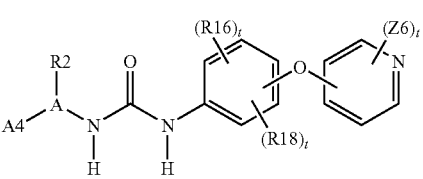
I-12d

1.12.4 More Preferred Compounds of Section 1.12

In a preferred embodiment of compounds from Section 1.12, said compounds have structures of formula I-12e:

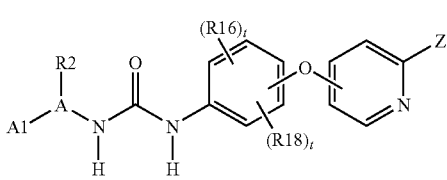
I-12e

1.12.5 Compounds of Section 1.12.4 with Preferred R16 Moieties

In a preferred embodiment of compounds from Section 1.12.4, said compounds have structures of formula I-12f:

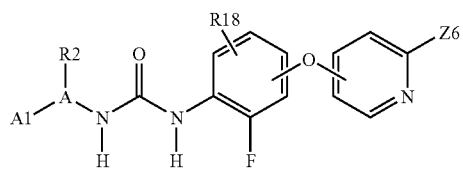

I-12f

1.12.6 Compounds of Section 1.12.5 with a More Preferred A1 Moieties

In a more preferred embodiment of compounds from Section 1.12.5, said compounds have structures of formula I-12g:

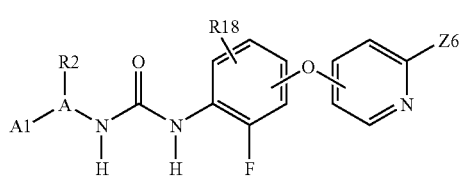

I-12g

Wherein A1 is selected from the group consisting of

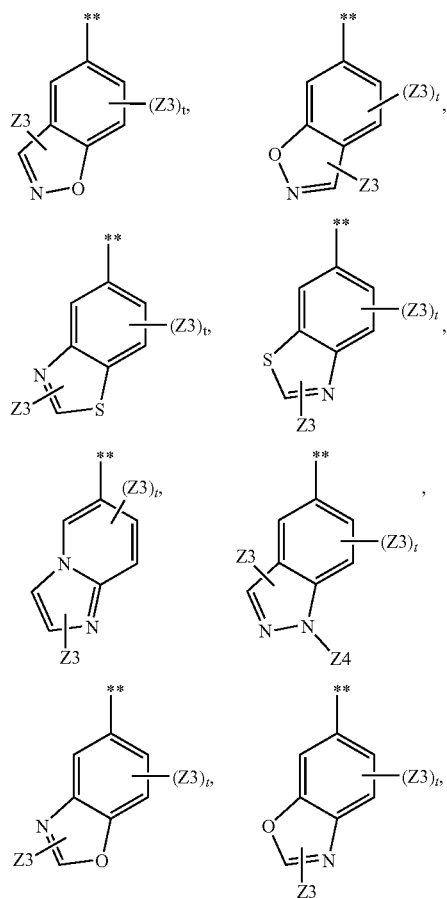

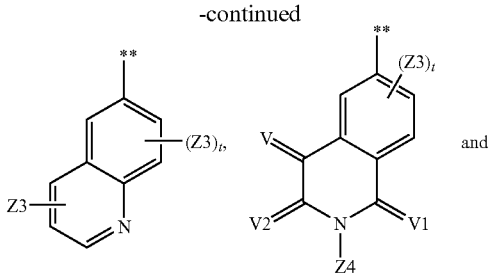

and

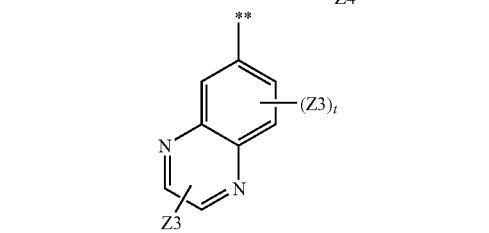

1.12.7 Compounds of Section 1.12.5 with a More Preferred Z6 Moieties

In a more preferred embodiment of compounds from Section 112.5, said compounds have structures of formula I-12h:

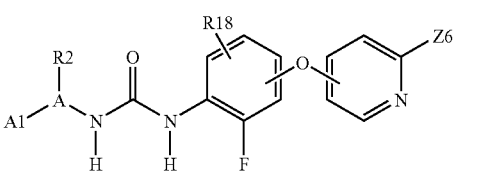

I-12h wherein Z6 is —C(O)NHR4, —NHR4 or R19 substituted pyrazole;

1.13 Methods

1.13a Methods of Protein Modulation

The invention includes methods of modulating kinase activity of a variety of kinases, e.g. C-Abl kinase, bcr-Abl kinase, Flt-3, c-Kit, PDGFR, VEGFR, c-MET, the HER family of kinases and the Raf family of kinases. The kinases may be wildtype kinases, oncogenic forms thereof, aberrant fusion proteins thereof or polymorphs of any of the foregoing. The method comprises the step of contacting the kinase species with compounds of the invention and especially those set forth in sections 1.1-1.12. The kinase species may be activated or unactivated, and the species may be modulated by phosphorylations, sulfation, fatty acid acylations glycosylations, nitrosylation, cystinylation (i.e. proximal cysteine residues in the kinase react with each other to form a disulfide bond) or oxidation. The kinase activity may be selected from the group consisting of catalysis of phospho transfer reactions, inhibition of phosphorylation, oxidation or nitrosylation of said kinase by another enzyme, enhancement of dephosphorylation, reduction or denitrosylation of said kinase by another enzyme, kinase cellular localization, and recruitment of other proteins into signaling complexes through modulation of kinase conformation.

1.13b Treatment Methods

The methods of the invention also include treating individuals suffering from a condition selected from the group consisting of cancer and hyperproliferative diseases. These methods comprise administering to such individuals compounds of the invention, and especially those of sections 1.1-1.12, said diseases including, but not limited to, a disease caused by c-Abl kinase, oncogenic forms thereof, aberrant fusion proteins thereof and polymorphs thereof, chronic myelogenous leukemia, acute lymphocytic leukemia, other myeloproliferative disorders, gastrointestinal stromal tumors, age-related macular degeneration, hypereosinophilic syndrome, glioblastomas, ovarian cancer, pancreatic cancer, prostate cancer, lung cancers, breast cancers, kidney cancers, cervical carcinomas, metastasis of primary solid tumor secondary sites, ocular diseases characterized by hyperproliferation leading to blindness including various retinopathies, i.e. diabetic retinopathy and age-related macular degeneration, rheumatoid arthritis, melanomas, colon cancer, thyroid cancer, a disease caused by a mutation in the RAS-RAF-MEK-ERK-MAP kinase pathway, human inflammation, rheumatoid spondylitis, ostero-arthritis, asthma, gouty arthritis, sepsis, septic shock, endotoxic shock, Gram-negative sepsis, toxic shock syndrome, adult respiratory distress syndrome, stroke, reperfusion injury, neural trauma, neural ischemia, psoriasis, restenosis, chronic obstructive pulmonary disease, bone resorptive diseases, graft-versus-host reaction, Chron's disease, ulcerative colitis, inflammatory bowel disease, pyresis, and combinations thereof. The administration method is not critical, and may be from the group consisting of oral, parenteral, inhalation, and subcutaneous.

1.14 Pharmaceutical Preparations

The compounds of the invention, especially those of sections 1.1-1.12, may form a part of a pharmaceutical composition by combining one or more such compounds with a pharmaceutically acceptable carrier. Additionally, the compositions may include an additive selected from the group consisting of adjuvants, excipients, diluents, and stabilizers.

2. Synthesis of Compounds of the Present Invention

The compounds of the invention are available by the procedures and teachings of WO 2006/071940, filed Dec. 23, 2005, incorporated by reference, and by the general synthetic methods illustrated in the schemes below and the accompanying examples.

As indicated in Scheme 1, ureas of general formula 1 can be readily prepared by the union of amines of general formula 2 with isocyanates 3 or isocyanate surrogates 4 (trichloroethyl carbamates) or 5 (isopropenyl carbamates). Preferred conditions for the preparation of compounds of general formula 1 involve heating a solution of 4 or 5 with 2 in the presence of a tertiary base such as diisopropylethylamine, triethylamine or N-methylpyrrolidine in a solvent such as dimethylformamide, dimethylsulfoxide, tetrahydrofuran or 1,4-dioxane at a temperature between 50 and 100° C. for a period of time ranging from 1 hour to 2 days.

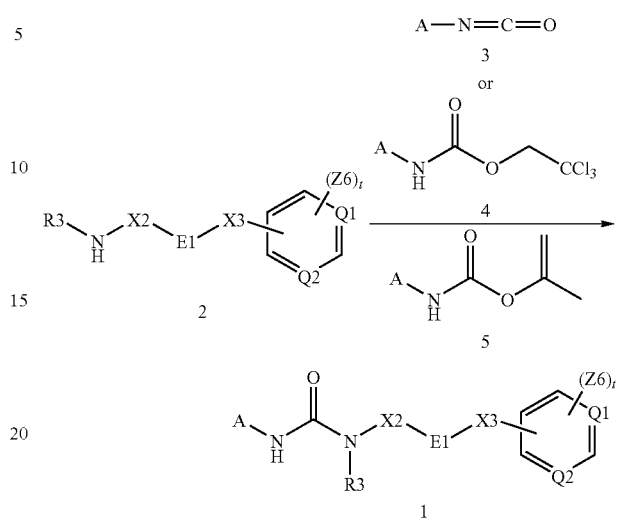

Scheme 1

As shown in Scheme 2, isocyanates 3 can be prepared from amines A-NH$_2$ 6 with phosgene, or a phosgene equivalent such as diphosgene, triphosgene, or N,N-dicarbonylimidazole. Trichloroethyl carbamates 4 and isopropenyl carbamates 5 are readily prepared from amines A-NH$_2$ (6) by acylation with trichloroethyl chloroformate or isopropenyl chloroformate by standard conditions familiar to those skilled in the art. Preferred conditions for the preparation of 4 and 5 include include treatment of compound 6 with the appropriate chloroformate in the presence of pyridine in an aprotic solvent such as dichloromethane or in the presence of aqueous hydroxide or carbonate in a biphasic aqueous/ethyl acetate solvent system.

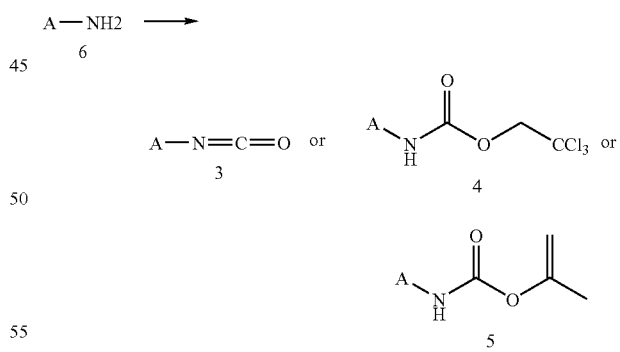

Scheme 2

Additionally, compounds of formula 1 can also be prepared from carboxylic acids 7 by the intermediacy of in-situ generated acyl azides (Curtius rearrangement) as indicated in Scheme 3. Preferred conditions for Scheme 3 include the mixing of acid 7 with amine 2 and diphenylphosphoryl azide in a solvent such as 1,4-dioxane or dimethylformamide in the presence of base, such as triethylamine, and raising the temperature of the reaction to about 80-120° C. to affect the Curtius rearrangement.

Scheme 3

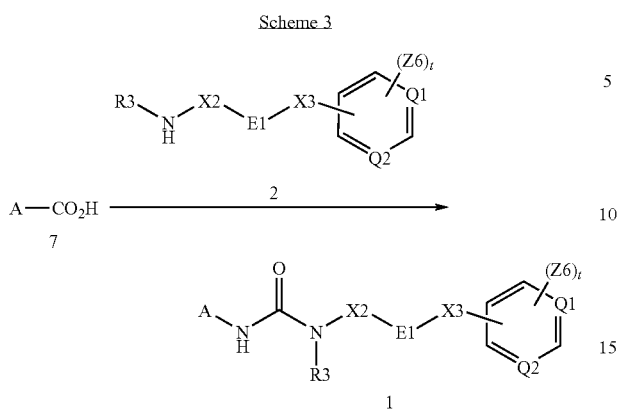

Many methods exist for the preparation of amines A-NH$_2$ 6 and acids A-CO$_2$H 7, depending on the nature of the A-moiety. Many such methods have been described in detail in WO 2006/071940, and are incorporated by reference here. Preferred synthetic methods are outlined in the following schemes for the non-limiting examples wherein A is a 1-substituted-pyrazole (optionally substituted by R2) or A and A1 are linked by C—C bond.

As illustrated in Scheme 4, A1-substituted, pyrazole amines 10 (a preferred aspect of A-NH$_2$ 6, Scheme 2) are available by the condensation of hydrazines 8 and beta-keto nitriles 9. Preferred conditions for this transformation are by heating in ethanolic HCl. Hydrazines 8 are in turn available by the diazotization of amines 11 followed by reduction or, alternately from the hydrolysis of hydrazones 13 obtained by the palladium mediated coupling of benzophenone hydrazone with compounds of formula A1-X 12, wherein X represents a halogen or triflate moiety.

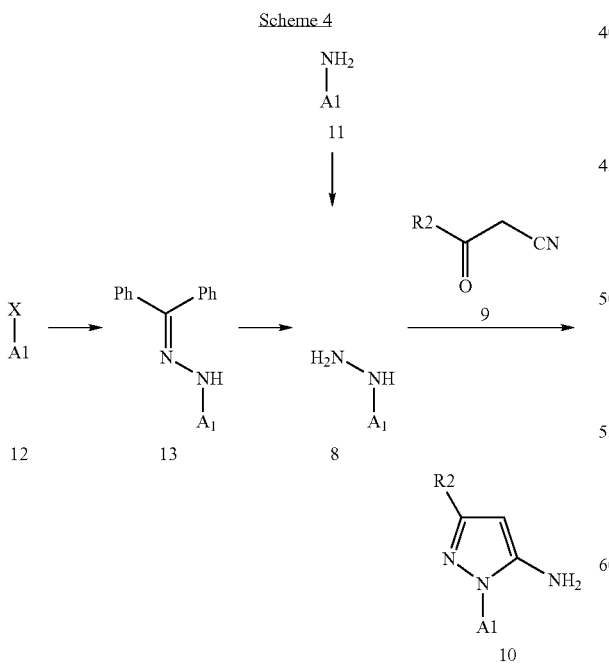

A non-limiting example of Scheme 4 is illustrated by the preparation of compound 19 (Scheme 5 and the accompanying examples). Thus commercially available 6-hydroxyquinoline 14 can be converted to trifluoromethanesulfonate 15 by treatment with triflic anhydride and pyridine. Reaction of 15 with benzophenone hydrazone in the presence of a palladium catalyst, preferably a catalyst containing the bis (diphenylphosphino)ferrocene ligand, provides the hydrazone 16. Reaction of 16 with ethanolic HCl at reflux provides the hydrazine 17, which can be combined with keto nitriles of general formula 18 by further heating in ethanolic HCl to provide quinoline pyrazole amines of formula 19. In another aspect of this synthetic sequence, hydrazone 16 can be converted directly to pyrazole 19 by the direct reaction with keto nitrile 18 upon heating in ethanolic HCl.

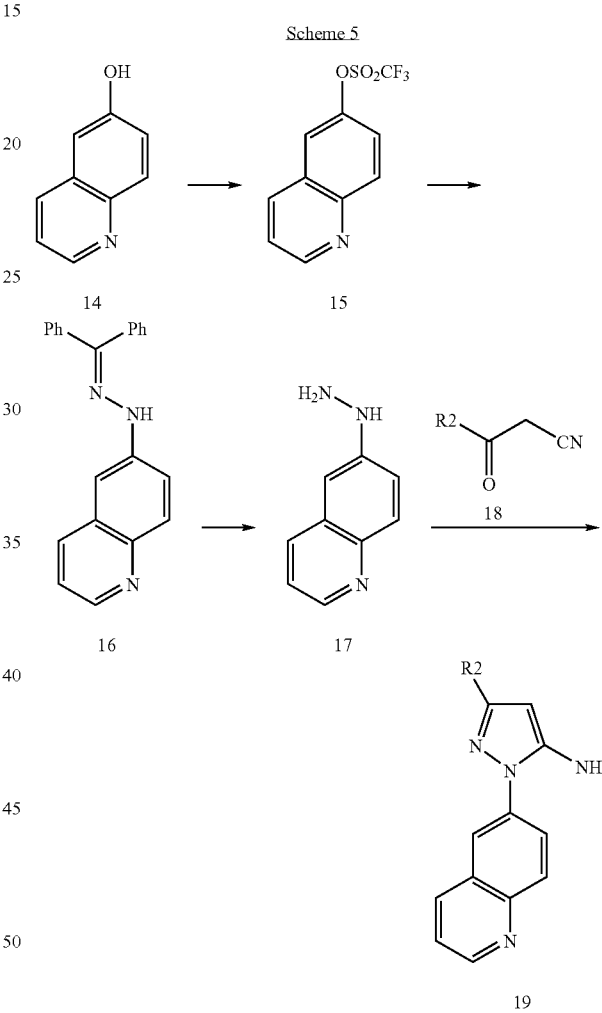

Another preferred method for constructing A1-substituted pyrazoles is illustrated by the general preparation of pyrazole acid 22 (Scheme 6), an aspect of A-CO$_2$H 7 (Scheme 3). As indicated in Scheme 6, the union of a pyrazole 5-carboxylic ester 20 with A1-X 12, wherein X reprepesents a halide, triflate, or boronic acid suitable for direct transition metal-catalyzed couplings with pyrazoles 20, provides A1-substituted pyrazole esters 21. Preferred conditions for such transformations involve mixing a boronic acid 11 [X=B(OH)$_2$] and esters 20 in dichloromethane with copper acetate and pyridine in the presence of crushed molecular sieves, with or without heating. Preferred esters for this transformation include ethyl, tert-butyl and benzyl esters. The esters 21 in turn can be converted to acids 22 by standard conditions familiar to those skilled in the art, such as saponification, acidic hydrolysis or hydrogenation.

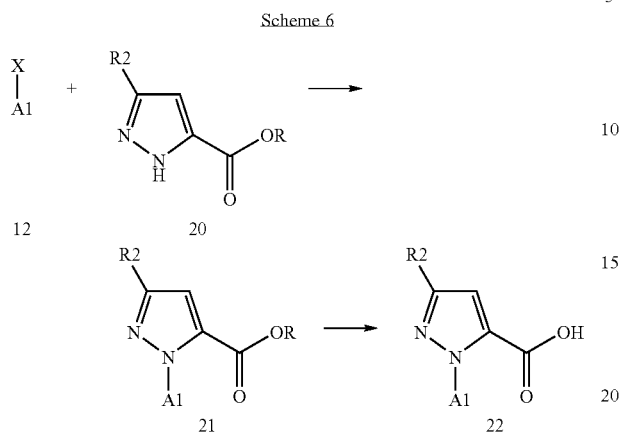

The synthesis of intermediates useful for the construction of compounds of formula 1 wherein A and A1 are linked by a C—C bond is shown in Scheme 7. In this case, palladium catalyzed reactions (for example, Suzuki or Stille reactions) of A1-X 12 with a complementary component 23 or 24 provides compounds 25 or 26, examples of general intermediates A-NH$_2$ 6 or A-CO$_2$H 7, respectively. In this synthetic sequence, the X-groups on the reactants 12 and 23 or 24 are moieties that undergo transition metal catalyzed cross coupling reactions, such as halides or triflates and boronic acids or esters, stannanes, silanes, organozincs or other organometallic moieties known by those skilled in the art to be suitable substrates for such processes. The X-groups in Scheme 7 are complementary moieties for cross coupling processes such that when A1-X 12 is a halide or triflate, A-X 23 or A-X 24 will be a complementary organometallic, such as a stannane or the like or a boronic acid or ester. Likewise, if A1-X 12 is an organometallic reagent or a boronic acid or ester, A-X will be a halide or triflate.

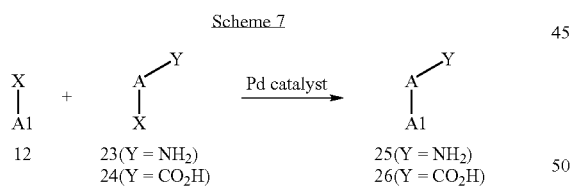

Within Scheme 7, it will be understood by those skilled in the art that there are additional synthetic equivalents for the Y-groups of 23 and 24 that can be used interchangeably with NH$_2$ and CO$_2$H with the addition of additional transforming steps. For example, the Y group of 23 might also be a protected amino group such as N-Boc or a surrogate amino group such as nitro that would give rise to compounds of formula 25 after acidic hydrolysis or reduction respectively. Similarly, it will be recognized that the Y group of 24 might also be an ester or nitrile which could be hydrolyzed to an acid of formula 26 by standard synthetic methods.

A non limiting example of Scheme 7 is illustrated by the preparation of compound 29, an example of general intermediate A-NH$_2$ 6, above. Thus, commercially available quinoline 6-boronic acid 27 can be combined with commercially available 5-fluoro-2-iodoaniline 28 in the presence of a palladium catalyst to provide compound 29, an example of general intermediate A-NH$_2$ 6, above.

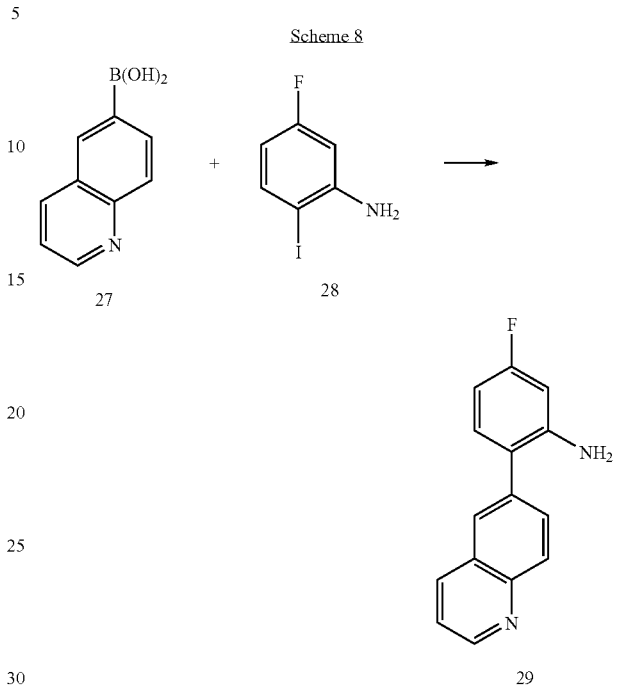

Amines 2 (Schemes 1 and 3, above) useful for the invention can be synthesized according to methods commonly known to those skilled in the art. Non-limiting examples are illustrated in the following schemes. A general preparation of aryl amine 32, an example of amine 2, above, is shown in Scheme 9. Thus, chloropyridines of formula 31 are reacted with phenols of formula 30 in the presence of base such as potassium tert-butoxide. Reactions are generally conducted at temperatures between 0° C. and 150° C. in solvents such as dimethylacetamide, dimethylformamide or dimethylsulfoxide. Some non-limiting examples of general synthetic Scheme 9 are shown in Schemes 10-12, below.

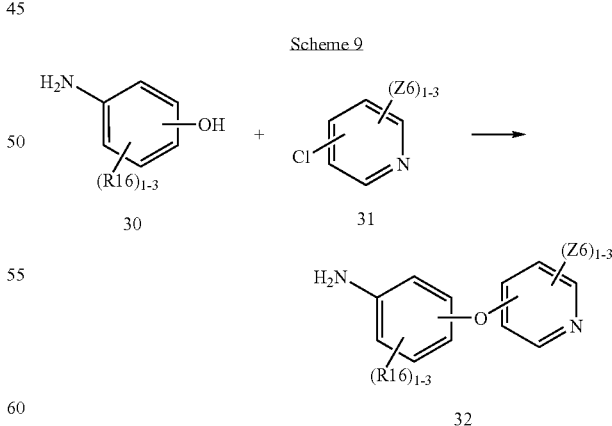

In Scheme 10, commercially available 3-fluoro-4-aminophenol is reacted with potassium tert-butoxide and chloropyridines 34 or 35 to provide amino ethers 36 and 37 respectively. The preferred solvent for this transformation is dimethylacetamide at a temperature between 80 and 100° C.

Scheme 10

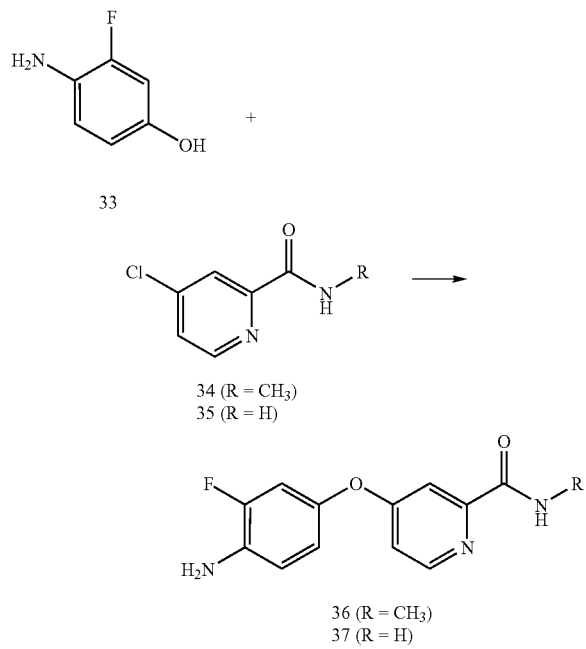

34 (R = CH₃)
35 (R = H)

36 (R = CH₃)
37 (R = H)

In a similar manner, commercially available 2-methyl-4-aminophenol 38 is combined with chloropyridines 34 and 35 to provide amino ethers 39 and 40, respectively (Scheme 11).

Scheme 11

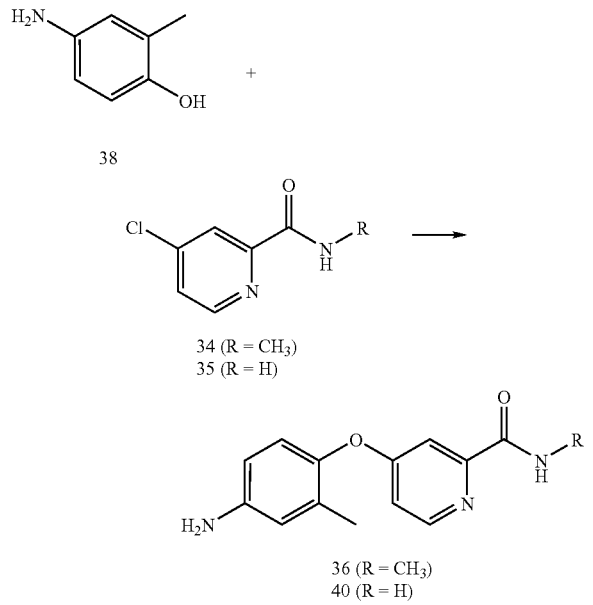

34 (R = CH₃)
35 (R = H)

36 (R = CH₃)
40 (R = H)

Scheme 12 illustrates the preparation of meta-substituted pyridyl ether amines 47 and 48, examples of general intermediate 2, above. As shown in Scheme 12, commercially available 2-chloro-4-fluorophenol 41 is treated with methyl chloroformate to provide carbonate 42. Nitration under standard conditions then provides adduct 43. Hydrolysis of the carbonate provides phenol 44. Concomitant reduction of both the nitro and chloro moieties provides aminophenol 45. Treatment of phenol 45 sequentially with potassium tert-butoxide and 3,5-dichloropyridine and heating in dimethylacetamide provides the compound 47. Removal of the chlorine atom of 47 by hydrogenation provides the amine of formula 48, an aspect of general amine 2.

Scheme 12

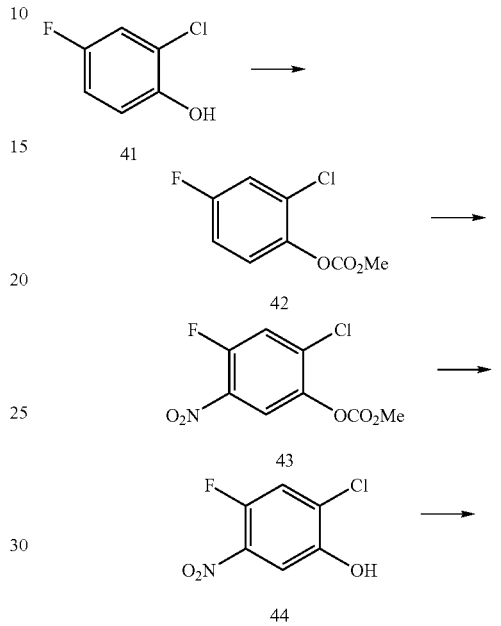

47 (R = Cl)
48 (R = H)

Amines of general formula 2 can also be prepared by the general route shown in Scheme 13. Thus, halo pyridine 49 (X is halogen) or halo pyrimidine 50 (X is halogen) can be converted to Z6-substituted pyridine 51 or Z6-substituted pyrimidine 52, respectively. There are several methods through which this can be accomplished, depending on the nature of the Z6. When the Z6 moiety is attached to the Q-containing ring through a Z6 nitrogen atom, preferred methods include heating compounds of formula 49 or 50 with an excess of the amine Z6-H either neat or in a solvent such as N-methylpyrrolidinone, DMF, DMSO or an alcoholic solvent at temperatures ranging from RT to 200° C. For the case of aryl and heteroaryl amines Z6-H, additional preferred methods include the heating of compounds 49 or 50 with an excess of the amine Z6-H and an acid catalyst (for example, TsOH, HCl, HOAc or the like) in a suitable solvent such as DMF, DMSO or an alcoholic solvent. Additional preferred methods for aryl and heteroarylamines Z6-H include combining Z6-H with compounds 49 or 50 in the presence of a transition metal catalyst such as a palladium catalyst in a suitable solvent like 1,4-dioxane or DMF with heating if necessary. When the Z6 moiety is attached to the Q-containing ring through a Z6 oxygen or sulfur atom, preferred methods include heating 49-50 with alcohol or thiol Z6-H in the presence of a strong base (for example, NaH or potassium tert-butoxide) either neat using Z6-H as the solvent, or in a polar solvent such as DMF or DMSO at temperatures ranging from RT to 200° C. When the Z6 moiety is attached to the Q-containing ring through a Z6 carbon atom, preferred methods include contacting compounds 49 or 50 with a species of formula Z6-M in the presence of a palladium catalyst, wherein M is a species that participates in transition-metal catalyzed cross-coupling reactions. Examples of suitable M groups include but are not limited to, boronic acids, boronic esters, zinc, trialkyltin, silicon, magnesium, lithium, and aluminum. Optionally, the transformations shown in Scheme 13 may be performed with microwave heating. It will be understood by those skilled in the art that the Z6 moieties introduced in Scheme 13 may contain optional protecting groups that will be removed in subsequent transformations (not shown). Some non-limiting examples of general Scheme 13 are shown in Schemes 14 and 15, below.

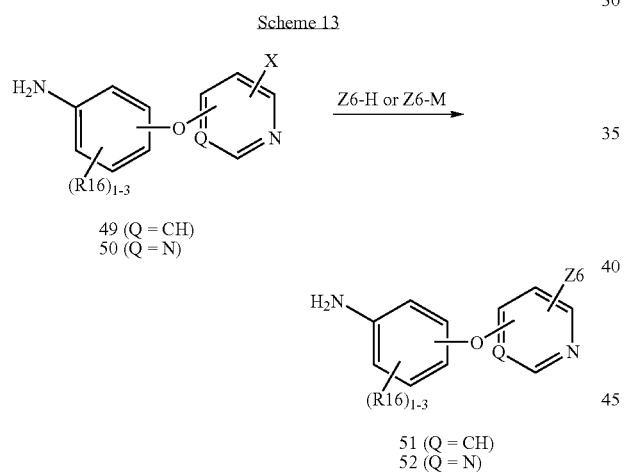

In Scheme 14, phenol 33 and 2,4-dichloropyridine (51) are combined using general Scheme 9 to provide the chloropyridine 52. Further reaction of chloropyridine 52 with the N-methylpyrazole boronate 53 in the presence of palladium tetrakis (triphenylphosphine) provides 54, an example of general amine 2.

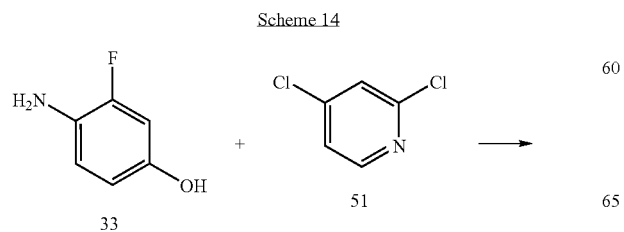

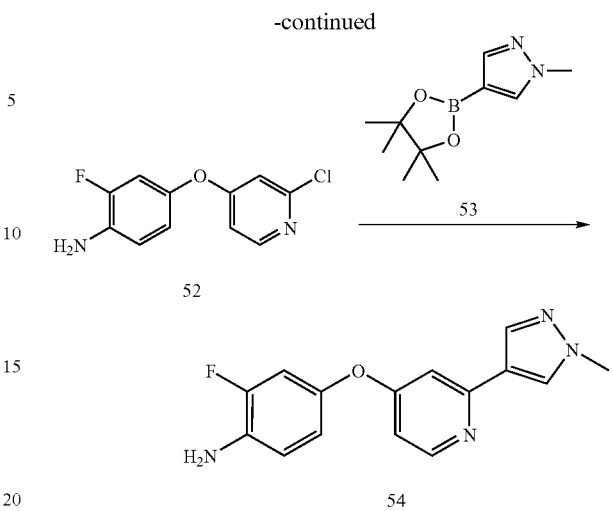

Scheme 15, shows the preparation of amino pyridine 55 from chloropyridine 52 by the general route of Scheme 13. Preferred conditions for this transformation include the contacting of chloropyridine 52 with isopropylamine in N-methylpyrrolidinone with microwave heating.

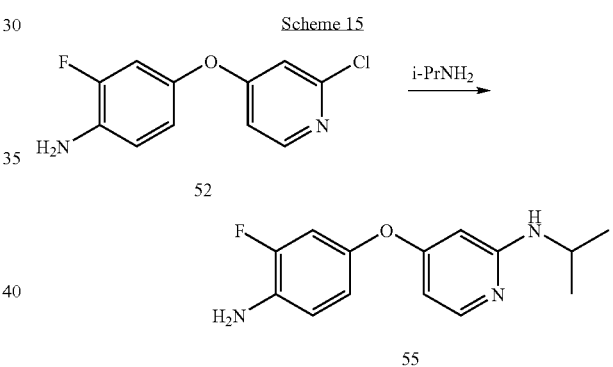

Scheme 16 illustrates an alternative preparation of compounds of general formula 1, represented by the preparation of urea 61. In the instance when general amine 2 is primary (R3=H), amine 2 can be converted to an isopropenyl carbamate 56, trichloroethyl carbamate 57, or 4-nitrophenyl carbamate 58 by reaction with isopropenyl chloroformate, trichloroethyl chloroformate or 4-nitrophenyl chloroformate, respectively. Alternatively, by analogy to Scheme 2, amine 2 (R3=H) can be converted to a discrete isocyanate 59. By analogy to Scheme 1, reaction of carbamates 56-58 or isocyanate 59 with R3-substituted amine 60 provides urea 61, an example of general formula 1.

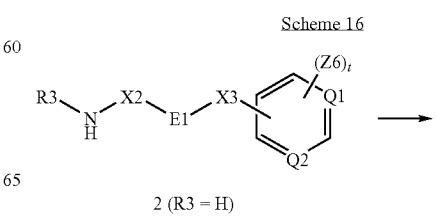

-continued

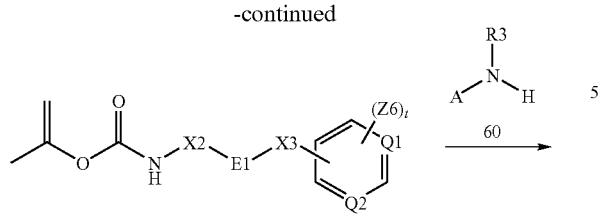

56 (R = NHCO₂C(CH₃)CH₂)
57 (R = NHCO₂CH₂CCl₃)
58 (R = NHCO₂(4-NO₂C₆H₄))
59 (R = NCO)

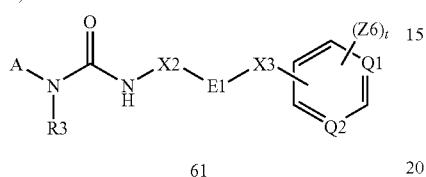

61

An additional subset of ureas of general formula 1 can be prepared as illustrated in Scheme 17. In the instances when R3 is not H, the mono-substituted ureas 1 or 61 can be optionally further transformed into bis-R3-substituted ureas 62 (Formula 1). Thus, in Scheme 17, exposure of 1 or 61 to alkyl halides or cycloalkyl halides in the presence of a base, for example potassium carbonate, sodium hydride or potassium tert-butoxide in a suitable solvent such as DMF provides ureas 62 wherein the newly incorporated R3 group is alkyl or cycloalkyl. Alternatively, exposure of ureas 1 or 61 to copper (II) acetate and Z3-substituted phenylboronic acids [See: Chan et. al, *Tetrahedron Lett.* 2003, 44, 3863-3865; Chan et. al, *Tetrahedron Lett.* 1998, 39, 2933-2936; Chan, D. M. T. *Tetrahedron Lett.* 1996, 37, 9013-9016] provides the analogous bis-R3-substituted ureas wherein the newly incorporated R3 is Z3-substituted phenyl.

Scheme 17

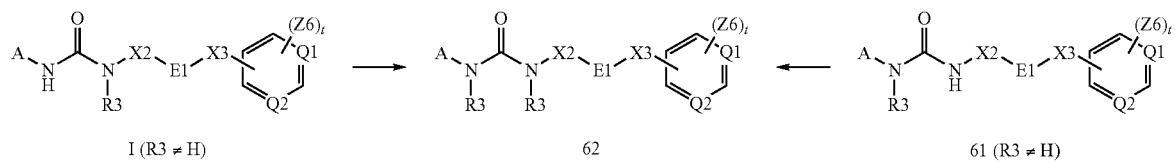

I (R3 ≠ H)    62    61 (R3 ≠ H)

General amines A-NH₂ (6) wherein the A-ring is isoxazole can be prepared by the methods described in Scheme 18. Many examples of R2-substituted aminoisoxazoles 64 and 65 are commercially available. They can also be prepared from common keto nitrile intermediates 63 by condensation with hydroxylamine either under acidic or alkaline conditions as described in the literature (Takase, et al. *Heterocycles*, (1991), 32, pp 1153-1158). Bromination of isoxazoles 64 or 65 using standard conditions (see: Sircar, et. al. *J. Org. Chem.* (1985), 50, pp 5723-7; Carr, et. al. *J. Med. Chem.* (1977), 20, pp 934-9; Chan et al., U.S. Pat. No. 5,514,691) provides bromo isoxazoles 66 and 67 respectively. By analogy to Schemes 7 and 8, 66 and 67 can be converted to A1-containing amino isoxazoles 68 and 69, examples of general amine 6 and 25, through palladium-mediated couplings with reagents of formula A1-M (70), wherein the "M" moiety of A1-M is a moiety that participates in transition metal catalyzed cross coupling reactions, such as a boronic acid or ester, stannane, silane, organozinc or other organometallic moiety known by those skilled in the art to be a suitable substrate for such processes. Using the general methods of Schemes 1 and 2, amines 68 and 69 can be converted to ureas of general formula 1. It will be understood by those skilled in the art that the A1-moiety of 68-70 may contain protecting groups that may be removed prior to or after conversion to ureas of formula 1 by appropriate de-protection conditions. It will be further understood that the amino group of 64-69 may be optionally protected with a suitable protecting group (such as a tert-butylcarbamate) if desired to facilitate the bromination or palladium coupling steps.

Scheme 18

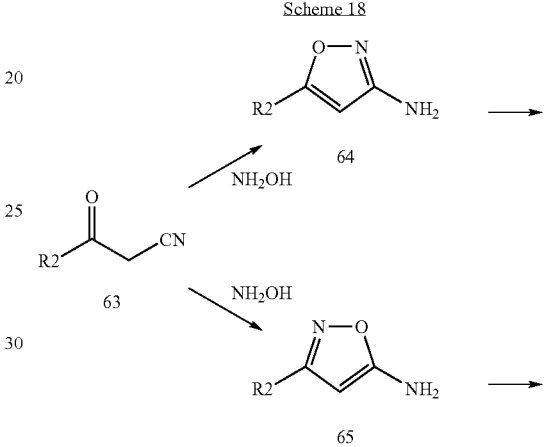

-continued

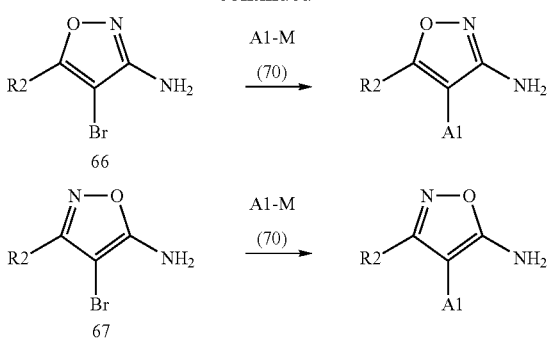

By analogy to Scheme 18, amines 73 and 74, examples of general amines A-NH$_2$ (6) wherein the A-ring is isothiazole, can be prepared as shown in Scheme 19 by the reaction of bromo isothiazoles 71 and 72 and A1-M (70). The requisite isothiazoles 71 and 72 are accessible by methods described in the literature (See; Hegde, V., WO 94/21647 (1994); Hackler, et. al. *J. Heterocyclic Chem.* (1989), 26, pp 1575-8). Using the general methods of Schemes 1 and 2, amines 73 and 74 can be converted to ureas of general formula 1.

Scheme 19

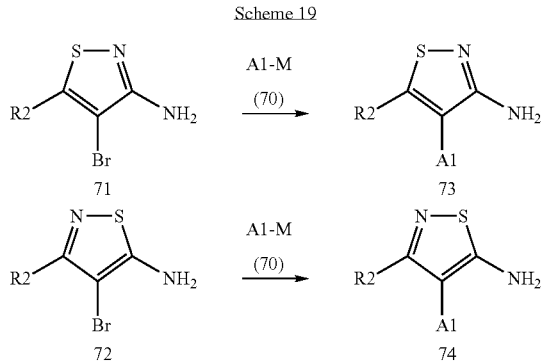

2.1 Examples

General Method A: To a stirring solution of carboxylic acid (0.50 mmol, 1.00 eq) and DPPA (0.75 mmol, 1.50 eq) in 1,4-dioxane (5.0 ml) at RT was added Et$_3$N (1.5 mmol, 3.00 eq). After stirring for 30 min at RT, the appropriate amine (0.76 mmol, 1.50 eq) in dioxane was added and the mixture was heated at 95-100° C. After 2 h, the completed reaction was cooled to RT, diluted with brine and extracted with EtOAc (2×). The combined organics were washed with 3M HCl (1×), satd. NaHCO$_3$ (2×), and brine (1×), dried (MgSO$_4$), filtered and evaporated to give the crude product which was purified by flash column chromatography to afford the target urea.

Example A1

4-Amino-2-fluorophenol (1.13 g, 8.9 mmol) and Example A22 (1.5 g, 8.9 mmol) were combined by the procedure of Example A2 to provide 4-(4-amino-2-fluorophenoxy)-N-methylpicolinamide (300 mg, 13% yield). $^1$H-NMR (DMSO-d$_6$) δ 8.78 (d, J=4.8 Hz, 1H), 8.47 (d, J=5.4 Hz, 1H), 7.32 (d, J=2.4 Hz, 1H), 7.11 (m, 1H), 7.01 (t, J=9.0 Hz, 1H), 6.51 (dd, J=13.2, 2.4 Hz, 1H), 6.42 (dd, J=8.4, 1.6 Hz, 1H), 5.51 (br s, 2H), 2.76 (d, J=4.8 Hz, 3H); MS (ESI) m/z: 262.1 (M+H$^+$).

Example A2

A solution of 4-amino-3-fluorophenol (2.00 g, 15.7 mmol) in anhydrous DMA (32 mL) was degassed by evacuation of the head space and backfilling with argon (repeated 3×). The solution was treated with potassium tert-butoxide (2.12 g, 18.9 mmol) and the resultant mixture was sonicated briefly to bring all solids into the solvent volume and was stirred at RT for 30 min. Example A22 (2.68 g, 15.7 mmol) was added. The reaction mixture was degassed a second time and the reaction mixture was heated to 100° C. overnight under argon. The reaction mixture was poured into ethyl acetate (400 mL) and washed with water (3×100 mL) and saturated brine (2×100 mL). The combined aqueous was extracted with EtOAc (100 mL). The combined organics were dried (MgSO$_4$), concentrated in vacuo to a brown oil and purified by silica gel chromatography to provide 4-(4-amino-3-fluorophenoxy)-N-methylpicolinamide (3.18 g, 77% yield). $^1$H NMR (400 MHz, DMSO-d$_6$) δ 8.76 (m, 1H), 8.48 (d, J=5.7 Hz, 1H), 7.36 (d, J=2.6 Hz, 1H), 7.10 (dd, J=5.7, 2.6 Hz, 1H), 7.02 (dd, J=11.8, 2.6 Hz, 1H), 6.86 (t, J=9.8 Hz, 1H), 6.79 (dd, J=8.9, 2.5 Hz, 1H), 5.23 (s, 2H), 2.79 (d, J=4.9 Hz, 3H); MS (ESI) m/z: 262.0 (M+H$^+$).

Example A3

In NMP (15 mL) was placed 3-amino-4-chlorophenol (1.70 g, 11.8 mmol) and potassium t-butoxide (1.40 g, 12.4 mmol) and the mixture was stirred overnight at RT. The dark solution was treated with the 3,5-difluoropyridine (2.73 g, 23.7 mmol) and powdered potassium carbonate (818 mg, 5.92 mmol) and the mixture was then warmed to 80° C. and stirred for 24 h. The resulting black mixture was cooled to RT, diluted with brine (100 mL) and extracted with ethyl acetate (3×50 mL). The combined ethyl acetate extracts were washed with saturated sodium bicarbonate (50 mL), water (50 mL) and brine (50 mL), dried (Na$_2$SO$_4$), concentrated in vacuo and purified via column chromatography to yield 2-chloro-5-(5-fluoropyridin-3-yloxy)benzenamine as a thick oil which was used without further purification. $^1$H-NMR (DMSO-d$_6$): δ 5.57 (br s, 2H), 6.26-6.30 (dd, 1H), 6.50 (s, 1H), 7.19-7.22 (m, 1H), 7.45-7.50 (m, 1H), 8.26 (s, 1H), 8.39 (s, 1H). MS (ESI) m/z: 239.0 (M+H$^+$).

Example A4

A mixture of Example A10 (4.6 g, 19.3 mmol) and 10% Pd(OH)$_2$/C (0.5 g, 0.35 mmol) in EtOH (50 mL) was stirred under a H$_2$ atmosphere at RT for 3 h. The mixture was filtered through Celite® and washed with EtOH. The filtrate was concentrated to give 2-fluoro-5-(pyridine-3-yloxy)aniline (3.5 g, 88% yield). $^1$H NMR (300 MHz, DMSO-d$_6$) δ 8.53 (d, J=2.4 Hz, 1H), 8.48 (d, J=3.9 Hz, 1H), 7.80-7.69 (m, 2H), 7.05 (dd, J=11.1, 8.7 Hz, 1H), 6.53 (dd, J=7.5, 3.0 Hz, 1H), 6.28 (dt, J=8.7, 3.3 Hz, 1H); MS (ESI) m/z: 205.3 (M+H$^+$).

Example A5

To a solution of 2,4-difluorophenol (2 g, 15.4 mmol) in CH$_2$Cl$_2$ (20 mL) was added triethyl amine (3.21 ml, 23 mmol) and ethyl chloroformate (1.77 ml, 18.4 mmol) at 0° C. After stirring the mixture for 1 h at RT, sat. NaHCO$_3$ solution (30 mL) was added, the organic layer was separated and the aqueous layer was extracted with CH$_2$Cl$_2$ (1×25 ml). The combined organic layers were washed with brine, dried (Na$_2$SO$_4$) and concentrated to afford 2,4-difluorophenyl ethyl carbonate (3.11 g, 100% yield) as a liquid.

To a solution of 2,4-difluorophenyl ethyl carbonate (3.1 g, 16 mmol) in sulphuric acid (10 mL) was added fuming HNO$_3$ (0.78 ml, 19 mmol) slowly, keeping the internal temperature around 0° C. After 15 min ice cold water (70 mL) was added, the product was extracted with ethyl acetate (2×50 mL), the combined organic layers were washed with brine, dried (Na$_2$SO$_4$) and concentrated to afford the nitro product as a thick syrup. This nitro product was dissolved in methanol (20 mL) and to this solution was added solid NaHCO$_3$ (4.0 g, 47 mmol) and the resultant mixture was stirred for 16 h at RT. The mixture was filtered and the filtrate was concentrated. The resulting solid was dissolved in water (20 ml) and acidified with 3M HCl solution to pH~5. The product was extracted with CH₂Cl₂ (3×25 mL), the combined organic layers were washed with brine, dried (Na₂SO₄) and concentrated to afford 2,4-difluoro-5-nitrophenol (2.34 g, 84% yield). ¹H NMR (400 MHz, Acetone-d₆) δ 9.59 (s, 1H), 7.78 (t, J=7.2 Hz, 1H), 7.45 (t, J=10.4 Hz, 1H); MS (ESI) m/z: 176.0 (M+H⁺).

To a suspension of 2,4-difluoro-5-nitrophenol (1.01 g, 5.77 mmol) in EtOAc was added palladium hydroxide (0.08 g, 0.57 mmol) and the resulting slurry was stirred under a hydrogen atmosphere for 6 h. The mixture was filtered through a Celite® pad, washing with EtOAc (2×10 mL) and the filtrate was concentrated to afford 5-amino-2,4-difluorophenol (0.8 g, 96% yield) as a solid. ¹H NMR (400 MHz, DMSO-d₆) δ 9.28 (s, 1H), 6.91 (t, J=7.2 Hz, 1H), 6.35 (t, J=8.8 Hz, 1H), 4.84 (brs, 2H); MS (ESI) m/z: 146.0 (M+H⁺).

To a solution of 5-amino-2,4-difluorophenol (0.3 g, 2.07 mmol) in DMSO (2 mL) was added potassium t-butoxide (0.23 g, 2.07 mmol) at RT. After stirring for 1 h, 3,5-dichloropyridine (0.37 g, 2.5 mmol) and potassium carbonate (0.14 g, 1 mmol) were added and the mixture was heated to 190° C. for 1 h in microwave reactor. Water (30 mL) was added, and the product was extracted with EtOAc (2×35 mL) and the combined organic layers were washed with brine solution, dried (Na₂SO₄), concentrated in vacuo and purified by chromatography (EtOAc/hexane) to afford 5-(5-chloropyridin-3-yloxy)-2,4-difluorobenzenamine (0.35 g, 66% yield) as a solid. ¹H NMR (400 MHz, Acetone-d₆) δ 8.33-8.30 (m, 2H), 7.44 (t, J=2.4 Hz, 1H), 7.13 (t, J=10.8 Hz, 1H), 6.78 (t, J=8.4 Hz, 1H), 4.85 (brs, 2H); MS (ESI) m/z: 257.0 (M+H⁺).

To a solution of 5-(5-chloropyridin-3-yloxy)-2,4-difluorobenzenamine (0.35 g, 1.4 mmol) in 1M HCl solution (10 mL) was added Pd/C (0.015 g) and mixture was shaken on a Parr apparatus under a hydrogen atmosphere (40 psi) for 24 h. The mixture was filtered through Celite® and the filter pad was washed with water (2×5 mL) and the filtrate was concentrated on the lyophilizer to afford the hydrochloride salt. This compound was neutralized with sat aq NaHCO₃ solution, the free amine extracted into EtOAc (2×35 mL) and the combined organic layers were washed with brine, dried (Na₂SO₄) and concentrated to yield 2,4-difluoro-5-(pyridin-3-yloxy) benzenamine (0.19 g, 63% yield) as a solid. ¹H NMR (400 MHz, Acetone-d₆) δ 8.33-8.30 (m, 2H), 7.37-7.29 (m, 2H), 7.09 (t, J=10.4 Hz, 1H), 6.70 (t, J=8.4 Hz, 1H), 4.78 (brs, 2H); MS (ESI) m/z: 223.0 (M+H⁺).

Example A6

A solution of 4-amino-o-cresol (0.301 g, 2.44 mmol) in anhydrous dimethylacetamide (6 mL) was de-gassed in vacuo and treated with potassium tert-butoxide (0.33 g, 2.93 mmol) under argon. The reaction mixture was sonicated briefly to suspend all solid matter in the liquid volume. The reaction was further stirred at RT for 30 min. Example A22 (0.417 g, 2.44 mmol) was added and the resultant mixture was heated to 100° C. overnight. The cooled reaction mixture was partitioned between ethyl acetate (50 mL) and water (20 mL). The organic layer was further washed with water (3×20 mL) and saturated brine (2×20 mL). The combined aqueous phases were extracted with ethyl acetate (2×20 mL). The combined organic phases were dried (MgSO₄), concentrated in vacuo, and purified by silica gel chromatography (EtOAc/hexanes) to provide 4-(4-amino-2-methylphenoxy)-N-methylpicolinamide (530 mg, 84% yield) as a yellow foam. ¹H NMR (400 MHz, DMSO-d₆) δ 8.75 (m, 1H), 8.45 (dd, J=4.6, 0.5 Hz, 1H), 7.27 (dd, J=2.6, 0.4 Hz, 1H), 7.04 (dd, J=5.5, 2.6 Hz, 1H), 6.78 (d, J=8.5 Hz, 1H), 6.53 (d, J=2.3 Hz, 1H), 6.48 (dd, J=8.6, 2.5 Hz, 1H), 5.10 (s, 2H), 2.78 (d, J=5.0 Hz, 3H), 1.93 (s, 3H); MS (ESI) m/z: 258.0 (M+H⁺).

Example A7

Using a procedure analogous to Example A2,4-amino-3-fluorophenol (14 g, 0.11 mmol) and Example A25 (16g, 0.10 mmol) were combined to provide 4-(4-amino-3-fluorophenoxy)picolinamide (8.8 g, 36% yield). ¹H NMR (300 MHz, DMSO-d₆) δ 8.46 (d, J=5.7 Hz, 1H), 8.09 (br s, 1H), 7.68 (br s, 1H), 7.34 (d, J=2.4 Hz, 1H), 7.10 (dd, J=5.6, 2.6 Hz, 1H), 7.01 (dd, J=5.7, 2.4 Hz, 1H), 6.84 (t, J=9.0 Hz, 1H), 6.77 (dd, J=5.7, 2.4 Hz, 1H), 5.22 (s, 2H); MS (ESI) m/z: 248.1 (M+H⁺).

Example A8

A solution of Example A23 (2.0 g, 8.4 mmol) in 2-aminoethanol (6.0 mL) was heated to 150° C. for 3 h. The solvent was removed under reduced pressure and the residue was purified by silica gel column chromatography to provide 2-(4-(4-amino-3-fluorophenoxy)-pyridin-2-ylamino)-ethanol (1.2 g, 54% yield). ¹H NMR (400 MHz, DMSO-d₆) δ 7.78 (d, J=5.6 Hz, 1H), 6.85 (dd, J=12.0, 2.4 Hz, 1H), 6.78 (t, J=8.8 Hz, 1H), 6.67 (dd, J=8.8, 2.0 Hz, 1H), 6.44 (t, J=5.2 Hz, 1H), 6.06 (dd, J=6.0, 2.4 Hz, 1H), 5.80 (d, J=2.0 Hz, 1H), 5.08 (s, 2H), 4.68 (br s, 1H), 3.43 (m, 2H), 3.25-3.20 (m, 2H); MS (ESI) m/z: (M+H⁺) 264.1

Example A9

A solution of Example A23 (4.0 g, 16.8 mmol) and N,O-dimethylhydroxylamine HCl (3.3 g, 34 mmol) were combined in 1,4-dioxane (50 mL) and the reaction mixture was heated overnight at 110° C. The reaction mixture was concentrated in vacuo, neutralized with 3M NaOH and extracted with EtOAc (3×). The combined organic phases were washed with brine, dried (MgSO₄) and concentrated in vacuo to obtain 4-(4-amino-3-fluorophenoxy)-N-methoxy-N-methylpyridin-2-amine (4.4 g, 99% yield). ¹H NMR (DMSO-d₆) δ 8.06 (d, J=5.2 Hz, 1H), 6.95 (dd, J=12.4, 2.8 Hz, 1H), 6.83 (dd, J=8.8, 8.4 Hz, 1H), 6.75 (dd, J=8.4, 2.4 Hz, 1H), 6.43 (d, J=2.4 Hz, 1H), 6.37 (dd, J=5.6, 2.4 Hz, 1H), 5.16 (s, 2H), 3.61 (s, 3H), 3.14 (s, 3H); MS (ESI) m/z: 264.2 (M+H⁺).

A mixture of 2-fluoro-4-(2-(methoxy(methyl)amino)pyridine-4-yloxy)aniline (2.0 g, 7.6 mmol) and 10% Pd/C (200 mg, 0.18 mmol) in MeOH (15 mL) was stirred under a H₂ atmosphere (50 psi) at RT for 48 h. The mixture was filtered through Celite® and the cake was washed with MeOH. The filtrate was concentrated to afford 4-(4-amino-3-fluorophenoxy)-N-methylpyridin-2-amine (1.2 g, 68% yield). ¹H NMR (DMSO-d₆) δ 7.86 (d, J=6.3 Hz, 1H), 6.82-6.69 (m, 3H), 6.18 (dd, J=6.0, 2.1 Hz, 1H), 5.84 (d, J=2.1 Hz, 1H), 5.41 (br s, 1H), 3.62 (s, 2H), 2.84 (d, J=3.0 Hz, 3H); MS (ESI) m/z: 234.2 (M+H⁺).

Example A10

A solution of Example A24 (0.95 g, 7.47 mmol) and potassium tert-butoxide (0.92 g, 8.2 mmol) in dimethylacetamide (2.0 mL) was degassed under vacuum and backfilled with N₂ (4×) and then stirred for 30 min. 3,5-Dichloropyridine was added and the resulting solution was heated to 80° C. overnight. The mixture was filtered and the filtrate was concentrated in vacuo and purified by silica gel chromatography to provide 5-(5-chloropyridin-3-yloxy)-2-fluoroaniline (0.5 g, 28% yield). ¹H NMR (400 MHz, DMSO-d₆) δ 8.37 (s, 1H), 8.29 (s, 1H), 7.51 (s, 1H), 7.00 (dd, J=10.8, 8.8 Hz, 1H), 6.46 (dd, J=7.6, 2.8 Hz, 1H), 6.22 (m, 1H), 5.38 (s, 2H); MS (ESI) m/z: 239.2 (M+H$^+$).

Example A11

A mixture of Example A8 (0.263 g, 1.0 mmol), imidazole (0.0749 g, 1.1 mmol) and TBSCl (0.181 g, 1.2 mmol) in DMF (10 mL) was stirred at RT overnight. Solvent was removed under reduced pressure. The residue was quenched with H$_2$O (10 mL) and the pH was adjusted to ~8 by using NaHCO$_3$. The aqueous solution was extracted with EtOAc (3×20 mL) and the combined organic layers were dried (MgSO$_4$), concentrated in vacuo and purified by chromatography to afford 4-(4-amino-3-fluorophenoxy)-N-(2-(tert-butyldimethylsilyloxy)ethyl)pyridin-2-amine (0.252 g, 67% yield) as a light yellow oil. MS (ESI) m/z: 378.3 (M+H$^+$).

Example A12

To a solution of Example A17 (7.5 g, 32.5 mmol) in EtOH (60 mL) was added 1.0 M aqueous NaOH (10 mL, 100 mmol). The resultant mixture was heated at 85° C. overnight. The majority of ethanol was removed in vacuo and the concentrate was diluted with water (50 mL) and washed with ethyl acetate. The aqueous layer was acidified to pH 1-2 by the addition of 3 M HCl. The acidic solution was extracted with EtOAc (3×200 mL) and the extracts were washed with brine, dried (MgSO$_4$) and concentrated in vacuo to give 5-(3-amino-4-fluorophenoxy)picolinic acid (6.2 g, 77%, yield). $^1$H-NMR (300 MHz, DMSO-d$_6$) δ 8.40 (d, J=2.7 Hz, 1H), 8.01 (d, J=8.4 Hz, 1H), 7.38 (dd, J=8.7, 2.7 Hz, 1H), 7.03 (dd, J=11.4, 8.7 Hz, 1H), 6.50 (dd, J=7.5, 3.0 Hz, 1H), 6.26 (m, 1H), 5.39 (br, s, 2H); MS (ESI) m/z: 249.1 (M+H$^+$).

5-(3-amino-4-fluorophenoxy)picolinic acid (0.14 g, 0.56 mmol) was dissolved in THF (3 mL) and stirred at 0° C. for 5 min. 1M Borane (3.4 mL) solution was added dropwise to the reaction mixture at 0° C. over a period of 30 min. The ice bath was removed and stirring continued at RT for 7 hours. The reaction mixture was cooled in an ice bath and treated with 3M HCl (5 mL). The solution was heated for 1 h at 50° C. The solution was washed with EtOAc (2×) and the aqueous layer was cooled in an ice bath and neutralized with 3M NaOH. The solution was extracted with EtOAc (3×), the combined organic layers were washed with brine, dried (Na$_2$SO$_4$) and concentrated in vacuo to obtain (5-(3-amino-4-fluorophenoxy)pyridin-2-yl)methanol (0.13 g, 98% yield). $^1$H NMR (400 MHz, DMSO-d$_6$) δ 8.24 (d, J=2.8 Hz, 1H), 7.46 (d, J=8.8 Hz, 1H), 7.40 (dd, J=2.8, 8.4 Hz, 1H), 6.99 (dd, J=8.8, 11.2 Hz, 1H), 6.40 (dd, J=2.8, 7.6 Hz, 1H), 6.15 (dt, J=3.2, 8.8 Hz, 1H), 5.40 (t, J=5.6 Hz, 1H), 5.33 (s, 2H), 4.54 (d, J=6.0 Hz, 2H); MS (ESI) m/z: 235.0 (M+H$^+$).

Example A13

NaH (100 mg, 3.3 mmol) was slowly added to a solution of Example A12 (0.50 g, 2.1 mmol) in dry THF (50 mL) at 0° C. After 30 min, CS$_2$ (0.49 g, 6.4 mmol) was added and the reaction mixture was stirred at 0° C. for 1 hour. Methyl iodide (2.4 g, 17 mmol) was added at 0° C. and the reaction mixture was allowed to warm to RT overnight. The solvent was removed under reduced pressure to obtain the crude product. The crude, O-(5-(3-amino-4-fluorophenoxy)pyridin-2-yl) methyl S-methyl carbonodithioate (0.69 g, 2.1 mmol) was dissolved in toluene (5 mL) and tributyltin hydride (1 mL) and AIBN (50 mg) were added. The reaction mixture was heated under reflux for 3 hours. The solvent was removed under reduced pressure and the residue was filtered and washed with CH$_2$Cl$_2$. The filtrate was evaporated and the residue was purified by silica gel column chromatography to obtain 2-fluoro-5-(6-methylpyridin-3-yloxy)benzenamine (0.26 g, 56% yield). $^1$H NMR (400 MHz, DMSO-d$_6$) δ 8.20 (d, J=2.8 Hz, 1H), 7.30 (dd, J=2.8, and 8.4 Hz, 1H), 7.25 (d, J=8.4 Hz, 1H), 6.97 (dd, J=8.8, 11.6 Hz, 1H), 6.38 (dd, J=3.2, 7.6 Hz, 1H), 6.13 (dt, J=3.2, 8.8 Hz, 1H), 5.31 (s, 1H), 2.44 (s, 3H); MS (ESI) m/z: 219.0 (M+H$^+$).

Example A14

A solution of 4-amino-3-fluorophenol (0.20 g, 1.6 mmol) in 4 mL of anhydrous DMA was treated with potassium tert-butoxide (0.24 g, 1.9 mmol). The resultant dark-red solution was stirred at RT for 1 hour in a capped vial. 4-Chloro-2-methoxypyridine (0.26 g, 1.6 mmol) was added and the reaction mixture was heated overnight at 100° C. Water (50 mL) was added and the solution was extracted with ethyl acetate (3×50 mL). The combined organic layers were washed with brine, dried (Na$_2$SO$_4$), concentrated in vacuo and purified by silica gel column chromatography to obtain 2-fluoro-4-(2-methoxypyridin-4-yloxy)benzenamine (0.20 g, 58% yield). $^1$H NMR (400 MHz, DMSO-d$_6$) δ 8.02 (d, J=6.0 Hz, 1H), 6.95 (dd, J=2.8, 12.0 Hz, 1H), 6.82 (dd, J=8.4, 8.8 Hz, 1H), 6.73 (dd, J=2.0, 8.4 Hz, 1H), 6.54 (dd, J=2.4, 6.0 Hz, 1H), 6.10 (d, J=2.4 Hz, 1H), 5.17 (s, 1H), 3.81 (s, 3H); MS (ESI) m/z: 235.0 (M+H$^+$).

Example A15

A teflon capped vial was charged with 4-amino-3-fluorophenol (0.291 g, 2.29 mmol) and anhydrous DMF (2.3 mL). The resultant solution was de-gassed in vacuo and backfilled with argon (3×). The vial was treated with sodium tert-butoxide (0.27 g, 2.41 mmol) under argon and quickly capped. The reaction mixture was stirred at RT for 1 h. After addition of 4-chloropicolinonitrile (0.317 g, 2.29 mmol) and K$_2$CO$_3$ (0.174 g, 1.26 mmol), the vial was de-gassed again and heated in a 90° C. oil bath overnight. The reaction mixture was diluted with EtOAc (60 mL) and washed with brine (25 mL). The aqueous phase was back-extracted with EtOAc (50 mL). The combined organic layers were washed with brine (25 mL), dried (MgSO$_4$), concentrated in vacuo and purified by chromatography to afford 4-(4-amino-3-fluorophenoxy)picolinonitrile (0.162 g, 31% yield) as a colorless oil. $^1$H NMR (DMSO-d$_6$) δ 8.56 (d, J=5.6 Hz, 1H), 7.62 (d, J=2.0 Hz, 1H), 7.14 (dd, J=6.0, 2.8 Hz, 1H), 7.03 (dd, J=11.6, 2.4 Hz, 1H), 6.88-6.77 (m, 2H), 5.25 (s, 2H); MS (ESI) m/z: 230.0 (M+H$^+$).

Example A16

A solution of 5-amino-2-chloro-4-fluorophenol (100 mg, 0.619 mmol) in degassed dimethylacetamide (2 mL) was treated with potassium t-butoxide (83 mg, 0.743 mmol) and 5-chloro-2-cyanopyridine (86 mg, 0.619 mmol). The resultant mixture was heated to 80° C. overnight, then cooled to RT and diluted with water (10 mL). The mixture was extracted with EtOAc (30 mL). The organic phase was washed with water (3×30 mL) and brine (30 mL) dried (Na$_2$SO$_4$) and concentrated in vacuo to provide 5-(5-amino-2-chloro-4-fluorophenoxy)picolinonitrile as a dark oil which was used without further purification. MS (ESI) m/z: 264.0 (M+H$^+$).

Example A17

A solution of 3-amino-4-fluoro-phenol (5.6 g, 44 mmol) in dimethylacetamide (60 mL) was degassed in vacuo and was treated with potassium tert-butoxide (5.3 g, 47 mmol). The resulting solution was stirred for 30 min. 5-Bromo-pyridine-2-carbonitrile (6.6 g, 36 mmol) was added in one-portion and the mixture was heated at 80° C. overnight. The solvent was removed in vacuo and the residue was purified by silica gel chromatography to provide 5-(3-amino-4-fluorophenoxy)picolinonitrile (3.5 g, 44% yield). $^1$H-NMR (300 MHz, DMSO-$d_6$) δ 8.47 (d, J=3.0 Hz, 1H), 7.98 (d, J=8.4 Hz, 1H), 7.44 (dd, J=8.8, 2.7 Hz, 1H), 7.06 (t, J=9.2 Hz, 1H), 6.52 (d, J=7.6 Hz, 1H), 6.28 (m, 1H), 5.44 (br s, 2H); MS (ESI) m/z: 230.0 (M+H$^+$).

Example A18

In DMA (10 mL) was placed 3-amino-4-fluorophenol (500 mg, 3.93 mmol), potassium t-butoxide (441 mg, 3.93 mmol) and 4-chloro-2-(methylthio)pyrimidine (632 mg, 3.93 mmol). The mixture was warmed to 50° C. and stirred overnight. The mixture was cooled to RT and diluted with water (30 mL), extracted with ethyl acetate (2×25 mL) and the combined organic phases washed with brine, dried (Na$_2$SO$_4$) and concentrated to yield a dark oil. The oil was purified by column chromatography to yield 2-fluoro-5-(2-(methylthio)pyrimidin-4-yloxy)benzenamine (841 mg, 85% yield) as an oil which was used without further purification. MS (ESI) m/z: 252.0 (M+H$^+$).

Example A19

A solution of pyridine-3-boronic acid (0.68 g, 5.5 mmol) and 2-methyl-5-nitro phenol (0.85 g, 5.5 mmol) in DCM (10 mL) was treated with pyridine (1.00 mL, 12.4 mmol), copper acetate (1.5 g, 8.3 mmol) and powdered 4A molecular sieves (330 mg). The reaction mixture was stirred for 7 days at RT open to air. The mixture was poured into water (50 mL) and extracted with DCM (2×50 mL). The combined organic phases were washed with saturated aq NaHCO$_3$ (25 mL), water (25 mL), satd NH$_4$Cl (2×25 mL) and brine (25 mL), dried (Na$_2$SO$_4$), concentrated in vacuo and purified via chromatography on silica gel to provide 3-(2-methyl-5-nitrophenoxy)pyridine (81 mg, 6% yield). $^1$H NMR (400 MHz, CDCl$_3$) δ 8.48 (dd, J=4.6, 1.0 Hz, 1H), 8.43 (d, J=2.4 Hz, 1H), 7.99 (dd, J=8.0, 2.0 Hz, 1H), 7.70 (d, J=2.4 Hz, 1H), 7.46 (d, J=8.4 Hz, 1H), 7.39-7.30 (m, 2H), 2.42 (s, 3H); MS (ESI) m/z: 231.0 (M+H$^+$).

A solution of 3-(2-methyl-5-nitrophenoxy)pyridine (80 mg, 0.35 mmol) and 10% Pd/C (50% wet, 165 mg, 0.08 mmol) in methanol (4 mL) was treated with formic acid (89%, 1 mL, 35 mmol) and the resultant solution was stirred at RT. After 1 h, the reaction mixture was filtered through Celite®, and the filter cake was washed with methanol. The filtrates were concentrated in vacuo, diluted with 40 mL of a pH 12 aqueous solution and extracted with ethyl acetate (3×25 mL). The extracts were dried (Na$_2$SO$_4$) and concentrated in vacuo to provide 4-methyl-3-(pyridin-3-yloxy)benzenamine (58 mg, 83% yield). $^1$H NMR (400 MHz, CDCl$_3$) δ 8.36 (m, 2H), 8.32 (dd, J=4.6, 1.4 Hz, 1H), 7.26-7.18 (m, 3H), 7.05 (d, J=8.0 Hz, 1H), 6.49 (dd, J=8.8, 2.4 Hz, 1H), 6.29 (d, J=2.4 Hz, 1H), 2.11 (s, 3H); MS (ESI) m/z: 201.0 (M+H$^+$).

Example A20

In DMA (8 mL) was placed 3-amino-4-fluorophenol (281 mg, 2.21 mmol), potassium t-butoxide (248 mg, 2.21 mmol) and 5-bromo-2-(trifluoromethyl)pyridine (500 mg, 2.21 mmol). The mixture was warmed to 75° C. overnight, then cooled to RT and diluted with water (75 mL). The mixture was extracted with ethyl acetate (2×40 mL) and the combined organic phases washed with brine (40 mL), dried (Na$_2$SO$_4$), concentrated in vacuo and purified by column chromatography to yield 2-fluoro-5-(6-(trifluoromethyl)pyridin-3-yloxy)benzenamine (161 mg, 26% yield) as an oil which was used without further purification. MS (ESI) m/z: 273.0 (M+H$^+$).

Example A21

In DMF (5 mL) was placed 5-(3-amino-4-fluorophenoxy)picolinic acid from Example A12 (500 mg, 2.01 mmol), 2.0 M methylamine solution/THF (10 mL, 20.1 mmol) and HOBt (324 mg, 2.12 mmol). To this was added N1-((ethylimino)methylene)-N3,N3-dimethylpropane-1,3-diamine hydrochloride (772 mg, 4.03 mmol) and the solution stirred overnight at RT. The solution was treated with an additional equiv of N1-((ethylimino)methylene)-N3,N3-dimethylpropane-1,3-diamine hydrochloride (775 mg) and warmed to 40° C., then cooled to RT and stirred overnight. The solution was diluted with ethyl acetate (30 mL) and washed with water (30 mL), brine (30 mL), dried (Na$_2$SO$_4$) and concentrated in vacuo to yield 5-(3-amino-4-fluorophenoxy)-N-methylpicolinamide (530 mg, 101% yield) as a thick oil, which was used without further purification. MS (ESI) m/z: 262.0 (M+H$^+$).

Example A22

To stirring anhydrous DMF (25 mL) was slowly added SOCl$_2$ (125 mL) at such a rate that the reaction temperature was maintained at 40-50° C. Pyridine-2-carboxylic acid (25 g, 0.2 mol) was added in portions over 30 min and the resulting mixture was heated at reflux for 16 h during which time a yellow solid precipitated. After cooling to RT, the mixture was diluted with toluene (80 mL) and concentrated. This process was repeated three times. The resulting dry residue was washed with toluene and dried under reduced pressure to yield 4-chloro-pyridine-2-carbonyl chloride (27.6 g, 79% yield), which was used in the next step without purification.

To a solution of 4-chloro-pyridine-2-carbonyl chloride (27.6 g, 0.16 mol) in anhydrous THF (100 mL) at 0° C. was added dropwise a solution of MeNH$_2$ in EtOH. The resulting mixture was stirred at 3° C. for 4 h. The reaction mixture was concentrated under reduced pressure to yield a solid, which was suspended in EtOAc and filtered. The filtrate was washed with brine (2×100 mL), dried and concentrated to yield 4-chloro-N-methylpicolinamide (16.4 g, 60% yield) as a yellow solid. $^1$H NMR (400 MHz, DMSO-$d_6$) δ 8.78 (br s, 1H), 8.55 (d, J=5.2 Hz, 1H), 7.97 (d, J=2.0 Hz, 1H), 7.66 (m, 1H), 2.82 (d, J=4.8 Hz, 3H); MS (ESI) m/z: 171.0 (M+H$^+$).

Example A23

Using a procedure analogous to Example A2, 2,4-dichloropyridine (8.0 g, 54 mmol) and 3-fluoro-4-aminophenol (8.0 g, 62.9 mmol) were combined to provide 4-(2-chloro-pyridin-4-yloxy)-2-fluorophenylamine (11g, 86% yield). $^1$H NMR (300 MHz, DMSO-$d_6$) δ 8.24 (d, J=5.7 Hz, 1H), 7.00 (dd, J=9.0, 2.7 Hz, 1H), 6.89-6.73 (m, 4H), 5.21 (br s, 2H); MS (ESI) m/z: 239.2 (M+H$^+$).

Example A24

Methyl chloroformate (77.3 g, 0.82 mol) was added dropwise to a −10° C. solution of 2-chloro-4-fluorophenol (100 g, 0.68 mol) and sodium hydroxide (32.8 g, 0.82 mol) in water (550 mL). After complete addition, the precipitated solid was collected by filtration and washed with water to give 2-chloro-4-fluorophenyl methyl carbonate (110 g, 79% yield). $^1$H NMR (300 MHz, DMSO-d$_6$) δ 7.62 (dd, J=8.1, 2.7 Hz, 1H), 7.50 (dd, J=9.0, 5.4 Hz, 1H), 7.30 (td, J=8.1, 3.0 Hz, 1H), 3.86 (s, 3H); MS (ESI) m/z: 205.2 (M+H$^+$).

To a suspension of 2-chloro-4-fluorophenyl methyl carbonate (110 g, 0.54 mol) in conc. H$_2$SO$_4$ (50 mL) was slowly added a mixture comprised of conc. H$_2$SO$_4$ (40 mL) and fuming HNO$_3$ (40.8 mL, 0.89 mol). The resultant mixture was stirred for 30 min at 0° C. The reaction mixture was poured into ice water and the precipitated solid was collected by filtration and washed with water to give 2-chloro-4-fluoro-5-nitrophenyl methyl carbonate (120g, 90% yield). $^1$H NMR (400 MHz, DMSO-d$_6$): δ 8.45 (d, J=7.2 Hz, 1H), 8.12 (d, J=10.8 Hz, 1H), 3.89 (s, 3H); MS (ESI) m/z: 250.1 (M+H$^+$).

A mixture of 2-chloro-4-fluoro-5-nitrophenyl methyl carbonate (120g 0.48 mol) and sodium hydroxide (22.7 g, 0.57 mol) in water (300 mL) was refluxed for 4 h. The insoluble solids were removed by filtration and the filtrate was acidified with dilute HCl. The precipitated solid was collected by filtration and washed with water to give 2-chloro-4-fluoro-5-nitrophenol (90g, 98% yield). $^1$H NMR (400 MHz, DMSO-d$_6$) δ 11.18 (s, 1H), 8.10 (d, J=10.4 Hz, 1H), 7.62 (d, J=7.2 Hz, 1H); MS (ESI) m/z: 192.1 (M+H$^+$)

2-Chloro-4-fluoro-5-nitrophenol (85 g, 0.45 mol) and 10% Pd/C (25 g, 0.023 mol) were combined in EtOH and hydrogenated (50 psi) for 12 h. The reaction mixture was filtered, concentrated in vacuo and purified by silica gel chromatography to provide 3-amino-4-fluorophenol (40 g 70% yield). $^1$H NMR (400 MHz, DMSO-d$_6$) δ 8.87 (s, 1H), 6.70 (dd, J=11.2, 8.8 Hz, 1H), 6.14 (dd, J=7.8, 2.4 Hz, 1H), 5.84 (m, 1H), 4.92 (s, 2H); MS (ESI) m/z: 128.2 (M+H$^+$).

Example A25

4-Chloropicolinamide was prepared using a procedure analogous to Example A22 by substituting NH$_3$ for MeNH$_2$. $^1$H NMR (300 MHz, DMSO-d$_6$) δ 8.59 (d, J=5.2 Hz, 1H), 8.18 (br s, 1H), 8.00 (d, J=2.0 Hz, 1H), 7.79 (br s, 1H), 7.72 (dd, J=5.2, 2.0 Hz, 1H); MS (ESI) m/z: 157.0 (M+H$^+$).

Example A26

Using a procedure analogous to Example A2, 2-fluoro-4-aminophenol (2.6 g, 24 mmol) and 2,4-dichloropyridine (2.88 g, 20 mol) were combined to provide 4-(2-chloropyridin-4-yloxy)-3-fluoro-phenylamine (3.2 g, 67% yield). $^1$H NMR (400 MHz, DMSO-d$_6$) δ 8.25 (d, J=5.6 Hz, 1H), 6.99 (m, 1H), 6.90 (m, 2H), 6.50 (d, J=1.6 Hz, 1H), 6.41 (d, J=10.4 Hz, 1H), 5.51 (s, 2H); MS (ESI) m/z: 239.1 (M+H$^+$).

A mixture of 4-(2-chloro-pyridin-4-yloxy)-3-fluoro-phenylamine (2.0 g, 8.4 mmol) and benzylmethylamine (20 mL) was heated to 200° C. overnight in a steel bomb. The reaction mixture was concentrated in vacuo and purified by silica gel chromatography to give 4-(4-amino-2-fluorophenoxy)-N-benzyl-N-methylpyridin-2-amine (1.0 g, 37% yield). MS (ESI) m/z: 324.2 (M+H$^+$).

To a solution of 4-(4-amino-2-fluorophenoxy)-N-benzyl-N-methylpyridin-2-amine (1.0 g, 3.1 mmol) in MeOH (10 mL) was added 10% Pd/C (0.25 g, 0.23 mmol). The reaction was stirred under a H$_2$ atmosphere (50 psi) at 75° C. for 12 h. The reaction mixture was filtered, concentrated under reduced pressure and purified by reverse phase prep-HPLC to provide 4-(4-amino-2-fluorophenoxy)-N-methylpyridin-2-amine (560 mg, 78% yield). $^1$H NMR (400 MHz, DMSO-d$_6$) δ 7.80 (d, J=5.6 Hz, 1H), 6.90 (t, J=9.0 Hz, 1H), 6.40-6.45 (m, 3H), 6.06 (dd, J=8.0, 2.8 Hz, 1H), 5.73 (d, J=2.8 Hz, 1H), 5.37 (s, 2H), 2.68 (d, J=4.8 Hz, 3H); MS (ESI) m/z: (M+H$^+$): 234.2.

Example A27

Example A23 (0.597 g, 2.5 mmol), 4-(4,4,5,5-tetramethyl-1,3,2-dioxaborolan-2-yl)-1H-pyrazole (0.728 g, 3.75 mmol), Cs$_2$CO$_3$ (3.10 g, 9.5 mmol) and Pd(PPh$_3$)$_4$ (0.289 g, 0.25 mmol) were combined in DMF/H$_2$O (20 mL). The reaction mixture was degassed, blanketed with N$_2$ and heated at 90° C. overnight. The completed reaction was diluted with H$_2$O (5 mL) and extracted with EtOAc (3×50 mL). The combined organics were washed with brine (20 mL), dried (MgSO$_4$), concentrated in vacuo and purified by chromatography to afford 4-(2-(1H-pyrazol-4-yl)pyridin-4-yloxy)-2-fluorobenzenamine (0.56 g, 83%) as a light yellow solid. $^1$H NMR (400 Hz, DMSO-d$_6$) δ 13.01 (s, 1H), 8.38 (d, J=5.6 Hz, 1H), 8.35 (s, 1H), 8.06 (s, 1H), 7.29 (d, J=2.4 Hz, 1H), 7.03 (dd, J=11.6, 2.4 Hz, 1H), 6.89 (t, J=8.8 Hz, 1H), 6.84 (m, J=8.4 Hz, 1H), 6.60 (m, 1H), 5.20 (s, 2H); MS (ESI) m/z: 271.0 (M+H$^+$).

Example A28

A solution of Example A23 (3 g, 12.6 mmol), 1-methyl-3-(4,4,5,5-tetramethyl-[1,3,2]dioxaborolan-2-yl)-1H-pyrazole (5.2 g, 25.2 mmol), and Na$_2$CO$_3$ (2.7 g, 25.2 mmol) in DME (18 mL) and water (6 mL) was sparged with nitrogen for 20 min. Pd(PPh$_3$)$_4$ (729 mg, 0.63 mmol) was added and the resulting mixture was heated to 100° C. for 16 h. The solvent was removed under reduced pressure and the crude product was suspended in water and extracted with EtOAc. The organic layer was washed with brine, dried (Na$_2$SO$_4$), concentrated in vacuo and purified by silica gel chromatography to give 2-fluoro-4-(2-(1-methyl-1H-pyrazol-4-yl)pyridin-4-yloxy)aniline (2 g, 56% yield). $^1$H NMR (300 MHz, DMSO-d$_6$) δ 8.31 (d, J=5.7 Hz, 1H), 8.21 (s, 1H), 7.92 (s, 1H), 7.12 (s, J=2.4 Hz, 1H), 6.96 (m, 1H), 6.85-6.72 (m, 2H), 6.56 (m, 1H), 5.15 (s, 2H), 3.84 (s, 3H); MS (ESI) m/z: 285.0 (M+H$^+$)

Example A29

By analogy to Example A2, 4-amino-3-fluorophenol (0.12 g, 0.53 mmol), potassium tert-butoxide (0.080 g, 0.71 mmol) and tert-butyl 4-chloropicolinate (159 mg, 0.53 mmol) were combined to provide tert-butyl 4-(4-amino-3-fluorophenoxy) picolinate (151 mg, 67% yield). MS (ESI) m/z: 305.0 (M+H$^+$).

To a solution of LiAlH$_4$ (699 mg, 18.4 mmol) in THF (15 mL) was added tert-butyl 4-(4-amino-3-fluorophenoxy)picolinate (1.4 g, 4.6 mmol) at 0° C. under N$_2$. The mixture was stirred at 0° C. for 2 h. The reaction mixture was quenched with 10% aq NaOH solution (4 mL), the resultant suspension was filtered and the filtrate was extracted with EtOAc (3×30 mL) to give (4-(4-amino-3-fluorophenoxy)pyridin-2-yl) methanol (700 mg, 70% yield). MS (ESI) m/z: 235.1 (M+H$^+$).

A solution of (4-(4-amino-3-fluorophenoxy)pyridin-2-yl) methanol (750 mg, 3.2 mmol) and Et$_3$N (821 mg, 8 mmol) in DMF (10 ml) at 0° C. was treated with tert-butyldimethylsilyl chloride (624 mg, 4.16 mmol). The resulting solution was stirred at RT for 4 hours. The solvent was removed in vacuo and the residue was purified by silica gel column chromatography to provide 4-(2-((tert-butyldimethylsilyloxy)methyl) pyridin-4-yloxy)-2-fluorobenzenamine (370 mg, 33% yield). $^1$H NMR (400 MHz, DMSO-d$_6$) δ 8.32 (d, J=5.6 Hz, 1H), 7.02 (s, 1H), 6.67-6.82 (m, 4H), 4.76 (s, 2H), 3.71 (s, 2H), 0.89 (s, 9H), 0.07 (s, 6H); MS (ESI) m/z: 349.2 (M+H$^+$).

Example A30

Example A23 (1 g, 4.2 mmol) and ethyl(4-methoxy-benzyl)amine (10 mL) were combined and heated to 200° C. for 30 hours. The reaction solution was poured into HOAc/water (20%, V/V) and extracted with EtOAc (3×100 mL). The combined organics were washed with brine (3×50 mL) and saturated NaHCO$_3$ solution (2×100 mL), dried (NaSO$_4$), concentrated in vacuo and purified by silica gel chromatography to give [4-(4-amino-3-fluoro-phenoxy)-pyridin-2-yl]-ethyl-(4-methoxybenzyl)amine (1.2 g, 78% yield). $^1$H NMR (400 MHz, DMSO-d$_6$) δ7.90 (d, J=5.6 Hz, 1H), 7.07 (d, J=8.4 Hz, 2H), 6.82 (d, J=8.0 Hz, 2H), 6.74 (m, 2H), 6.63 (d, J=7.2 Hz, 1H), 6.02 (d, J=4.0 Hz, 1H), 5.90 (s, 1H), 5.09 (s, 2H), 4.53 (s, 2H), 3.67 (s, 3H), 3.44 (m, 2H), 1.00 (t, J=6.8, 3H); MS (ESI) m/z: 368.2 (M+H$^+$).

Trifluoroacetic acid (10 mL) was added to a solution of [4-(4-amino-3-fluoro-phenoxy)-pyridin-2-yl]-ethyl-(4-methoxybenzyl)amine (1.2 g, 3.27 mmol) in CH$_2$Cl$_2$ (50 mL) and the resulting solution was heated to 40° C. overnight. The reaction mixture was concentrated under reduced pressure and the residue was treated with HCl (5 mL, 12M, 60 mmol) and water (50 mL). The solution was washed with EtOAc (4×50 mL). The aqueous layer was treated with NaHCO$_3$ until pH=8 and then extracted with EtOAc (3×50 mL). The combined extracts were washed with brine (3×50 mL), dried (NaSO$_4$) and concentrated in vacuo to give 4-(4-amino-3-fluorophenoxy)-N-ethylpyridin-2-amine (0.45 g, 67% yield). $^1$H NMR (300 MHz, DMSO-d$_6$) δ7.79 (d, J=5.7, 1H), 6.85 (dd, J=11.7, 2.4 Hz, 1H), 6.78 (t, J=8.7 Hz, 1H), 6.67 (dd, J=8.7, 2.4 Hz, 1H), 6.39 (m, 1H), 6.05 (dd, J=5.7, 2.1 Hz, 1H), 5.72 (d, J=2.1 Hz, 1H), 5.09 (s, 2H), 3.15 (m, 2H), 1.03 (t, J=7.2, 3H); MS (ESI) m/z: 248.2 (M+H$^+$).

Example A31

To a solution of Example A23 (0.30 g, 1.3 mmol) in NMP (5 mL) was added isopropylamine (0.54 mL, 6.3 mmol) and it was heated under microwave at 200° C. for 6 hours. Water was added and the solution was extracted with ethyl acetate. The organic layer was washed with brine, dried (MgSO$_4$), concentrated in vacuo and purified by silica gel column chromatography (EtOAc/hexane: EtOAc: MeOH/CH$_2$Cl$_2$) to obtain 4-(4-amino-3-fluorophenoxy)-N-isopropylpyridin-2-amine (0.16 g, 49% yield). MS (ESI) m/z: 262.2 (M+H$^+$).

Example A32

A solution of 3,5-dinitro-benzonitrile (5 g, 25.9 mol), 5-chloro-pyridin-3-ol (3.35 g, 25.9 mol) and K$_2$CO$_3$ (7.2 g, 52 mol) in DMF (150 mL) was heated at 100° C. overnight. The mixture was concentrated in vacuo and the residue was poured into water. The aqueous layer was extracted with ethyl acetate (3×150 mL) and the combined organics were washed with brine, dried (Na$_2$SO$_4$), concentrated in vacuo and purified by silica gel chromatography to afford 3-(5-chloro-pyridin-3-yloxy)-5-nitro-benzonitrile (3.1 g, 44% yield). $^1$H NMR (400 MHz, DMSO-d$_6$) δ 8.56 (s, 1H), 8.51 (s, 1H), 8.47 (s, 1H), 8.22 (s, 1H), 8.19 (s, 1H), 7.87 (s, 1H).

Iron powder (6.3 g, 112 mmol) was added to a mixture of 3-(5-chloro-pyridin-3-yloxy)-5-nitro-benzonitrile (3.1 g, 11.2 mol) in acetic acid (100 mL) and the reaction was stirred at RT for 6 h. Water (200 mL) was added and the mixture was neutralized to pH 7 with saturated Na$_2$CO$_3$ solution and extracted with EtOAc (3×150 mL). The combined organics were washed with brine, dried (Na$_2$SO$_4$), concentrated in vacuo and purified on silica gel to give 3-amino-5-(5-chloro-pyridin-3-yloxy)benzonitrile (1.92 g, 71% yield). $^1$H NMR (400 MHz, DMSO-d$_6$) δ 8.53 (d, J=1.6 Hz, 1H), 8.44 (d, J=2.4 Hz, 1H), 7.80 (t, J=2.4 Hz, 1H), 6.77 (s, 1H), 6.72 (d, J=1.6 Hz, 1H), 6.56 (d, J=2.0 Hz, 1H), 5.92 (s, 2H); MS (ESI) m/z: 246.2 [M+H]$^+$.

Example A33

3,5-dinitro-benzonitrile (3 g, 16 mmol), 6-methylpyridin-3-ol (1.7 g, 16 mmol), and K$_2$CO$_3$ (4.3 g, 31 mmol) were dissolved in DMF and heated to 110° C. overnight. The reaction mixture was poured into water and the mixture was extracted with EtOAc. The combined organics were washed with brine, dried (Na$_2$SO$_4$), concentrated in vacuo and purified by silica gel chromatography to provide 3-(6-methylpyridin-3-yloxy)-5-nitrobenzonitrile (3 g, 76% yield). $^1$H NMR (400 MHz, DMSO) δ 8.50 (s, 1H), 8.38 (s, 1H), 8.08 (s, 1H), 8.01 (s, 1H), 7.59-7.56 (d, J=10 Hz, 1H), 7.38-7.36 (d, J=8.4 Hz, 1H), 1.98 (s, 3H); MS (ESI) m/z: 256.3 [M+H]$^+$.

A mixture of 3-(6-methylpyridin-3-yloxy)-5-nitrobenzonitrile (3 g, 0.012 mol) and iron powder in acetic acid (200 mL) was stirred at RT for 6 h. H$_2$O was added and the mixture was adjusted to pH 7 with saturated Na$_2$CO$_3$ solution. The aqueous layer was extracted with EtOAc, and the combined organics were washed with brine, dried (MgSO$_4$), concentrated in vacuo and purified by silica gel chromatography to afford 3-amino-5-(6-methylpyridin-3-yloxy)benzonitrile (2 g, 76% yield). $^1$H NMR (400 MHz, DMSO) δ 8.25 (s, 1H), 7.42 (d, J=10 Hz, 1H), 7.30 (d, J=8.4 Hz, 1H), 6.62 (s, 1H), 6.51 (s, 1H), 6.38 (s, 1H), 5.78 (s, 2H), 2.49 (s, 3H); MS (ESI) m/z: 226.2 [M+H]$^+$.

Example A34

3,5-Dinitrobenzonitrile (1.50 g, 7.77 mmol) was added to a slurry of pyridin-3-ol (739 mg, 7.77 mmol) and potassium carbonate (10.7 g, 77.7 mmol) in DMF (15 mL), the mixture was warmed to 60° C. and stirred overnight. After cooling to RT the reaction was diluted with ethyl acetate (50 mL) and water (100 mL). The organic phase was separated, washed with saturated sodium bicarbonate (50 mL) and brine (50 mL), dried (Na$_2$SO$_4$), concentrated in vacuo and purified by chromatography (Si-40 column, ethyl acetate/hexanes) to give a light yellow solid identified as 3-nitro-5-(pyridin-3-yloxy)benzonitrile (1.31 g, 69% yield). MS (ESI) m/z: 242.0 (M+H$^+$).

A solution of 3-nitro-5-(pyridin-3-yloxy)benzonitrile (1.31 g, 9.42 mmol) and tin(II) chloride dehydrate (6.13 g, 27.2 mmol) in ethanol (20 mL) was warmed to 70° C. for 2 hrs. After cooling to RT, the reaction was poured onto ice/water (100 mL). The aqueous mixture was made basic (pH~=8) with sodium hydroxide, diluted with ethyl acetate (50 mL) and filtered through paper to remove most salts. This solution was extracted with ethyl acetate (2×75 mL) and the combined organics washed with brine, dried (Na2SO4) and concentrated in vacuo to give a light yellow solid identified as 3-amino-5-(pyridin-3-yloxy)benzonitrile (660 mg, 57% yield). MS (ESI) m/z: 212.0 (M+H$^+$).

Example A35

Using a procedure analogous to Example A3, 3-amino-4-fluorophenol (491 mg, 3.86 mmol) and 4-chloropyrimidin-2-amine (500 mg, 3.86 mmol) were combined to give 4-(3-amino-4-fluorophenoxy)pyrimidin-2-amine (509 mg, 59% yield). MS (ESI) m/z: 221.0 (M+H$^+$).

Example A36

A solution of 1,3-difluoro-2-methylbenzene (15 g, 0.12 mol) in H₂SO₄ (100 mL) was treated dropwise with HNO₃ (65%, 11.4 g, 0.12 mol) at −10° C. The resultant mixture was stirred for about 30 min. The mixture was poured into ice-water and extracted with EtOAc (3×200 mL). The combined organics were washed with brine, dried (NaSO₄) and concentrated in vacuo to give 1,3-difluoro-2-methyl-4-nitrobenzene (16 g, 78% yield). $^1$H NMR (400 MHz, CDCl₃) δ 7.80 (m, 1H), 6.8-7.1 (m, 1H), 2.30 (s, 3H).

1,3-difluoro-2-methyl-4-nitrobenzene (16 g, 0.092 mol), benzyl alcohol (10 g, 0.092 mol) and K₂CO₃ (25.3 g, 0.18 mol) were combined in DMF (250 mL) and heated to 100° C. overnight. The mixture was poured into water and extracted with EtOAc (3×200 mL). The combined organics were washed with brine, dried (Na₂SO₄), concentrated in vacuo and purified by column chromatography on silica gel to give 1-benzyloxy-3-fluoro-2-methyl-4-nitrobenzene (8 g, 33% yield). $^1$H NMR (400 MHz, DMSO-d₆) δ 8.04 (t, J=8.8 Hz, 1H), 7.30-7.46 (m, 5H), 7.08 (d, J=9.2 Hz, 1H), 5.28 (s, 2H), 2.13 (s, 3H).

1-Benzyloxy-3-fluoro-2-methyl-4-nitrobenzene (8 g, 0.031 mol) and 10% Pd—C (1 g) were combined in methanol (100 mL) and the mixture was stirred under an H₂ atmosphere (1 atm) overnight. The reaction mixture was filtered and the filtrate was concentrated in vacuo to give 4-amino-3-fluoro-2-methylphenol (4.2 g, 96% yield). $^1$H NMR (300 MHz, DMSO-d₆) δ 8.61 (s, 1H), 6.42 (t, J=8.4 Hz, 1H), 7.11 (d, J=8.4 Hz, 1H), 4.28 (s, 2H), 1.96 (s, 3H); MS (ESI) m/z: 142.1 [M+H]⁺.

Potassium tert-butoxide (3.5 g, 0.031 mol) was added to a solution of 4-amino-3-fluoro-2-methylphenol (4.2 g, 0.03 mol) in DMAc and the resultant mixture was stirred for 30 min at RT. To this mixture was added a solution of 2,4-dichloropyridine (4.38 g, 0.03 mol) in DMAc and the mixture was heated at 100° C. overnight. The reaction mixture was concentrated in vacuo and the residue was dissolved in ethyl acetate (200 mL) and filtered through silica gel, washing forward with EtOAc. The filtrate was concentrated and purified by silica gel chromatography to give 4-(2-chloropyridin-4-yloxy)-2-fluoro-3-methylbenzenamine (3.2 g, 42% yield). $^1$H NMR (300 MHz, DMSO-d₆) δ 8.21 (d, J=6.0 Hz, 1H), 6.84 (s, 1H), 6.81 (dd, J=5.6, 2.4 Hz, 1H), 6.67 (m, 2H), 5.12 (s, 2H), 1.91 (s, 3H); MS (ESI) m/z 253.1 [M+H]⁺.

4-(2-Chloropyridin-4-yloxy)-2-fluoro-3-methylbenzenamine (1.0 g, 3.3 mmol), 1-methyl-4-(4,4,5,5-tetramethyl-[1,3,2]dioxaborolan-2-yl)-1H-pyrazole (1 g, 4.8 mmol), Na₂CO₃ (0.84 g, 6.6 mmol) and Pd(PPh₃)₄ (0.25 g, 0.2 mmol) were combined in DME (75 mL) and water (25 mL). The mixture was sparged with nitrogen for 15 min and was heated to reflux overnight. The reaction mixture was extracted with EtOAc (3×100 mL) and the combined organics were washed with brine, concentrated in vacuo and purified by silica gel chromatography to give 2-fluoro-3-methyl-4-(2-(1-methyl-1H-pyrazol-4-yl)pyridin-4-yloxy)aniline (0.74 g, 75% yield). $^1$H NMR (300 MHz, DMSO-d₆) δ 8.27 (d, J=6.0 Hz, 1H), 8.18 (s, 1H), 7.90 (s, 1H), 7.07 (s, 1H), 6.63 (m, 2H), 6.45 (dd, J=5.6, 2.4 Hz, 1H), 5.06 (s, 2H), 3.82 (s, 3H), 1.95 (s, 3H); MS (ESI) m/z: 299.2 [M+H]⁺.

Example A37

A solution of 1,2,3-trifluoro-4-nitro-benzene (30 g, 0.17 mol) and benzyl alcohol (18.4 g, 0.17 mol) in DMF (300 mL) was treated with K₂CO₃ (35 g, 0.25 mol) and the resulting mixture was stirred at RT for 8 h. Water (300 mL) was added, and the mixture was extracted with EtOAc (3×500 mL). The combined organics were washed with brine, dried (MgSO₄), concentrated in vacuo and chromatographed on silica gel to give 1-benzyloxy-2,3-difluoro-4-nitrobenzene (16 g, 36% yield). $^1$H NMR (400 MHz, DMSO-d₆): δ 8.06 (m, 1H), 7.49-7.30 (m, 6H), 5.37 (s, 2H).

A mixture of 1-benzyloxy-2,3-difluoro-4-nitrobenzene (14 g, 52.8 mmol) and Pd/C (10%, 1.4 g) in MeOH (200 mL) was stirred under a hydrogen atmosphere (30 psi) for 2 h. The catalyst was removed by filtration and the filtrate was concentrated in vacuo to afford 4-amino-2,3-difluoro-phenol (7 g, 92% yield). $^1$H NMR (400 MHz, DMSO-d₆) δ 9.05 (s, 1H), 6.45 (t, J=8.8 Hz, 1H), 6.34 (t, J=9.2 Hz, 1H), 4.67 (s, 2H).

Using a procedure analogous to Example A2, 4-amino-2,3-difluorophenol (6 g, 41.4 mmol), potassium tert-butoxide (4.9 g, 43.5 mmol) and 2,4-dichloropyridine (6.1 g, 41.4 mmol) were combined to afford 4-(2-chloro-pyridin-4-yloxy)-2,3-difluorophenylamine (7 g, 66% yield). $^1$H NMR (400 MHz, DMSO-d₆) δ 8.27 (d, J=6.0 Hz, 1H), 7.05 (s, 1H), 6.95 (m, 1H), 6.92 (d, J=8.8 Hz, 1H), 6.62 (d, J=8.8 Hz, 1H), 5.60 (s, 2H).

Example A38

A solution of Example A37 (2 g, 7.8 mmol), 1-methyl-4-(4,4,5,5-tetramethyl-[1,3,2]dioxaborolan-2-yl)-1H-pyrazole (1.6 g, 7.8 mmol) and Na₂CO₃ (1.65 mg, 15.6 mmol) in DME (12 mL) and H₂O (4 mL) was sparged with nitrogen for 20 min. Pd(PPh₃)₄ (450 mg, 0.4 mmol) was added and the resulting mixture was heated to 70° C. under nitrogen for 16 h. The solvent was removed under reduced pressure and the crude product was suspended in water and extracted with EtOAc (3×10 mL). The organic layer was washed with brine, dried (MgSO₄), concentrated in vacuo and purified by column chromatography on silica gel to give 2,3-difluoro-4-[2-(1-methyl-1H-pyrazol-4-yl)-pyridin-4-yloxy]phenylamine (1.3 g, 55% yield). $^1$H NMR (400 MHz, DMSO-d₆) δ 8.40 (d, J=6.0 Hz, 1H), 8.32 (s, 1H), 8.02 (s, 1H), 7.26 (s, 1H), 6.96 (t, J=8.8 Hz, 1H), 6.70-6.67 (m, 2H), 5.62 (s, 2H), 3.92 (s, 3H); MS (ESI) m/z: 303.2[M+H]⁺.

Example A39

Example A23 (2.0 g, 8.4 mmol) and 4-methoxybenzylamine (50 mL) were combined in a steel bomb and heated to 160° C. for 3 h. The reaction mixture was concentrated under reduced pressure and purified by reverse prep-HPLC to give N-(4-methoxybenzyl)-4-(4-amino-3-fluorophenoxy)pyridin-2-amine (1.0 g, 35% yield).

A solution of N-(4-methoxybenzyl)-4-(4-amino-3-fluorophenoxy)pyridin-2-amine (500 mg, 1.47 mmol) in CH₂Cl₂ (10 mL) was treated with ammonium cerium(IV) nitrate (1.64 g, 2.99 mmol) and the resultant mixture was stirred at RT overnight. The reaction mixture was washed with water, concentrated in vacuo and purified by silica gel chromatography to yield 4-(4-amino-3-fluorophenoxy)pyridin-2-amine (250 mg, 77% yield). $^1$H NMR (300 MHz, DMSO-d₆) δ 7.73 (d, J=6.0 Hz, 1H), 6.88 (dd, J=9.0, 2.0 Hz, 1H), 6.80 (t, J=8.7 Hz, 1H), 6.68 (m, 1H), 6.06 (dd, J=4.5, 1.8 Hz, 1H), 5.84 (s, 2H), 5.75 (d, J=1.5 Hz, 1H), 5.08 (s, 2H); MS (ESI) m/z: 220.3 (M+H⁺).

Example A40

A solution of 4-amino-2-methyl-phenol (4.25 g, 34.5 mmol) in dimethylacetamide (50 mL) was degassed in vacuo and blanketed with argon. Potassium tert-butoxide (5.0 g, 44.6 mmol) was added and the reaction mixture was degassed a second time and stirred at RT under argon for 30 min. 2,4-Dichloro-pyridine (4.6 g, 31.3 mmol) was added and the mixture was heated to 100° C. overnight. The solvent was removed under reduced pressure and the residue was purified by silica gel chromatography to give 4-(2-chloropyridin-4-yloxy)-3-methylbenzenamine (4.5 g, 56% yield). $^1$H NMR (400 MHz, DMSO-$d_6$) δ 8.21 (d, J=5.2 Hz, 1H), 6.75-6.80 (m, 3H), 6.45-6.50 (m, 2H), 5.15 (s, 2H), 1.92 (s, 3H); MS (ESI) m/z: 235.1 (M+H$^+$).

A solution of 4-(2-chloropyridin-4-yloxy)-3-methylbenzenamine (595 mg, 2.54 mmol), 1-methyl-4-(4,4,5,5-tetramethyl)-[1,3,2]dioxaborolan-2-yl)-4H-pyrazole (790 mg, 3.80 mmol) and $Cs_2CO_3$ (2.53 g, 7.77 mmol) in 10 mL of DMF (10 mL) and water (3 mL) was de-gassed under vacuum and blanketed with nitrogen. Pd(PPh$_3$)$_4$ (295 mg, 0.26 mmol) was added and the reaction mixture was heated to 90° C. overnight. The reaction mixture was diluted with EtOAc (30 mL) and washed with water (2×10 mL) and brine (2×10 mL). The aqueous portion was extracted with EtOAc (2×15 mL) and the combined organics were washed with brine (10 mL), concentrated in vacuo and purified on silica gel to provide 3-methyl-4-(2-(1-methyl-1H-pyrazol-4-yl)pyridin-4-yloxy)benzenamine as a pale yellow colored foam (627 mg, 88% yield). $^1$H NMR (400 MHz, DMSO-$d_6$): δ 8.27 (d, J=6.0 Hz, 1H), 8.18 (s, 1H), 7.90 (d, J=0.7 Hz, 1H), 7.07 (d, J=2.2 Hz, 1H), 6.74 (d, J=8.6 Hz, 1H), 6.49 (d, J=2.5 Hz, 1H), 6.46-6.40 (m, 2H), 5.02 (s, 2H), 3.84 (s, 3H), 1.94 (s, 3H); MS (ESI) m/z: 281.2 (M+H$^+$).

Example A41

4-Chloro-2-methylsulfanyl-pyrimidine (1.4 g, 8.8 mmol), 4-(4,4,5,5-tetramethyl-[1,3,2]dioxaborolan-2-yl)-1H-pyrazole (2.0 g, 10.3 mmol), $Na_2CO_3$ (2.8 g, 26.4) and Pd(PPh$_3$)$_4$ (500 mg, 0.43 mmol) were combined in a solvent comprised of toluene/EtOH/H$_2$O (4/4/1, 20 mL). The mixture was degassed by applying a vacuum and backfilling the headspace with argon. The reaction mixture was heated overnight at 100° C. The insoluble portion was filtered and the filtrate was concentrated and purified by silica gel chromatography to provide 2-(methylthio)-4-(1H-pyrazol-4-yl)pyrimidine (1.2 g, 71% yield). $^1$H NMR (400 MHz, CDCl$_3$) δ 8.45 (d, J=6.4 Hz, 1H), 8.24 (s, 1H), 7.23 (s, 1H), 7.05 (d, J=6.4 Hz, 1H), 2.51 (s, 3H).

To a solution of 2-(methylthio)-4-(1H-pyrazol-4-yl)pyrimidine (200 mg, 1 mmol) in dichloromethane (3 mL) and H$_2$O (1 mL) was added 4-methoxybenzylchloride (200 mg, 1.28 mmol) at 0° C. The mixture was stirred at RT overnight. The organic layer was separated, washed with brine and concentrated in vacuo to give crude 4-(1-(4-methoxybenzyl)-1H-pyrazol-4-yl)-2-(methylthio)pyrimidine. $^1$H NMR (300 MHz, DMSO-$d_6$) δ 8.58 (s, 1H), 8.50, (d, J=5.4 Hz, 1H), 8.16 (s, 1H), 7.40 (d, J=5.4 Hz, 1H), 7.27 (d, J=8.4 Hz, 2H), 7.22 (d, J=8.4 Hz, 2H), 5.30 (s, 2H), 3.72 (s, 3H), 2.51 (s, 3H); MS (ESI) m/z: 313 (M+H$^+$).

To a solution of 4-(1-(4-methoxybenzyl)-1H-pyrazol-4-yl)-2-(methylthio)pyrimidine (200 mg, 0.64 mmol) in dichloromethane was added m-CPBA (220 mg, 1.28 mmol). The reaction was stirred for 2 hour at RT. Water was added, the organic layer was separated and the aqueous layer was extracted with dichloromethane. The combined organics were washed with brine and concentrated in vacuo. The residue was combined with 3-amino-4-fluorophenol (165 mg, 1.28 mmol) and $K_2CO_3$ (176 mg, 1.28 mmol) in DMF (5 mL) and the resultant mixture was heated at 90° C. overnight. After filtration and concentration, the residue was purified by silica gel column chromatography to give 5-(4-(1-(4-methoxybenzyl)-1H-pyrazol-4-yl)pyrimidin-2-yloxy)-2-fluorobenzenamine (210 mg, 84% yield). $^1$H NMR (300 MHz, DMSO-$d_6$) δ 8.50 (s, 1H), 8.44, (d, J=5.4 Hz, 1H), 8.10 (s, 1H), 7.42 (d, J=5.4 Hz, 1H), 7.25 (d, J=8.4 Hz, 2H), 6.98 (t, J=9.6 Hz, 1H), 6.91 (d, J=8.4 Hz, 2H), 6.52 (dd, J=2.7, 8.7 Hz, 1H), 6.28 (m, 1H), 5.30 (br s, 2H), 5.26 (s, 2H), 3.72 (s, 3H); MS (ESI) m/z: 392.2 (M+H$^+$).

To a solution of 5-(4-(1-(4-methoxybenzyl)-1H-pyrazol-4-yl)pyrimidin-2-yloxy)-2-fluorobenzenamine (50 mg, 0.13 mmol) in dichloromethane (3 mL) was added TFA (0.3 mL) at 0° C. and the reaction stirred at RT for 12 h. The solvent was removed in vacuo, the residue was washed with ether and treated with saturated ammonia solution. The solid was collected via filtration and dried under vacuum to give 5-(4-(1H-pyrazol-4-yl)pyrimidin-2-yloxy)-2-fluorobenzenamine (15 mg, 43% yield). $^1$H NMR (300 MHz, MeOD) δ 8.44 (d, J=5.1 Hz, 1H), 8.23 (br s, 2H), 7.40 (d, J=5.4, 1H), 7.02 (dd, J=10.8, 8.7 Hz, 1H), 6.73 (dd, J=2.7, 7.2 Hz, 1H), 6.50 (m, 1H); MS (ESI) m/z: 272.2 (M+H$^+$).

Example A42

Using a procedure analogous to Example A3, 3-amino-4-fluorophenol (0.127 g, 1.0 mmol) and 5-bromo-2-nitropyridine (0.203 g, 1.0 mmol) were combined to afford 2-fluoro-5-(6-nitropyridin-3-yloxy)benzenamine (0.098 g, 39% yield) as a yellow solid. $^1$H NMR (400 MHz, DMSO-d6) δ 8.36 (d, J=2.8 Hz, 1H), 8.30 (d, J=8.8 Hz, 1H), 7.56 (dd, J=8.8, 2.8 Hz, 1H), 7.07 (m, 1H), 6.53 (dd, J=7.6, 3.2 Hz, 1H), 6.31 (s, 1H), 5.48 (s, 2H); MS (ESI) m/z: 250.0 (M+H$^+$).

Example B1

To a stirring solution of benzyl 6-(4,4,5,5-tetramethyl-1,3,2-dioxaborolan-2-yl)-3,4-dihydroisoquinoline-2(1H)-carboxylate (0.991 g, 2.52 mmol, 1.00 eq) in THF (10 ml) and H$_2$O (2.5 ml) was added NaIO$_4$ (1.62 g, 7.56 mmol, 3.00 eq). The resulting suspension was stirred at 25° C. for 30 min and then treated with 3M HCl (1.68 ml, 5.04 mmol, 2.0 eq). The mixture was stirred for 2.5 h. The supernatant was decanted away from the solids, rinsing forward with THF. The combined organic phases were washed with brine (2×), dried (MgSO$_4$) and concentrated in vacuo to give crude 2-(benzyloxycarbonyl)-1,2,3,4-tetrahydroisoquinolin-6-ylboronic acid (0.640 g, 82% yield) as a foam which was used as is in the next reaction. $^1$H NMR (400 MHz, DMSO-$d_6$) δ 7.68-7.58 (m, 2H), 7.45-7.29 (m, 6H), 7.17 (m, 1H), 5.13 (s, 2H), 4.62-4.56 (brm, 2H), 3.65 (brs, 2H), 2.86 (t, 2H, J=5.60 Hz); MS (ESI) m/z: 312.0 (M+H$^+$).

To a stirring suspension of 2-(benzyloxycarbonyl)-1,2,3,4-tetrahydroisoquinolin-6-ylboronic acid (0.640 g, 2.06 mmol, 1.00 eq) and 4 ÅMS (0.64 g) in CH$_2$Cl$_2$ (20 ml) was added pyridine (0.168 ml, 2.06 mmol, 1.00 eq) followed by ethyl 3-t-butyl-1H-pyrazole-5-carboxylate (0.404 g, 2.06 mmol, 1.00 eq) and Cu(OAc)$_2$ (0.374 g, 2.06 mmol, 1.00 eq). The resulting blue-green mixture was stirred at 25° C. After 40 h, the mixture was diluted with H$_2$O and decanted away from the molecular sieves. The layers were separated and the organic phase was washed with H$_2$O (2×). The combined aqueous phases were extracted with CH$_2$Cl$_2$ (1×). The combined organic phases were dried (MgSO$_4$), concentrated in vacuo and purified by flash chromatography (EtOAc/hexanes) to afford benzyl 6-(3-t-butyl-5-(ethoxycarbonyl)-1H-pyrazol-1-yl)-3,4-dihydroisoquinoline-2(1H)-carboxylate (0.46 g, 48% yield). $^1$H NMR (400 MHz, DMSO-$d_6$) δ 7.41-7.28 (m, 5H), 7.24-7.20 (m, 3H), 6.96 (s, 1H), 5.15 (s, 2H), 4.67 (brm, 2H), 4.17 (q, 2H, J=7.2 Hz), 3.66 (brs, 2H), 2.86 (t, 2H, J=6.0 Hz), 1.29 (s, 9H), 1.18 (t, 3H, J=7.2 Hz); MS (ESI) m/z: 462.3 (M+H$^+$).

To a stirring solution of benzyl 6-(3-t-butyl-5-(ethoxycarbonyl)-1H-pyrazol-1-yl)-3,4-dihydroisoquinoline-2(1H)-carboxylate (0.160 g, 0.347 mmol) in 1:1:1 THF/EtOH/H$_2$O (3 ml) at 22° C. was added LiOH.H$_2$O (0.0727 g, 1.73 mmol). After 3 h, the completed reaction was acidified (pH 2-3) with 1M HCl and extracted with EtOAc (3×). The combined organic phases were washed with brine (2×), dried (MgSO$_4$), filtered and evaporated to afford 1-(2-(benzyloxycarbonyl)-1,2,3,4-tetrahydroisoquinolin-6-yl)-3-t-butyl-1H-pyrazole-5-carboxylic acid (0.16 g, 106% yield) as an oil which was used without further purification. $^1$H NMR (400 MHz, DMSO-d$_6$) δ 7.41-7.31 (m, 5H), 7.328-7.20 (m, 3H), 6.91 (s, 1H), 5.15 (s, 2H), 4.65 (brm, 2H), 3.66 (brs, 2H), 2.86 (t, 2H, J=6.0 Hz), 1.29 (s, 9H); MS (ESI) m/z: 434.2 (M+H$^+$).

Example B2

Ethyl 3-t-butyl-1-(2-(trifluoromethylsulfonyloxy)quinolin-6-yl)-1H-pyrazole-5-carboxylate (see WO 2006/071940A2, 0.380 g, 0.806 mmol), MeNH$_2$.HCl (0.109 g, 1.61 mmol) and Et$_3$N (0.449 ml, 3.22 mmol) were combined DMF (8 mL) and stirred at RT overnight. Additional portions of MeNH$_2$.HCl (0.109 g, 1.61 mmol) and Et$_3$N (0.449 ml, 3.22 mmol) were added and the reaction was stirred an additional 4 h at RT and 3 h at 60° C. The completed reaction was diluted with brine and extracted with EtOAc. The extracts were washed with brine, dried (Na$_2$SO$_4$), concentrated in vacuo and purified by silica gel chromatography to provide ethyl 3-tert-butyl-1-(2-(methylamino)quinolin-6-yl)-1H-pyrazole-5-carboxylate (240 mg, 85% yield). $^1$H NMR (400 MHz, DMSO-d$_6$) δ 7.90 (d, J=9.2 Hz, 1H), 7.68 (d, J=2.8 Hz, 1H), 7.53 (d, J=9.2 Hz, 1H), 7.46 (dd, J=8.8, 2.0 Hz, 1H), 7.17 (q, J=4.8 Hz, 1H), 6.98 (s, 1H), 6.80 (d, J=8.8 Hz, 1H), 4.16 (q, J=7.2 Hz, 2H), 2.92 (d, J=4.8 Hz, 3H), 1.32 (s, 9H), 1.13 (t, J=7.2 Hz, 3H); MS (ESI) m/z: 353.2 (M+H$^+$).

LiOH.H$_2$O (0.143 g, 3.40 mmol) was added to a solution of ethyl 3-tert-butyl-1-(2-(methylamino)quinolin-6-yl)-1H-pyrazole-5-carboxylate (0.240 g, 0.68 mmol) in a mixture of water/THF/EtOH (1:1:1, 9 mL). The reaction mixture was stirred overnight at RT, diluted with 3 M HCl and extracted with EtOAc and THF. The combined organics were washed with brine, dried (MgSO$_4$) and concentrated under vacuum to obtain 3-tert-butyl-1-(2-(methylamino)quinolin-6-yl)-1H-pyrazole-5-carboxylic acid (0.22 g, 100% yield). $^1$H-NMR (DMSO-d$_6$) δ 7.90 (d, J=9.2 Hz, 1H), 7.66 (d, J=2.4 Hz, 1H), 7.52 (d, J=8.8 Hz, 1H), 7.46 (dd, J=9.2, 2.8 Hz, 1H), 7.14 (m, 1H), 6.88 (brs, 1H), 6.79 (d, J=9.2 Hz, 1H), 2.92 (d, J=4.8 Hz, 3H), 1.31 (s, 9H); MS (ESI) m/z: 325.2 (M+H$^+$).

Example B3

A solution of triflic anhydride (42.8 g, 0.15 mol) in CH$_2$Cl$_2$ (100 mL) was added dropwise to a 0° C. solution of 6-hydroxyquinoline (20.00 g, 0.138 mol) and pyridine (23 g, 0.277 mol) in CH$_2$Cl$_2$ (500 mL). The cooling bath was removed and the resulting solution was stirred at RT for 4 h. The reaction mixture was washed with water (3×300 mL) and the organic phase was dried (MgSO$_4$) and concentrated under vacuum to afford crude quinolin-6-yl trifluoromethanesulfonate (40 g, >100% yield) as an oil. $^1$H-NMR (400 MHz, DMSO-d$_6$) δ 9.00 (d, 1H, J=2.8 Hz), 8.50 (d, 1H, J=8.0 Hz), 8.21 (d, J=2.8 Hz, 1H), 8.18 (d, J=9.2 Hz, 1H), 7.80 (m, 1H), 7.64 (m, 1H); MS (ESI) m/z: 277.9 (M+H$^+$).

To a suspension of quinolin-6-yl trifluoromethanesulfonate (40 g, 0.14 mol), benzophenone hydrazone (35.6 g, 0.18 mol), cesium carbonate (74 g, 0.23 mol) and 1,1'-bis(diphenylphosphino)ferrocene (2.5 g, 4.5 mmol) in degassed toluene (1 L) was added palladium acetate (0.013 g, 0.058 mmol). The resultant mixture was heated to 90° C. under a nitrogen atmosphere. After 16 h, the mixture was concentrated in vacuo and the residue was purified via silica gel column chromatography (EtOAc/pet ether) to provide 1-(diphenylmethylene)-2-(quinolin-6-yl)hydrazine (32 g, 68.6% yield). $^1$H-NMR (300 MHz, DMSO-d$_6$) δ 9.22 (s, 1H), 8.58 (t, J=1.8 Hz, 1H), 8.13 (d, J=3.6 Hz, 1H), 7.80 (d, J=3.6 Hz, 1H), 7.61 (d, J=3.9 Hz, 1H), 7.59-7.51 (m, 4H), 7.50 (d, J=3.6 Hz, 2H), 7.33-7.39 (m, 6H); MS (ESI) m/z: 324 (M+H$^+$).

A solution of 1-(diphenylmethylene)-2-(quinolin-6-yl)hydrazine (32 g, 99 mmol) and 4,4-dimethyl-3-oxo-pentanenitrile (26 g, 0.15 mol) in ethanol (500 mL) was treated with conc HCl (80 ml, 12 N, 0.96 mol) and the mixture was heated to reflux overnight. The cooled reaction mixture was concentrated under vacuum and the residue was washed with Et$_2$O to remove the diphenylketone. The crude product was dissolved in EtOAc and neutralized (pH 8) with saturated Na$_2$CO$_3$ solution. The organic layer was dried (Na$_2$SO$_4$), concentrated in vacuo and purified by silica gel chromatography to give 5-tert-butyl-2-quinolin-6-yl-2H-pyrazol-3-ylamine (23 g, 87% yield). $^1$H-NMR (300 MHz, DMSO-d$_6$) δ 8.86 (m, 1H), 8.39 (d, J=5.7 Hz, 1H), 8.11-8.02 (m, 3H), 7.54 (m, 1H), 5.46 (s, 1H), 5.42 (br s, 2H), 1.23 (s, 9H); MS (ESI) m/z: 267.2 (M+H$^+$).

To a cold solution (−10° C.) of 5-tert-butyl-2-quinolin-6-yl-2H-pyrazol-3-ylamine (8.00 g, 30 mmol) in 100 ml of CH$_2$Cl$_2$ was added pyridine (8.0 ml, 99 mmol) and DMAP (100 mg), followed by a solution of trichloroethyl chloroformate (8.9 ml, 42 mmol) in 30 ml of CH$_2$Cl$_2$ over a period of 20 minutes. After stirring for 1 hour, water (100 ml) was added, stirring continued for 10 more minutes and the organic layer separated. The organic layer was washed with brine, dried and the dark brown residue obtained after removal of the solvent crystallized from acetonitrile to furnish 2,2,2-trichloroethyl 3-tert-butyl-1-(quinolin-6-yl)-1H-pyrazol-5-ylcarbamate as a white solid (8.23 g, 62% yield). $^1$H NMR (DMSO-d$_6$) δ 10.15 (br s, 1H) 8.93 (m, 1H), 8.41 (d, J=8 Hz, 1H), 8.11 (m, 2H), 7.90 (dd, J=8, 2 Hz, 1H), 7.60 (dd, J=6.4, 4.2 Hz, 1H), 6.39 (s, 1H), 4.85 (s, 2H), 1.32 (s, 9H); MS (ESI) m/z: 442 (M+H$^+$).

Example B4

Quinolin-6-ylboronic acid (0.34 g, 2.0 mmol) was dissolved in CH$_2$Cl$_2$ (30 mL) and pyridine (1 mL) with MS (activated 4 Å) and stirred at RT for 6 hours. Ethyl 3-tert-butyl-1H-pyrazole-5-carboxylate (0.39 g, 2.0 mmol) and copper(II) acetate (0.36 g, 2.0 mmol) were added and the reaction was stirred at RT for 3 days open to air. The reaction mixture was filtered through a pad of Celite®, the filtrate was concentrated in vacuo and purified by silica gel chromatography to obtain ethyl 3-tert-butyl-1-(quinolin-6-yl)-1H-pyrazole-5-carboxylate (0.21 g, 33% yield). MS (ESI) m/z: 324.0 (M+H$^+$).

Lithium hydroxide (62 mg, 2.6 mmol) was added to a solution of ethyl 3-tert-butyl-1-(quinolin-6-yl)-1H-pyrazole-5-carboxylate (0.21 g, 0.65 mmol) in dioxane-H$_2$O-EtOH (1:1:1, 6 mL). The reaction mixture was stirred overnight at RT. The solution was concentrated and the residue was dissolved in H$_2$O (2 mL). 3M HCl was added and the precipitate was collected by filtration and washed with water. The solid was dried under vacuum to obtain 3-tert-butyl-1-(quinolin-6-yl)-1H-pyrazole-5-carboxylic acid (0.18 g, 94% yield) as a white solid. $^1$H NMR (400 MHz, DMSO-d$_6$) δ 8.96 (dd, J=2.0, 4.0 Hz, 1H), 8.47 (dd, J=1.2, 8.4 Hz, 1H), 8.09 (m, 1H), 8.06 (s, 1H), 7.82 (dd, J=2.8, 9.2 Hz, 1H), 7.61 (dd, J=4.8, 8.8 Hz, 1H), 7.01 (s, 1H), 1.33 (s, 9H); MS (ESI) m/z: 296.0 (M+H$^+$).

Example B5

[3-(5-amino-3-t-butyl-pyrazol-1-yl)naphthalen-1-yl]acetic acid ethyl ester hydrochloride (see WO 2006/071940, 1.60 g, 4.55 mmol) was treated with ammonia in methanol (7 M, 13 mL, 91 mmol) and the reaction mixture was heated in a sealed tube for 6 days. The solvent was removed in vacuo and the residue was chromatographed to provide 2-(3-(5-amino-3-tert-butyl-1H-pyrazol-1-yl)naphthalen-1-yl)acetamide (610 mg, 41% yield). MS (ESI) m/z: 323.3 (M+H$^+$).

To a mixture of saturated sodium bicarbonate (20 mL), ethyl acetate (20 mL) and 2-(3-(5-amino-3-tert-butyl-1H-pyrazol-1-yl)naphthalen-1-yl)acetamide (300 mg, 0.931 mmol) was added Troc-Cl (296 mg, 1.40 mmol). The mixture was stirred vigorously overnight. The mixture was diluted with ethyl acetate (30 mL) and the organic phase was separated, washed with 5% citric acid (30 mL) and brine (30 mL), dried (Na$_2$SO$_4$) and concentrated in vacuo to give a solid which was triturated with ethyl acetate and filtered to provide 2,2,2-trichloroethyl 1-(4-(2-amino-2-oxoethyl)naphthalen-2-yl)-3-tert-butyl-1H-pyrazol-5-ylcarbamate (241 mg, 52% yield). MS (ESI) m/z: 499.0 (M+H$^+$).

Example B6

To a stirring suspension of tert-butyl 5-(5-amino-3-tert-butyl-1H-pyrazol-1-yl)-1H-indazole-1-carboxylate (see WO 2006/071940A2, 0.250 g, 0.70 mmol) and Troc-Cl (0.10 ml, 0.74 mmol) in EtOAc (7 ml) at RT was added sat'd. NaHCO$_3$ (2.9 ml, 2.1 mmol). After 3 h, the completed reaction was diluted with hexanes (35 ml) and filtered. The solid was rinsed well with hexanes and dried to afford tert-butyl 5-(3-tert-butyl-5-((2,2,2-trichloroethoxy)carbonyl)-1H-pyrazol-1-yl)-1H-indazole-1-carboxylate (0.36 g, 97% yield). MS (ESI) m/z: 532.0 (M+H$^+$).

Example B7

To a stirring solution of t-butyl 6-(5-amino-3-t-butyl-1H-pyrazol-1-yl)-3,4-dihydroisoquinoline-2(1H)-carboxylate (see WO 2006/071940A2, 0.075 g, 0.20 mmol) and Troc-Cl (0.028 ml, 0.21 mmol) in EtOAc (2 ml) was added sat'd. NaHCO$_3$ (0.82 ml, 0.61 mmol). The resulting biphasic solution was stirred at RT overnight. The layers were separated and the aqueous phase was extracted with EtOAc (2×). The combined organic phases were washed with brine (1×), dried (MgSO$_4$) and concentrated in vacuo to give crude t-butyl 6-(3-t-butyl-5-((2,2,2-trichloroethoxy)carbonyl)-1H-pyrazol-1-yl)-3,4-dihydroisoquinoline-2(1H)-carboxylate (0.110 g, 100% yield). $^1$H NMR (DMSO-d$_6$) δ 9.93 (brs, 1H), 7.29-7.24 (m, 2H), 6.83-6.80 (m, 1H), 6.27 (s, 1H), 4.85 (s, 2H), 4.52 (brs, 2H), 3.57-3.53 (m, 2H), 2.82-2.79 (m, 2H), 1.44 (s, 9H), 1.27 (s, 9H); MS (ESI) m/z: 545.0 (M+H$^+$).

Example B8

A solution of tert-butyl 5-(5-amino-3-tert-butyl-1H-pyrazol-1-yl)-1H-indazole-1-carboxylate (see WO 2006/071940A2, 0.64 g, 1.80 mmol) in EtOAc (6 mL) was treated with 1M aq NaOH (2.7 mL). To the stirring biphasic reaction mixture at 0° C. was added isopropenyl chloroformate (0.26 mL) dropwise over 1 min. The reaction mixture was stirred for 4 h at RT. The reaction was diluted with EtOAc (20 ml). The organic layer was washed with H$_2$O (2×10 ml), brine (10 ml) dried (MgSO$_4$) and concentrated to afford tert-butyl 5-(3-tert-butyl-5-((prop-1-en-2-yloxy)carbonylamino)-1H-pyrazol-1-yl)-1H-indazole-1-carboxylate (0.69 g, 87% yield) as a light yellow foam. $^1$H NMR (DMSO-d$_6$) δ 9.77 (s, 1H), 8.52 (s, 1H), 8.17 (d, J=9 Hz, 1H), 7.97 (d, J=2 Hz, 1H), 7.74 (dd, J=9, 2 Hz 1H), 6.34 (s, 1H), 4.7 (m, 2H), 1.80 (s, 3H), 1.67 (s, 9H), 1.30 (s, 9H); MS (ESI) m/z: 440.2 (M+H$^+$).

Example B9

Using a procedure analogous to Example B3, 6-(2-(diphenylmethylene)hydrazinyl)quinoline (4.0 g, 12.3 mmol) and 4-methyl-3-oxo-pentanenitrile (1.5 g, 13.5 mmol) were combined to provide to 3-isopropyl-1-(quinolin-6-yl)-1H-pyrazol-5-amine. (1.1 g, 36% yield). $^1$H NMR (400 MHz, CDCl$_3$) δ 8.93 (dd, J=4.4, 1.6 Hz, 1H), 8.21-8.18 (m, 2H), 8.05-8.02 (m, 2H), 7.44 (dd, J=8.4, 4.4 Hz, 1H), 5.56 (s, 1H), 3.85 (br s, 2H), 2.97 (m, 1H), 1.31 (d, J=6.8 Hz, 6H); MS (ESI) m/z: 253.2 (M+H$^+$).

Using a procedure analogous to Example B3 3-isopropyl-1-(quinolin-6-yl)-1H-pyrazol-5-amine (0.378 g, 1.5 mmol) was converted to 2,2,2-trichloroethyl 3-isopropyl-1-(quinolin-6-yl)-1H-pyrazol-5-ylcarbamate (0.391 g, 61% yield). MS (ESI) m/z: 427.0 (M+H$^+$).

Example B10

Using a procedure analogous to Example B3, 6-(2-(diphenylmethylene)hydrazinyl)quinoline (4.0 g, 12.3 mmol) and 3-oxo-pentanenitrile (1.3 g, 1.1 eq) were combined to yield 5-ethyl-2-quinolin-6-yl-2H-pyrazol-3-ylamine (2.5 g, 85% yield). $^1$H NMR (300 MHz, DMSO-d$_6$) δ 8.87 (dd, J=7.8, 1.8 Hz, 1H), 8.39 (dd, J=8.4, 1.5 Hz, 1H), 8.12 (s, 1H), 8.06-8.03 (m, 2H), 7.54 (dd, J=8.4, 1.2 Hz, 1H), 5.46 (br s, 2H), 5.40 (s, 1H), 2.49 (q, J=7.5 Hz, 2H), 1.16 (t, J=7.5 Hz, 3H); MS (ESI) m/z: 239.2 (M+H$^+$).

Using a procedure analogous to Example B3, 5-ethyl-2-quinolin-6-yl-2H-pyrazol-3-ylamine (0.378 g, 1.5 mmol) was converted to 2,2,2-trichloroethyl 3-ethyl-1-(quinolin-6-yl)-1H-pyrazol-5-ylcarbamate (0.287 g, 41% yield) as a white foam. MS (ESI) m/z: 413.0 (M+H$^+$).

Example B11

Using a procedure analogous to a procedure analogous to Example B3, 6-(2-(diphenylmethylene)hydrazinyl)quinoline (5.0 g, 15.5 mmol) and 4,4,4-trifluoro-3-oxo-butyronitrile (2.3 g, 16.8 mmol) were combined to yield 2-quinolin-6-yl-5-trifluoromethyl-2H-pyrazol-3-ylamine (2.3 g, 53% yield). $^1$H NMR (300 MHz, DMSO-d$_6$) δ 8.95 (dd, J=1.5, 4.2 Hz, 1H), 8.47 (d, J=7.2 Hz, 1H), 8.22 (d, J=2.4 Hz, 1H), 8.14 (d, J=9.3 Hz, 1H), 7.97 (dd, J=2.4, 9.0 Hz, 1H), 7.60 (dd, J=7.2, 4.2 Hz, 1H), 5.96 (br s, 2H), 5.85 (s, 1H); MS (ESI) m/z: 279.2 (M+H$^+$).

Using a procedure analogous to Example B3, 2-quinolin-6-yl-5-trifluoromethyl-2H-pyrazol-3-ylamine (0.47 g, 1.7 mmol) was converted to 2,2,2-trichloroethyl 1-(quinolin-6-yl)-3-(trifluoromethyl)-1H-pyrazol-5-ylcarbamate (0.333 g, 43% yield). MS (ESI) m/z: 453.0 (M+H$^+$).

Example B12

Using a procedure analogous to Example B3, 6-(2-(diphenylmethylene)hydrazinyl)quinoline (5.0 g, 15.5 mmol) and 3-cyclopentyl-3-oxopropanenitrile (3.0 g, 1.1 eq) were combined to yield 3-cyclopentyl-1-(quinolin-6-yl)-1H-pyrazol-5-amine (2.3 g, 53% yield). $^1$H NMR (300 MHz, DMSO-d$_6$) δ 8.87 (m, 1H), 8.38 (dd, J=1.5, 8.4 Hz, 1H), 8.10 (s, 1H), 8.04-8.02 (m, 2H), 7.55 (dd, J=4.2, 8.1 Hz, 1H), 5.41 (br s, 2H), 5.38 (s, 1H), 2.90 (m, 1H), 1.85-1.96 (m, 2H), 1.53-1.70 (m, 6H); MS (ESI) m/z: 279.3 (M+H$^+$).

Using a procedure analogous to Example B3, 3-cyclopentyl-1-(quinolin-6-yl)-1H-pyrazol-5-amine (0.418 g, 1.5 mmol) was converted to 2,2,2-trichloroethyl 3-cyclopentyl-1-(quinolin-6-yl)-1H-pyrazol-5-ylcarbamate (0.394 g, 58% yield). MS (ESI) m/z: 453.0 (M+H$^+$).

Example B13

Using a procedure analogous to Example B3, 6-(2-(diphenylmethylene)hydrazinyl)quinoline (4.0 g, 12.3 mmol) and 3-cyclobutyl-3-oxo-propionitrile (1.7 g, 1.1 eq) were combined to provide 5-cyclobutyl-2-quinolin-6-yl-2H-pyrazol-3-ylamine (1.3 g, 40% yield). $^1$H NMR (300 MHz, CDCl$_3$) δ 8.92 (dd, J=4.5, 1.2 Hz, 1H), 8.16-8.20 (m, 2H), 8.00-8.04 (m, 2H), 7.43 (dd, J=8.4, 1.2 Hz, 1H), 5.64 (s, 1H), 3.83 (br s, 2H), 3.53 (m, 1H), 2.40-2.20 (m, 4H), 2.08-1.92 (m, 2H); MS (ESI) m/z: 265.1 (M+H$^+$).

Using a procedure analogous to Example B3, 5-cyclobutyl-2-quinolin-6-yl-2H-pyrazol-3-ylamine (0.396 g, 1.5 mmol) was converted to 2,2,2-trichloroethyl 3-cyclobutyl-1-(quinolin-6-yl)-1H-pyrazol-5-ylcarbamate (0.412 g, 63% yield). MS (ESI) m/z: 439.0 (M+H$^+$).

Example B14

A degassed mixture of ethyl 5-chloro-2-iodobenzoate (0.621 g, 2.00 mmol), Pd(PPh$_3$)$_4$ (0.116 mg, 0.1 mmol), quinolin-6-ylboronic acid (0.381 g, 2.2 mmol), K$_2$CO$_3$ (0.553 g, 4.0 mmol), dimethoxyethane (20 mL), and water (5 mL) was heated under reflux overnight. Solvents were removed under reduced pressure. The residue was diluted with sat'd NH$_4$Cl (15 mL) and extracted with EtOAc (3×30 mL). The combined organic layers were dried (MgSO$_4$), concentrated in vacuo and purified by chromatography to afford ethyl 5-chloro-2-(quinolin-6-yl)benzoate (0.244 g, 39% yield) as a colorless oil. MS (ESI) m/z: 312.0 (M+H$^+$).

To a stirring solution of ethyl 5-chloro-2-(quinolin-6-yl) benzoate (0.244 g, 0.78 mmol) in 1:1:1 THF/EtOH/H$_2$O (21 ml) at RT was added LiOH—H$_2$O (0.164 g, 3.91 mmol). The resulting reaction mixture was stirred at RT overnight. Solvent was removed under reduced pressure and the residue was diluted with H$_2$O (10 mL). The aqueous solution was acidified to pH~4 with 3M HCl and extracted with EtOAc (3×30 mL). The combined organic layers were washed with brine (20 mL), dried (MgSO$_4$) and concentrated to afford 5-chloro-2-(quinolin-6-yl)benzoic acid (0.201 g, 91% yield) as a white solid. MS (ESI) m/z: 284.0 (M+H$^+$).

To a stirring solution of 5-chloro-2-(quinolin-6-yl)benzoic acid (0.201 g, 0.708 mmol) and TEA (0.148 ml, 1.06 mmol) in 1,4-dioxane (10 ml) at RT, was added DPPA (0.191 ml, 0.244 mmol). After stirring for 30 min at RT, 2,2,2-trichloroethanol (0.680 ml, 7.08 mmol) was added and the reaction was stirred with heating at 100° C. for 2 h. The completed reaction was diluted with brine (10 ml) and extracted with EtOAc (3×25 ml). The combined organics were washed with 5% citric acid (10 ml), sat'd. NaHCO$_3$ (10 ml) and brine (10 ml), dried (MgSO$_4$), concentrated in vacuo and purified by chromatography to afford 2,2,2-trichloroethyl 5-chloro-2-(quinolin-6-yl)phenylcarbamate (0.25 g, 82% yield) as a white solid. MS (ESI) m/z: 431.0 (M+H$^+$).

Example B15

2,2,2-Trichloroethyl 4-chloro-2-(quinolin-6-yl)phenylcarbamate was prepared from ethyl 4-chloro-2-iodobenzoate using a procedure analogous to Example B14. MS (ESI) m/z: 431.0 (M+H$^+$).

Example B16

A mixture of 5-nitro-1H-indazole (50 g, 0.31 mol) and 10% Pd/C (5.0 g) in MeOH (400 mL) was heated under H$_2$ (30 psi) atmosphere overnight. After the mixture was filtered, the filtrate was concentrated to give 1H-indazol-5-ylamine as a yellow solid (40 g, 97% yield). $^1$H NMR (300 MHz, DMSO-d$_6$) δ 12.50 (br s, 1H), 7.70 (s, 1H), 7.22 (d, J=6.6 Hz, 1H), 6.77 (d, J=6.6 Hz, 1H), 6.74 (s, 1H), 4.72 (br s, 1H); MS (ESI) m/z: 134.2 (M+H$^+$).

To a solution of 1H-indazol-5-ylamine (8.0 g, 60.1 mmol) in concentrated HCl (20 mL, 240 mmol) was added an aqueous solution (50 mL) of NaNO$_2$ (4.2 g, 60.1 mmol) at 0° C. and the resulting mixture was stirred for 1 h. A solution of SnCl$_2$.2H$_2$O (27 g, 120 mmol) in conc HCl (30 mL) was then added at 0° C. The reaction was stirred for an additional 2 h at RT. A solution of 4-methyl-3-oxo-pentanenitrile (8.0 g, 1.1 eq) in ethanol (50 mL) was added and the resultant mixture was heated to reflux overnight. The reaction mixture was concentrated under reduced pressure and was purified by silica gel chromatography to provide 2-(1H-indazol-5-yl)-5-isopropyl-2H-pyrazol-3-ylamine (8.5 g, 59% yield, two steps). $^1$H NMR (300 MHz, DMSO-d$_6$) 8.09 (s, 1H), 7.82 (s, 1H), 7.57 (d, J=6.6 Hz, 1H), 7.51 (d, J=6.6 Hz, 1H), 5.31 (s, 1H), 5.12 (s, 2H), 2.74 (m, 1H), 1.15 (d, J=5.1 Hz, 6H); MS (ESI) m/z: 242.3 (M+H$^+$).

A stirring solution of 2-(1H-indazol-5-yl)-5-isopropyl-2H-pyrazol-3-ylamine (8.0 g, 33 mmol) in dioxane (80 mL)/10% NaOH (30 mL) was treated with (Boc)$_2$O (8.6 g, 39.4 mmol). The resultant mixture was stirred for 3 h and was then extracted with DCM (3×100 mL). The organic layer was concentrated in vacuo and the residue was purified by silica gel chromatography to give 5-(5-amino-3-isopropyl-pyrazol-1-yl)-indazole-1-carboxylic acid tert-butyl ester (6.8 g, 47%) as a white solid. $^1$H NMR (300 MHz, DMSO-d$_6$) δ 8.43 (s, 1H), 8.10 (d, J=9.3 Hz, 1H), 8.00 (br s, 1H), 7.82 (d, J=9.3 Hz, 1H), 5.36 (s, 1H), 5.29 (br s, 2H), 2.76 (m, 1H), 1.64 (s, 9H), 1.16 (d, J=7.2 Hz, 6H). MS (ESI) m/z: 442.2 (M+H$^+$).

A solution of tent-butyl 5-(5-amino-3-isopropyl-1H-pyrazol-1-yl)-1H-indazole-1-carboxylate (1.50 g) in EtOAc (15 mL) was treated with 1M aq NaOH (6.8 mL). To the stirred biphasic reaction mixture at 0° C. was added isopropenyl chloroformate (0.64 mL) drop-wise over 1 min. The reaction mixture was stirred at RT overnight. The reaction mixture was diluted with EtOAc (100 mL), washed with H$_2$O (2×30 mL), brine (30 mL), dried (MgSO$_4$) and concentrated to afford tert-butyl 5-(3-isopropyl-5-((prop-1-en-2-yloxy)carbonylamino)-1H-pyrazol-1-yl)-1H-indazole-1-carboxylate (1.90 g, 99% yield) as a white foam. MS (ESI) m/z: 425.8 (M+H$^+$).

Example B17

Using a procedure analogous to Example B16, 1H-indazol-5-ylamine (5.0 g, 37.5 mmol) and 3-oxo-pentanenitrile (4.0 g, 1.1 eq) were combined and purified by silica gel chromatography to give 5-ethyl-2-(1H-indazol-5-yl)-2H-pyrazol-3-ylamine (5.2 g, 61% yield, two steps). $^1$H NMR (300 MHz, DMSO-d$_6$) δ 8.04 (s, 1H), 7.58 (s, 1H), 7.57 (d, J=6.6 Hz, 1H), 7.50 (d, J=6.6 Hz, 1H), 5.30 (s, 1H), 5.13 (br s, 2H), 2.47 (q, J=6.9 Hz, 2H), 1.14 (t, J=6.9 Hz, 3H); MS (ESI) m/z: 228.3 (M+H$^+$).

Using a procedure analogous to Example B16, 5-ethyl-2-(1H-indazol-5-yl)-2H-pyrazol-3-ylamine (5.0 g, 22 mmol) was converted to 5-(5-amino-3-ethyl-pyrazol-1-yl)-indazole-1-carboxylic acid tert-butyl ester (3.0 g, 42% yield) as a white solid. $^1$H NMR (300 MHz, DMSO-d$_6$): δ 8.42 (s, 1H), 8.09 (d, J=6.6 Hz, 1H), 7.98 (s, 1H), 7.81 (d, J=6.6 Hz, 1H), 5.35 (s, 1H), 5.29 (br s, 2H), 2.44 tert-Butyl 5-(5-amino-3-ethyl-1H-pyrazol-1-yl)-1H-indazole-1-carboxylate (0.50 g) was converted to tert-butyl 5-(3-ethyl-5-((prop-1-en-2-yloxy)carbonylamino)-1H-pyrazol-1-yl)-1H-indazole-1-carboxylate (0.55 g, 88% yield) using a procedure analogous to Example 16. MS (ESI) m/z: 412.3 (M+H$^+$).

Example B18

A solution of N-benzhydrylidene-N'-quinolin-6-yl-hydrazine (32 g, 0.099 mol) in EtOH (500 mL) was treated with conc. HCl (80 ml, 0.96 mmol). After stirring for 10 min, 5,5-dimethyl-2,4-dioxo-hexanoic acid ethyl ester (26 g, 0.15 mol) was added, and the mixture was heated to 80° C. overnight. The reaction was concentrated in vacuo to give a residue which was washed with Et$_2$O to afford ethyl 5-tert-butyl-1-(quinolin-6-yl)-1H-pyrazole-3-carboxylate hydrochloride (40 g, 0.11 mol, 112% yield). MS (ESI) m/z: 324.1 (M+H$^+$).

A suspension of ethyl 5-tert-butyl-1-(quinolin-6-yl)-1H-pyrazole-3-carboxylate hydrochloride (32 g, 0.089 mol) in THF (300 mL) was treated with aqueous LiOH (2 N, 100 mL, 0.20 mmol) and the resultant mixture was heated to 40° C. for 3 hours. The reaction was concentrated under reduced pressure and the remaining aqueous layer was washed with EtOAc. The aqueous phase was acidified to pH 3 and the resultant precipitate was collected by filtration, washed with cold ether and dried in vacuo to provide 5-tert-butyl-1-(quinolin-6-yl)-1H-pyrazole-3-carboxylic acid (21 g, 71% yield). $^1$H-NMR (400 MHz, DMSO-d$_6$) δ 9.03 (m, 1H), 8.50 (d, J=8.7 Hz, 1H), 8.20 (d, J=2.4 Hz, 1H), 8.15 (d, J=8.8 Hz, 1H), 7.79 (dd, J=8.7 Hz, 2.4 Hz, 1H), 7.67 (dd, J=8.4, 4.4 Hz, 1H), 6.68 (s, 1H), 1.17 (s, 9H); MS (ESI) m/z: 296.3 (M+H$^+$).

Example B19

A solution of sodium nitrite (502 mg, 7.27 mmol) in H$_2$O (8 ml) was added dropwise to a well-stirred 0° C. mixture of 2-methylquinolin-6-amine (1.00 g, 6.32 mmol) in conc. HCl (10 ml). The resulting mixture was stirred at 0° C. for 1 h. Tin(II) chloride dihydrate (6.13 g, 27.2 mmol) in conc. HCl (8 ml) was added and stirring was continued at 0° C. for 1 h and then RT for 2 h. Ethanol (60 ml) and 4,4-dimethyl-3-oxopentanenitrile (1.03 g, 8.22 mmol) were added and the mixture was heated at reflux overnight. The completed reaction mixture was concentrated in vacuo and diluted with ethyl acetate (100 mL). The mixture was cooled in an ice/water bath and made basic (pH~8) with solid sodium hydroxide. The solution was filtered through Celite, and the filter cake was washed with water (50 mL) and ethyl acetate (100 mL). The organic phase was separated, washed with brine, dried (Na$_2$SO$_4$), and concentrated to yield a foam. The foam was stirred in ether (50 mL) and allowed to stand for several hours. The resultant solid was collected by filtration and dried in vacuo to yield 3-tert-butyl-1-(2-methylquinolin-6-yl)-1H-pyrazol-5-amine (428 mg, 24% yield). MS (ESI) m/z: 281.2 (M+H$^+$).

A solution of 3-tert-butyl-1-(2-methylquinolin-6-yl)-1H-pyrazol-5-amine (420 mg, 1.50 mmol) in CH$_2$Cl$_2$ (15 mL) was treated with pyridine (592 mg, 7.49 mmol) and TROC-Cl (333 mg, 1.57 mmol). The mixture was stirred at RT for 16 h, then washed with 5% citric acid (2×20 mL), saturated aq NaHCO$_3$ (20 mL) and brine (20 mL). The organic phase was dried (Na$_2$SO$_4$) and concentrated to provide a mixture of 2,2,2-trichloroethyl 3-tert-butyl-1-(2-methylquinolin-6-yl)-1H-pyrazol-5-ylcarbamate (73% yield) contaminated with 16% of the bis-Troc adduct. The mixture was used without further purification. MS (ESI) m/z: 456.5 (M+H$^+$).

Example B20

Using a procedure analogous to Example B4, imidazo[1,2-a]pyridin-6-ylboronic acid (0.200 g, 1.23 mmol) and ethyl 3-tert-butyl-1H-pyrazole-5-carboxylate (0.267 g, 1.36 mmol) were combined to afford ethyl 3-tert-butyl-1-(H-imidazo[1,2-a]pyridin-6-yl)-1H-pyrazole-5-carboxylate (0.0355 g, 9% yield) as a colorless oil. MS (ESI) m/z: 313.2 (M+H$^+$).

Using a procedure analogous to Example B4, ethyl 3-tert-butyl-1-(H-imidazo[1,2-a]pyridin-6-yl)-1H-pyrazole-5-carboxylate (0.071 g, 0.23 mmol) was converted to 3-tert-butyl-1-(H-imidazo[1,2-a]pyridin-6-yl)-1H-pyrazole-5-carboxylic acid (0.0643 g, 99% yield) as a white solid. MS (ESI) m/z: 285.0 (M+H$^+$).

Example B21

Using a procedure analogous to Example B4, imidazo[1,2-a]pyridin-6-ylboronic acid (0.500 g, 3.09 mmol) and ethyl 3-isopropyl-1H-pyrazole-5-carboxylate (0.619 g, 3.40 mmol) were combined to afford ethyl 3-isopropyl-1-(H-imidazo[1,2-a]pyridin-6-yl)-1H-pyrazole-5-carboxylate (0.098 g, 11% yield) as a colorless oil. MS (ESI) m/z: 299.3 (M+H$^+$).

Using a procedure analogous to Example B4, ethyl 3-isopropyl-1-(H-imidazo[1,2-a]pyridin-6-yl)-1H-pyrazole-5-carboxylate (0.098 g, 0.33 mmol) was converted to 3-isopropyl-1-(H-imidazo[1,2-a]pyridin-6-yl)-1H-pyrazole-5-carboxylic acid (0.087 g, 98% yield) as a white solid. MS (ESI) m/z: 271.0 (M+H$^+$).

Example B22

To a stirring suspension of 6-aminobenzothiazole (0.500 g, 3.33 mmol) in conc. HCl (5 ml) at 0-5° C. was added a solution of NaNO$_2$ (0.276 g, 3.99 mmol) in H$_2$O (5 ml). The mixture was stirred at 0-5° C. for 75 min until a clear yellow solution was obtained. To this was then added a solution of SnCl$_2$.2H$_2$O (2.76 g, 13.3 mmol) in conc. HCl (5 ml). After completing the addition, the suspension was stirred at RT for 2 h. 4-Methyl-3-oxopentanenitrile (0.444 g, 3.99 mmol) and EtOH (50 ml) were added and the reaction was stirred with heating at 75° C. After 18 h, the completed reaction was cooled to RT and concentrated to an aqueous residue. This was chilled thoroughly in ice and made strongly basic (pH 12-13) by the addition of 6M NaOH. While still cold the mixture was extracted with EtOAc (2×). The combined organics were washed with H$_2$O (2×), brine (1×), dried (MgSO$_4$), filtered and evaporated to afford crude 1-(benzo[d]thiazol-6-yl)-3-isopropyl-1H-pyrazol-5-amine (0.8 g, 93% yield) as an oil which was used as is in the next reaction. $^1$H NMR (400 MHz, DMSO-d$_6$) δ 9.36 (s, 1H), 8.30 (d, J=2.4 Hz, 1H); 8.10 (d, J=8.8 Hz, 1H), 7.74 (dd, J=2.4 and 8.8 Hz, 1H), 5.36 (s, 1H), 5.33 (brs, 2H), 2.76 (septet, J=6.8 Hz, 1H), 1.17 (d, J=6.8 Hz, 6H); MS (ESI) m/z: 259.0 (M+H$^+$).

To a stirring solution of 1-(benzo[d]thiazol-6-yl)-3-isopropyl-1H-pyrazol-5-amine (0.80 g, 3.1 mmol) and pyridine (0.51 ml, 6.2 mmol) in CH$_2$Cl$_2$ (30 ml) at RT was added Troc-Cl (0.51 ml, 3.7 mmol). After 2 h, the completed reaction was washed with 10% $CuSO_4$ (2×), $H_2O$ (1×), brine (1×), dried ($MgSO_4$), evaporated and purified by flash column chromatography (EtOAc/hexanes) to afford 2,2,2-trichloroethyl 1-(benzo[d]thiazol-6-yl)-3-isopropyl-1H-pyrazol-5-ylcarbamate (0.31 g, 23% yield) as an oil. MS (ESI) m/z: 433.0 ($M+H^+$), 435.0 ($M+2+H^+$).

Example B23

1-Methyl-5-nitro-1H-benzo[d]imidazole (prepared as described in WO 2005/092899; 1.14 g, 6.43 mmol) in EtOH (50 ml) was stirred under $H_2$ (1 atm) at RT in the presence of 10% Pd/C (50 wt % $H_2O$, 1.37 g, 0.643 mmol). After 18 h, the completed reaction was filtered on Celite, rinsing forward with EtOH. The combined filtrates were concentrated to afford crude 1-methyl-1H-benzo[d]imidazol-5-amine (1.02 g, 108% yield) as a dark orange oil which was used as is in the next reaction. $^1H$ NMR (400 MHz, DMSO-$d_6$) δ 7.87 (s, 1H), 7.17 (d, J=8.4 Hz, 1H), 6.75 (d, J=2.0 Hz, 1H), 6.59 (dd, J=2.0 and 8.4 Hz, 1H), 4.73 (brs, 2H), 3.69 (s, 3H); MS (ESI) m/z: 148.0 ($M+H^+$).

Using a procedure analogous to Example B22, 1-methyl-1H-benzo[d]imidazol-5-amine (0.50 g, 3.4 mmol), $NaNO_2$ (0.28 g, 4.1 mmol), $SnCl_2.2H_2O$ (2.8 g, 14 mmol) and 4-methyl-3-oxopentanenitrile (0.45 g, 4.1 mmol) were combined to afford crude 3-isopropyl-1-(1-methyl-1H-benzo[d]imidazol-5-yl)-1H-pyrazol-5-amine (0.63 g, 73% yield) as a foam which was used as is in the next reaction. $^1H$ NMR (400 MHz, DMSO-$d_6$): δ 8.22 (s, 1H), 7.72 (dd, J=0.40 and 1.2 Hz, 1H), 7.60 (dd, J=0.40 and 8.4 Hz, 1H), 7.42 (dd, J=2.0 and 8.4 Hz, 1H), 5.32 (s, 1H), 5.08 (brs, 2H), 3.85 (s, 3H), 2.75 (septet, J=6.8 Hz, 1H), 1.16 (d, J=6.8 Hz, 6H); MS (ESI) m/z: 250.0 ($M+H^+$).

Using a procedure analogous to Example B22, 3-isopropyl-1-(1-methyl-1H-benzo[d]imidazol-5-yl)-1H-pyrazol-5-amine (0.63 g, 2.5 mmol) was converted to 2,2,2-trichloroethyl 3-isopropyl-1-(1-methyl-1H-benzo[d]imidazol-5-yl)-1H-pyrazol-5-ylcarbamate (0.5 g, 47% yield) and isolated as an oil. $^1H$ NMR (400 MHz, DMSO-$d_6$) δ 9.86 (brs, 1H), 8.24 (s, 1H), 7.67 (brs, 1H), 7.62 (d, J=8.4 Hz, 1H), 7.36 (dd, J=2.0 and 8.4 Hz, 1H), 6.23 (s, 1H), 4.81 (s, 2H), 3.85 (s, 3H), 2.90 (septet, J=6.8 Hz, 1H), 1.22 (d, J=6.8 Hz, 6H); MS (ESI) m/z: 430.0 ($M+H^+$), 432.0 ($M+2+H^+$).

Example B24

To a stirring solution of 1-(2-(benzyloxycarbonyl)-1,2,3,4-tetrahydroisoquinolin-6-yl)-3-tert-butyl-1H-pyrazole-5-carboxylic acid from Example B1 (0.320 g, 0.738 mmol, 1.0 eq) and TEA (0.118 ml, 0.849 mmol, 1.15 eq) in 1,4-dioxane (7.5 ml) at 20° C. was added DPPA (0.183 ml, 0.849 mmol, 1.15 eq). After 30 min, 2,2,2-trichloroethanol (1.0 ml, 10.4 mmol, 14 eq) was added and the reaction was stirred with heating at 100° C. After 4 h, the completed reaction was diluted with brine and extracted with EtOAc (2×). The combined organics were washed with 5% citric acid (1×), satd. $NaHCO_3$ (1×) and brine (1×), dried ($MgSO_4$), concentrated in vacuo and purified by silica gel chromatography to afford benzyl 6-(3-tert-butyl-5-((2,2,2-trichloroethoxy)carbonyl)amino-1H-pyrazol-1-yl)-3,4-dihydroisoquinoline-2(1H)-carboxylate (0.260 g, 61% yield) as an oil. MS (ESI) m/z: 579.0 ($M+H^+$), 581.0 ($M+2+H^+$).

Example B25

Using the procedure of Example B26, 3-isopropyl-1-(quinolin-6-yl)-1H-pyrazol-5-amine from Example B9 (1.00 g, 4.0 mmol), lithium bis(trimethylsilyl)amide (1.0 M in THF, 7.9 mL, 7.9 mmol) and isopropenyl chloroformate (0.48 mL, 4.4 mmol) were combined to provide prop-1-en-2-yl 3-isopropyl-1-(quinolin-6-yl)-1H-pyrazol-5-ylcarbamate (0.85 g, 65% yield). MS (ESI) m/z: 337.2 ($M+H^+$).

Example B26

A solution of 5-tert-butyl-2-quinolin-6-yl-2H-pyrazol-3-ylamine from Example B3 (1.00 g, 3.8 mmol) in THF (20 mL) was cooled to −78° C. and treated with lithium bis(trimethylsilyl)amide (1.0 M in THF, 7.5 mL, 7.5 mmol). The resultant mixture was stirred at −78° C. for 30 min. Isopropenyl chloroformate (0.45 mL, 0.41 mmol) was added and stirring was continued at −78° C. for 30 min. The reaction mixture was quenched at −78° C. with aq HCl (2 N, 4 mL, 8 mmol), was warmed to RT and partitioned between water (200 mL) and EtOAc (200 mL). The organic layer was separated, washed with brine, dried ($MgSO_4$), concentrated in vacuo and purified by silica gel chromatography to provide prop-1-en-2-yl 3-tert-butyl-1-(quinolin-6-yl)-1H-pyrazol-5-ylcarbamate (0.5 g, 38% yield). MS (ESI) m/z: 351.2 ($M+H^+$).

Example B27

4-Fluoro-3-nitrophenylboronic acid (0.9 g, 4.9 mmol) was dissolved in $CH_2Cl_2$ (10 mL) and pyridine (1 mL) with MS (activated 4A) and dried for 6 hours. A mixture of 4-fluoro-3-nitrophenylboronic acid, tert-butyl 3-isopropyl-1H-pyrazole-5-carboxylate (1.0 g, 4.9 mmol), copper(II) acetate (0.88 g, 4.9 mmol) and molecular sieves (4A activated, powder) was stirred at RT for 7 days open to the air. The reaction mixture was filtered through a pad of Celite. The filtrate was concentrated in vacuo and purified by silica gel column chromatography (EtOAc/hexane) to obtain tert-butyl 1-(4-fluoro-3-nitrophenyl)-3-isopropyl-1H-pyrazole-5-carboxylate (0.74 g, 44% yield). MS (ESI) m/z: 350.3 ($M+H^+$).

To a solution of tert-butyl 1-(4-fluoro-3-nitrophenyl)-3-isopropyl-1H-pyrazole-5-carboxylate (0.74 g, 2.1 mmol) in THF/water (12 mL) was added LiOH (300 mg, 13 mmol) and $H_2O_2$ (30% wt, 0.96 mL). The reaction mixture was heated overnight at 60° C. $Na_2S_2O_3$ solution was added until the peroxide test (starch-iodide paper) was negative. Acetic acid was added until the pH was 4-5. The solution was extracted with EtOAc and the organic layer was washed with brine, dried ($MgSO_4$), concentrated in vacuo and purified by silica gel column chromatography (EtOAc/hexanes) to obtain tert-butyl 1-(4-hydroxy-3-nitrophenyl)-3-isopropyl-1H-pyrazole-5-carboxylate (0.27 g, 37% yield). MS (ESI) m/z: 348.3 ($M+H^+$).

To a solution of tert-butyl 1-(4-hydroxy-3-nitrophenyl)-3-isopropyl-1H-pyrazole-5-carboxylate (0.27 g, 0.78 mmol) in ethyl acetate/methanol (1:1, 10 mL) was added palladium on carbon (30 mg) and the mixture was hydrogenated (50 psi) overnight under Parr. The solution was filtered and washed with methanol. The combined filtrate was concentrated to afford tert-butyl 1-(3-amino-4-hydroxyphenyl)-3-isopropyl-1H-pyrazole-5-carboxylate. The crude tert-butyl 1-(3-amino-4-hydroxyphenyl)-3-isopropyl-1H-pyrazole-5-carboxylate was treated with 25% TFA in $CH_2Cl_2$ (2 mL) and stirred overnight at RT. The solvent was evaporated to obtain 1-(benzo[d]oxazol-5-yl)-3-tert-butyl-1H-pyrazole-5-carboxylic acid. To a solution of 1-(benzo[d]oxazol-5-yl)-3-tert-butyl-1H-pyrazole-5-carboxylic acid in xylenes (3 mL) was added triethyl orthoformate (0.16 mL, 0.96 mmol) and a catalytic amount of PPTS. The reaction mixture was heated at 140° C. for 4 hours. The solvent was evaporated and the residue was treated with methylene chloride with stirring for 1 hour. The resulting solid was filtered and washed with methylene chloride to obtain 1-(benzo[d]oxazol-5-yl)-3-isopropyl-1H-pyrazole-5-carboxylic acid (0.1 g, 45% yield: for three steps). MS (ESI) m/z: 272.0 (M+H$^+$).

Example B28

In toluene (8 mL) was placed 1-(diphenylmethylene)hydrazine (1.00 g, 5.10 mmol), palladium acetate (10.4 mg, 0.0464 mmol) and 2-(diphenylphosphino)-1-(2-(diphenylphosphino)naphthalen-1-yl)naphthalene (44 mg, 0.0696 mmol) and the reaction was stirred at 100° C. under Ar for 5 min and then cooled to RT. To this dark purple solution was added 6-bromoquinoxaline (970 mg, 4.64 mmol), sodium t-butoxide (624 mg, 6.50 mmol) and toluene (2 mL). The reaction was placed under Ar and warmed to 100° C. for 5 hrs, cooled to RT and stirred overnight. The reaction was diluted with ether (50 mL) and water (30 mL) and filtered through a Celite pad. The pad was washed with ether (20 mL) and water (20 mL). The combined organic layers were washed with brine (50 mL), dried (Na$_2$SO$_4$), concentrated in vacuo and purified by chromatography (ethyl acetate/hexanes) to give 1-(diphenylmethylene)-2-(quinoxalin-6-yl)hydrazine (305 mg, 20% yield) as a bright yellow foam. $^1$H NMR (300 MHz, DMSO-d$_6$) δ 7.35-7.41 (m, 5H), 7.51-7.53 (m, 2H), 7.58-7.65 (m, 3H), 7.75 (s, 1H), 7.89 (s, 2H), 8.61 (s, 1H), 8.74 (s, 1H), 9.60 (s, 1H); MS (ESI) m/z: 325.0 (M+H$^+$).

In ethanol (10 mL) was placed 1-(diphenylmethylene)-2-(quinoxalin-6-yl)hydrazine (300 mg, 0.925 mmol), pivaloylacetonitrile (156 mg, 1.25 mmol) and p-toluenesulfonic acid hydrate (704 mg, 3.70 mmol). The reaction was brought to reflux and stirred overnight. The reaction was cooled to RT, diluted with ethyl acetate (50 mL) and saturated sodium bicarbonate (50 mL). The organic phase was separated, washed with 1N NaOH (30 mL) and brine (30 mL), dried (Na$_2$SO$_4$), concentrated in vacuo and purified by chromatography (Si-25 column, ethyl acetate/hexanes) to give a tan foam, identified as 3-tert-butyl-1-(quinoxalin-6-yl)-1H-pyrazol-5-amine (57 mg, 23% yield). MS (ESI) m/z: 268.2 (M+H$^+$).

Example B29

To a solution of phenethylamine (60.5 g, 0.5 mol) and Na$_2$CO$_3$ (63.6 g, 0.6 mol) in EtOAc/H$_2$O (800 mL, 4:1) was added ethyl chloroformate, dropwise, (65.1 g, 0.6 mol) at 0° C. during a period of 1 h. The mixture was warmed to RT and stirred for an additional 1 h. The organic phase was separated and the aqueous layer was extracted with EtOAc. The combined organic phases were washed with H$_2$O and brine, dried (Na$_2$SO$_4$), concentrated in vacuo and purified by flash chromatography to afford ethyl phenethylcarbamate (90.2 g). $^1$H NMR (400 MHz, CDCl$_3$) δ 7.32-7.18 (m, 5H), 4.73 (brs, 1H), 4.14-4.08 (q, J=6.8 Hz, 2H), 3.44-3.43 (m, 2H), 2.83-2.79 (t, J=6.8 Hz, 2H), 1.26-1.21 (t, J=6.8 Hz, 3H).

A suspension of ethyl phenethylcarbamate (77.2 g, 40 mmol) in polyphosphoric acid (300 mL) was heated to 140-160° C. and stirred for 2.5 h. The reaction mixture was cooled to RT, carefully poured into ice-H$_2$O and stirred for 1 h. The aqueous solution was extracted with EtOAc (3×300 mL). The combined organic phases were washed with H$_2$O, 5% K$_2$CO$_3$ and brine, dried (Na$_2$SO$_4$), concentrated in vacuo and purified by flash chromatography to afford 3,4-dihydro-2H-isoquinolin-1-one (24 g). $^1$H NMR (400 MHz, DMSO-d$_6$) δ 7.91 (brs, 1H), 7.83 (d, J=7.5 Hz, 1H), 7.43 (t, J=7.5 Hz, 1H), 7.33-7.25 (m, 2H), 3.37-3.32 (m, 2H), 2.87 (t, J=6.6 Hz, 2H).

To an ice-salt bath cooled mixture of conc. HNO$_3$ and conc. H$_2$SO$_4$ (200 mL, 1:1) was added 4-dihydro-2H-isoquinolin-1-one (15 g, 0.102 mol) dropwise over 15 min. After stirring for 2 h, the resulting mixture was poured into ice-H$_2$O and stirred for 30 min. The precipitate was filtered, washed with H$_2$O, and dried in air to afford 7-nitro-3,4-dihydro-2H-isoquinolin-1-one (13 g). $^1$H NMR (300 MHz, DMSO-d$_6$) δ 8.53 (d, J=2.4 Hz, 1H), 8.31 (d, J=2.4 Hz, 1H), 8.29 (d, J=2.4 Hz, 1H), 7.62 (d, J=8.4 Hz, 1H), 3.44-3.39 (m, 2H), 3.04 (t, J=6.6 Hz, 2H).

A suspension of 7-nitro-3,4-dihydro-2H-isoquinolin-1-one (11.6 g, 60 mmol) and 10% Pd/C (1.2 g) in MeOH was stirred overnight at RT under H$_2$ (40 psi). The mixture was filtered through Celite® and washed with MeOH. The filtrate was evaporated under vacuum to afford 8.2 g of 7-amino-3,4-dihydro-2H-isoquinolin-1-one, which was used without further purification.

To a suspension of 7-amino-3,4-dihydro-2H-isoquinolin-1-one (8.1 g, 50 mmol) in conc. HCl (100 mL) in an ice-H$_2$O bath was added a solution of NaNO$_2$ (3.45 g, 50 mmol) in H$_2$O dropwise at such a rate that the reaction mixture never rose above 5° C. A solution of SnCl$_2$.2H$_2$O(22.5 g, 0.1 mol) in conc. HCl (150 mL) was added dropwise after 30 min. The resulting mixture was stirred for another 2 h at 0° C. The precipitate was collected by suction, washed with ether to afford 7-hydrazino-3,4-dihydro-2H-isoquinolin-1-one (8.3 g), which was used for the next reaction without further purification.

A mixture of 7-hydrazino-3,4-dihydro-2H-isoquinolin-1-one (8.0 g, 37.6 mmol) and 4,4-dimethyl-3-oxo-pentanenitrile (5.64 g, 45 mmol) in EtOH (100 mL) and conc. HCl (10 mL) was heated at reflux overnight. After removal of the solvent, the residue was washed with ether to afford 7-(5-amino-3-t-butyl-pyrazol-1-yl)-3,4-dihydro-2H-isoquinolin-1-one hydrochloride as a yellow solid (11.5 g, 96% yield), which was used without further purification.

To a solution of 7-(5-amino-3-t-butyl-pyrazol-1-yl)-3,4-dihydro-2H-isoquinolin-1-one hydrochloride (0.5 g, 1.76 mmol) in CH$_2$Cl$_2$ (25 mL) were added pyridine (0.22 mL) and trichloroethyl chloroformate (0.27 mL) at 0° C. and the mixture was stirred overnight at RT. LCMS showed the reaction was incomplete. Pyridine (0.25 mL) and TROC-Cl (0.25 mL) were added and then the mixture stirred at RT for 2 hours. The reaction mixture was diluted with CH$_2$Cl$_2$, the organic layer was washed with 3M HCl and brine, dried (Na$_2$SO$_4$) and concentrated in vacuo. The residue was dissolved in EtOAc and hexane was added. The solid was filtered to obtain 2,2,2-trichloroethyl 3-tert-butyl-1-(1-oxo-1,2,3,4-tetrahydroisoquinolin-7-yl)-1H-pyrazol-5-ylcarbamate (0.46 g, 57% yield). MS (ESI) m/z: 458.0 (M+H$^+$).

Example B30

To a solution of 7-(5-amino-3-t-butyl-pyrazol-1-yl)-3,4-dihydro-2H-isoquinolin-1-one hydrochloride from Example B29 (20 g, 0.070 mol) in THF (400 mL) was added LAH (15 g, 0.395 mol) in portions at 0-5° C. The resulting mixture was heated at reflux overnight, followed by the addition of 10% NaOH solution. After stirring for 1 h at RT, Boc$_2$O (23 g, 0.106 mol) was added and the solution stirred overnight. After filtration, the filtrate was concentrated to afford the crude product, which was purified by reverse phase chromatography to give 7-(5-amino-3-t-butyl-pyrazol-1-yl)-3,4-dihydro-1H-isoquinoline-2-carboxylic acid t-butyl ester (12 g, 75% yield). $^1$H NMR (300 MHz, DMSO-d$_6$) δ 7.32 (s, 1H), 7.29 (d, J=2.7 Hz, 1H), 7.18 (d, J=8.4 Hz, 1H), 5.32 (s, 1H), 5.15

(s, 1H), 4.51 (s, 2H), 3.52 (t, J=5.6 Hz, 2H), 2.75 (t, J=5.6 Hz, 2H), 1.40 (s, 9H), 1.17 (s, 9H); MS (ESI) m/z: 371 (M+H$^+$).

To a stirring solution of tert-butyl 7-(5-amino-3-tert-butyl-1H-pyrazol-1-yl)-3,4-dihydroisoquinoline-2(1H)-carboxylate (0.50 g, 1.35 mmol) and Troc-Cl (0.19 ml, 1.38 mmol) in EtOAc (15 mL) was added satd. NaHCO$_3$ (2.75 ml, 2.02 mmol). The resulting biphasic mixture was stirred at RT for 5 h. The layers were separated and the organic washed with sat'd. NaHCO$_3$ (1×) and brine (1×), dried (Na$_2$SO$_4$) and concentrated in vacuo to obtain tert-butyl 7-(3-tert-butyl-5-((2,2,2-trichloroethoxy)carbonyl)-1H-pyrazol-1-yl)-3,4-dihydroisoquinoline-2(1H)-carboxylate (0.69 g, 94% yield). MS (ESI) m/z: 545.0 (M+H$^+$).

Example 1

A solution of Example B3 (7.0 g, 15.8 mmol), Example A2 (4.14 g, 15.8 mmol) and DIEA (4.5 g, 34.9 mmol) in DMSO (70 ml) was heated in an oil-bath at 70° C. for 8 hrs. The reaction mixture was poured into water (500 ml), stirred overnight and the solids were separated by filtration. Successive crystallization of the crude product from toluene and acetone provided 1-(3-tert-butyl-1-(quinolin-6-yl)-1H-pyrazol-5-yl)-3-(2-fluoro-4-(2-(methylcarbamoyl)pyridin-4-yloxy)phenyl)urea as a white crystalline solid (4.06 g, 46% yield). $^1$H NMR (DMSO-d$_6$) δ 8.90 (m, 2H), 8.79 (m, 1H), 8.52 (m, 2H), 8.2 (m, 3H), 7.96 (dd, J=9, 2 Hz, 1H), 7.63 (dd, J=8, 4 Hz, 1H), 7.40 (br s, 1H), 7.30 (dd, J=3, 12 Hz, 1H), 7.17 (m, 1H), 7.05 (d, J=9 Hz, 1H), 6.50 (s, 1H), 2.80 (d, J=5 Hz), 1.32 (s, 9H); MS (ESI) m/z: 554 (M+H$^+$). The free base was treated with 0.1 M HCl to provide 1-(3-tert-butyl-1-(quinolin-6-yl)-1H-pyrazol-5-yl)-3-(2-fluoro-4-(2-(methylcarbamoyl)pyridin-4-yloxy)phenyl)urea bis hydrochloride salt as a pale yellow fluffy solid (2.40 g). $^1$H NMR (DMSO-d$_6$) δ 9.56 (s, 1H), 9.26 (m, 2H), 9.10 (d, J=8 Hz, 1H), 8.85 (m, 1H), 8.55 (m, 2H), 8.46 (d, J=9 Hz, 1H), 8.33 (dd, J=9, 2 Hz, 1H), 8.11 (t, J=9 Hz, 1H), 8.03 (dd, dd, J=9, 2 Hz, 1H), 7.46 (d, J=3 Hz, 1H), 7.30 (dd, J=3, 12 Hz, 1H), 7.20 (dd, J=3, 6 Hz, 1H), 7.04 (brd, J=7 Hz, 1H), 6.49 (s, 1H), 2.80 (d, J=4.5 Hz), 1.33 (s, 9H).

Example 2

Example B1 (142 mg, 0.33 mmol) and Et$_3$N (0.15 mL, 0.72 mmol) were combined in dioxane (3 mL). DPPA (0.13 mL, 0.59 mmol) was added and the reaction mixture was stirred at RT for 90 min. Example A2 (94 mg, 0.36 mmol) was added and the resultant mixture was heated to 95° C. for 4 h. The reaction mixture was concentrated in vacuo and purified by silica gel chromatography to provide benzyl 6-(3-tert-butyl-5-(3-(2-fluoro-4-(2-(methylcarbamoyl)pyridin-4-yloxy)phenyl)ureido)-1H-pyrazol-1-yl)-3,4-dihydroisoquinoline-2(1H)-carboxylate (95 mg, 42% yield). $^1$H NMR (400 MHz, DMSO-d$_6$) δ 9.00 (br s, 1H), 8.84 (s, 1H), 8.79 (q, J=4.8 Hz, 1H), 8.52 (d, J=5.6 Hz, 1H), 8.20 (t, J=9.2 Hz, 1H), 7.40-7.28 (m, 10H), 7.17 (dd, J=5.6, 2.8 Hz, 1H), 7.05 (m, 1H), 6.40 (s, 1H), 5.14 (s, 2H), 4.66 (m, 2H), 3.68 (m, 2H), 2.91 (t, J=5.6 Hz, 2H), 2.79 (d, J=4.8 Hz, 3H), 1.27 (s, 9H); MS (ESI) m/z: 692.2 (M+H$^+$).

A solution of benzyl 6-(3-tert-butyl-5-(3-(2-fluoro-4-(2-(methylcarbamoyl)pyridin-4-yloxy)phenyl)ureido)-1H-pyrazol-1-yl)-3,4-dihydroisoquinoline-2(1H)-carboxylate (93 mg, 0.13 mmol) in methanol (3 mL) was treated with 10% Pd/C (50% wet, 74 mg, 0.03 mmol) and formic acid (88%, 0.60 mL, 14 mmol). The resultant reaction mixture was stirred for 90 min and filtered through Celite, washing forward with methanol. The filtrate was concentrated in vacuo and purified on silica gel to provide 1-(3-tert-butyl-1-(1,2,3,4-tetrahydroisoquinolin-6-yl)-1H-pyrazol-5-yl)-3-(2-fluoro-4-(2-(methylcarbamoyl)pyridin-4-yloxy)phenyl)urea (42 mg, 56% yield). The product was treated with aqueous HCl (0.1 M, 0.75 mL) to provide 1-(3-tert-butyl-1-(1,2,3,4-tetrahydroisoquinolin-6-yl)-1H-pyrazol-5-yl)-3-(2-fluoro-4-(2-(methylcarbamoyl)pyridin-4-yloxy)phenyl)urea hydrochloride. $^1$H NMR (400 MHz, DMSO-d$_6$) δ 9.38 (br s, 2H), 9.10 (d, J=1.8 Hz, 1H), 9.05 (s, 1H), 8.80 (m, 1H), 8.53 (d, J=5.4 Hz, 1H), 8.15 (t, J=9.1 Hz, 1H), 7.46-7.34 (m, 4H), 7.32 (dd, J=11.6, 2.8 Hz, 1H), 7.18 (m, 1H), 7.05 (m, 1H), 6.39 (s, 1H), 4.33 (br s, 2H), 3.40 (2H obscured by H$_2$O), 3.09 (t, J=6.0 Hz, 2H), 2.79 (d, J=5.0 Hz, 3H), 1.28 (s, 9H); MS (ESI) m/z: 558.3 (M+H$^+$).

Example 3

Using general method A, Example B4 (80 mg, 0.27 mmol), Example A1 (0.18 g, 0.68 mmol), triethyl amine (30 mg, 0.30 mmol), and DPPA (82 mg, 0.30 mmol) were combined to yield 1-(3-tert-butyl-1-(quinolin-6-yl)-1H-pyrazol-5-yl)-3-(3-fluoro-4-(2-(methylcarbamoyl)pyridin-4-yloxy)phenyl)urea which was treated with 3M HCl/EtOAc to obtain its HCl salt (125 mg, 78% yield). $^1$H NMR (400 MHz, DMSO-d$_6$): δ 9.79 (brm, 1H), 9.16 (brm, 1H), 9.05 (brm, 1H), 8.93 (brm, 1H), 8.79 (brm, 1H), 8.53 (d, J=5.6 Hz, 1H), 8.42 (brm, 1H), 8.33 (brm, 1H), 8.22 (brm, 1H), 7.91 (brm, 1H), 7.68 (dd, J=2.4, and 14.4 Hz, 1H), 7.37 (d, J=2.4 Hz, 1H), 7.34 (t, J=9.2 Hz, 1H), 7.19 (brm, 1H), 6.49 (s, 1H), 2.79 (d, J=5.2 Hz, 3H), 1.31 (s, 9H); MS (ESI) m/z: 554.2 (M+H$^+$).

Example 4

To a solution of Example B8 (0.132 g, 0.30 mmol) in THF (1.0 ml) were added Example A2 (0.083 g, 0.315 mmol) and 1-methylpyrrolidine (2.6 mg, 0.03 mmol). The mixture was heated at 55° C. overnight. Solvent was removed and the residue was dissolved in MeOH (4.5 ml), to which 3M HCl/EtOAc (1.3 ml, 3.8 mmol) was added. The resulting mixture was stirred at RT overnight, followed by heating at 55° C. for 3 h. The reaction mixture was concentrated to dryness, diluted with sat'd. NaHCO$_3$ (7 ml) and extracted with EtOAc (3×20 ml). The combined organic layers was washed with sat'd. NaHCO$_3$ (7 ml), H$_2$O (7 ml) and brine (7 ml), dried (MgSO$_4$), concentrated in vacuo and purified by chromatography to afford 1-(3-tert-butyl-1-(1H-indazol-5-yl)-1H-pyrazol-5-yl)-3-(2-fluoro-4-(2-(methylcarbamoyl)pyridin-4-yloxy)phenyl)urea (80 mg, 49% yield) as a white solid. This was converted to corresponding HCl salt by reacting with HCl (4.0 M in dioxane, 1.0 eq.). $^1$H NMR (DMSO-d$_6$) δ 9.17 (s, 1H), 9.13 (s, 1H), 8.99 (m, 1H), 8.56 (d, J=5.6 Hz, 1H), 8.23-8.18 (m, 2H), 7.96 (d, J=2.0 Hz, 1H), 7.72 (d, J=8.8 Hz, 1H), 7.58 (d, J=2.4 Hz, 1H), 7.49 (dd, J=8.8, 1.6 Hz, 1H), 7.32 (dd, J=11.6, 2.8 Hz, 1H), 7.24 (dd, J=6.0, 3.0 Hz, 1H), 7.07 (dd, J=8.8, 1.6 Hz, 1H), 6.47 (s, 1H), 2.81 (d, J=4.8 Hz, 3H), 1.30 (s, 9H); MS (ESI) m/z: 543.2 (M+H$^+$).

Example 5

Using general method A, Example B4 (80 mg, 0.27 mmol) and Example A6 (99 mg, 0.38 mmol) were combined to provide 1-(3-tert-butyl-1-(quinolin-6-yl)-1H-pyrazol-5-yl)-3-(3-methyl-4-(2-(methylcarbamoyl)pyridin-4-yloxy)phenyl)urea (149 mg, 99% yield). $^1$H NMR (400 MHz, DMSO-d$_6$) δ 9.08 (s, 1H), 8.97 (dd, J=4.1, 1.2 Hz, 1H), 8.77 (q, J=4.6 Hz, 1H), 8.62 (s, 1H), 8.51-8.48 (m, 2H), 8.20-8.16 (m, 2H), 7.97 (d, J=8.9, 2.0 Hz, 1H), 7.63 (dd, J=8.5, 4.2 Hz, 1H), 7.46

(d, J=2.4 Hz, 1H), 7.32 (dd, J=8.7, 2.5 Hz, 1H), 7.27 (d, J=2.6 Hz, 1H), 7.08 (m, 1H), 7.06 (d, J=8.7 Hz, 1H), 6.47 (s, 1H), 2.78 (d, J=4.6 Hz, 3H), 2.04 (s, 3H), 1.33 (s, 9H); MS (ESI) m/z: 550.2 (M+H$^+$).

Example 6

Using a procedure analogous to Example 1, Example B3 (0.19 g, 0.43 mmol) and Example A7 (0.11 g, 0.43 mmol) were combined to provide 1-(3-tert-butyl-1-(quinolin-6-yl)-1H-pyrazol-5-yl)-3-(4-(2-carbamoyl)pyridin-4-yloxy)-2-fluorophenyl)urea hydrochloride (0.160 g, 64% yield). $^1$H NMR (DMSO-d$_6$) δ 9.55 (s, 1H), 9.27-9.24 (m, 2H), 9.10 (d, J=8.8 Hz, 1H), 8.56-8.54 (m, 2H), 8.46 (d, J=9.2 Hz, 1H), 8.32 (dd, J=9.6, 2.4 Hz, 1H), 8.27 (s, 1H), 8.13 (t, J=9.2 Hz, 1H), 8.04 (dd, J=8.4, 5.2 Hz, 1H), 7.85 (s, 1H), 7.52 (d, J=2.4 Hz, 1H), 7.32 (dd, J=11.6, 2.4 Hz, 1H), 7.24 (dd, J=6.0, 2.8 Hz, 1H), 7.05 (dq, J=8.8, 1.2 Hz, 1H), 6.50 (s, 1H), 1.33 (s, 9H); MS (ESI) m/z: 540.3 (M+H$^+$).

Example 7

Example B3 (0.12 g, 0.27 mmol), Example A9 (63 mg, 0.27 mmol) and DIEA (77 mg, 0.60 mmol) were combined in DMSO (1 mL) and heated overnight at 50-55° C. Water was added (50 mL) and the mixture was extracted with EtOAc (3×100 mL), dried (MgSO$_4$), concentrated in vacuo and purified by silica gel column chromatography (EtOAc/hexane) to obtain 1-(3-tert-butyl-1-(quinolin-6-yl)-1H-pyrazol-5-yl)-3-(2-fluoro-4-(2-(methylamino)pyridin-4-yloxy)phenyl)urea. The solid was treated with 0.100M HCl (2 equiv.) to obtain and 1-(3-tert-butyl-1-(quinolin-6-yl)-1H-pyrazol-5-yl)-3-(2-fluoro-4-(2-(methylamino)pyridin-4-yloxy)phenyl)urea hydrochloride (52 mg, 32% yield). $^1$H NMR (400 MHz, DMSO-d$_6$) δ 9.23 (brs, 1H), 9.17 (brs, 1H), 9.06 (brm, 1H), 8.66 (brm, 1H), 8.53 (brs, 1H), 8.0-8.3 (m, 4H), 7.92 (d, J=6.8 Hz, 1H), 7.74 (m, 1H), 7.35 (dd, J=2.8, and 11.6 Hz, 1H), 7.07 (m, 1H), 6.62 (d, J=6.4 Hz, 1H), 6.48 (s, 1H), 6.18 (brs, 1H), 2.88 (d, J=4.8 Hz, 2H), 1.32 (s, 9H); LC-MS (EI) m/z: 526.2 (M+H$^+$).

Example 8

Using a procedure analogous to Example 1, Example B6 (0.178 g, 0.335 mmol), Example A10 (0.0840 g, 0.352 mmol) and DIEA (0.0701 ml, 0.402 mmol) were combined, purified by flash column chromatography (EtOAc/hexanes) and purified a second time by flash column chromatography (EtOAc/CH$_2$Cl$_2$) to afford t-butyl 5-(3-t-butyl-5-(3-(5-(5-chloropyridin-3-yloxy)-2-fluorophenyl)ureido)-1H-pyrazol-1-yl)-1H-indazole-1-carboxylate (0.0486 g, 23% yield) as a solid. $^1$H NMR (400 MHz, acetone-d$_6$) δ 8.52 (brd, 1H, J=2.8 Hz), 8.46 (s, 1H), 8.37 (d, 1H, J=2.0 Hz), 8.35-8.32 (m, 2H), 8.24 (dt, 1H, J=0.8 and 8.8 Hz), 8.818 (dd, 1H, J=2.8 and 6.8 Hz), 7.22 (dd, 1H, J=8.8 and 10.8 Hz), 6.81 (ddd, 1H, J=3.2, 4.0 and 8.8 Hz), 1.73 (s, 9H), 1.34 (s, 9H); MS (ESI) m/z: 620.2 (M+H$^+$).

The material from the previous step (0.0486 g, 0.078 mmol) and 4M HCl in dioxane (5.0 ml) were combined at RT. A little MeOH was added to give a homogeneous solution. The mixture was heated overnight at 40° C. The completed reaction was concentrated in vacuo, dissolved in MeCN/H$_2$O, frozen and lyophilized to afford 1-(3-t-butyl-1-(1H-indazol-5-yl)-1H-pyrazol-5-yl)-3-(5-(5-chloropyridin-3-yloxy)-2-fluorophenyl)urea (0.0475 g, 103% yield) as the bis-HCl salt. $^1$H NMR (400 MHz, DMSO-d$_6$) δ 9.14 (s, 1H), 8.95 (s, 1H), 8.43-8.42 (m, 1H), 8.34-8.33 (m, 1H), 8.20 (s, 1H), 8.00-7.97 (m, 1H), 7.88-7.87 (m, 1H), 7.70-7.67 (m, 1H), 7.60-7.59 (m, 1H), 7.45-7.42 (m, 1H), 7.32-7.27 (m, 1H), 6.81-6.77 (m, 1H), 6.38 (s, 1H), 1.27 (s, 9H); MS (ESI) m/z: 520.2 (M+H$^+$).

Example 9

Using a procedure analogous to Example 1, Example B7 (0.300 g, 0.550 mmol), Example A10 (0.138 g, 0.577 mmol) and DIEA (0.115 ml, 0.659 mmol) were combined and purified by flash column chromatography (EtOAc/hexanes) to afford tert-butyl 6-(3-tert-butyl-5-(3-(5-(5-chloropyridin-3-yloxy)-2-fluorophenyl)ureido)-1H-pyrazol-1-yl)-3,4-dihydroisoquinoline-2(1H)-carboxylate (0.090 g, 26% yield) as a film. $^1$H NMR (400 MHz, acetone-d$_6$) δ 8.50 (brs, 1H), 8.36 (s, 1H), 8.35-8.32 (m, 2H), 8.19-8.16 (m, 1H), 7.47-7.46 (m, 1H), 7.38-7.36 (m, 2H), 7.31-7.29 (m, 1H), 7.27-7.22 (m, 1H), 6.83-6.79 (m, 1H), 6.46 (s, 1H), 4.63 (brs, 2H), 3.68-3.65 (m, 2H), 2.89-2.86 (m, 2H), 1.50 (s, 9H), 1.32 (s, 9H); MS (ESI) m/z: 635.2 (M+H$^+$).

The material from the previous reaction (0.090 g, 0.14 mmol, 1.00 eq) and 4M HCl in dioxane (5.00 ml) were combined at 22° C. A little MeOH was added to make the mixture homogeneous. After 2.5 h, the completed reaction was concentrated in vacuo, dissolved in MeCN/H$_2$O, frozen and lyophilized to afford 1-(3-tert-butyl-1-(1,2,3,4-tetrahydroisoquinolin-6-yl)-1H-pyrazol-5-yl)-3-(5-(5-chloropyridin-3-yloxy)-2-fluorophenyl)urea (76 mg, 89% yield) as the bis-HCl salt. $^1$H NMR (400 MHz, DMSO-d$_6$) δ 9.51 (brs, 2H), 9.26 (brs, 1H), 9.22 (s, 1H), 8.42-8.41 (m, 1H), 8.33-8.32 (m, 1H), 7.95-7.92 (m, 1H), 7.60-7.59 (m, 1H), 7.42-7.29 (m, 4H), 6.82-6.78 (m, 1H), 6.34 (s, 1H), 4.32-4.30 (m, 2H), 3.39-3.35 (m, 2H), 3.10-3.06 (m, 2H), 1.26 (s, 9H); MS (ESI) m/z: 535.2 (M+H$^+$).

Example 10

Using a procedure analogous to Example 1, Example B9 (0.150 g, 0.351 mmol) and Example A2 (0.101 g, 0.386 mmol) were combined to provide 1-(2-fluoro-4-(2-(methylcarbamoyl)pyridin-4-yloxy)phenyl)-3-(3-isopropyl-1-(quinolin-6-yl)-1H-pyrazol-5-yl)urea hydrochloride (0.126 g, 62% yield). $^1$H NMR (DMSO-d$_6$) δ 9.36 (s, 1H), 9.18-9.15 (m, 2H), 8.92 (d, J=8.4 Hz, 1H), 8.85-8.80 (m, 1H), 8.53 (d, J=5.6 Hz, 1H), 8.44 (d, J=2.4 Hz, 1H), 8.36 (d, J=9.2 Hz, 1H), 8.22 (dd, J=9.2, 2.4 Hz, 1H), 8.14 (t, J=9.2 Hz, 1H), 7.92 (dd, J=8.4, 4.8 Hz, 1H), 7.42 (d, J=2.4 Hz, 1H), 7.31 (dd, J=11.6, 2.8 Hz, 1H), 7.19 (dd, J=5.6, 2.8 Hz, 1H), 7.04 (dd, J=8.8, 2.0 Hz, 1H), 6.45 (s, 1H), 2.96 (m, 1H), 2.79 (d, J=4.8 Hz, 3H), 1.28 (d, J=6.8 Hz, 6H); MS (ESI) m/z: 540.3 (M+H$^+$).

Example 11

Using a procedure analogous to Example 1, Example B10 (0.15 g, 0.363 mmol) and Example A2 (0.100 g, 0.38 mmol) were combined to provide 1-(3-ethyl-1-(quinolin-6-yl)-1H-pyrazol-5-yl)-3-(2-fluoro-4-(2-(methylcarbamoyl)pyridin-4-yloxy)phenyl)urea hydrochloride (0.120 g, 58% yield). $^1$H NMR (DMSO-d$_6$) δ 9.42 (s, 1H), 9.21-9.18 (m, 2H), 8.96 (d, J=8.4 Hz, 1H), 8.87-8.82 (m, 1H), 8.53 (d, J=5.6 Hz, 1H), 8.48 (d, J=1.6 Hz, 1H), 8.38 (d, J=9.2 Hz, 1H), 8.25 (dd, J=9.2, 1.6 Hz, 1H), 8.14 (t, J=8.8 Hz, 1H), 7.95 (dd, J=8.0, 4.8 Hz, 1H), 7.43 (d, J=2.0 Hz, 1H), 7.31 (dd, J=12.0, 2.4 Hz, 1H), 7.19 (dd, J=5.2, 2.0 Hz, 1H), 7.05 (dt, J=8.8, 1.6 Hz, 1H), 6.44 (s, 1H), 2.79 (d, J=4.8 Hz, 3H), 2.64 (q, J=7.6 Hz, 2H), 1.25 (t, J=7.6 Hz, 3H); MS (ESI) m/z: 526.2 (M+H$^+$).

Example 12

Using a procedure analogous to Example 1, Example B3 (0.195 g, 0.441 mmol), Example A10 (0.111 g, 0.464 mmol)

and DIEA (0.0923 ml, 0.530 mmol) were combined and purified first by flash column chromatography (EtOAc/hexanes) and then by reverse phase chromatography (MeCN (w/0.1% TFA)/H$_2$O (w/0.1% TFA)) to provide an aqueous solution of the TFA salt of the desired product. The aqueous residue was treated with satd. NaHCO$_3$ (pH 8) and extracted with EtOAc (3×). The combined organics were washed with brine (1×), dried (MgSO$_4$), and evaporated to afford product (0.0258 g, 11% yield) as the free base. The free base was treated with certified 0.1N HCl (0.97 ml, 2.0 eq) to afford 1-(3-t-butyl-1-(quinolin-6-yl)-1H-pyrazol-5-yl)-3-(5-(5-chloropyridin-3-yloxy)-2-fluorophenyl)urea (0.0262 g, 10% yield) as the bis-HCl salt. $^1$H NMR (400 MHz, DMSO-d$_6$) δ 9.33 (s, 1H), 9.22-9.21 (m, 1H), 9.14-9.13 (m, 1H), 8.83-8.81 (m, 1H), 8.42-8.41 (m, 1H), 8.36 (brs, 1H), 8.33-8.29 (m, 2H), 8.15-8.12 (m, 1H), 7.94-7.91 (m, 1H), 7.88-7.84 (m, 1H), 7.59-7.57 (m, 1H), 7.34-7.28 (m, 1H), 6.82-6.78 (m, 1H), 6.46 (s, 1H), 1.30 (s, 9H); MS (ESI) m/z: 531.0 (M+H$^+$).

Example 13

Using a procedure analogous to Example 1, Example B3 (100 mg, 0.226 mmol), DIEA (73 mg, 0.566 mmol) and Example A18 (63 mg, 0.25 mmol) were combined to yield 1-(3-tert-butyl-1-(quinolin-6-yl)-1H-pyrazol-5-yl)-3-(2-fluoro-5-(2-(methylthio)pyrimidin-4-yloxy)phenyl)urea hydrochloride (61 mg, 50% yield). $^1$H-NMR (DMSO-d$_6$) δ 1.30 (s, 9H), 2.50 (s, 3H), 6.47 (s, 1H), 6.76 (d, 1H), 6.86-6.90 (m, 1H), 7.29-7.34 (m, 1H), 7.92-7.98 (m, 2H), 8.20-8.23 (m, 1H), 8.37 (d, 1H), 8.44 (s, 1H), 8.50 (d, 1H), 8.95 (d, 1H), 9.19-9.20 (m, 1H), 9.28 (s, 1H), 9.46 (s, 1H); MS (ESI) m/z: 544.2 (M+H$^+$).

Example 14

Using a procedure analogous to Example 1, Example B3 (0.10 g, 0.23 mmol), Example A12 (53 mg, 0.23 mmol) and DIEA (64 mg, 0.50 mmol) were combined and purified by reverse phase column chromatography to obtain 1-(3-tert-butyl-1-(quinolin-6-yl)-1H-pyrazol-5-yl)-3-(2-fluoro-5-(6-(hydroxymethyl)pyridin-3-yloxy)phenyl)urea TFA salt. The residue was dissolved in 3M HCl and co-evaporated with isopropyl alcohol (3×). EtOAc was added to the residue and the solid was filtered, washed with EtOAc, and dried under vacuum to obtain 1-(3-tert-butyl-1-(quinolin-6-yl)-1H-pyrazol-5-yl)-3-(2-fluoro-5-(6-(hydroxymethyl)pyridin-3-yloxy)phenyl)urea HCl salt (40 mg, 34% yield). $^1$H NMR (400 MHz, DMSO-d$_6$) δ 9.15 (brm, 1H), 9.05 (brm, 1H), 8.63 (brm, 1H), 8.32 (brm, 1H), 8.23 (brm, 2H), 8.03 (m, 1H), 7.90 (m, 1H), 7.73 (brm, 1H), 7.56 (m, 2H), 7.28 (dd, J=9.2, 12.4 Hz, 1H), 6.74 (m, 1H), 6.44 (s, 1H), 4.60 (m, 2H), 1.30 (s, 9H); MS (ESI) m/z: 527.2 (M+H$^+$).

Example 15

Using a procedure analogous to Example 1, Example B9 (0.120 g, 0.281 mmol) and Example A7 (0.0763 g, 0.309 mmol) were combined to provide 1-(4-(2-carbamoylpyridin-4-yloxy)-2-fluorophenyl)-3-(3-isopropyl-1-(quinolin-6-yl)-1H-pyrazol-5-yl)urea hydrochloride (0.101 g, 65% yield). $^1$H NMR (DMSO-d$_6$) δ 9.23 (s, 1H), 9.11-9.08 (m, 2H), 8.77 (d, J=4.8 Hz, 1H), 8.53 (d, J=6.0 Hz, 1H), 8.35 (d, J=2.0 Hz, 1H), 8.29 (d, J=8.8 Hz, 1H), 8.18-8.11 (m, 3H), 7.84-7.80 (m, 1H), 7.75 (s, 1H), 7.43 (d, J=2.4 Hz, 1H), 7.31 (dd, J=11.6, 2.4 Hz, 1H), 7.20 (dd, J=6.0, 2.4 Hz, 1H), 7.05 (dd, J=9.6, 2.8 Hz, 1H), 6.45 (s, 1H); MS (ESI) m/z: 526.2 (M+H$^+$).

Example 16

Using a procedure analogous to Example 1, Example B3 (85 mg, 0.19 mmol), Example A13 (42 mg, 0.19 mmol) and DIEA (55 mg, 0.42 mmol) were combined in DMSO (1 mL) and heated overnight at 50-55° C. Water was added (50 mL) and the mixture was extracted with EtOAc (3×100 mL), dried (MgSO$_4$), concentrated in vacuo and purified by silica gel column chromatography to obtain 1-(3-tert-butyl-1-(quinolin-6-yl)-1H-pyrazol-5-yl)-3-(2-fluoro-5-(6-methylpyridin-3-yloxy)phenyl)urea. The product treated with 0.10M aq HCl solution to obtain 1-(3-tert-butyl-1-(quinolin-6-yl)-1H-pyrazol-5-yl)-3-(2-fluoro-5-(6-methylpyridin-3-yloxy)phenyl)urea salt HCl salt (56 mg, 52% yield). $^1$H NMR (400 MHz, DMSO-d$_6$) δ 9.38 (brs, 1H), 9.27 (d, J=2.4 Hz, 1H), 9.11 (dd, J=1.6, and 4.8 Hz, 1H), 8.77 (d, J=8.0 Hz, 1H), 8.50 (d, J=3.2 Hz, 1H), 8.34 (d, J=2.4 Hz, 1H), 8.29 (d, J=9.2 Hz, 1H), 8.11 (dd, J=2.4, and 9.2 Hz, 1H), 7.94 (dd, J=3.2, and 6.8 Hz, 1H), 7.83 (m, 2H), 7.68 (d, J=8.8 Hz, 1H), 7.32 (dd, J=9.2, 10.8 Hz, 1H), 6.79 (m, 1H), 6.44 (s, 1H), 2.61 (s, 3H), 1.30 (s, 9H); MS (ESI) m/z: 511.2 (M+H$^+$).

Example 17

Using a procedure analogous to Example 1, Example B9 (213 mg, 0.50 mmol), Example A6 (145 mg, 0.56 mmol) and DIEA (0.09 mL, 0.517 mmol) were combined in DMF (2 mL) to provide 1-(3-isopropyl-1-(quinolin-6-yl)-1H-pyrazol-5-yl)-3-(3-methyl-4-(2-(methylcarbamoyl)pyridin-4-yloxy)phenyl)urea (194 mg, 73% yield). $^1$H NMR (400 MHz, DMSO-d$_6$): δ 9.07 (s, 1H), 8.97 (dd, J=4.2, 1.8 Hz, 1H), 8.76 (q, J=4.9 Hz, 1H), 8.64 (s, 1H), 8.51-8.48 (m, 2H), 8.19-8.16 (m, 2H), 7.97 (dd, J=9.0, 2.4 Hz, 1H), 7.63 (dd, J=8.3, 4.2 Hz, 1H), 7.45 (d, J=2.4 Hz, 1H), 7.33 (dd, J=8.9, 2.6 Hz, 1H), 7.28 (d, J=2.6 Hz, 1H), 7.10-7.04 (m, 2H), 6.43 (s, 1H), 2.95 (m, 1H), 2.78 (d, J=4.9 Hz, 3H), 2.04 (s, 3H), 1.28 (d, J=6.7 Hz, 6H); MS (ESI) m/z: 536.2 (M+H$^+$).

Example 18 mCPBA (1.07 g of ~70%, 4.34 mmol) was added to a solution of Example A18 (545 mg, 2.17 mmol) in CH$_2$Cl$_2$ (15 mL) and the solution was stirred at RT. The mixture was washed with saturated sodium bicarbonate (3×20 mL) and brine (30 mL), dried (Na$_2$SO$_4$) and concentrated in vacuo to yield 0.65 g of a tan foam, which proved to be a mixture of the sulfoxide and sulfone, and which was used as is. In 2.0N methylamine/THF (22 mL) was placed the crude sulfoxide/sulfone mixture (0.61 g, 2.2 mmol) with stirring overnight at 40° C. The mixture was cooled to RT, diluted with ethyl acetate (25 mL), washed with 5% citric acid (25 mL), saturated sodium bicarbonate (25 mL) and brine (25 mL), dried (Na$_2$SO$_4$), concentrated in vacuo and purified by reverse phase chromatography to yield 4-(3-amino-4-fluorophenoxy)-N-methylpyrimidin-2-amine trifluoroacetic acid salt (301 mg, 60% yield). MS (ESI) m/z: 235.0 (M+H$^+$).

In DMSO (2 mL) was placed Example B3 (159 mg, 0.359 mmol), DIEA (139 mg, 1.08 mmol) and 4-(3-amino-4-fluorophenoxy)-N-methylpyrimidin-2-amine trifluoroacetic acid salt (150 mg, 0.431 mmol). The mixture was warmed to 50° C. overnight, then diluted with ethyl acetate (25 mL), washed with 5% citric acid (50 mL), saturated sodium bicarbonate (50 mL) and brine (50 mL), dried (Na$_2$SO$_4$), concentrated in vacuo and purified by column chromatography to yield 1-(3- tert-butyl-1-(quinolin-6-yl)-1H-pyrazol-5-yl)-3-(2-fluoro-5-(2-(methylamino)pyrimidin-4-yloxy)phenyl)urea (93 mg, 49% yield). $^1$H-NMR (DMSO-$d_6$) 1.31 (s, 9H), 2.54-2.86 (br d, 3H), 6.46 (s, 1H), 6.57-6.61 (br m, 1H), 6.91-6.93 (br m, 1H), 7.32-7.37 (m, 1H), 7.94-8.05 (m, 2H), 8.23-8.33 (m, 2H), 8.40 (d, 1H), 8.48 (s, 1H), 8.98 (d, 1H), 9.19-9.21 (m, 1H), 9.43-9.47 (br m, 1H), 9.68-9.73 (br m, 1H); MS (ESI) m/z: 527.2 (M+H$^+$).

Example 19

Using a procedure analogous to Example 1, Example B9 (85 mg, 0.20 mmol), Example A9 (46 mg, 0.20 mmol) and DIEA (57 mg, 0.44 mmol) were combined in DMSO (1 mL) to obtain 1-(2-fluoro-4-(2-(methylamino)pyridin-4-yloxy)phenyl)-3-(3-isopropyl-1-(quinolin-6-yl)-1H-pyrazol-5-yl)urea. The product was treated with 0.100M aq HCl solution to obtain 1-(2-fluoro-4-(2-(methylamino)pyridin-4-yloxy)phenyl)-3-(3-isopropyl-1-(quinolin-6-yl)-1H-pyrazol-5-yl)urea HCl salt (52 mg, 48% yield). $^1$H NMR (400 MHz, DMSO-$d_6$) δ 9.17 (s, 1H), 9.14 (brs, 1H), 8.98 (dd, J=1.2, and 4.0 Hz, 1H), 8.50 (d, J=8.4 Hz, 1H), 8.42 (brs, 1H), 8.20 (d, J=2.8 Hz, 1H), 8.17 (d, J=9.2 Hz, 1H), 7.97 (dd, J=2.4, and 9.2 Hz, 1H), 7.91 (d, J=7.2 Hz, 1H), 7.64 (dd, J=4.0, and 8.4 Hz, 1H), 7.34 (dd, J=2.4, and 11.6 Hz, 1H), 7.07 (dd, J=1.2, and 8.8 Hz, 1H), 6.60 (d, J=6.4 Hz, 1H), 6.43 (s, 1H), 6.17 (brs, 1H), 2.95 (m, 1H), 2.87 (d, J=4.4 Hz, 3H), 1.27 (d, J=6.8 Hz, 6H); MS (ESI) m/z: 512.3 (M+H$^+$).

Example 20

Using a procedure analogous to Example 1, Example B10 (0.13 g, 0.314 mmol), Example A7 (0.086 g, 0.346 mmol) and DIEA (0.12 mL, 0.69 mmol) were dissolved in DMSO (1.5 mL) and the mixture was heated at 55° C. overnight to afford 1-(4-(2-carbamoylpyridin-4-yloxy)-2-fluorophenyl)-3-(3-ethyl-1-(quinolin-6-yl)-1H-pyrazol-5-yl)urea (0.088 g, 55% yield). This was converted to corresponding HCl salt by reacting with HCl (4.0 M HCl/dioxane, 1.0 eq.). $^1$H NMR (DMSO-$d_6$) δ 9.37 (s, 1H), 9.18-9.15 (m, 2H), 8.90 (d, J=8.0 Hz, 1H), 8.54 (d, J=5.6 Hz, 1H), 8.43 (s, 1H), 8.21 (d, J=8.8 Hz, 1H), 8.22-8.12 (m, 3H), 7.91 (m, 1H), 7.78 (s, 1H), 7.45 (d, J=1.6 Hz, 1H), 7.31 (dd, J=12, 2.0 Hz, 1H), 7.21 (dd, J=5.2, 1.4 Hz, 1H), 7.05 (d, J=9.2 Hz, 1H), 6.44 (s, 1H), 2.64 (q, J=7.6 Hz, 2H), 1.25 (t, J=7.2 Hz, 3H); MS (ESI) m/z: 512.3 (M+H$^+$).

Example 21

Using a procedure analogous to Example 1, Example B3 (198 mg, 373 mmol), DIEA (121 mg, 0.933 mmol) and Example A21 (117 mg, 0.448 mmol) were combined to yield 1-(3-tert-butyl-1-(quinolin-6-yl)-1H-pyrazol-5-yl)-3-(2-fluoro-5-(6-(methylcarbamoyl)pyridin-3-yloxy)phenyl)urea (140 mg, 67% yield) as the hydrochloride salt. $^1$H-NMR (DMSO-$d_6$) δ 1.30 (s, 9H), 2.81 (d, 3H), 6.45 (s, 1H), 6.81-6.83 (m, 1H), 7.30-7.35 (m, 1H), 7.43-7.46 (m, 1H), 7.91-8.02 (m, 3H), 8.19-8.21 (m, 1H), 8.34-8.43 (m, 3H), 8.65-8.66 (m, 1H), 8.91 (d, 1H), 9.17-9.19 (m, 1H), 9.28 (br s, 1H), 9.44 (s, 1H); MS (ESI) m/z: 554.2 (M+H$^+$).

Example 22

Using a procedure analogous to Example 1, Example B14 (0.125 g, 0.291 mmol) and Example A7 (0.079 g, 0.320 mmol) were combined to provide 1-(4-(2-carbamoylpyridin-4-yloxy)-2-fluorophenyl)-3-(5-chloro-2-(quinolin-6-yl)phenyl)urea hydrochloride (0.070 g, 43% yield). $^1$H NMR (DMSO-$d_6$) δ 9.20 (d, J=3.6 Hz, 1H), 9.04 (d, J=1.6 Hz, 1H), 8.92 (d, J=8.0 Hz, 1H), 8.54-8.52 (m, 2H), 8.36 (d, J=9.2 Hz, 1H), 8.32 (d, J=1.6 Hz, 1H), 8.23 (t, J=8.8 Hz, 1H), 8.18-8.17 (m, 2H), 8.02 (dd, J=8.4, 1.6 Hz, 1H), 7.93-7.90 (m, 1H), 7.76 (s, 1H), 7.43-7.39 (m, 2H), 7.31-7.26 (m, 2H), 7.20 (dd, J=5.6, 2.4 Hz, 1H), 7.06 (dd, J=8.8, 1.2 Hz, 1H); MS (ESI) m/z: 528.0 (M+H$^+$).

Example 23

Using a procedure analogous to Example 1, Example B9 (35 mg, 0.02 mmol), Example A14 (47 mg, 0.20 mmol) and DIEA were combined in DMSO and heated overnight at 60° C. to obtain 1-(2-fluoro-4-(2-methoxypyridin-4-yloxy)phenyl)-3-(3-isopropyl-1-(quinolin-6-yl)-1H-pyrazol-5-yl)urea HCl salt (54 mg, 49% yield). $^1$H NMR (400 MHz, DMSO-$d_6$) δ 9.35 (brs, 1H), 9.13 (brs, 1H), 8.85 (d, J=2.0 Hz, 1H), 8.74 (s, 1H), 8.35 (dd, J=1.6, and 8.4 Hz, 1H), 8.25 (m, 1H), 7.90 (s, 1H), 7.74 (d, J=8.4 Hz, 1H), 7.71 (brs, 1H), 7.29 (m, 2H), 6.46 (s, 1H), 4.31 (q, J=7.2 Hz, 2H), 2.66 (s, 3H), 1.29 (s, 9H), 1.22 (t, J=7.2 Hz, 3H); MS (ESI) m/z: 556.3 (M+H$^+$).

Example 24

Using a procedure analogous to Example 1, Example B19 (150 mg, 0.329 mmol) and Example A2 (94 mg, 0.362 mmol) were combined to provide 1-(3-tert-butyl-1-(2-methylquinolin-6-yl)-1H-pyrazol-5-yl)-3-(2-fluoro-4-(2-(methylcarbamoyl)pyridin-4-yloxy)phenyl)urea hydrochloride (113 mg, 60% yield). $^1$H-NMR (DMSO-$d_6$) δ 1.33 (s, 9H), 2.79 (d, 3H), 3.00 (s, 3H), 6.49 (s, 1H), 7.02-7.04 (m, 1H), 7.19-7.20 (m, 1H), 7.30 (d, 1H), 7.45 (s, 1H), 8.01 (d, 1H), 8.07-8.09 (m, 1H), 8.34-8.37 (m, 1H), 8.50-8.57 (m, 3H), 8.85-8.87 (m, 1H), 9.10 (d, 1H), 9.29 (s, 1H), 9.61 (s, 1H); MS (ESI) m/z: 568.2 (M+H$^+$).

Example 25

Using a procedure analogous to Example 1, Example B9 (120 mg, 0.28 mmol), Example A20 (80 mg, 0.29 mmol), and DIEA (110 mg, 0.84 mmol) were combined to yield 1-(2-fluoro-5-(6-(trifluoromethyl)pyridin-3-yloxy)phenyl)-3-(3-isopropyl-1-(quinolin-6-yl)-1H-pyrazol-5-yl)urea hydrochloride (62 mg, 40% yield). $^1$H-NMR (DMSO-$d_6$) δ 1.25 (d, 6H), 2.93 (pen, 1H), 6.41 (s, 1H), 6.85-6.88 (m, 1H), 7.32-7.37 (m, 1H), 7.51-7.54 (m, 1H), 7.87-7.90 (m, 2H), 7.96-7.98 (m, 1H), 8.16-8.18 (m, 1H), 8.33 (d, 1H), 8.40 (s, 1H), 8.52 (s, 1H), 8.87 (d, 1H), 9.15-9.16 (m, 1H), 9.28 (s, 1H), 9.42 (s, 1H); MS (ESI) m/z: 551.2 (M+H$^+$).

Example 26

Using a procedure analogous to Example 1, Example B9 (0.200 g, 0.468 mmol) and Example A15 (0.113 g, 0.491 mmol) were combined to provide 1-(4-(2-cyanopyridin-4-yloxy)-2-fluorophenyl)-3-(3-isopropyl-1-(quinolin-6-yl)-1H-pyrazol-5-yl)urea (0.238 g, 100%). MS (ESI) m/z: 508.3 (M+H$^+$)

1-(4-(2-Cyanopyridin-4-yloxy)-2-fluorophenyl)-3-(3-isopropyl-1-(quinolin-6-yl)-1H-pyrazol-5-yl)urea (0.108 g, 0.221 mmol) and N-acetylcysteine (0.072 g, 0.441 mmol) were dissolved in MeOH (0.3 mL). Ammonium acetate (0.041 g, 0.0.529 mmol) was added and the reaction mixture was heated at 60° C. under $N_2$ overnight. The completed reaction was diluted with $H_2O$ (10 ml), basified by $K_2CO_3$, extracted with EtOAc (2×30 mL) and THF (20 mL). The combined organic layers were washed with brine (20 mL), dried (MgSO$_4$), concentrated in vacuo and purified by chromatography to afford 1-(4-(2-carbamimidoylpyridin-4-yloxy)-2-fluorophenyl)-3-(3-isopropyl-1-(quinolin-6-yl)-1H-pyrazol-5-yl)urea (0.019 g, 17% yield) as a white solid. This was converted to corresponding HCl salt by reacting with HCl (4.0 M HCl/dioxane, 1.0 eq.). $^1$H NMR (DMSO-d$_6$) δ 9.57 (s, 2H), 9.36-9.34 (m, 2H), 9.20 (d, J=1.2 Hz, 1H), 9.09 (dd, J=4.4, 1.2 Hz, 1H), 8.74 (d, J=8.0 Hz, 1H), 8.68 (d, J=5.2 Hz, 1H), 8.35 (d, J=2.0 Hz, 1H), 8.28 (d, J=9.2 Hz, 1H), 8.18-8.10 (m, 2H), 7.92 (d, J=2.4 Hz, 1H), 7.80 (dd, J=8.4, 4.8 Hz, 1H), 7.32-7.26 (m, 2H), 7.05 (dd, J=8.8, 1.2 Hz, 1H), 6.44 (s, 1H), 2.97-2.93 (m, 1H), 1.28 (d, J=6.8 Hz, 6H); MS (ESI) m/z: 525.3 (M+H$^+$).

Example 27

Using a procedure analogous to Example 1, Example B7 (159 mg, 0.291 mmol), DIEA (45 mg, 0.35 mmol) and Example A34 (74 mg, 0.35 mmol) were combined to give tert-butyl 6-(3-tert-butyl-5-(3-(3-cyano-5-(pyridin-3-yloxy)phenyl)ureido)-1H-pyrazol-1-yl)-3,4-dihydroisoquinoline-2(1H)-carboxylate (83 mg, 47% yield). MS (ESI) m/z: 608.3 (M+H$^+$).

In CH$_2$Cl$_2$ (8 mL) was placed tert-butyl 6-(3-tert-butyl-5-(3-(3-cyano-5-(pyridin-3-yloxy)phenyl)ureido)-1H-pyrazol-1-yl)-3,4-dihydroisoquinoline-2(1H)-carboxylate (83 mg, 0.14 mmol). HCl (g) was bubbled into reaction mixture until the solution was saturated and the solution was then stirred at RT for 4 hrs. Concentration in vacuo gave a solid which was triturated with ether (10 mL). The solid was collected by filtration, washed with ether (2 mL) and dried to afford 1-(3-tert-butyl-1-(1,2,3,4-tetrahydroisoquinolin-6-yl)-1H-pyrazol-5-yl)-3-(3-cyano-5-(pyridin-3-yloxy)phenyl)urea hydrochloric acid salt (69 mg, 93% yield). $^1$H NMR (300 MHz, DMSO-d$_6$) δ 1.26 (s, 9H), 3.06-3.09 (m, 2H), 3.35-3.40 (m, 2H), 4.28-4.30 (m, 2H), 6.33 (s, 1H), 7.23-7.24 (m, 1H), 7.31-7.34 (m, 1H), 7.39-7.47 (m, 4H), 7.63-7.67 (m, 2H), 7.77-7.78 (m, 1H), 8.52-8.54 (m, 1H), 8.59 (m, 1H), 8.93 (s, 1H), 9.42-9.43 (m, 2H), 10.16 (s, 1H); MS (ESI) m/z: 527.2 (M+H$^+$).

Example 28

Using a procedure analogous to Example 1, Example A35 (95 mg, 0.428 mmol), DIEA (158 mg, 1.22 mmol) and Example B3 (180 mg, 0.407 mmol) were combined to give 1-(5-(2-aminopyrimidin-4-yloxy)-2-fluorophenyl)-3-(3-tert-butyl-1-(quinolin-6-yl)-1H-pyrazol-5-yl)urea hydrochloride salt (102 mg, 48% yield). $^1$H NMR (300 MHz, DMSO-d$_6$) δ 1.31 (s, 9H), 6.46 (s, 1H), 6.65 (d, J=6.8 Hz, 1H), 6.91-6.94 (m, 1H), 7.32-7.37 (m, 1H), 7.91-7.94 (m, 1H), 7.97-8.00 (m, 1H), 8.20-8.23 (m, 1H), 8.31-8.33 (m, 1H), 8.36-8.39 (m, 1H), 8.45-8.46 (m, 1H), 8.92-8.94 (m, 1H), 9.18 (m, 1H), 9.45 (m, 1H), 9.66 (s, 1H), NH2 missing; MS (ESI) m/z: 513.3 (M+H$^+$).

Example 29

Using a procedure analogous to Example 1, Example B9 (0.200 g, 0.468 mmol) and Example A15 (0.113 g, 0.491 mmol) in presence of DIEA (0.179 mL, 0.1.03 mmol) were combined to afford 1-(4-(2-cyanopyridin-4-yloxy)-2-fluorophenyl)-3-(3-isopropyl-1-(quinolin-6-yl)-1H-pyrazol-5-yl)urea (0.238 g, 100%) as a colorless oil. It was converted to corresponding HCl salt by reacting with HCl (4.0 M in dioxane, 1.0 eq.). $^1$H NMR (400 MHz, DMSO-d$_6$) δ 9.19 (s, 1H), 9.09-9.08 (m, 2H), 8.73 (d, J=8.0 Hz, 1H), 8.60 (d, J=6.0 Hz, 1H), 8.32 (d, J=2.4 Hz, 1H), 8.27 (d, J=8.8 Hz, 1H), 8.16 (t, J=9.2 Hz, 1H), 8.10 (dd, J=9.2, 2.4 Hz, 1H), 7.80 (dd, J=8.0, 4.4 Hz, 1H), 7.72 (d, J=2.8 Hz, 1H), 7.31 (dd, J=11.6, 2.8 Hz, 1H), 7.23 (dd, J=5.6, 2.8 Hz, 1H), 7.05 (dd, J=9.2, 2.8 Hz, 1H), 6.45 (s, 1H), 2.95 (m, 1H), 1.27 (d, J=7.2 Hz, 6H); MS (ESI) m/z: 508.3 (M+H$^+$).

Example 30

Using a procedure analogous to Example 1, Example B3 (0.2 g, 0.453 mmol) and Example A29 (0.158 g, 0.453 mmol) were combined in DMSO (4 mL) at 70° C. in presence of DIEA (0.176 g, 1.36 mmol) to provide 1-(3-tert-butyl-1-(quinolin-6-yl)-1H-pyrazol-5-yl)-3-(4-(2-((tert-butyldimethylsilyloxy)methyl)pyridin-4-yloxy)-2-fluorophenyl)urea (0.12 g, 43% yield). $^1$H NMR (400 MHz, CDCl$_3$) δ 9.02 (brs, 1H), 8.86 (d, J=8.5 Hz, 1H), 7.65 (m, 3H), 7.27 (dd, J=8, 4.4 Hz, 1H), 6.99 (s, 1H), 6.89 (brd, J=9.0 Hz, 1H), 6.73 (dd, J=12, 2.5 Hz, 1H), 6.65 (s, 1H), 6.60 (m, 1H), 4.71 (s, 2H), 1.36 (s, 9H), 0.85 (s, 9H), 0.05 (s, 6H); MS (ESI) m/z: 641.3 (M+H$^+$).

A solution of 1-(3-tert-butyl-1-(quinolin-6-yl)-1H-pyrazol-5-yl)-3-(4-(2-((tert-butyldimethylsilyloxy)methyl)pyridin-4-yloxy)-2-fluorophenyl)urea (0.12 g, 0.19 mmol) in THF (2 ml) was treated with TBAF (1.0 ml, 1.0 M solution in THF) at RT for 1 hour. Water (10 ml) was added and the separated solid was filtered, washed with water and dried to give desilylated product 1-(3-tert-butyl-1-(quinolin-6-yl)-1H-pyrazol-5-yl)-3-(2-fluoro-4-(2-(hydroxymethyl)pyridin-4-yloxy)phenyl)urea as a white solid (0.090 g, 91% yield). $^1$H NMR (400 MHz, DMSO-d$_6$) δ 9.01 (brs, 1H), 8.97 (dd, J=4.2, 1.6 Hz, 2H), 8.50 (brd, J=8.3 Hz, 1H), 8.36 (d, J=5.5 Hz, 2H), 8.18 (m, 2H), 7.97 (dd, J=9, 2 Hz, 1H), 7.63 (dd, J=9, 4.4 Hz, 1H), 7.22 (dd, J=12, 2.5 Hz, 1H), 6.99 (m, 1H), 6.93 (d, J=2.5 Hz, 1H), 6.82 (dd, J=5.7, 2.5 Hz, 1H), 6.48 (s, 1H), 5.40 (t, J=6 Hz, 1H), 4.50 (d, J=8 Hz, 2H), 1.32 (s, 9H); MS (ESI) m/z: 527.2 (M+H$^+$). The free base was converted to hydrochloride salt. $^1$H NMR (400 MHz, DMSO-d$_6$) δ 9.31 (brs, 1H), 9.23 (m, 1H), 9.07 (dd, J=4.2, 1.6 Hz, 1H), 8.70 (brd, J=8.3 Hz, 1H), 8.65 (d, J=6.8 Hz, 2H), 8.32 (d, J=2 Hz, 1H), 8.27 (d, J=9 Hz, 1H), 8.22 (d, J=9 Hz, 1H), 8.09 (dd, J=9, 2.3 Hz, 1H), 7.75 (dd, J=8, 4.5 Hz, 1H), 7.43-7.37 (m, 2H), 7.34 (d, 2.8 Hz, 1H), 7.12 (m, 1H), 6.48 (s, 1H), 4.77 (s, 2H), 1.32 (s, 9H); MS (ESI) m/z: 527.2 (M+H$^+$).

Example 31

Using a procedure analogous to Example 4, Example B25 (0.30 g, 0.89 mmol) and Example A31 (0.26 g, 0.98 mmol) in presence of N-methylpyrrolidine (catalytic amount) were combined to afford 1-(2-fluoro-4-(2-(isopropylamino)pyridin-4-yloxy)phenyl)-3-(3-isopropyl-1-(quinolin-6-yl)-1H-pyrazol-5-yl)urea (0.26 g, 54% yield). The product was treated with methanesulfonic acid to afford 1-(2-fluoro-4-(2-(isopropylamino)pyridin-4-yloxy)phenyl)-3-(3-isopropyl-1-(quinolin-6-yl)-1H-pyrazol-5-yl)urea mesylate salt (260 mg, 88% yield). $^1$H NMR (400 MHz, DMSO-d$_6$) δ 9.03 (m, 1H), 9.01 (s, 1H), 8.96 (dd, J=1.6, and 4.0 Hz, 1H), 8.49 (brd, J=8.4 Hz, 1H), 8.33 (brm, 1H), 8.17 (m, 2H), 7.95 (dd, J=2.8, and 9.2 Hz, 1H), 7.87 (d, J=7.6 Hz, 1H), 7.63 (d, J=4.4, and 8.4 Hz, 1H), 7.33 (dd, J=2.8, and 11.6 Hz, 1H), 7.06 (m, 1H), 6.61 (dd, J=2.4, and 7.2 Hz, 1H), 6.41 (s, 1H), 6.09 (brs, 1H), 3.81

(m, 1H), 2.91 (m, 1H), 2.30 (s, 3H), 1.25 (d, J=6.8 Hz, 6H), 1.13 (d, J=6.0 Hz, 6H); MS (ESI) m/z: 540.3 (M+H$^+$).

Example 32

Using general method A, Example B20 (0.0643 g, 0.226 mmol) and Example A7 (0.168 g, 0.678 mmol) were combined to afford 1-(3-tert-butyl-1-(H-imidazo[1,2-a]pyridin-6-yl)-1H-pyrazol-5-yl)-3-(4-(2-carbamoylpyridin-4-yloxy)-2-fluorophenyl)urea (0.071 g, 59%) as a white solid. It was converted to corresponding HCl salt by reacting with HCl (4.0 M in dioxane, 1.0 eq.). $^1$H NMR (400 MHz, DMSO-d$_6$) δ 9.48 (s, 1H), 9.33 (d, J=0.8 Hz, 1H), 9.13 (d, J=1.6 Hz, 1H), 8.53 (d, J=5.2 Hz, 1H), 8.41 (d, J=2.4 Hz, 1H), 8.26 (d, J=2.0 Hz, 1H), 8.17-8.09 (m, 4H), 7.72 (s, 1H), 7.39 (d, J=2.4 Hz, 1H), 7.32 (dd, J=12.0, 2.8 Hz, 1H), 7.20 (dd, J=5.6, 2.8 Hz, 1H), 7.05 (dd, J=9.2, 1.6 Hz, 1H), 6.49 (s, 1H), 1.32 (s, 9H); MS (ESI) m/z: 529.3 (M+H$^+$).

Example 33

Using a procedure analogous to Example 1, Example B9 (100 mg, 0.23 mmol) and Example A12 (55 mg, 0.23 mmol) in presence of DIEA (90 µL, 0.51 mmol) were combined to afford 1-(2-fluoro-5-(6-(hydroxymethyl)pyridin-3-yloxy)phenyl)-3-(3-isopropyl-1-(quinolin-6-yl)-1H-pyrazol-5-yl)urea (30 mg, 25% yield). The product was treated with methanesulfonic acid to afford 1-(2-fluoro-5-(6-(hydroxymethyl)pyridin-3-yloxy)phenyl)-3-(3-isopropyl-1-(quinolin-6-yl)-1H-pyrazol-5-yl)urea mesylate salt (23 mg, 65% yield). $^1$H NMR (400 MHz, DMSO-d$_6$) δ 9.11 (brs, 1H), 9.10 (m, 1H), 9.06 (m, 1H), 8.65 (d, J=8.4 Hz, 1H), 8.34 (s, 1H), 8.25 (d, J=1.6 Hz, 1H), 8.21 (d, J=9.2 Hz, 1H), 8.03 (dd, J=2.4, and 9.2 Hz, 1H), 7.91 (dd, J=2.8, and 6.4 Hz, 1H), 7.75 (dd, J=4.8, and 8.4 Hz, 1H), 7.58 (s, 1H), 7.30 (m, 1H), 6.75 (m, 1H), 6.40 (s, 1H), 4.61 (s, 2H), 2.92 (m, 1H), 2.32 (s, 3H), 1.25 (d, J=6.8 Hz, 6H); MS (ESI) m/z: 513.3 (M+H$^+$).

Example 34

Using a procedure analogous to Example B19 step 2, Example A2 (1.00 g, 3.83 mmol) and 2,2,2-trichloroethyl carbonochloridate (1.30 g, 6.12 mmol) were combined to give 2,2,2-trichloroethyl 2-fluoro-4-(2-(methylcarbamoyl)pyridin-4-yloxy)phenylcarbamate. MS (ESI) m/z: 436.0, 438.0 (M+H).

A solution of Example B28 (57 mg, 0.213 mmol), 2,2,2-trichloroethyl 2-fluoro-4-(2-(methylcarbamoyl)pyridin-4-yloxy)phenylcarbamate (102 mg, 0.235 mmol) and DIEA (110 mg, 0.853 mmol) in DMSO (1.5 mL) was placed was warmed to 60° C. overnight. It was then treated with additional 2,2,2-trichloroethyl 2-fluoro-4-(2-(methylcarbamoyl)pyridin-4-yloxy)phenylcarbamate (~200 mg), warmed to 60° C. overnight. The reaction was diluted with ethyl acetate (25 mL) and 5% citric acid (20 mL). The organic phase was separated, washed with saturated sodium bicarbonate (20 mL) and brine (20 mL), dried (Na$_2$SO$_4$), concentrated in vacuo and purified by chromatography (Si-25 column, MeOH/EtOAc) to afford impure product. Repurification via reverse phase chromatography (C18-25 column, CH$_3$CN/H$_2$O) gave a residue which was treated with 1N sodium hydroxide (3 mL) and extracted with ethyl acetate (2×20 mL). The combined organic phases were dried (Na$_2$SO$_4$), concentrated in vacuo and treated with 4N HCl/dioxane (0.1 mL) to afford 1-(3-tert-butyl-1-(quinoxalin-6-yl)-1H-pyrazol-5-yl)-3-(2-fluoro-4-(2-(methylcarbamoyl)pyridin-4-yloxy)phenyl)urea hydrochloric acid salt (14 mg, 12% yield). $^1$H NMR (300 MHz, DMSO-d$_6$) δ 1.31 (s, 9H), 2.77 (d, 3H), 6.47 (s, 1H), 7.00-7.05 (m, 1H), 7.15-7.18 (m, 1H), 7.26-7.28 (m, 1H), 7.39 (m, 1H), 7.65 (m, 1H), 8.08-8.13 (m, 2H), 8.21-8.25 (m, 2H), 8.50 (m, 1H), 8.78 (m, 1H), 8.97-9.03 (m, 3H), 9.13 (s, 1H); MS (ESI) m/z: 555.2 (M+H$^+$).

Example 35

Using a procedure analogous to Example 1, Example B9 (0.145 g, 0.339 mmol) and Example A27 (0.087 g, 0.323 mmol) in presence of DIEA (0.124 mL, 0.710 mmol) were combined to afford 1-(4-(2-(1H-pyrazol-4-yl)pyridin-4-yloxy)-2-fluorophenyl)-3-(3-isopropyl-1-(quinolin-6-yl)-1H-pyrazol-5-yl)urea (0.112 g, 63%) as a white foam. It was converted to corresponding mesylate salt by reacting with MsOH (1.0 eq.). $^1$H NMR (400 MHz, DMSO-d$_6$) δ 9.10-9.03 (m, 3H), 8.63-8.52 (m, 4H), 8.26-8.20 (m, 2H), 8.03 (d, J=3.6 Hz, 1H), 7.78-7.70 (m, 2H), 7.40 (d, J=10.8 Hz, 1H), 7.14-7.09 (m, 2H), 6.44 (s, 1H), 2.95 (m, 1H), 2.33 (s, 3H), 1.27 (d, J=7.2 Hz, 6H); MS (ESI) m/z: 549.3 (M+H$^+$).

Example 36

Example B22 (0.310 g, 0.715 mmol), Example A2 (0.187 g, 0.715 mmol) and DIEA (0.274 ml, 1.57 mmol) were combined in DMSO (3 ml) and stirred at 70° C. After 18 h, the completed reaction was cooled to RT, diluted with brine and extracted with EtOAc (3×). The combined organics were washed with brine (2×), dried (MgSO$_4$), evaporated and purified by flash column chromatography (EtOAc/hexanes) to afford the free base (84.1 mg, 22% yield). The free base thus obtained was treated with certified 0.1N HCl (3.1 ml, 2.0 eq) to afford 1-(1-(benzo[d]thiazol-6-yl)-3-isopropyl-1H-pyrazol-5-yl)-3-(2-fluoro-4-(2-(methylcarbamoyl)pyridin-4-yloxy)phenyl)urea (45 mg) as the bis-HCl salt. $^1$H NMR (400 MHz, DMSO-d$_6$) δ 9.49 (s, 1H), 9.00 (s, 2H), 8.81 (q, J=4.8 Hz, 1H), 8.52 (d, J=5.6 Hz, 1H), 8.39 (d, J=1.6 Hz, 1H), 8.24 (d, J=8.80 Hz, 1H), 8.19 (t, J=9.2 Hz, 1H), 7.70 (dd, J=2.4 and 8.8 Hz, 1H), 7.42 (d, J=2.4 Hz), 7.31 (dd, J=3.2 and 12.0 Hz, 1H), 7.18 (dd, J=2.8 and 6.0 Hz, 1H), 7.06 (ddd, J=1.2, 2.8 and 8.8 Hz, 1H), 6.42 (s, 1H), 2.92 (septet, J=7.2 Hz, 1H), 2.79 (d, J=4.8 Hz, 3H), 1.26 (d, J=7.2 Hz, 6H); MS (ESI) m/z: 546.3 (M+H$^+$).

Example 37

Example B23 (0.200 g, 0.464 mmol), Example A2 (0.121 g, 0.464 mmol) and i-Pr$_2$NEt (0.178 ml, 1.02 mmol) were combined in DMSO (2 ml) and stirred with heating at 70° C. After 18 h, the completed reaction was cooled to RT, diluted with brine and extracted with EtOAc (3×). The combined organics were washed with brine (2×), dried (MgSO$_4$), concentrated in vacuo and purified by flash column chromatography (EtOAc/hexanes to EtOAc to THF) to afford impure product. This was purified a second time by reverse phase chromatography (MeCN (w/0.1% TFA)/H$_2$O (w/0.1% TFA)) to afford desired product (110 mg, 36% yield) as the TFA salt following lyophilization. The TFA salt thus obtained was dissolved in THF and shaken orbitally with MP-carbonate resin (110 mg) for 2 h. The supernatant was decanted away and the beads washed with THF (2×). The combined decants were concentrated, diluted with MeCN/H$_2$O and then treated with certified 0.1N HCl (3.3 ml, 2.0 eq) to afford 1-(2-fluoro-4-(2-(methylcarbamoyl)pyridin-4-yloxy)phenyl)-3-(3-isopropyl-1-(1-methyl-1H-benzo[d]imidazol-5-yl)-1H-pyrazol-5-yl)urea (31 mg) as the bis-HCl salt. $^1$H NMR (400 MHz, DMSO-d$_6$) δ 9.46 (brs, 1H), 9.11 (s, 1H), 9.07 (s, 1H), 8.76 (brq, J=4.8 Hz, 1H), 8.50 (d, J=5.6 Hz, 1H), 8.11 (t, J=9.2 Hz, 1H), 8.06 (d, J=8.8 Hz), 7.98 (d, J=2.0 Hz, 1H), 7.78 (m, 1H), 7.37 (d, J=2.8 Hz, 1H), 7.28 (dd, J=2.4 and 11.2 Hz, 1H), 7.16 (dd, J=2.4 and 5.6 Hz, 1H), 7.02 (ddd, J=1.2, 2.8 and 8.8 Hz, 1H), 6.38 (s, 1H), 4.08 (s, 3H), 2.92 (septet, J=6.8 Hz, 1H), 2.76 (d, J=4.8 Hz, 3H), 1.24 (d, J=6.8 Hz, 6H); MS (ESI) m/z: 543.2 (M+H$^+$).

Example 38

Using general method A, Example B21 (0.0.054 g, 0.20 mmol) and Example A2 (0.16 g, 0.60 mmol) were combined to afford 1-(1-(H-imidazo[1,2-a]pyridin-6-yl)-3-isopropyl-1H-pyrazol-5-yl)-3-(2-fluoro-4-(2-(methylcarbamoyl)pyridin-4-yloxy)phenyl)urea (0.045 g, 43% yield) as a white solid. It was converted to corresponding mesylate salt by reacting with MsOH (1.0 eq.). $^1$H NMR (400 MHz, DMSO-d$_6$) δ 9.19 (m, 1H), 8.49 (d, J=6.0 Hz, 1H), 8.33 (d, J=2.0 Hz, 1H), 8.24 (dd, J=9.6, 3.0 Hz, 1H), 7.15 (d, J=2.0 Hz, 1H), 8.08 (d, J=10.0 Hz, 1H), 8.01 (t, J=8.8 Hz, 1H), 7.53 (d, J=3.5 Hz, 1H), 7.12 (dd, J=6.0, 3.0 Hz, 1H), 7.06 (dd, J=11.6, 2.8 Hz, 1H), 6.96 (m, 1H), 6.45 (s, 1H), 3.01 (m, 1H), 2.94 (s, 3H), 2.70 (s, 3H), 1.33 (d, J=6.4 Hz, 6H); MS (ESI) m/z: 529.3 (M+H$^+$).

Example 39

Using general method A, Example B21 (0.030 g, 0.11 mmol) and Example A7 (0.082 g, 0.33 mmol) were combined to afford 1-(1-(H-imidazo[1,2-a]pyridin-6-yl)-3-isopropyl-1H-pyrazol-5-yl)-3-(4-(2-carbamoylpyridin-4-yloxy)-2-fluorophenyl)urea (0.0245 g, 43% yield) as a white solid. It was converted to corresponding HCl salt by reacting with HCl (4.0 M in dioxane, 1.0 eq.). $^1$H NMR (400 MHz, DMSO-d$_6$) δ 9.26 (d, J=0.8 Hz, 1H), 8.69 (d, J=6.4 Hz, 1H), 8.38 (d, J=1.6 Hz, 1H), 8.26 (dd, J=9.6, 1.2 Hz, 1H), 8.20-8.11 (m, 3H), 7.96 (s, 1H), 7.48 (d, J=5.6 Hz, 1H), 7.23 (dd, J=11.6, 2.8 Hz, 1H), 7.10 (d, J=9.2 Hz, 1H), 6.51 (s, 1H), 3.03 (m, 1H), 1.37 (d, J=6.8 Hz, 6H); MS (ESI) m/z: 515.2 (M+H$^+$).

Example 40

Using a procedure analogous to Example 1, Example A39 (63 mg, 0.29 mmol) and Example B9 (122 mg, 0.29 mmol) were combined to provide 1-(4-(2-aminopyridin-4-yloxy)-2-fluorophenyl)-3-(3-isopropyl-1-(quinolin-6-yl)-1H-pyrazol-5-yl)urea contaminated with 2,2,2-trichloroethanol (56 mg, 28% yield). $^1$H NMR (400 MHz, DMSO-d$_6$) δ 8.99-8.96 (m, 2H), 8.93 (d, J=1.5 Hz, 1H), 8.49 (m, 1H), 8.19-8.16 (m, 2H), 8.10 (t, J=9.2 Hz, 1H), 7.95 (dd, J=9.1, 2.3 Hz, 1H), 7.80 (d, J=5.8 Hz, 1H), 7.63 (dd, J=8.3, 4.0 Hz, 1H), 7.15 (dd, J=11.8, 2.8 Hz, 1H), 6.95 (m, 1H), 6.44 (s, 1H), 6.13 (dd, J=5.9, 2.2 Hz, 1H), 5.94 (s, 2H), 5.82 (d, J=2.0 Hz, 1H), 2.94 (m, 1H), 1.27 (d, J=6.8 Hz, 6H); MS (ESI) m/z: 498.2 (M+H$^+$).

A solution of the above 1-(4-(2-aminopyridin-4-yloxy)-2-fluorophenyl)-3-(3-isopropyl-1-(quinolin-6-yl)-1H-pyrazol-5-yl)urea (44 mg, 0.061 mmol theory) and pyridine (0.30 mL, 3.7 mmol) in CH$_2$Cl$_2$ (1 mL) was treated with acetic anhydride (0.040 mL, 0.39 mmol). The reaction was stirred for 60 h and then partitioned between EtOAc and 2 M aq Na$_2$CO$_3$. The organic layer was washed with water and brine. The aqueous phases were back extracted with EtOAc. The combined organic phases were dried (Na$_2$SO$_4$), concentrated in vacuo and purified by reverse-phase chromatography to provide 1-(4-(2-acetamidopyridin-4-yloxy)-2-fluorophenyl)-3-(3-isopropyl-1-(quinolin-6-yl)-1H-pyrazol-5-yl)urea (25 mg, 76% yield). $^1$H NMR (400 MHz, DMSO-d$_6$) δ 10.53 (s, 1H), 9.01 (s, 1H), 8.96-8.94 (m, 2H), 8.49 (m, 1H), 8.18-8.11 (m, 4H), 7.95 (dd, J=8.8, 2.4 Hz, 1H), 7.64-7.59 (m, 2H), 7.21 (dd, J=11.8, 2.7 Hz, 1H), 6.98 (m, 1H), 6.65 (dd, J=5.8, 2.4 Hz, 1H), 6.43 (s, 1H), 2.93 (m, 1H), 2.03 (s, 3H), 1.26 (d, J=6.8 Hz, 6H); MS (ESI) m/z: 540.3 (M+H$^+$).

Example 41

Using as procedure analogous to Example 4, Example B25 (100 mg, 0.30 mmol) and Example A30 (74 mg, 0.30 mmol) in presence of N-methylpyrrolidine (catalytic amount) were combined to afford 1-(4-(2-(ethylamino)pyridin-4-yloxy)-2-fluorophenyl)-3-(3-isopropyl-1-(quinolin-6-yl)-1H-pyrazol-5-yl)urea (70 mg, 45% yield). The product was treated with methanesulfonic acid to afford 1-(4-(2-(ethylamino)pyridin-4-yloxy)-2-fluorophenyl)-3-(3-isopropyl-1-(quinolin-6-yl)-1H-pyrazol-5-yl)urea mesylate salt (71 mg, 87% yield). $^1$H NMR (400 MHz, DMSO-d$_6$) δ 9.02 (m, 1H), 9.01 (s, 1H), 8.97 (dd, J=1.6, and 4.0 Hz, 1H), 8.49 (brd, J=8.4 Hz, 1H), 8.37 (brs, 1H), 8.17 (m, 2H), 7.95 (dd, J=2.4, and 8.8 Hz, 1H), 7.88 (d, J=7.2 Hz, 1H), 7.63 (d, J=4.4, and 8.4 Hz, 1H), 7.33 (dd, J=2.8, and 11.6 Hz, 1H), 7.06 (m, 1H), 6.61 (dd, J=2.0, and 7.2 Hz, 1H), 6.41 (s, 1H), 6.13 (brs, 1H), 3.23 (m, 2H), 2.92 (m, 1H), 2.28 (s, 3H), 1.25 (d, J=6.8 Hz, 6H), 1.13 (t, J=7.2 Hz, 3H); MS (ESI) m/z: 526.2 (M+H$^+$).

Example 42

Using a procedure analogous to Example 1, Example B9 (295 mg, 0.69 mmol) and Example A40 (214 mg, 0.763 mmol) were combined in DMF (3 mL) to provide 1-(3-isopropyl-1-(quinolin-6-yl)-1H-pyrazol-5-yl)-3-(3-methyl-4-(2-(1-methyl-1H-pyrazol-4-yl)pyridin-4-yloxy)phenyl)urea (278 mg, 72% yield). $^1$H NMR (400 MHz, DMSO-d$_6$) δ 9.00 (s, 1H), 8.94 (dd, J=4.2, 1.6 Hz, 1H), 8.59 (s, 1H), 8.45 (dd, J=8.6, 1.0 Hz, 1H), 8.29 (d, J=6.0 Hz, 1H), 8.20 (s, 1H), 8.15-8.13 (m, 2H), 7.94 (dd, J=9.1, 2.4 Hz, 1H), 7.91 (s, 1H), 7.60 (dd, J=8.5, 4.1 Hz, 1H), 7.40 (d, J=2.3 Hz, 1H), 7.27 (dd, J=8.6, 2.4 Hz, 1H), 7.11 (d, J=2.2 Hz, 1H), 6.99 (d, J=8.8 Hz, 1H), 6.45 (dd, J=5.7, 2.4 Hz, 1H), 6.39 (s, 1H), 3.83 (s, 3H), 2.92 (m, 1H), 2.05 (s, 3H), 1.25 (d, J=6.9 Hz, 6H); MS (ESI) m/z: 559.2 (M+H$^+$).

Example 43

Using a procedure analogous to Example 1, Example B3 (0.711 g, 1.66 mmol) and Example A28 (0.450 g, 1.58 mmol) in presence of DIEA (0.61 mL, 3.48 mmol) were combined to afford 1-(2-fluoro-4-(2-(1-methyl-1H-pyrazol-4-yl)pyridin-4-yloxy)phenyl)-3-(3-isopropyl-1-(quinolin-6-yl)-1H-pyrazol-5-yl)urea (0.431 g, 48% yield) as a white solid. It was converted to corresponding mesylate salt by reacting with MsOH (1.0 eq.). $^1$H NMR (400 MHz, DMSO-d$_6$) δ 9.08-9.04 (m, 3H), 8.66 (d, J=8.8 Hz, 1H), 8.57-8.54 (m, 2H), 8.26-8.16 (m, 4H), 8.05 (dd, J=9.2, 2.4 Hz, 1H), 7.75 (q, J=4.4 Hz, 1H), 7.64 (s, 1H), 7.37 (dd, J=11.6, 2.0 Hz, 1H), 7.12-7.08 (m, 2H), 6.41 (s, 1H), 3.90 (s, 3H), 2.92 (m, 1H), 2.33 (s, 3H), 1.24 (d, J=7.2 Hz, 6H); MS (ESI) m/z: 563.3 (M+H$^+$).

Example 44

Using a procedure analogous to Example 4, Example B26 (100 mg, 0.29 mmol) and Example A31 (75 mg, 0.29 mmol) in presence of N-methylpyrrolidine (catalytic amount) were combined to afford 1-(3-tert-butyl-1-(quinolin-6-yl)-1H-pyrazol-5-yl)-3-(2-fluoro-4-(2-(isopropylamino)pyridin-4-yloxy)phenyl)urea (59 mg, 32% yield). The product was treated with methanesulfonic acid to afford 1-(3-tert-butyl-1-(quinolin-6-yl)-1H-pyrazol-5-yl)-3-(2-fluoro-4-(2-(isopropylamino)pyridin-4-yloxy)phenyl)urea mesylate salt (63 mg, 93% yield). $^1$H NMR (400 MHz, DMSO-d$_6$) δ 9.03 (m, 1H), 9.00 (s, 1H), 8.98 (m, 1H), 8.54 (brd, J=8.4 Hz, 1H), 8.35 (brm, 1H), 8.17 (m, 2H), 7.97 (dd, J=2.4, and 9.2 Hz, 1H), 7.86 (d, J=7.2 Hz, 1H), 7.66 (d, J=4.4, and 8.4 Hz, 1H), 7.33 (dd, J=2.8, and 11.6 Hz, 1H), 7.05 (m, 1H), 6.61 (dd, J=2.4, and 6.8 Hz, 1H), 6.45 (s, 1H), 6.08 (brs, 1H), 3.81 (m, 1H), 2.29 (s, 3H), 1.29 (s, 9H), 1.13 (d, J=6.0 Hz, 6H); MS (ESI) m/z: 554.2 (M+H$^+$).

Example 45

Using a procedure analogous to Example 1, Example B10 (0.060 g, 0.15 mmol) and Example A28 (0.041 g, 0.15 mmol) in presence of DIEA (0.056 mL, 0.32 mmol) were combined to afford 1-(3-ethyl-1-(quinolin-6-yl)-1H-pyrazol-5-yl)-3-(2-fluoro-4-(2-(1-methyl-1H-pyrazol-4-yl)pyridin-4-yloxy)phenyl)urea (47.6 mg, 60% yield) as a white foam. It was converted to corresponding mesylate salt by reacting with MsOH (1.0 eq.). $^1$H NMR (400 MHz, DMSO-d$_6$) δ 9.03-8.95 (m, 3H), 8.55-8.48 (m, 3H), 8.19-8.13 (m, 3H), 7.95 (dd, J=9.2, 2.4 Hz, 1H), 7.64 (dd, J=8.4, 4.4 Hz, 1H), 7.55 (s, 1H), 7.32 (dd, J=12.0, 2.8 Hz, 1H), 7.07-7.01 (m, 2H), 6.36 (s, 1H), 3.86 (s, 3H), 2.56 (q, J=7.2 Hz, 2H), 2.25 (s, 3H), 1.18 (t, J=7.6 Hz, 3H); MS (ESI) m/z: 549.3 (M+H$^+$).

Example 46

Using general method A, Example B27 (77 mg, 0.28 mmol) and Example A2 (150 mg, 0.57 mmol) in presence of DPPA (67 µL, 0.31 mmol) and Et$_3$N (44 µL, 0.31 mmol) were combined to afford 1-(1-(benzo[d]oxazol-5-yl)-3-isopropyl-1H-pyrazol-5-yl)-3-(2-fluoro-4-(2-(methylcarbamoyl)pyridin-4-yloxy)phenyl)urea (105 mg, 70% yield). $^1$H NMR (400 MHz, DMSO-d$_6$) δ 8.96 (d, J=2.0 Hz, 1H), 8.88 (s, 1H), 8.86 (s, 1H), 8.77 (q, J=4.8 Hz, 1H), 8.49 (d, J=6.0 Hz, 1H), 8.16 (t, J=9.2 Hz, 1H), 7.94 (dd, J=3.2 and 5.2 Hz, 1H), 7.57 (dd, J=2, and 8.8 Hz, 1H), 7.38 (d, J=2.8 Hz, 1H), 7.28 (dd, J=2.4 and 11.6 Hz, 1H), 7.14 (dd, J=2.8 and 5.6 Hz, 1H), 7.03 (m, 1H), 6.37 (s, 1H), 2.76 (d, J=4.8 Hz, 3H), 1.23 (d, J=6.8 Hz, 6H); MS (ESI) m/z: 530.2 (M+H$^+$).

Example 47

To a suspension of 5-amino-2-fluorobenzonitrile (1.00 g, 7.38 mmol) in conc HCl (15 mL) at 0° C. was added a solution of NaNO$_2$ (0.64 g, 9.28 mmol) in water (15 mL) slowly over 15 min. The resultant mixture was stirred for 90 min at 0° C. A solution comprised of SnCl$_2$.2H$_2$O (3.37 g, 14.9 mmol), conc HCl (5 mL) and water (5 mL) was added drop wise over 20 min. The mixture was stirred for 2 h at 0° C., and was extracted with EtOAc (4×25 mL). The aqueous portion was cooled with an ice bath and cautiously treated with 70 mL of 3 M NaOH (70 mL) to a final pH of 5. The aqueous was extracted with EtOAc (2×50 mL). All organics were combined and concentrated in vacuo to afford a brown oil (2.58 g), which was combined with pivaloylacetonitrile (1.00 g, 8.0 mmol) in isopropanol (15 mL). The resultant solution was heated to reflux for 28 h. The reaction mixture was concentrated in vacuo, diluted with EtOAc (30 mL) and washed with water (20 mL), satd aq NaHCO$_3$ (20 mL), water (20 mL) and brine (20 mL). The aqueous was further extracted with EtOAc (2×20 mL). The combined organics were dried (MgSO$_4$), concentrated in vacuo and purified by chromatography on silica gel to provide 5-(5-amino-3-tert-butyl-1H-pyrazol-1-yl)-2-fluorobenzonitrile (1.24 g, 65% yield). $^1$H NMR (400 MHz, DMSO-d$_6$) δ 8.05 (m, 1H), 7.97 (m, 1H), 7.61 (t, J=9.0 Hz, 1H), 5.43 (s, 1H), 5.42 (s, 2H); MS (ESI) m/z: 259.3 (M+H$^+$).

A solution 5-(5-amino-3-tert-butyl-1H-pyrazol-1-yl)-2-fluorobenzonitrile (86 mg, 0.33 mmol) and acetone oxime (37 mg, 0.50 mmol) in DMAc (1 mL) was treated with potassium tert-butoxide (56 mg, 0.50 mmol). The reaction mixture was stirred 45 min at RT. The mixture was diluted with EtOAc (30 mL), washed with water (10 mL) and brine (2×10 mL), dried (Na$_2$SO$_4$), concentrated in vacuo and purified via silica gel chromatography to provide propan-2-one O-2-cyano-4-(5-amino-3-tert-butyl-1H-pyrazol-1-yl)phenyl oxime (47 mg, 45% yield). $^1$H NMR (400 MHz, Acetone-d$_6$) δ 7.93-7.89 (m, 2H), 7.63 (dd, J=8.8, 0.8 Hz, 1H), 5.52 (s, 1H), 4.87 (s, 2H), 2.17 (s, 3H), 2.08)s, 3H), 1.26 (s, 9H); MS (ESI) m/z: 312.3 (M+H$^+$).

A solution of propan-2-one O-2-cyano-4-(5-amino-3-tert-butyl-1H-pyrazol-1-yl)phenyl oxime (47 mg, 0.15 mmol) in ethyl acetate (5 mL) was treated with 2 M aq Na$_2$CO$_3$ (0.67 mL) and isopropenyl chloroformate (0.050 mL, 0.46 mmol). The reaction was stirred at RT. After 2 h, additional isopropenyl chloroformate (0.1 mL, 0.92 mmol) was added. After1 h, additional isopropenyl chloroformate (0.1 mL, 0.92 mmol) and 2 M aq Na$_2$CO$_3$ (0.5 mL, 1 mmol) were added. After another hour, the reaction was diluted with EtOAc (10 mL), washed with water (10 mL) and brine (10 mL), dried (MgSO$_4$) and concentrated in vacuo to provide the isopropenyl carbamate of propan-2-one O-2-cyano-4-(5-amino-3-tert-butyl-1H-pyrazol-1-yl)phenyl oxime (62 mg, 58% yield) that was used without further purification. MS (ESI) m/z: 396.2 (M+H$^+$).

The isopropenyl carbamate from the previous step (60 mg, 0.15 mmol), Example A2 (40 mg, 0.15 mmol) and N-methylpyrrolidine (1 mg, 0.015 mmol) were combined in THF (1 mL) and heated to 55° C. overnight. The reaction was concentrated and chromatographed to provide the corresponding urea (97 mg, >100% yield) as a dark foam. MS (ESI) m/z: 599.2 (M+H$^+$).

The above urea was dissolved in ethanol and treated with 3 M aq HCl (0.5 mL). After 24 h, another 0.5 mL of 3 M aq HCL was added and the stirring was continued for 3 days. The reaction mixture was partitioned aqueous 2 M Na$_2$CO$_3$ and EtOAc. The organic layer was washed with sat aq NaHCO3, water, and brine, dried (Na$_2$SO$_4$), concentrated in vacuo and purified by silica gel chromatography and recrystallization from acetone to provide 1-(1-(3-aminobenzo[d]isoxazol-5-yl)-3-tert-butyl-1H-pyrazol-5-yl)-3-(2-fluoro-4-(2-(methylcarbamoyl)pyridin-4-yloxy)phenyl)urea (33 mg, 39% yield over 2 steps). $^1$H NMR (400 MHz, DMSO-d$_6$) δ 8.93 (d, J=2.2 Hz, 1H), 8.86 (s, 1H), 7.77 (q, J=4.8 Hz, 1H), 8.50 (d, J=5.4 Hz, 1H), 8.20 (t, J=9.3 Hz, 1H), 7.99 (d, J=1.2 Hz, 1H), 7.64-7.59 (m, 2H), 7.37 (d, J=2.4 Hz, 1H), 7.29 (dd, J=11.9, 2.6 Hz, 1H), 7.15 (dd, J=5.6, 2.6 Hz, 1H), 7.03 (m, 1H), 6.55 (s, 2H), 6.41 (s, 1H), 2.77 (d, J=4.7 Hz, 3H), 1.27 (s, 9H); MS (ESI) m/z: 559.2 (M+H$^+$).

Example 48

Using a procedure analogous to Example 1, Example B9 (0.175 g, 0.41 mmol) and Example A42 (0.097 g, 0.389 mmol) were combined to afford 1-(2-fluoro-5-(6-nitropyridin-3-yloxy)phenyl)-3-(3-isopropyl-1-(quinolin-6-yl)-1H-pyrazol-5-yl)urea (0.129 g, 63% yield) as a light yellow oil. $^1$H NMR (400 MHz, DMSO-d$_6$) δ 8.94 (dd, J=4.4, 2.0 Hz, 1H), 8.48 (d, J=8.4 Hz, 1H), 8.31 (d, J=8.8 Hz, 1H), 8.26 (d, J=2.8 Hz, 1H), 8.20 (d, J=8.8 Hz, 1H), 8.11 (d, J=2.4 Hz, 1H), 8.00 (m, 1H), 7.91 (dd, J=9.2, 2.4 Hz, 1H), 7.63 (m, 1H), 7.58 (dd, J=8.8, 2.8 Hz, 1H), 7.22 (m, 1H), 6.84 (m, 1H), 6.46 (s, 1H), 2.98 (m, 1H), 1.30 (d, J=7.2 Hz, 6H); MS (ESI) m/z: 528.3 (M+H$^+$).

1-(2-fluoro-5-(6-nitropyridin-3-yloxy)phenyl)-3-(3-isopropyl-1-(quinolin-6-yl)-1H-pyrazol-5-yl)urea (0.129 g, 0.245 mmol) was dissolved in MeOH (2.0 mL), to which NH$_4$Cl (0.131 g, 2.45 mmol) and zinc power (0.160 g, 2.45 mmol) were added and the reaction mixture was stirred at RT for 4 h. The reaction mixture was filtered through Celite and washed with methanol (30 mL) and EtOAc (50 mL). The filtrate was concentrated in vacuum, partitioned between EtOAc (30 mL) and water (20 mL). The separated organic phase was washed with brine (10 mL), dried (MgSO$_4$) and concentrated to afford 1-(5-(6-aminopyridin-3-yloxy)-2-fluorophenyl)-3-(3-isopropyl-1-(quinolin-6-yl)-1H-pyrazol-5-yl)urea (0.0495 g, 41% yield) as a white foam. MS (ESI) m/z: 498.2 (M+H$^+$).

1-(5-(6-aminopyridin-3-yloxy)-2-fluorophenyl)-3-(3-isopropyl-1-(quinolin-6-yl)-1H-pyrazol-5-yl)urea (0.0495 g, 0.099 mmol) was dissolved in DCM (1.0 mL), to which pyridine (0.49 mL, 6.0 mmol) and acetic anhydride (0.066 mL, 0.65 mmol) were added. The reaction mixture was stirred at RT for 12 h. The completed reaction was quenched with 2M NaHCO$_3$ (12 mL) and extracted with EtOAc (25 mL). The organic layer was washed with H$_2$O (15 mL) and brine (10 mL), dried (MgSO$_4$), concentrated in vacuo and purified by chromatography to afford 1-(5-(6-acetamidopyridin-3-yloxy)-2-fluorophenyl)-3-(3-isopropyl-1-(quinolin-6-yl)-1H-pyrazol-5-yl)urea (0.0234 g, 44% yield) as a yellow foam. It was converted to corresponding mesylate salt by reacting with MsOH (1.0 eq.). $^1$H NMR (400 MHz, DMSO-d$_6$) δ 10.54 (s, 1H), 9.09 (s, 1H), 9.07-9.04 (m, 2H), 8.65 (d, J=8.0 Hz, 1H), 8.25 (d, J=2.0 Hz, 1H), 8.21 (d, J=8.8 Hz, 1H), 8.11-8.07 (m, 2H), 8.02 (dd, J=8.8, 2.4 Hz, 1H), 7.85 (m, 1H), 7.75 (m, 1H), 4.48 (dd, J=8.8, 3.2 Hz, 1H), 7.24 (m, 1H), 6.67 (m, 1H), 6.40 (s, 1H), 2.92 (m, 1H), 2.31 (s, 3H), 2.08 (s, 3H), 1.24 (d, J=7.2 Hz, 6H); MS (ESI) m/z: 540.0 (M+H$^+$).

Example 49

Using a procedure analogous to Example 1, Example B24 (150 mg, 0.26 mmol) and Example A28 (74 mg, 0.26 mmol) in presence of DIEA (90 µL, 0.52 mmol) were combined to afford benzyl 6-(3-tert-butyl-5-(3-(2-fluoro-4-(2-(1-methyl-1H-pyrazol-4-yl)pyridin-4-yloxy)phenyl)ureido)-1H-pyrazol-1-yl)-3,4-dihydroisoquinoline-2(1H)-carboxylate (100 mg, 56% yield).

To a solution of benzyl 6-(3-tert-butyl-5-(3-(2-fluoro-4-(2-(1-methyl-1H-pyrazol-4-yl)pyridin-4-yloxy)phenyl)ureido)-1H-pyrazol-1-yl)-3,4-dihydroisoquinoline-2(1H)-carboxylate (100 mg, 0.14 mmol) in methanol/EtOAc (1:1, 10 mL) was added 10% Pd/C. The solution was stirred overnight under H$_2$ (1 atm) at RT. The solution was filtered and concentrated in vacuo to obtain 1-(3-tert-butyl-1-(1,2,3,4-tetrahydroisoquinolin-6-yl)-1H-pyrazol-5-yl)-3-(2-fluoro-4-(2-(1-methyl-1H-pyrazol-4-yl)pyridin-4-yloxy)phenyl)urea (73 mg, 90% yield) $^1$H NMR (400 MHz, DMSO-d$_6$) δ 9.00 (brs, 1H), 8.02 (m, 1H), 8.35 (d, J=5.6 Hz, 1H), 8.25 (s, 1H), 8.15 (dt, J=2.4, and 8.8, 1H), 7.95 (s, 1H), 7.1-7.3 (m, 3H), 7.99 (m, 1H), 6.65 (m, 1H), 6.36 (d, J=2.8 Hz, 1H), 3.95 (m, 1H), 3.84 (s, 3H), 3.53 (m, 1H), 3.01 (m, 1H), 2.88 (m, 1H), 2.79 (m, 1H), 2.60 (m, 1H), 1.25 (s, 9H); MS (ESI) m/z: 581.3 (M+H$^+$).

Example 50

Using a procedure analogous to Example 1, Example B29 (0.20 g, 0.43 mmol) and Example A27 (118 mg, 0.43 mmol) were combined to afford 1-(4-(2-(1H-pyrazol-4-yl)pyridin-4-yloxy)-2-fluorophenyl)-3-(3-tert-butyl-1-(1-oxo-1,2,3,4-tetrahydroisoquinolin-7-yl)-1H-pyrazol-5-yl)urea (123 mg, 47% yield). $^1$H NMR (400 MHz, DMSO-d$_6$) δ 8.88 (brs, 1H), 8.83 (s, 1H), 8.33 (d, J=5.6 Hz, 1H), 8.10 (d, J=8.8 Hz, 1H), 8.07 (m, 2H), 7.85 (d, J=2.0 Hz, 1H), 7.57 (dd, J=2.4, and 8.0 Hz, 1H), 7.42 (d, J=8.0 Hz, 1H), 7.31 (brs, 1H), 7.18 (dd, J=2.4, and 12.0 Hz, 1H), 6.95 (m, 1H), 6.65 (m, 1H), 6.33 (s, 1H), 3.35 (m, 2H), 2.91 (m, 2H), 1.22 (s, 9H); MS (ESI) m/z: 581.3 (M+H$^+$).

Example 51

Using a procedure analogous to Example 1, Example B30 (0.20 g, 0.37 mmol) and Example A27 (100 mg, 0.37 mmol) were combined to afford tert-butyl 7-(5-(3-(4-(2-(1H-pyrazol-4-yl)pyridin-4-yloxy)-2-fluorophenyl)ureido)-3-tert-butyl-1H-pyrazol-1-yl)-3,4-dihydroisoquinoline-2(1H)-carboxylate (130 mg, 53% yield) which was treated with 4.0 M HCl/dioxane (2 mL) and it was stirred at RT for 4 hours. The solid was filtered, washed with ethyl acetate, and dried under vacuum to obtain 1-(4-(2-(1H-pyrazol-4-yl)pyridin-4-yloxy)-2-fluorophenyl)-3-(3-tert-butyl-1-(1,2,3,4-tetrahydroisoquinolin-7-yl)-1H-pyrazol-5-yl)urea HCl salt (120 mg, 96% yield). $^1$H NMR (400 MHz, DMSO-d$_6$) δ 9.51 (brs, 2H), 9.27 (brs, 1H), 9.21 (brs, 1H), 8.69 (brs, 2H), 8.54 (d, J=7.2 Hz, 1H), 8.22 (t, J=9.2 Hz, 1H), 7.84 (m, 1H), 7.3-7.5 (m, 4H), 7.13 (m 1H), 7.10 (dd, J=2.4, and 6.4 Hz, 1H), 6.37 (s, 1H), 4.38 (m, 2H), 3.38 (m, 2H), 3.05 (m, 2H), 1.28 (s, 9H); MS (ESI) m/z: 567.3 (M+H).

Example 52

Using a procedure analogous to Example 1, Example A36 (110 mg, 0.363 mmol) and Example B10 (150 mg, 0.363 mmol) were combined and purified by chromatography (Si-25 column, methanol/ethyl acetate) to give 1-(2,3-difluoro-4-(2-(1-methyl-1H-pyrazol-4-yl)pyridin-4-yloxy)phenyl)-3-(3-ethyl-1-(quinolin-6-yl)-1H-pyrazol-5-yl)urea as a white foam (66 mg, 32% yield). $^1$H NMR (400 MHz, dimethylsulfoxide-d$_6$) δ 1.27 (t, 3H), 2.65 (q, 2H), 3.89 (s, 3H), 6.46 (s, 1H), 6.74-6.76 (m, 1H), 7.22 (t, 1H), 7.29 (s, 1H), 7.65-7.68 (s, 1H), 7.97-8.02 (m, 3H), 8.20-8.22 (m, 2H), 8.31 (s, 1H), 8.40-8.42 (m, 1H), 8.50-8.53 (m, 1H), 9.00-9.01 (m, 1H), 9.11 (s, 1H), 9.19 (s, 1H); MS (ESI) m/z: 567.0 (M+H$^+$).

Example 53

Using a procedure analogous to Example 1, Example A38 (108 mg, 0.363 mmol) and Example B10 (150 mg, 0.363 mmol) were combined and purified by chromatography (Si-25 column, methanol/ethyl acetate) to give 1-(3-ethyl-1-(quinolin-6-yl)-1H-pyrazol-5-yl)-3-(2-fluoro-3-methyl-4-(2-(1-methyl-1H-pyrazol-4-yl)pyridin-4-yloxy)phenyl)urea as a white foam (78 mg, 38% yield). $^1$H NMR (400 MHz, dimethylsulfoxide-d$_6$) δ 1.29 (t, 3H), 2.09 (s, 3H), 2.67 (q, 2H), 3.91 (s, 3H), 6.47 (s, 1H), 6.59-6.61 (m, 1H), 7.00-7.02 (m, 1H), 7.22 (s, 1H), 7.67-7.70 (m, 1H), 7.99-8.10 (m, 3H), 8.22-8.24 (m, 2H), 8.30 (s, 1H), 8.39 (d, 1H), 8.53-8.55 (m, 1H), 9.00-9.03 (m, 2H), 9.10 (s, 1H); MS (ESI) m/z: 563.3 (M+H$^+$).

Example 54

Using a procedure analogous to Example 1, Example B3 (0.10 g, 0.23 mmol) and Example A32 (56 mg, 0.23 mmol) in the presence of DIEA (68 µL) were combined to afford 1-(3-tert-butyl-1-(quinolin-6-yl)-1H-pyrazol-5-yl)-3-(3-(5-chloropyridin-3-yloxy)-5-cyanophenyl)urea (39 mg, 32% yield). $^1$H NMR (400 MHz, DMSO-d$_6$) δ 9.47 (s, 1H), 8.98 (dd, J=2.0 and 4.4 Hz, 1H), 8.82 (s, 1H), 8.53 (d, J=2.0 Hz, 1H), 8.49 (m, 1H), 8.45 (d, J=2.4 Hz, 1H), 8.17 (m, 2H), 7.97 (dd, J=2.8 and 9.2 Hz, 1H), 7.84 (t, J=2.0 Hz, 1H), 7.70 (t, J=1.6 Hz, 1H), 7.65 (dd, J=4.0 and 8.0 Hz, 1H), 7.45 (t, J=2.0 Hz, 1H), 7.31 (m, 1H), 6.48 (s, 1H), 2.50 (s, 3H), 1.34 (s, 9H); MS (ESI) m/z: 538.0 (M+H$^+$).

Example 55

Using a procedure analogous to Example 1, Example B3 (0.10 g, 0.23 mmol) and Example A33 (51 mg, 0.23 mmol) in presence of DIEA (68 µL) were combined to afford 1-(3-tert-butyl-1-(quinolin-6-yl)-1H-pyrazol-5-yl)-3-(3-cyano-5-(6-methylpyridin-3-yloxy)phenyl)urea (31 mg, 27% yield). $^1$H NMR (400 MHz, DMSO-d$_6$) δ 9.43 (s, 1H), 8.98 (dd, J=2.0 and 4.4 Hz, 1H), 8.74 (s, 1H), 8.48 (m, 1H), 8.33 (d, J=2.8 Hz, 1H), 8.16 (m, 2H), 7.96 (dd, J=2.8 and 9.2 Hz, 1H), 7.63 (m, 2H), 7.50 (dd, J=2.8 and 8.0 Hz, 1H), 7.34 (d, J=8.4 Hz, 1H), 7.29 (t, J=2.0 Hz, 1H), 7.17 (m, 1H), 6.46 (s, 1H), 2.50 (s, 3H), 1.33 (s, 9H); MS (ESI) m/z: 518.0 (M+H$^+$).

Example 56

Using a procedure analogous to Example 1, Example A41 (15 mg, 0.055 mmol) and Example B9 (24 mg, 0.056 mmol) were combined to provide 1-(5-(4-(1H-pyrazol-4-yl)pyrimidin-2-yloxy)-2-fluorophenyl)-3-(3-isopropyl-1-(quinolin-6-yl)-1H-pyrazol-5-yl)urea (9 mg, 29% yield) $^1$H NMR (400 MHz, DMSO-d$_6$) δ 13.36 (s, 1H), 9.09 (s, 1H), 9.07 (s, 1H), 8.95 (m, 1H), 8.50-8.45 (m, 2H), 8.17-8.12 (m, 2H), 8.01 (dd, J=6.8, 2.9 Hz, 1H), 7.92 (dd, J=9.0, 2.1 Hz, 1H), 7.61 (dd, J=8.2, 4.1 Hz, 1H), 7.51 (d, J=5.0 Hz, 1H), 7.27 (dd, J=11.0, 8.9 Hz, 1H), 6.85 (m, 1H), 6.40 (s, 1H), 2.89 (m, 1H), 1.22 (d, J=6.8 Hz, 6H); MS (ESI) m/z: 550.2 (M+H$^+$).

The following examples were prepared by the methods described in Schemes 1-17, General Method A, the above Examples and the methods described in WO 2006/071940, filed Dec. 23, 2005, incorporated by reference: 1-(3-tert-butyl-1-(1,2,3,4-tetrahydroisoquinolin-6-yl)-1H-pyrazol-5-yl)-3-(3-fluoro-4-(2-(methylcarbamoyl)pyridin-4-yloxy) phenyl)urea, 1-(3-tert-butyl-1-(2-(methylamino)quinolin-6-yl)-1H-pyrazol-5-yl)-3-(2-fluoro-4-(2-(methylcarbamoyl) pyridin-4-yloxy)phenyl)urea, 1-(1-(4-(2-amino-2-oxoethyl) naphthalen-2-yl)-3-tert-butyl-1H-pyrazol-5-yl)-3-(2-chloro-5-(5-fluoropyridin-3-yloxy)phenyl)urea, 1-(3-tert-butyl-1-(quinolin-6-yl)-1H-pyrazol-5-yl)-3-(2-fluoro-5-(pyridin-3-yloxy)phenyl)urea, 1-(3-tert-butyl-1-(quinolin-6-yl)-1H-pyrazol-5-yl)-3-(2,4-difluoro-5-(pyridin-3-yloxy)phenyl) urea, 1-(3-tert-butyl-1-(1,2,3,4-tetrahydroisoquino lin-6-yl)-1H-pyrazol-5-yl)-3-(2,4-difluoro-5-(pyridin-3-yloxy) phenyl)urea, 1-(3-tert-butyl-1-(1H-indazol-5-yl)-1H-pyrazol-5-yl)-3-(2-fluoro-5-(pyridin-3-yloxy)phenyl)urea, 1-(5-tert-butyl-1-(quinolin-6-yl)-1H-pyrazol-3-yl)-3-(2-fluoro-4-(2-(methylcarbamoyl)pyridin-4-yloxy)phenyl) urea, 1-(3-tert-butyl-1-(quinolin-6-yl)-1H-pyrazol-5-yl)-3-(2-fluoro-4-(2-(2-hydroxyethylamino)pyridin-4-yloxy) phenyl)urea, 1-(3-tert-butyl-1-(quinolin-6-yl)-1H-pyrazol-5-yl)-3-(4-chloro-5-(6-cyanopyridin-3-yloxy)-2-fluorophenyl)urea, 1-(2-fluoro-4-(2-(methylcarbamoyl) pyridin-4-yloxy)phenyl)-3-(1-(quinolin-6-yl)-3-(trifluoromethyl)-1H-pyrazol-5-yl)urea, 1-(3-cyclopentyl-1-(quinolin-6-yl)-1H-pyrazol-5-yl)-3-(2-fluoro-4-(2-(methylcarbamoyl)pyridin-4-yloxy)phenyl)urea, 1-(3-cyclobutyl-1-(quinolin-6-yl)-1H-pyrazol-5-yl)-3-(2-fluoro-4-(2-(methylcarbamoyl)pyridin-4-yloxy)phenyl)urea, 1-(3-tert-butyl-1-(quino lin-6-yl)-1H-pyrazol-5-yl)-3-(5-(6-cyanopyridin-3-yloxy)-2-fluorophenyl)urea, 1-(3-tert-butyl-1-(quinolin-6-yl)-1H-pyrazol-5-yl)-3-(3-fluoro-4-(2-(methylamino)pyridin-4-yloxy)phenyl)urea, 1-(3-tert-butyl-1-(1,2,3,4-tetrahydroisoquinolin-6-yl)-1H-pyrazol-5-yl)-3-(4-methyl-3-(pyridin-3-yloxy)phenyl)urea, 1-(2-fluoro-5-(6-methylpyridin-3-yloxy)phenyl)-3-(3-isopropyl-1-(quinolin-6-yl)-1H-pyrazol-5-yl)urea, 1-(3-ethyl-1-(quinolin-6-yl)-1H-pyrazol-5-yl)-3-(2-fluoro-4-(2-(methylamino)pyridin-4-yloxy)phenyl)urea, 1-(3-tert-butyl-1-(1H-indazol-5-yl)-1H-pyrazol-5-yl)-3-(2-fluoro-5-(2-(methylamino)pyrimidin-4-yloxy)phenyl)urea, 1-(4-(2-carbamoylpyridin-4-yloxy)-2-fluorophenyl)-3-(4-chloro-2-(quinolin-6-yl)phenyl)urea, 1-(1-(1H-indazol-5-yl)-3-isopropyl-1H-pyrazol-5-yl)-3-(4-(2-carbamoylpyridin-4-yloxy)-2-fluorophenyl)urea, 1-(3-tert-butyl-1-(2-methylquinolin-6-yl)-1H-pyrazol-5-yl)-3-(4-(2-carbamoylpyridin-4-yloxy)-2-fluorophenyl)urea, 1-(4-(2-carbamoylpyridin-4-yloxy)-3-methylphenyl)-3-(3-isopropyl-1-(quinolin-6-yl)-1H-pyrazol-5-yl)urea, 1-(2-fluoro-4-(2-(methylcarbamoyl)pyridin-4-yloxy)phenyl)-3-(3-isopropyl-1-(2-methylquinolin-6-yl)-1H-pyrazol-5-yl) urea, 1-(3-isopropyl-1-(quinolin-6-yl)-1H-pyrazol-5-yl)-3-(3-methyl-4-(2-(methylcarbamoyl)pyridin-4-yloxy)phenyl) urea, 1-(4-(2-carbamoylpyridin-4-yloxy)-2-fluorophenyl)-3-(3-isopropyl-1-(2-methylquinolin-6-yl)-1H-pyrazol-5-yl) urea, 1-(4-(2-(dimethylamino)pyridin-4-yloxy)-2-fluorophenyl)-3-(3-isopropyl-1-(quinolin-6-yl)-1H-pyrazol-5-yl)urea, 1-(3-isopropyl-1-(quinolin-6-yl)-1H-pyrazol-5-yl)-3-(3-methyl-4-(2-(methylamino)pyridin-4-yloxy) phenyl)urea, 1-(3-tert-butyl-1-(quinolin-6-yl)-1H-pyrazol-5-yl)-3-(4-(2-carbamoylpyridin-4-yloxy)-3-methylphenyl) urea, 1-(5-(2-aminopyrimidin-4-yloxy)-2-fluorophenyl)-3-(3-isopropyl-1-(2-methylquinolin-6-yl)-1H-pyrazol-5-yl) urea, 1-(2-fluoro-4-(2-(methylamino)pyrimidin-4-yloxy) phenyl)-3-(3-isopropyl-1-(quinolin-6-yl)-1H-pyrazol-5-yl) urea, 1-(2-fluoro-5-(6-(methylcarbamoyl)pyridin-3-yloxy) phenyl)-3-(3-isopropyl-1-(quinolin-6-yl)-1H-pyrazol-5-yl) urea, 1-(3-isopropyl-1-(quinolin-6-yl)-1H-pyrazol-5-yl)-3-(2-methyl-4-(2-(methylcarbamoyl)pyridin-4-yloxy)phenyl) urea, 1-(3-tert-butyl-1-(2-methylquinolin-6-yl)-1H-pyrazol-5-yl)-3-(2-fluoro-4-(2-(methylamino)pyridin-4-yloxy) phenyl)urea, 1-(4-(2-(1H-pyrazol-4-yl)pyridin-4-yloxy)-2-fluorophenyl)-3-(3-methyl-1-(quinolin-6-yl)-1H-pyrazol-5-yl)urea, 1-(2-fluoro-4-(2-(methylcarbamoyl)pyridin-4-yloxy)phenyl)-3-(3-isopropyl-1-(quinoxalin-6-yl)-1H-pyrazol-5-yl)urea, 1-(4-(2-carbamoylpyridin-4-yloxy)-2-fluorophenyl)-3-(3-isopropyl-1-(quinoxalin-6-yl)-1H-pyrazol-5-yl)urea, 1-(1-(benzo[d]oxazol-5-yl)-3-tert-butyl-1H-pyrazol-5-yl)-3-(2-fluoro-4-(2-(methylcarbamoyl) pyridin-4-yloxy)phenyl)urea, 1-(4-(2-(1H-pyrazol-4-yl) pyridin-4-yloxy)-3-methylphenyl)-3-(3-isopropyl-1-(quinolin-6-yl)-1H-pyrazol-5-yl)urea, 1-(4-(2-(1H-pyrazol-4-yl)pyridin-4-yloxy)-2-fluorophenyl)-3-(3-tert-butyl-1-(1,2,3,4-tetrahydroisoquinolin-6-yl)-1H-pyrazol-5-yl)urea, 1-(3-fluoro-4-(2-(isopropylamino)pyridin-4-yloxy)phenyl)-3-(3-isopropyl-1-(quinolin-6-yl)-1H-pyrazol-5-yl)urea, 1-(3-isopropyl-1-(quinolin-6-yl)-1H-pyrazol-5-yl)-3-(4-(2-(isopropylamino)pyridin-4-yloxy)-3-methylphenyl)urea, 1-(4-(2-(cyclopentylamino)pyridin-4-yloxy)-2-fluorophenyl)-3-(3-isopropyl-1-(quinolin-6-yl)-1H-pyrazol-5-yl)urea and 1-(2-fluoro-4-(2-(1-methyl-1H-pyrazol-4-yl)pyridin-4-yloxy)phenyl)-3-(3-methyl-1-(quinolin-6-yl)-1H-pyrazol-5-yl)urea.

The following examples are prepared by the methods described in Schemes 1-17, General Method A, the above Examples and the methods described in WO 2006/071940, filed Dec. 23, 2005, incorporated by reference: 1-(3-tert-butyl-1-(1,2,3,4-tetrahydroisoquinolin-6-yl)-1H-pyrazol-5-yl)-3-(4-methyl-3-(4-(pyridin-3-yl)pyrimidin-2-yloxy)phenyl)urea, 1-(5-(4-(1H-pyrazol-4-yl)pyrimidin-2-yloxy)-2-fluorophenyl)-3-(3-isopropyl-1-(quinolin-6-yl)-1H-pyrazol-5-yl)urea, 1-(2-fluoro-4-methyl-5-(4-(1-methyl-1H-pyrazol-4-yl)pyrimidin-2-yloxy)phenyl)-3-(3-isopropyl-1-(quinolin-6-yl)-1H-pyrazol-5-yl)urea, 1-(2-fluoro-5-(4-(1-methyl-1H-pyrazol-4-yl)pyrimidin-2-yloxy)phenyl)-3-(3-isopropyl-1-(quinolin-6-yl)-1H-pyrazol-5-yl)urea, 1-(2-fluoro-4-(2-(1-methyl-1H-pyrazol-4-yl)pyridin-4-yloxy)phenyl)-3-(1-isopropyl-3-(quinolin-6-yl)-1H-pyrazol-4-yl)urea, 1-(2-fluoro-4-(2-(1-methyl-1H-pyrazol-4-yl)pyridin-4-yloxy)phenyl)-3-(1-isopropyl-4-(quinolin-6-yl)-1H-pyrrol-3-yl)urea, 1-(2-fluoro-4-(2-(1-methyl-1H-pyrazol-4-yl)pyridin-4-yloxy)phenyl)-3-(1-isopropyl-5-methyl-3-(quinolin-6-yl)-1H-pyrazol-4-yl)urea, 1-(2-fluoro-4-(2-(1-methyl-1H-pyrazol-4-yl)pyridin-4-yloxy)phenyl)-3-(2-isopropyl-5-(quinolin-6-yl)oxazol-4-yl)urea, 1-(2-fluoro-4-(2-(1-methyl-1H-pyrazol-4-yl)pyridin-4-yloxy)phenyl)-3-(2-isopropyl-5-(quinolin-6-yl)thiazol-4-yl)urea, 1-(2-fluoro-4-(2-(1-methyl-1H-pyrazol-4-yl)pyridin-4-yloxy)phenyl)-3-(5-isopropyl-2-(quinolin-6-yl)furan-3-yl)urea, 1-(2-fluoro-4-(2-(1-methyl-1H-pyrazol-4-yl)pyridin-4-yloxy)phenyl)-3-(5-isopropyl-2-(quinolin-6-yl)thiophen-3-yl)urea, 1-(2-fluoro-4-(2-(1-methyl-1H-pyrazol-4-yl)pyridin-4-yloxy)phenyl)-3-(4-isopropyl-1-(quinolin-6-yl)-1H-imidazol-2-yl)urea, 1-(2-fluoro-4-(2-(1-methyl-1H-pyrazol-4-yl)pyridin-4-yloxy)phenyl)-3-(5-isopropyl-2-(quinolin-6-yl)-1H-pyrrol-3-yl)urea, 1-(2-fluoro-4-(2-(1-methyl-1H-pyrazol-4-yl)pyridin-4-yloxy)phenyl)-3-(4-isopropyl-1-(quinolin-6-yl)-1H-pyrrol-2-yl)urea, 1-(2-fluoro-4-(2-(1-methyl-1H-pyrazol-4-yl)pyridin-4-yloxy)phenyl)-3-(5-methyl-2-(quinolin-6-yl)pyridin-3-yl)urea, 1-(2-fluoro-4-(2-(1-methyl-1H-pyrazol-4-yl)pyridin-4-yloxy)phenyl)-3-(1-isopropyl-3-(1,2,3,4-tetrahydroisoquinolin-6-yl)-1H-pyrazol-4-yl)urea, 1-(2-fluoro-4-(2-(1-methyl-1H-pyrazol-4-yl)pyridin-4-yloxy)phenyl)-3-(1-isopropyl-4-(1,2,3,4-tetrahydroisoquinolin-6-yl)-1H-pyrrol-3-yl)urea, 1-(2-fluoro-4-(2-(1-methyl-1H-pyrazol-4-yl)pyridin-4-yloxy)phenyl)-3-(2-isopropyl-5-(1,2,3,4-tetrahydroisoquinolin-6-yl)oxazol-4-yl)urea, 1-(2-fluoro-4-(2-(1-methyl-1H-pyrazol-4-yl)pyridin-4-yloxy)phenyl)-3-(2-isopropyl-5-(1,2,3,4-tetrahydroisoquinolin-6-yl)thiazol-4-yl)urea, 1-(2-fluoro-4-(2-(1-methyl-1H-pyrazol-4-yl)pyridin-4-yloxy)phenyl)-3-(5-isopropyl-2-(1,2,3,4-tetrahydroisoquinolin-6-yl)furan-3-yl)urea, 1-(2-fluoro-4-(2-(1-methyl-1H-pyrazol-4-yl)pyridin-4-yloxy)phenyl)-3-(5-isopropyl-2-(1,2,3,4-tetrahydroisoquinolin-6-yl)thiophen-3-yl)urea, 1-(2-fluoro-4-(2-(1-methyl-1H-pyrazol-4-yl)pyridin-4-yloxy)phenyl)-3-(4-isopropyl-1-(1,2,3,4-tetrahydroisoquinolin-6-yl)-1H-imidazol-2-yl)urea, 1-(2-fluoro-4-(2-(1-methyl-1H-pyrazol-4-yl)pyridin-4-yloxy)phenyl)-3-(5-isopropyl-2-(1,2,3,4-tetrahydroisoquinolin-6-yl)-1H-pyrrol-3-yl)urea, 1-(2-fluoro-4-(2-(1-methyl-1H-pyrazol-4-yl)pyridin-4-yloxy)phenyl)-3-(4-isopropyl-1-(1,2,3,4-tetrahydroisoquinolin-6-yl)-1H-pyrrol-2-yl)urea, 1-(2-fluoro-4-(2-(1-methyl-1H-pyrazol-4-yl)pyridin-4-yloxy)phenyl)-3-(5-methyl-2-(1,2,3,4-tetrahydroisoquinolin-6-yl)pyridin-3-yl)urea, 4-(3-fluoro-4-(3-(1-isopropyl-3-(quinolin-6-yl)-1H-pyrazol-4-yl)ureido)phenoxy)-N-methylpicolinamide, 4-(3-fluoro-4-(3-(1-isopropyl-4-(quinolin-6-yl)-1H-pyrrol-3-yl)ureido)phenoxy)-N-methylpicolinamide, 4-(3-fluoro-4-(3-(2-isopropyl-5-(quinolin-6-yl)oxazol-4-yl)ureido)phenoxy)-N-methylpicolinamide, 4-(3-fluoro-4-(3-(2-isopropyl-5-(quinolin-6-yl)thiazol-4-yl)ureido)phenoxy)-N-methylpicolinamide, 4-(3-fluoro-4-(3-(5-isopropyl-2-(quinolin-6-yl)thiophen-3-yl)ureido)phenoxy)-N-methylpicolinamide, 4-(3-fluoro-4-(3-(4-isopropyl-1-(quinolin-6-yl)-1H-imidazol-2-yl)ureido)phenoxy)-N-methylpicolinamide, 4-(3-fluoro-4-(3-(5-isopropyl-2-(quinolin-6-yl)-1H-pyrrol-3-yl)ureido)phenoxy)-N-methylpicolinamide, 4-(3-fluoro-4-(3-(4-isopropyl-1-(quinolin-6-yl)-1H-pyrrol-2-yl)ureido)phenoxy)-N-methylpicolinamide, 4-(3-fluoro-4-(3-(5-methyl-2-(quinolin-6-yl)pyridin-3-yl)ureido)phenoxy)-N-methylpicolinamide, 4-(3-fluoro-4-(3-(5-isopropyl-2-(quinolin-6-yl)furan-3-yl)ureido)phenoxy)-N-methylpicolinamide, 1-(5-(4-(1H-pyrazol-4-yl)pyrimidin-2-yloxy)-2-fluoro-4-methylphenyl)-3-(3-isopropyl-1-(quinolin-6-yl)-1H-pyrazol-5-yl)urea, 1-(2-fluoro-5-(4-(1-methyl-1H-pyrazol-4-yl)pyrimidin-2-yloxy)phenyl)-3-(3-isopropyl-1-(quinolin-6-yl)-1H-pyrazol-5-yl)urea, 145-(4-(1H-pyrazol-4-yl)pyrimidin-2-yloxy)-2-fluoro-4-methylphenyl)-3-(1-(benzo[d]oxazol-5-yl)-3-isopropyl-1H-pyrazol-5-yl)urea, 1-(2-fluoro-4-methyl-5-(4-(1-methyl-1H-pyrazol-4-yl)pyrimidin-2-yloxy)phenyl)-3-(3-isopropyl-1-(quinolin-6-yl)-1H-pyrazol-5-yl)urea, 1-(1-(benzo[d]oxazol-5-yl)-3-isopropyl-1H-pyrazol-5-yl)-3-(2-fluoro-5-(4-(1-methyl-1H-pyrazol-4-yl)pyrimidin-2-yloxy)phenyl)urea, 1-(5-(4-(1H-pyrazol-4-yl)pyrimidin-2-yloxy)-2-fluoro-4-methylphenyl)-3-(1-(imidazo[1,2-a]pyridin-6-yl)-3-isopropyl-1H-pyrazol-5-yl)urea, 1-(2-fluoro-5-(4-(1-methyl-1H-pyrazol-4-yl)pyrimidin-2-yloxy)phenyl)-3-(1-(imidazo[1,2-a]pyridin-6-yl)-3-isopropyl-1H-pyrazol-5-yl)urea.

Section 3

Abl kinase (Seq. ID No. 1) Assay

Activity of Abl kinase (Seq. ID no. 1) was determined by following the production of ADP from the kinase reaction through coupling with the pyruvate kinase/lactate dehydrogenase system (e.g., Schindler, et al. Science (2000) 289, 1938-1942). In this assay, the oxidation of NADH (thus the decrease at $A_{340nm}$) was continuously monitored spectrophotometrically. The reaction mixture (100 µl) contained Abl kinase (1 nM. Abl from deCode Genetics), peptide substrate (EAIYAAPFAKKK, 0.2 mM), $MgCl_2$ (10 mM), pyruvate kinase (4 units), lactate dehydrogenase (0.7 units), phosphoenol pyruvate (1 mM), and NADH (0.28 mM) in 90 mM Tris buffer containing 0.2% octyl-glucoside and 3.5% DMSO, pH 7.5. Test compounds were incubated with Abl (Seq. ID no. 1) and other reaction reagents at 30 C for 2 h before ATP (500 µM) was added to start the reaction. The absorption at 340 nm was monitored continuously for 2 hours at 30° C. on Polarstar Optima plate reader (BMG). The reaction rate was calculated using the 1.0 to 2.0 h time frame. Percent inhibition was obtained by comparison of reaction rate with that of a control (i.e. with no test compound). $IC_{50}$ values were calculated from a series of percent inhibition values determined at a range of inhibitor concentrations using software routines as implemented in the GraphPad Prism software package.

pAbl Kinase Assay

Activity of pAbl kinase (Seq. ID no. 1) was determined by following the production of ADP from the kinase reaction through coupling with the pyruvate kinase/lactate dehydrogenase system (e.g., Schindler, et al. Science (2000) 289, 1938-1942). In this assay, the oxidation of NADH (thus the decrease at $A_{340nm}$) was continuously monitored spectrophotometrically. The reaction mixture (100 μl) contained pAbl kinase (2 nM. pAbl from deCode Genetics), peptide substrate (EAIYAAPFAKKK, 0.2 mM), $MgCl_2$ (10 mM), pyruvate kinase (4 units), lactate dehydrogenase (0.7 units), phosphoenol pyruvate (1 mM), and NADH (0.28 mM) in 90 mM Tris buffer containing 0.2% octyl-glucoside and 3.5% DMSO, pH 7.5. Test compounds were incubated with pAbl (Seq. ID no. 1) and other reaction reagents at 30 C for 2 h before ATP (500 μM) was added to start the reaction. The absorption at 340 nm was monitored continuously for 2 hours at 30° C. on Polarstar Optima plate reader (BMG). The reaction rate was calculated using the 1.0 to 2.0 h time frame. Percent inhibition was obtained by comparison of reaction rate with that of a control (i.e. with no test compound). $IC_{50}$ values were calculated from a series of percent inhibition values determined at a range of inhibitor concentrations using software routines as implemented in the GraphPad Prism software package. pAbl was obtained as a phosphorylated form of the enzyme used in the Abl assay (see above).

Abl(T315I) (Seq. ID no. 2) Kinase Assay

Activity of Abl(T315I) (Seq. ID no. 2) kinase was determined by following the production of ADP from the kinase reaction through coupling with the pyruvate kinase/lactate dehydrogenase system (e.g., Schindler, et al. Science (2000) 289, 1938-1942). In this assay, the oxidation of NADH (thus the decrease at $A_{340nm}$) was continuously monitored spectrophometrically. The reaction mixture (100 μl) contained Abl (T315I) kinase (Seq. ID no. 2) (6 nM. Abl(T315I) from decode Genetics), peptide substrate (EAIYAAPFAKKK, 0.2 mM), $MgCl_2$ (10 mM), pyruvate kinase (4 units), lactate dehydrogenase (0.7 units), phosphoenol pyruvate (1 mM), and NADH (0.28 mM) in 90 mM Tris buffer containing 0.2% octyl-glucoside and 3.5% DMSO, pH 7.5. Test compounds were incubated with Abl(T315I) and other reaction reagents at 30 C for 2 h before ATP (500 μM) was added to start the reaction. The absorption at 340 nm was monitored continuously for 2 hours at 30° C. on Polarstar Optima plate reader (BMG). The reaction rate was calculated using the 1.0 to 2.0 h time frame. Percent inhibition was obtained by comparison of reaction rate with that of a control (i.e. with no test compound). $IC_{50}$ values were calculated from a series of percent inhibition values determined at a range of inhibitor concentrations using software routines as implemented in the GraphPad Prism software package.

```
Abl kinase                                                              (Seq. ID no. 1)
        MSYYHHHHHHDYDIPTTENLYFQGAMDPSSPNYDKWEMERTDITMKHKLGGGQYGEVYEGVW

KKYSLTVAVKTLKEDTMEVEEFLKEAAVMKEIKHPNLVQLLGVCTREPPFYIITEFMTYGNLLDYLRECN

RQEVNAVVLLYMATQISSAMEYLEKKNFIHRDLAARNCLVGENHLVKVADFGLSRLMTGDTYTAHAGAKF

PIKWTAPESLAYNKFSIKSDVWAFGVLLWEIATYGMSPYPGIDLSQVYELLEKDYRMERPEGCPEKVYEL

MRACWQWNPSDRPSFAEIHQAFETMFQESSISDEVEKELGKRGT

Abl(T315I) kinase                                                       (Seq. ID no. 2)
        MSYYHHHHHHDYDIPTTENLYFQGAMDPSSPNYDKWEMERTDITMKHKLGGGQYGEVYEGVW

KKYSLTVAVKTLKEDTMEVEEFLKEAAVMKEIKHPNLVQLLGVCTREPPFYIIIEFMTYGNLLDYLRECN

RQEVNAVVLLYMATQISSAMEYLEKKNFIHRDLAARNCLVGENHLVKVADFGLSRLMTGDTYTAHAGAKF

PIKWTAPESLAYNKFSIKSDVWAFGVLLWEIATYGMSPYPGIDLSQVYELLEKDYRMERPEGCPEKVYEL

MRACWQWNPSDRPSFAEIHQAFETMRGT
```

Cell Culture

BaF3 cells (parental or transfected with the following: wild type bcr-Abl or bcr-Abl point mutants T315I, E255K, Y253F, M351T) were obtained from Professor Richard Van Etten (New England Medical Center, Boston, Mass.). Briefly, cells were grown in RPMI 1640 supplemented with 10% characterized fetal bovine serum (HyClone, Logan, Utah) at 37 degrees Celsius, 5% $CO_2$, 95% humidity. Cells were allowed to expand until reaching 80% saturation at which point they were subcultured or harvested for assay use.

Cell Proliferation Assay

A serial dilution of test compound was dispensed into a 96 well black clear bottom plate (Corning, Corning, N.Y.). For each cell line, three thousand cells were added per well in complete growth medium. Plates were incubated for 72 hours at 37 degrees Celsius, 5% CO2, 95% humidity. At the end of the incubation period Cell Titer Blue (Promega, Madison, Wis.) was added to each well and an additional 4.5 hour incubation at 37 degrees Celsius, 5% CO2, 95% humidity was performed. Plates were then read on a BMG Fluostar Optima (BMG, Durham, N.C.) using an excitation of 544 nM and an emission of 612 nM. Data was analyzed using Prism software (Graphpad, San Diego, Calif.) to calculate $IC_{50}$'s.

Biological Data Summary. Biochemical $IC_{50}$ Values of Compounds of Formula Ia.

In general, compounds 1-56 disclosed herein exhibited >50% inhibition activity at 0.1-2 uM concentration against Abl kinase and T315I Abl kinase.

Biological Data Summary. Whole cell $IC_{50}$ Values of Compounds of Formula Ia.

In general, compounds 1-56 disclosed herein exhibited >50% inhibition of proliferation at 1-10 uM concentration against BaF/3 cells harboring wt bcr-Abl and or bcr-Abl point mutants including T315I, E255K, Y253F, and M351T.

Section 4—Important Structural Comparisons vs. Biological Activity

WO 2006/071940A2 describes inhibitors of kinases, including C-Abl kinase, B-Raf kinase, c-MET, VEGF kinase, and the HER family wherein a central phenyl ring is unsubstituted. An example of these inhibitors is shown below, wherein the central phenyl ring is unsubstituted (R16 and R18=H). Compounds A, B and C, discussed below, are taken from WO 2006/071940A2.

Representative Key Structures

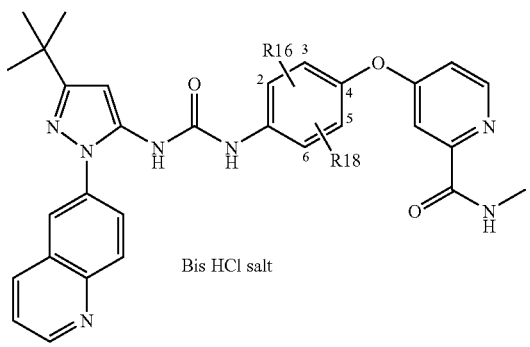

Bis HCl salt

Example 1 (R16 = 2-F, R18 = H),
Example 5 (R16 = 3-Me, R18 = H)
Compound A (R16 = H, R18 = H)

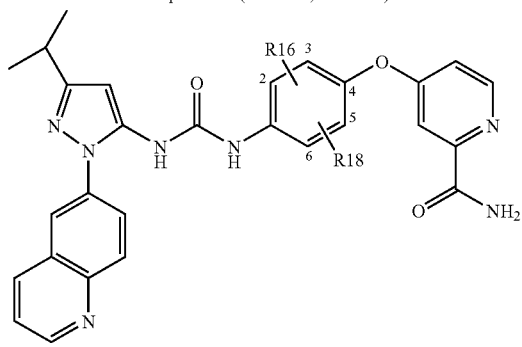

Example 15 (R16 = 2-F, R18 = H)
Compound B (R16 = H, R18 = H)

It has unexpectedly been found that inhibitors that contain R16 substituents other than H have superior potency as measured by in vitro kinase inhibition and also as measured by in vivo whole cell anti-proliferation potencies in cancer cells. By way of illustration in Table 1, Example 1 of the present invention containing a 2-F moiety as the R16 substituent is 5.5-times more potent vs. phosphorylated-Abl kinase (p-Abl) than the unsubstituted Compound A containing R16=H. Example 1 is 6.3 times more potent than Compound A vs. the T315I mutant Abl kinase, a clinical isolate of oncogenic Abl kinase found in patients with chronic myelogenous leukemia and in whom treatment is resistant to currently available therapies including Gleevec® (M. E. Gorre et al, *Science* (2001) 293: 876; S. Branford et al, *Blood* (2002) 99: 3472; N. von Bubnoff et al, *Lancet* (2002) 359: 487) and dasatinib (N. P. Shah et al, *Science* (2004) 305: 399). Example 5 containing a 3-methyl moiety as the R16 substituent is 4 times more potent vs. p-Abl kinase than the unsubstituted (R16=H) Compound A. Example 15 containing a 2-F moiety as the R16 substituent is 8-times more potent vs. unphosphorylated-Abl kinase (u-Abl) than the unsubstituted (R16=H) Compound B (from WO 2006/071940A2). Example 15 is >14-times more potent than Compound B vs. p-Abl kinase, and 18 times more potent than Compound B vs. the T315I mutant Abl kinase.

TABLE 1

|  | R16 | u-Abl IC$_{50}$ | p-Abl IC$_{50}$ | T315I Abl IC$_{50}$ |
|---|---|---|---|---|
| Example 1 | 2-F | 0.8 nM | 4 nM | 6 nM |
| Example 5 | 5-Me | 0.7 nM | 6 nM | 250 nM |
| Compound A | H | 1 nM | 22 | 38 |
| Example 15 | 2-F | 1 nM | 35 nM | 56 nM |
| Compound B | H | 8 nM | >500 nM | 1,000 nM |
| Example 4 | 2-F | 0.7 nM | 20 nM | 12 nM |
| Compound C | H | 1.6 nM | 350 nM | 160 nM |

Structures of Example 4 (R16=2-F, R18=H) and Compound C(R16, R18=H)

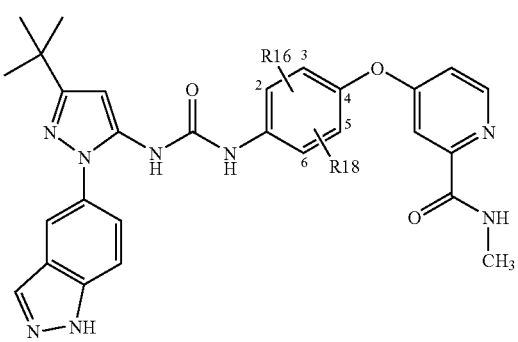

This trend is also evident in other analogs related to those mentioned above. As shown in Table 1, the indazolyl-containing compound Example 4 containing a 2-F moiety as the R16 substituent is 2.2 times more potent than the unsubstituted (R16=H) Compound C vs. u-Abl kinase, 18 times more potent than Compound C vs. p-Abl kinase, and 13 times more potent than Compound C vs. T315I mutant Abl kinase.

This unexpected increase in potency vs. these kinases is also revealed in whole cell assays which measure the effectiveness of these Abl kinase inhibitors to block proliferation of cells containing oncogenic forms of Abl kinase: the fusion protein bcr-Abl kinases (C. L. Sawyers, *New England Journal of Medicine* (1999) 340: 1330; S. Faderl et al, *New England Journal of Medicine* (1999) 341: 164; J. B. Konopka et al, *Proceeding of the National Academy of Sciences USA* (1985) 82: 1810). Table 2 illustrates the increased potency of substituted R16-containing compounds of Examples 1, 5, and 15 vs. their unsubstituted analogs Compounds A and B. The R16-substituted analogs are 2.6-4.5 times more potent than the unsubstituted analogs in BaF3 cells expressing oncogenic bcr-abl kinase, 1.5-3.5 times more potent in BaF3 cells expressing the T315I mutant oncogenic form of bcr-abl kinase, 3.5-7.2 times more potent in BaF3 cells expressing the Y253F mutant oncogenic form of bcr-abl kinase, 4.4-6 times more potent in BaF3 cells expressing the E255K mutant oncogenic form of bcr-abl kinase, and 3.2-4.2 times more potent in BaF3 cells expressing the M351T mutant oncogenic form of bcr-abl kinase. These five forms of bcr-abl kinase are oncogenic and are causative of human chronic myelogenous leukemia. Moreover, the four mutant forms of bcr-abl kinase are resistant to the currently available bcr-abl inhibitor Gleevec®.

TABLE 2

| | R16 | BaF3 wt bcr-abl IC$_{50}$ | BaF3 T315I bcr-abl IC$_{50}$ | BaF3 Y253F bcr-abl IC$_{50}$ | BaF3 E255K bcr-abl IC$_{50}$ | BaF3 M351T bcr-abl IC$_{50}$ |
|---|---|---|---|---|---|---|
| Example 1 | 2-F | 6 nM | 8 nM | 26 nM | 83 nM | 11 nM |
| Example 5 | 5-Me | 8 nM | 25 nM | 15 nM | 62 nM | 10 nM |
| Compound A | H | 16 nM | 12 nM | 108 nM | 368 nM | 35 nM |
| Example 15 | 2-F | 11 nM | 25 nM | 86 nM | 238 nM | 13 nM |
| Compound B | H | 49 nM | 87 nM | 297 nM | 1,109 nM | 54 nM |

The invention claimed is:

1. Compounds of the formula Ia

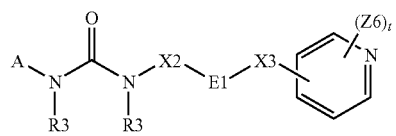

and pharmaceutically acceptable salts thereof;

wherein E1 is phenyl, and wherein the E1 ring is substituted with one to three R16 moieties;

wherein A is selected from the group consisting of imidazolyl, and pyrazolyl;

G1 is a heteroaryl taken from the group consisting of pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl, pyridinyl, and pyrimidinyl;

G4 is a heterocyclyl taken from the group consisting of oxetanyl, azetadinyl, tetrahydrofuranyl, pyrrolidinyl, oxazolinyl, oxazolidinyl, imidazolonyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl;

The A ring is substituted at any substitutable position with one A1 moiety, wherein A1 is selected from the group consisting of:

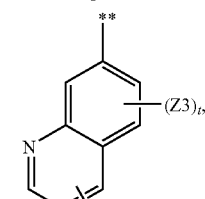

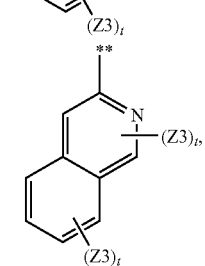

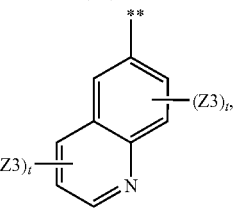

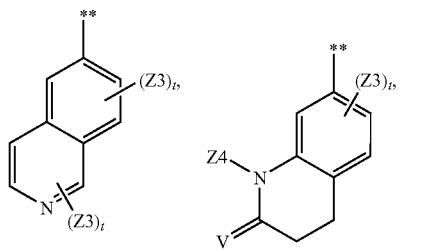

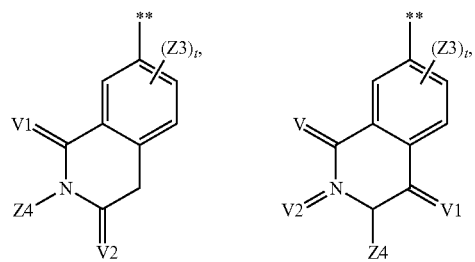

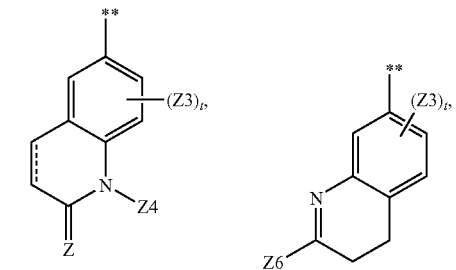

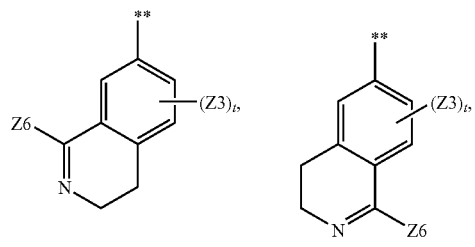

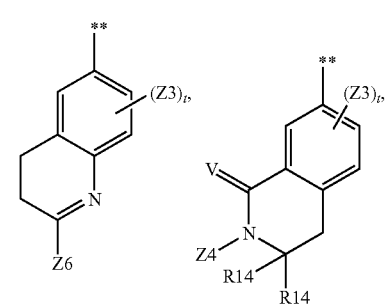

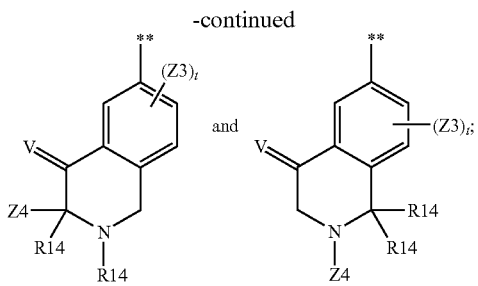

and wherein the symbol (**) is the point of attachment to the A ring of formula Ia;

and wherein ---- indicates either a saturated or unsaturated bond;

the A ring is optionally substituted with one or more R2 moieties;

X2 is a direct bond wherein E1 is directly linked to the NR3 group of formula Ia;

X3 is —O—;

V, V1, and V2 are each independently O or represent two hydrogens attached to the methylene carbon to which the V, V1, or V2 is attached;

each Z3 is independently and individually selected from the group consisting of H, C1-C6alkyl, branched C3-C7alkyl, C3-C8carbocyclyl, halogen, fluoroC1-C6alkyl wherein the alkyl moiety can be partially or fully fluorinated, cyano, hydroxyl, methoxy, oxo, $(R3)_2NC(O)$—, $(R4)_2NC(O)$—, —N(R4)C(O)R8, $(R3)_2NSO_2$—, $(R4)_2NSO_2$—, —N(R4)SO$_2$R5, —N(R4)SO$_2$R8, —(CH$_2$)N(R3)$_2$, —(CH$_2$)$_q$N(R4)$_2$, —O(CH$_2$)$_q$N(R4)$_2$, —O(CH$_2$)$_q$O—C1-C6alkyl, —N(R3)(CH$_2$)$_q$O—C1-C6alkyl, —N(R3)(CH$_2$)$_q$N(R4)$_2$, —O(CH$_2$)$_q$R5, —N(R3)(CH$_2$)$_q$R5, —C(O)R5, —C(O)R8, and nitro;

in the event that Z3 contains an alkyl or alkylene moiety, such moieties may be further substituted with one or more C1-C6alkyls;

each Z4 is independently and individually selected from the group consisting of H, C1-C6alkyl, hydroxyC2-C6alkyl, C1-C6alkoxyC2-C6alkyl, $(R4)_2N$—C2-C6alkyl, $(R4)_2N$—C2-C6alkylN(R4)-C2-C6alkyl, $(R4)_2N$—C2-C6alkyl-O—C2-C6alkyl, $(R4)_2NC(O)$—C1-C6alkyl, carboxyC1-C6alkyl-, C1-C6alkoxycarbonylC1-C6alkyl-, —C2-C6alkylN(R4)C(O)R8, R8-C(=NR3)-, —SO$_2$R8, —C(O)R8, —(CH$_2$)$_n$G1, —(CH$_2$)$_n$G4, —(CH$_2$)$_q$O(CH$_2$)$_n$G1, —(CH$_2$)$_q$O(CH$_2$)$_n$G4, —(CH$_2$)$_q$N(R3)(CH$_2$)$_n$G1, —(CH$_2$)$_q$N(R3)(CH$_2$)$_n$G4, —(CH$_2$)$_q$NHC(O)(CH$_2$)$_n$R5, —(CH$_2$)$_q$C(O)NH(CH$_2$)$_q$R5, —(CH$_2$)$_q$C(O)R5, —(CH$_2$)$_q$OC(O)R5, —(CH$_2$)$_q$R5, —(CH$_2$)$_q$NR4(CH$_2$)$_q$R5, and —(CH$_2$)$_q$O(CH$_2$)$_q$R5;

in the event that Z4 contains an alkyl or alkylene moiety, such moieties may be further substituted with one or more C1-C6alkyls;

each Z6 is independently and individually selected from the group consisting of H, C1-C6alkyl, branched C3-C7alkyl, hydroxyl, hydroxyC1-C6alkyl, hydroxyC2-C6 branched alkyl, C1-C6alkoxy, C1-C6alkoxyC1-C6alkyl-, C1-C6alkoxyC2-C6 branched alkyl-, C2-C6 branched alkoxy-, C1-C6alkylthio-, $(R3)_2N$—, —N(R3)C(O)R8, $(R4)_2N$—, —R5, —N(R4)C(O)R8, —N(R3)SO$_2$R6, —C(O)N(R3)$_2$, —C(O)N(R4)$_2$, —C(O)R5, —SO$_2$NH(R4), halogen, fluoroC1-C6alkyl wherein the alkyl is fully or partially fluorinated, cyano, fluoroC1-C6alkoxy wherein the alkyl is fully or partially fluorinated, —O(CH$_2$)$_q$N(R4)$_2$, —N(R3)(CH$_2$)$_q$N(R4)$_2$, —O(CH$_2$)$_q$O—C1-C6alkyl, —O(CH$_2$)$_q$N(R4)$_2$, —N(R3)(CH$_2$)$_q$O—C1-C6alkyl, —N(R3)(CH$_2$)$_q$N(R4)$_2$, —O(CH$_2$)$_q$R5, N(R3)(CH$_2$)$_q$R5, —(NR3)$_r$R17, —(O)$_r$R17, —(S)$_r$R17, —(CH$_2$)$_r$R17, —R17, —(CH$_2$)$_n$G1, —(CH$_2$)$_n$G4, —(CH$_2$)$_n$O(CH$_2$)$_n$G1, —(CH$_2$)$_n$O(CH$_2$)$_n$G4, —(CH$_2$)$_n$N(R3)(CH$_2$)$_n$G1, and —(CH$_2$)$_n$N(R3)(CH$_2$)$_n$G4;

each R2 is selected from the group consisting of Z3-substituted aryl, Z3-substituted G1-, Z3-substituted G4-, C1-C6 alkyl, branched C3-C8alkyl, R19 substituted C3-C8cycloalkyl fluoroC1-C6alkyl wherein the alkyl is fully or partially fluorinated, cyano, C1-C6alkoxy, and fluoroC1-C6alkoxy wherein the alkyl group is fully or partially fluorinated;

wherein each R3 is independently and individually selected from the group consisting of H, C1-C6alkyl, branched C3-C7alkyl, C3-C7-carbocyclyl, and Z3-substituted phenyl;

each R4 is independently and individually selected from the group consisting of H, C1-C6alkyl, hydroxyC1-C6alkyl-, dihydroxyC1-C6alkyl-, C1-C6alkoxyC1-C6alkyl-, branched C3-C7alkyl-, branched hydroxyC1-C6alkyl-, branched C1-C6alkoxyC1-C6alkyl-, branched dihydroxyC2-C6alkyl-, —(CH$_2$)$_p$N(R7)$_2$, —(CH$_2$)$_p$R5, —(CH$_2$)$_p$C(O)N(R7)$_2$, —(CH$_2$)$_n$C(O)R5, —(CH$_2$)$_n$C(O)OR3, C3-C7-carbocyclyl, hydroxyl substituted C3-C7-carbocyclyl-, alkoxy substituted C3-C7-carbocyclyl-, dihydroxyl substituted C3-C7-carbocyclyl-, and —(CH$_2$)$_n$R17;

each R5 is independently and individually selected from the group consisting of

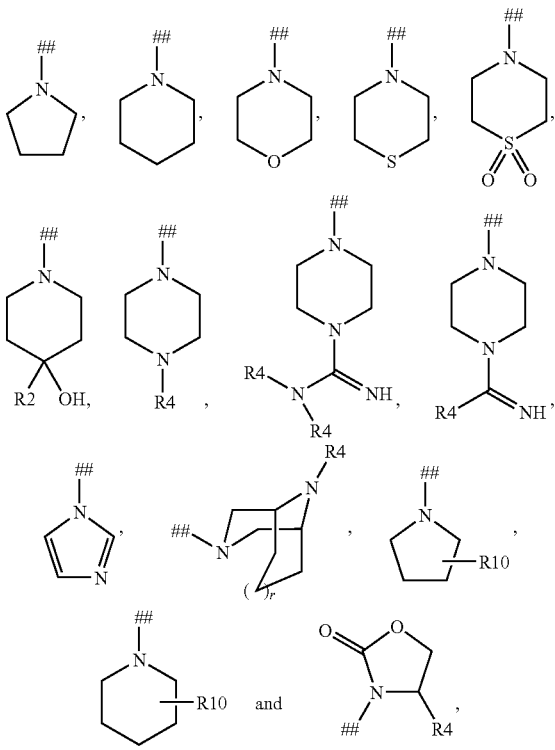

and wherein the symbol (##) is the point of attachment of the R5 moiety;

each R6 is independently and individually selected from the group consisting of C1-C6alkyl, branched C3-C7alkyl, C3-C7-carbocyclyl, phenyl, G1, and G4;

each R7 is independently and individually selected from the group consisting of H, C1-C6alkyl, hydroxyC2-C6alkyl-, dihydroxyC2-C6alkyl-, C2-C6alkoxyC2-C6alkyl-, branched C3-C7alkyl-, branched hydroxyC2-C6 alkyl-, branched C2-C6alkoxyC2-C6alkyl-, branched dihydroxyC2-C6alkyl-, —(CH$_2$)$_q$R5, —(CH$_2$)$_n$C(O)R5, —(CH$_2$)$_n$C(O)OR3, C3-C7-carbocyclyl, hydroxyl substituted C3-C7-carbocyclyl-, alkoxy substituted C3-C7-carbocyclyl-, dihydroxy substituted C3-C7-carbocyclyl, and —(CH$_2$)$_n$R17;

each R8 is independently and individually selected from the group consisting of C1-C6alkyl, branched C3-C7alkyl, fluoroC1-C6alkyl wherein the alkyl moiety is partially or fully fluorinated, C3-C7-carbocyclyl, phenyl-, phenylC1-C6alkyl-, G1, G1-C1-C6alkyl-, G4, G4-C1-C6alkyl-, OH, C1-C6alkoxy, N(R3)$_2$, N(R4)$_2$, and R5;

each R9 is independently and individually selected from the group consisting of H, F, C1-C6alkyl, branched C3-C7alkyl, C3-C7-carbocyclyl, phenyl, phenyl-C1-C6alkyl-, —(CH$_2$)$_n$G1, and —(CH$_2$)$_n$G4;

each R10 is independently and individually selected from the group consisting of CO$_2$H, CO$_2$C1-C6alkyl, —C(O)N(R4)$_2$, OH, C1-C6alkoxy, and —N(R4)$_2$;

each R14 is independently and respectively selected from the group consisting of H, C1-C6alkyl, branched C3-C6alkyl, and C3-C7-carbocyclyl;

R16 is independently and individually selected from the group consisting of fluorine and methyl;

each R17 is taken from the group comprising phenyl, naphthyl, pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl, oxetanyl, azetadinyl, tetrahydrofuranyl, oxazolinyl, oxazolidinyl, pyranyl, thiopyranyl, tetrahydropyranyl, dioxalinyl, azepinyl, oxepinyl, and diazepinyl;

wherein R17 can be optionally substituted with an R3 substituent;

R19 is H or C1-C6 alkyl;

n is 0-6; p is 1-4; q is 2-6; r is 0 or 1; t is 1-3, and v is 1 or 2.

2. Compounds of claim 1 having the formula Ib

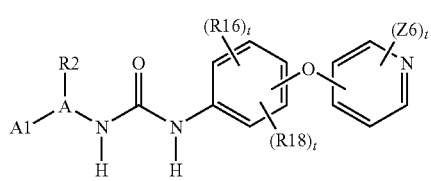

wherein A is pyrazolyl.

3. A compound of claim 1 having the formula Iv:

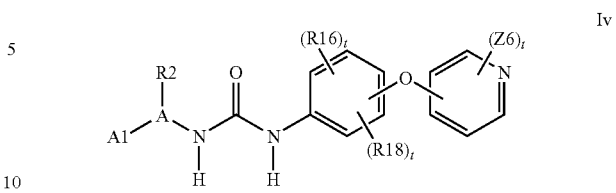

wherein A is imidazolyl.

4. A pharmaceutical composition comprising a compound of claim 1 together with a pharmaceutically acceptable carrier, said carrier including an additive selected from the group consisting of adjuvants, excipients, diluents, and stablilizers.

5. A compound selected from the group consisting of
1-(3-tert-butyl-1-(1,2,3,4-tetrahydroisoquinolin-6-yl)-1H-pyrazol-5-yl)-3-(3-fluoro-4-(2-(methylcarbamoyl)pyridin-4-yloxy)phenyl)urea,
1-(3-tert-butyl-1-(quinolin-6-yl)-1H-pyrazol-5-yl)-3-(2-fluoro-4-(2-(methylcarbamoyl)pyridin-4-yloxy)phenyl)urea,
1-(3-tert-butyl-1-(1,2,3,4-tetrahydroisoquinolin-6-yl)-1H-pyrazol-5-yl)-3-(2-fluoro-4-(2-(methylcarbamoyl)pyridin-4-yloxy)phenyl)urea,
1-(3-tert-butyl-1-(quinolin-6-yl)-1H-pyrazol-5-yl)-3-(3-fluoro-4-(2-(methylcarbamoyl)pyridin-4-yloxy)phenyl)urea,
1-(3-tert-butyl-1-(quinolin-6-yl)-1H-pyrazol-5-yl)-3-(2-fluoro-5-(pyridin-3-yloxy)phenyl)urea,
1-(3-tert-butyl-1-(quinolin-6-yl)-1H-pyrazol-5-yl)-3-(3-methyl-4-(2-(methylcarbamoyl)pyridin-4-yloxy)phenyl)urea,
1-(3-tert-butyl-1-(quinolin-6-yl)-1H-pyrazol-5-yl)-3-(4-(2-carbamoylpyridin-4-yloxy)-2-fluorophenyl)urea,
1-(3-tert-butyl-1-(quinolin-6-yl)-1H-pyrazol-5-yl)-3-(2-fluoro-4-(2-(methylamino)pyridin-4-yloxy)phenyl)urea,
1-(2-fluoro-4-(2-(methylcarbamoyl)pyridin-4-yloxy)phenyl)-3-(3-isopropyl-1-(quinolin-6-yl)-1H-pyrazol-5-yl)urea,
1-(3-ethyl-1-(quinolin-6-yl)-1H-pyrazol-5-yl)-3-(2-fluoro-4-(2-(methylcarbamoyl)pyridin-4-yloxy)phenyl)urea,
1-(3-cyclopentyl-1-(quinolin-6-yl)-1H-pyrazol-5-yl)-3-(2-fluoro-4-(2-(methylcarbamoyl)pyridin-4-yloxy)phenyl)urea,
1-(3-tert-butyl-1-(quinolin-6-yl)-1H-pyrazol-5-yl)-3-(2-fluoro-5-(6-(hydroxymethyl)pyridin-3-yloxy)phenyl)urea,
1-(3-tert-butyl-1-(1,2,3,4-tetrahydroisoquinolin-6-yl)-1H-pyrazol-5-yl)-3-(4-methyl-3-(pyridin-3-yloxy)phenyl)urea,
1-(4-(2-carbamoylpyridin-4-yloxy)-2-fluorophenyl)-3-(3-isopropyl-1-(quinolin-6-yl)-1H-pyrazol-5-yl)urea,
1-(3-isopropyl-1-(quinolin-6-yl)-1H-pyrazol-5-yl)-3-(3-methyl-4-(2-(methylcarbamoyl)pyridin-4-yloxy)phenyl)urea,
1-(4-(2-carbamoylpyridin-4-yloxy)-2-fluorophenyl)-3-(3-ethyl-1-(quinolin-6-yl)-1H-pyrazol-5-yl)urea,
1-(3-tert-butyl-1-(quinolin-6-yl)-1H-pyrazol-5-yl)-3-(2-fluoro-5-(6-(methylcarbamoyl)pyridin-3-yloxy)phenyl)urea,
1-(4-(2-carbamoylpyridin-4-yloxy)-3-methylphenyl)-3-(3-isopropyl-1-(quinolin-6-yl)-1H-pyrazol-5-yl)urea, 1-(2-fluoro-4-(2-(1-methyl-1H-pyrazol-4-yl)pyridin-4-yloxy)phenyl)-3-(3-isopropyl-1-(quinolin-6-yl)-1H-pyrazol-5-yl)urea, 1-(3-ethyl-1-(quinolin-6-yl)-1H-pyrazol-5-yl)-3-(2-fluoro-4-(2-(1-methyl-1H-pyrazol-4-yl)pyridin-4-yloxy)phenyl)urea, 1-(4-(2-(1H-pyrazol-4-yl)pyridin-4-yloxy)-3-methylphenyl)-3-(3-isopropyl-1-(quinolin-6-yl)-1H-pyrazol-5-yl)urea, 1-(3-tert-butyl-1-(1,2,3,4-tetrahydroisoquinolin-6-yl)-1H-pyrazol-5-yl)-3-(2-fluoro-4-(2-(1-methyl-1H-pyrazol-4-yl)pyridin-4-yloxy)phenyl)urea, 1-(4-(2-(1H-pyrazol-4-yl)pyridin-4-yloxy)-2-fluorophenyl)-3-(3-tert-butyl-1-(1,2,3,4-tetrahydroisoquinolin-6-yl)-1H-pyrazol-5-yl)urea, 1-(4-(2-(1H-pyrazol-4-yl)pyridin-4-yloxy)-2-fluorophenyl)-3-(3-tert-butyl-1-(1,2,3,4-tetrahydroisoquinolin-7-yl)-1H-pyrazol-5-yl)urea, 1-(3-fluoro-4-(2-(isopropylamino)pyridin-4-yloxy)phenyl)-3-(3-isopropyl-1-(quinolin-6-yl)-1H-pyrazol-5-yl)urea, 1-(3-isopropyl-1-(quinolin-6-yl)-1H-pyrazol-5-yl)-3-(4-(2-(isopropylamino)pyridin-4-yloxy)-3-methylphenyl)urea, 1-(3-ethyl-1-(quinolin-6-yl)-1H-pyrazol-5-yl)-3-(2-fluoro-3-methyl-4-(2-(1-methyl-1H-pyrazol-4-yl)pyridin-4-yloxy)phenyl)urea, and 1-(2,3-difluoro-4-(2-(1-methyl-1H-pyrazol-4-yl)pyridin-4-yloxy)phenyl)-3-(3-ethyl-1-(quinolin-6-yl)-1H-pyrazol-5-yl)urea and pharmaceutically acceptable salts, and tautomers thereof.

6. The compound 1-(4-(2-carbamoylpyridin-4-yloxy)-2-fluorophenyl)-3-(3-isopropyl-1-(quinolin-6-yl)-1H-pyrazol-5-yl)urea and pharmaceutically acceptable salts, and tautomers thereof.

7. The compound 1-(3-tert-butyl-1-(quinolin-6-yl)-1H-pyrazol-5-yl)-3-(3-methyl-4-(2-(methylcarbamoyl)pyridin-4-yloxy)phenyl)urea and pharmaceutically acceptable salts, and tautomers thereof.

8. The compound 1-(3-tert-butyl-1-(quinolin-6-yl)-1H-pyrazol-5-yl)-3-(2-fluoro-4-(2-(methylcarbamoyl)pyridin-4-yloxy)phenyl)urea and pharmaceutically acceptable salts, and tautomers thereof.

9. The compound 1-(3-tert-butyl-1-(quinolin-6-yl)-1H-pyrazol-5-yl)-3-(4-(2-carbamoylpyridin-4-yloxy)-2-fluorophenyl)urea and pharmaceutically acceptable salts, and tautomers thereof.

10. The compound 1-(2-fluoro-4-(2-(methylcarbamoyl)pyridin-4-yloxy)phenyl)-3-(3-isopropyl-1-(quinolin-6-yl)-1H-pyrazol-5-yl)urea and pharmaceutically acceptable salts, and tautomers thereof.

11. A pharmaceutical composition comprising a compound of claim 5, or a pharmaceutically acceptable salt thereof, and a pharmaceutically acceptable carrier.

12. A pharmaceutical composition comprising the compound of claim 6, or a pharmaceutically acceptable salt thereof, and a pharmaceutically acceptable carrier.

13. A pharmaceutical composition comprising the compound of claim 7, or a pharmaceutically acceptable salt thereof, and a pharmaceutically acceptable carrier.

14. A pharmaceutical composition comprising the compound of claim 8, or a pharmaceutically acceptable salt thereof, and a pharmaceutically acceptable carrier.

15. A pharmaceutical composition comprising the compound of claim 9, or a pharmaceutically acceptable salt thereof, and a pharmaceutically acceptable carrier.

16. A pharmaceutical composition comprising the compound of claim 10, or a pharmaceutically acceptable salt thereof, and a pharmaceutically acceptable carrier.

17. The pharmaceutical composition of claim 11, further comprising an additive selected from the group consisting of adjuvants, excipients, diluents, and stablilizers.

18. A pharmaceutical composition of claim 12, further comprising an additive selected from the group consisting of adjuvants, excipients, diluents, and stablilizers.

19. A pharmaceutical composition of claim 13, further comprising an additive selected from the group consisting of adjuvants, excipients, diluents, and stablilizers.

20. A pharmaceutical composition of claim 14, further comprising an additive selected from the group consisting of adjuvants, excipients, diluents, and stablilizers.

21. A pharmaceutical composition of claim 15, further comprising an additive selected from the group consisting of adjuvants, excipients, diluents, and stablilizers.

22. A pharmaceutical composition of claim 16, further comprising an additive selected from the group consisting of adjuvants, excipients, diluents, and stablilizers.

* * * * *

SEQUENCE LISTING

<160> NUMBER OF SEQ ID NOS: 3

<210> SEQ ID NO 1
<211> LENGTH: 316
<212> TYPE: PRT
<213> ORGANISM: Homo sapiens

<400> SEQUENCE: 1

```
Met Ser Tyr Tyr His His His His His His Asp Tyr Asp Ile Pro Thr
1               5                   10                  15

Thr Glu Asn Leu Tyr Phe Gln Gly Ala Met Asp Pro Ser Ser Pro Asn
            20                  25                  30

Tyr Asp Lys Trp Glu Met Glu Arg Thr Asp Ile Thr Met Lys His Lys
        35                  40                  45

Leu Gly Gly Gly Gln Tyr Gly Glu Val Tyr Glu Gly Val Trp Lys Lys
    50                  55                  60

Tyr Ser Leu Thr Val Ala Val Lys Thr Leu Lys Glu Asp Thr Met Glu
65                  70                  75                  80

Val Glu Glu Phe Leu Lys Glu Ala Ala Val Met Lys Glu Ile Lys His
                85                  90                  95

Pro Asn Leu Val Gln Leu Leu Gly Val Cys Thr Arg Glu Pro Pro Phe
            100                 105                 110

Tyr Ile Ile Thr Glu Phe Met Thr Tyr Gly Asn Leu Leu Asp Tyr Leu
        115                 120                 125

Arg Glu Cys Asn Arg Gln Glu Val Asn Ala Val Val Leu Leu Tyr Met
    130                 135                 140

Ala Thr Gln Ile Ser Ser Ala Met Glu Tyr Leu Glu Lys Lys Asn Phe
145                 150                 155                 160

Ile His Arg Asp Leu Ala Ala Arg Asn Cys Leu Val Gly Glu Asn His
                165                 170                 175

Leu Val Lys Val Ala Asp Phe Gly Leu Ser Arg Leu Met Thr Gly Asp
            180                 185                 190

Thr Tyr Thr Ala His Ala Gly Ala Lys Phe Pro Ile Lys Trp Thr Ala
        195                 200                 205

Pro Glu Ser Leu Ala Tyr Asn Lys Phe Ser Ile Lys Ser Asp Val Trp
    210                 215                 220

Ala Phe Gly Val Leu Leu Trp Glu Ile Ala Thr Tyr Gly Met Ser Pro
225                 230                 235                 240

Tyr Pro Gly Ile Asp Leu Ser Gln Val Tyr Glu Leu Leu Glu Lys Asp
                245                 250                 255

Tyr Arg Met Glu Arg Pro Glu Gly Cys Pro Glu Lys Val Tyr Glu Leu
            260                 265                 270
```

Met Arg Ala Cys Trp Gln Trp Asn Pro Ser Asp Arg Pro Ser Phe Ala
        275                 280                 285

Glu Ile His Gln Ala Phe Glu Thr Met Phe Gln Glu Ser Ser Ile Ser
        290                 295                 300

Asp Glu Val Glu Lys Glu Leu Gly Lys Arg Gly Thr
305                 310                 315

<210> SEQ ID NO 2
<211> LENGTH: 300
<212> TYPE: PRT
<213> ORGANISM: Homo sapiens

<400> SEQUENCE: 2

Met Ser Tyr Tyr His His His His Asp Tyr Asp Ile Pro Thr
1               5                   10                  15

Thr Glu Asn Leu Tyr Phe Gln Gly Ala Met Asp Pro Ser Ser Pro Asn
            20                  25                  30

Tyr Asp Lys Trp Glu Met Glu Arg Thr Asp Ile Thr Met Lys His Lys
        35                  40                  45

Leu Gly Gly Gly Gln Tyr Gly Glu Val Tyr Glu Gly Val Trp Lys Lys
    50                  55                  60

Tyr Ser Leu Thr Val Ala Val Lys Thr Leu Lys Glu Asp Thr Met Glu
65                  70                  75                  80

Val Glu Glu Phe Leu Lys Glu Ala Ala Val Met Lys Glu Ile Lys His
                85                  90                  95

Pro Asn Leu Val Gln Leu Leu Gly Val Cys Thr Arg Glu Pro Pro Phe
            100                 105                 110

Tyr Ile Ile Ile Glu Phe Met Thr Tyr Gly Asn Leu Leu Asp Tyr Leu
        115                 120                 125

Arg Glu Cys Asn Arg Gln Glu Val Asn Ala Val Val Leu Leu Tyr Met
    130                 135                 140

Ala Thr Gln Ile Ser Ser Ala Met Glu Tyr Leu Glu Lys Lys Asn Phe
145                 150                 155                 160

Ile His Arg Asp Leu Ala Ala Arg Asn Cys Leu Val Gly Glu Asn His
                165                 170                 175

Leu Val Lys Val Ala Asp Phe Gly Leu Ser Arg Leu Met Thr Gly Asp
            180                 185                 190

Thr Tyr Thr Ala His Ala Gly Ala Lys Phe Pro Ile Lys Trp Thr Ala
        195                 200                 205

Pro Glu Ser Leu Ala Tyr Asn Lys Phe Ser Ile Lys Ser Asp Val Trp
    210                 215                 220

Ala Phe Gly Val Leu Leu Trp Glu Ile Ala Thr Tyr Gly Met Ser Pro
225                 230                 235                 240

Tyr Pro Gly Ile Asp Leu Ser Gln Val Tyr Glu Leu Leu Glu Lys Asp
                245                 250                 255

Tyr Arg Met Glu Arg Pro Glu Gly Cys Pro Glu Lys Val Tyr Glu Leu
            260                 265                 270

Met Arg Ala Cys Trp Gln Trp Asn Pro Ser Asp Arg Pro Ser Phe Ala
        275                 280                 285

Glu Ile His Gln Ala Phe Glu Thr Met Arg Gly Thr
    290                 295                 300

<210> SEQ ID NO 3
<211> LENGTH: 12
<212> TYPE: PRT
<213> ORGANISM: Homo sapiens

```
<400> SEQUENCE: 3

Glu Ala Ile Tyr Ala Ala Pro Phe Ala Lys Lys Lys
1               5                   10
```